United States Patent
Hanson

(10) Patent No.: US 10,487,326 B2
(45) Date of Patent: *Nov. 26, 2019

(54) PEPTIDE OLIGONUCLEOTIDE CONJUGATES

(71) Applicant: Sarepta Therapeutics, Inc., Cambridge, MA (US)

(72) Inventor: Gunnar J. Hanson, Cambridge, MA (US)

(73) Assignee: SAREPTA THERAPEUTICS, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/827,431

(22) Filed: Nov. 30, 2017

(65) Prior Publication Data

US 2018/0298383 A1    Oct. 18, 2018

Related U.S. Application Data

(60) Continuation of application No. 14/851,434, filed on Sep. 11, 2015, now Pat. No. 9,862,946, which is a division of application No. 13/299,310, filed on Nov. 17, 2011, now Pat. No. 9,161,948, which is a continuation-in-part of application No. 13/107,528, filed on May 13, 2011, now Pat. No. 9,238,042, and a continuation-in-part of application No. 13/101,942, filed on May 5, 2011, now abandoned.

(51) Int. Cl.
| | |
|---|---|
| *C12N 15/113* | (2010.01) |
| *A61K 31/713* | (2006.01) |
| *C12N 15/87* | (2006.01) |
| *A61K 31/712* | (2006.01) |
| *A61K 47/64* | (2017.01) |

(52) U.S. Cl.
CPC .......... *C12N 15/113* (2013.01); *A61K 31/712* (2013.01); *A61K 31/713* (2013.01); *A61K 47/64* (2017.08); *A61K 47/645* (2017.08); *C12N 15/1136* (2013.01); *C12N 15/1138* (2013.01); *C12N 15/87* (2013.01); *C12N 2310/11* (2013.01); *C12N 2310/3233* (2013.01); *C12N 2310/33* (2013.01); *C12N 2310/3513* (2013.01); *C12N 2320/33* (2013.01)

(58) Field of Classification Search
CPC .... A61K 31/712; A61K 31/713; A61K 47/64; A61K 47/645; C12N 15/113; C12N 15/87
USPC ..... 435/6.1, 91.1, 91.31, 455, 458; 530/300; 536/23.1, 24.5
See application file for complete search history.

(56) References Cited

U.S. PATENT DOCUMENTS

| | | | |
|---|---|---|---|
| 5,087,617 A | 2/1992 | Smith | |
| 5,525,465 A | 6/1996 | Haralambidis et al. | |
| 5,686,564 A | 11/1997 | Brundish et al. | |
| 5,747,641 A | 5/1998 | Frankel et al. | |
| 5,849,727 A | 12/1998 | Porter et al. | |
| 6,159,946 A | 12/2000 | Zalewski et al. | |
| 6,303,573 B1 | 10/2001 | Rouslahti et al. | |
| 6,306,993 B1 | 10/2001 | Rothbard et al. | |
| 6,329,501 B1 | 12/2001 | Smith et al. | |
| 6,365,351 B1 | 4/2002 | Iversen | |
| 6,495,663 B1 | 12/2002 | Rothbard et al. | |
| 6,559,279 B1 | 5/2003 | Manoharan et al. | |
| 6,593,292 B1 | 7/2003 | Rothbard et al. | |
| 6,645,974 B2 | 11/2003 | Hutchinson et al. | |
| 6,669,951 B2 | 12/2003 | Rothbard et al. | |
| 7,138,238 B2 | 11/2006 | Vodyanoy et al. | |
| 7,169,814 B2 | 1/2007 | Rothbard et al. | |
| 7,229,961 B2 | 6/2007 | Rothbard et al. | |
| 7,456,146 B2 | 11/2008 | Yu et al. | |
| 7,468,418 B2 | 12/2008 | Iversen et al. | |
| 7,482,016 B2 | 1/2009 | Doerr et al. | |
| 7,507,196 B2 | 3/2009 | Stein et al. | |
| 7,524,829 B2 | 4/2009 | Stein et al. | |
| 7,582,615 B2 | 9/2009 | Neuman et al. | |
| 7,585,834 B2 | 9/2009 | Wender et al. | |
| 7,786,151 B2 | 8/2010 | Hagiwara et al. | |
| 7,790,694 B2 | 9/2010 | Geller et al. | |
| 7,855,283 B2 | 12/2010 | Iversen | |
| 7,888,012 B2 | 2/2011 | Iversen et al. | |
| 7,943,762 B2 | 5/2011 | Weller et al. | |
| 7,973,015 B2 | 7/2011 | Van Ommen et al. | |
| 7,989,608 B2 | 8/2011 | Mourich et al. | |
| 8,008,469 B2 | 8/2011 | Mourich et al. | |
| 8,030,291 B2 | 10/2011 | Stein et al. | |
| 8,030,292 B2 | 10/2011 | Stein et al. | |

(Continued)

FOREIGN PATENT DOCUMENTS

| | | |
|---|---|---|
| EP | 1 938 802 A1 | 7/2008 |
| JP | 2002-511885 A | 4/2002 |

(Continued)

OTHER PUBLICATIONS

Spence et al. (2001) "Generation of cellular immunity to lymphocytic choriomeningitis virus is independent of CD1d1 expression," Immunology. 104:168-174.

(Continued)

*Primary Examiner* — Jane J Zara

(74) *Attorney, Agent, or Firm* — Lathrop Gage LLP; Brian C. Trinque; Andrew R. Ehle

(57) ABSTRACT

Oligonucleotide analogs conjugated to carrier peptides are provided. The disclosed compounds are useful for the treatment of various diseases, for example diseases where inhibition of protein expression or correction of aberrant mRNA splice products produces beneficial therapeutic effects.

37 Claims, 21 Drawing Sheets

Specification includes a Sequence Listing.

(56) References Cited

U.S. PATENT DOCUMENTS

| | | | |
|---|---|---|---|
| 8,053,420 | B2 | 11/2011 | Iversen et al. |
| 8,067,571 | B2 | 11/2011 | Weller et al. |
| 8,084,433 | B2 | 12/2011 | Iversen et al. |
| 8,129,352 | B2 | 3/2012 | Iversen et al. |
| 8,168,604 | B2 | 5/2012 | Stein et al. |
| 8,741,863 | B2 | 6/2014 | Moulton et al. |
| 8,835,402 | B2 | 9/2014 | Kole et al. |
| 8,865,883 | B2 | 10/2014 | Sazani et al. |
| 8,871,918 | B2 | 10/2014 | Sazani et al. |
| 8,877,725 | B2 | 11/2014 | Iversen et al. |
| 9,068,185 | B2 | 6/2015 | Iversen |
| 9,161,948 | B2 * | 10/2015 | Hanson ............... A61K 31/713 |
| 9,238,042 | B2 | 1/2016 | Schnell et al. |
| 9,862,946 | B2 | 1/2018 | Hanson |
| 2001/0021700 | A1 | 9/2001 | Moore et al. |
| 2002/0127198 | A1 | 9/2002 | Rothbard et al. |
| 2003/0031655 | A1 | 2/2003 | Woolf |
| 2003/0045488 | A1 | 3/2003 | Brown et al. |
| 2003/0087861 | A1 | 5/2003 | Iversen |
| 2003/0185788 | A1 | 10/2003 | Rothbard et al. |
| 2003/0228348 | A1 | 12/2003 | Hirayama et al. |
| 2004/0170955 | A1 | 9/2004 | Arap et al. |
| 2005/0171026 | A1 | 8/2005 | Hagiwara et al. |
| 2005/0203041 | A1 | 9/2005 | Mourich et al. |
| 2006/0014712 | A1 | 1/2006 | Neuman |
| 2006/0078542 | A1 | 4/2006 | Mah et al. |
| 2006/0127981 | A1 | 6/2006 | Bergman et al. |
| 2006/0148747 | A1 | 7/2006 | Stein et al. |
| 2006/0269911 | A1 | 11/2006 | Iversen et al. |
| 2006/0276425 | A1 | 12/2006 | Mourich et al. |
| 2007/0004661 | A1 | 1/2007 | Stein et al. |
| 2007/0066556 | A1 | 3/2007 | Stein et al. |
| 2007/0129323 | A1 | 6/2007 | Stein et al. |
| 2007/0265214 | A1 | 11/2007 | Stein et al. |
| 2008/0267978 | A1 | 10/2008 | Zutter |
| 2009/0075377 | A1 | 3/2009 | Lu et al. |
| 2009/0082547 | A1 | 3/2009 | Iversen et al. |
| 2009/0088562 | A1 | 4/2009 | Weller et al. |
| 2009/0099066 | A1 | 4/2009 | Moulton et al. |
| 2009/0110689 | A1 | 4/2009 | Mourich et al. |
| 2009/0180958 | A1 | 7/2009 | Koivistoinen et al. |
| 2009/0318676 | A1 | 12/2009 | Manoharan et al. |
| 2010/0016215 | A1 | 1/2010 | Moulton et al. |
| 2010/0021456 | A1 | 1/2010 | Miossec et al. |
| 2010/0130591 | A1 | 5/2010 | Sazani et al. |
| 2010/0184670 | A1 | 7/2010 | Mourich et al. |
| 2010/0184833 | A1 | 7/2010 | De Kimpe et al. |
| 2010/0190689 | A1 | 7/2010 | Thornton et al. |
| 2010/0234280 | A1 | 9/2010 | Geller et al. |
| 2010/0234281 | A1 | 9/2010 | Weller et al. |
| 2011/0118334 | A1 | 5/2011 | Iversen |
| 2011/0269665 | A1 | 11/2011 | Kole |
| 2011/0289608 | A1 | 11/2011 | Schnell et al. |
| 2011/0306550 | A1 | 12/2011 | Vitek et al. |
| 2012/0065169 | A1 | 3/2012 | Hanson et al. |
| 2012/0141463 | A1 | 6/2012 | Wu et al. |
| 2012/0148622 | A1 | 6/2012 | Tenoever |
| 2013/0005792 | A1 | 1/2013 | Haining et al. |
| 2013/0045202 | A1 | 2/2013 | Irving et al. |
| 2013/0089517 | A1 | 4/2013 | Brady et al. |
| 2013/0131312 | A1 | 5/2013 | Iversen et al. |
| 2015/0141321 | A1 | 5/2015 | Kole et al. |
| 2015/0152415 | A1 | 6/2015 | Sazani et al. |

FOREIGN PATENT DOCUMENTS

| | | |
|---|---|---|
| JP | 2003-504417 A | 2/2003 |
| JP | 2007-536253 A | 12/2007 |
| JP | 2008-509701 A | 4/2008 |
| JP | 2010-532168 A | 10/2010 |
| JP | 2011-505846 A | 3/2011 |
| WO | 1994/004686 A1 | 2/1999 |
| WO | 1999/005302 A1 | 2/1999 |
| WO | 2000/044897 A1 | 8/2000 |
| WO | 2000/071706 A1 | 11/2000 |
| WO | 2001/062297 A1 | 8/2001 |
| WO | 2002/038764 A2 | 5/2002 |
| WO | 2003/068942 A2 | 8/2003 |
| WO | 2004/097017 A2 | 11/2004 |
| WO | 2005/010044 A2 | 2/2005 |
| WO | 2005/030799 A1 | 4/2005 |
| WO | 2005/072527 A2 | 8/2005 |
| WO | 2005/089247 A2 | 9/2005 |
| WO | 2005/115479 A2 | 12/2005 |
| WO | 2006/000057 A1 | 1/2006 |
| WO | 2006/033933 A2 | 3/2006 |
| WO | 2006/047683 A2 | 5/2006 |
| WO | 2006/050414 A2 | 5/2006 |
| WO | 2006/083183 A1 | 8/2006 |
| WO | 2006/086667 A2 | 8/2006 |
| WO | 2006/088833 A2 | 8/2006 |
| WO | 2007/009094 A2 | 1/2007 |
| WO | 2007/030576 A2 | 3/2007 |
| WO | 2007/030691 A2 | 3/2007 |
| WO | 2007/056466 A2 | 5/2007 |
| WO | 2007/103529 A2 | 9/2007 |
| WO | 2008/005002 A1 | 1/2008 |
| WO | 2008/008113 A1 | 1/2008 |
| WO | 2008/025025 A2 | 2/2008 |
| WO | 2008/036127 A2 | 3/2008 |
| WO | 2009/005793 A2 | 1/2009 |
| WO | 2009/026412 A1 | 2/2009 |
| WO | 2009/079790 A1 | 7/2009 |
| WO | 2009/086469 A2 | 7/2009 |
| WO | 2009/144481 A2 | 12/2009 |
| WO | 2010/048586 A1 | 4/2010 |
| WO | 2010/054267 A1 | 5/2010 |
| WO | 2010/072405 A1 | 7/2010 |
| WO | 2010/080554 A1 | 7/2010 |
| WO | 2011/143608 A1 | 11/2011 |

OTHER PUBLICATIONS

Stein et al. (1997) "A Specificity Comparison of Four Antisense Types: Morpholino, 2'-0-Methyl RNA, DNA, and Phosphorothioate DNA," Antisense & Nucleic Acid Drug Development. 7:151-157.

Stein et al. (2001) "Inhibition of Vesivirus Infections in Mammalian Tissue Culture with Antisense Morpholino Oligomers," Antisense & Nucleic Acid Drug Development. 11:317-325.

Summerton (1999) "Morpholino antisense oligomers: the case for an RNase H-independent structural type," Biochimica et Biophysica Acta. 1489:141-158.

Summerton et al. (1997) "Morpholino Antisense Oligomers: Design, Preparation, and Properties," Antisense & Nucleic Acid Drug Development. 7:187-195.

Vanin et al. (1981) "Synthesis and Application of Cleavable Photoactivable Heterobifunctional reagents," Biochemistry. 20:6754-6760.

Vives et al. (2003) "TAT Peptide Internalization: Seeking the Mechanism of Entry," Current Protein and Peptide Science. 4:125-132.

Wender et al. (2000) "The design, synthesis, and evaluation of molecules that enable or enhance cellular uptake: peptoid molecular transporters," Proc. Natl. Acad. Sci. USA. 97(24):13003-13008.

Wender et al. (2002) "Oligocarbamate Molecular Transporters: Design, Synthesis, and Biological Evaluation of a New Class of Transporters for Drug Delivery," J. Am. Chem. Soc. 124:13382-13383.

Wherry et al. (2003) "Viral Persistence Alters CD8 T-Cell Immunodominance and Tissue Distribution and Results in Distinct Stages of Functional Impairment," Journal of Virology. 77(8):4911-4927.

Wilton et al. (2007) "Antisense Oligonucleotide-induced Exon Skipping Across the Human Dystrophin Gene Transcript," Molecular Therapy 15(7):1288-1296.

Wright et al. (2008) "The Human IL-17F/IL-17A Heterodimeric Cytokine Signals through the IL-17RA/IL-17RC Receptor Complex," The Journal of Immunology. 181:2799-2805.

Wu et al. (2007) "Cell-penetrating peptides as transporters for morpholino oligomers: effects of amino acid composition on intracellular delivery and cytotoxicity," Nucleic Acids Research. 35(15):5182-5191.

(56) References Cited

OTHER PUBLICATIONS

Yauch et al. (2008) "Mouse models of dengue virus infection and disease," Antiviral Research. 80:87-93.
Yin et al. (2008) "Effective Exon Skipping and Restoration of Dystrophin Expression by Peptide Nucleic Acid Antisense Oligonucleotides in mdx Mice," Molecular Therapy. 16(1):38-45.
Yoo et al. (1999) "PAMAM Dendrimers as Delivery Agents for Antisense Oligonucleotides," Pharmaceutical Research. 16(12):1799-1804.
Youngblood et al. (2007) "Stability of Cell-Penetrating Peptide-Morpholino Oligomer Conjugates in Human Serum and in Cells," Bioconjugate Chem. 18:50-60.
Zhang et al. (2006) "Construction of a novel chimera consisting of a chelator-containing Tat peptide conjugated to a morpholino antisense oligomers for technetium-99m labeling and accelerating cellular kinetics," Nuclear Medicine and Biology. 33:263-269.
Zhou et al. (2007) "IL-17A versus IL-17F induced intracellular signal transduction pathways and modulation by IL-17RA and IL-17RC RNA interference in AGS gastric adenocarcinoma cells," Cytokine. 38:157-164.
Zubin et al. (1999) "Oligonucleotide-peptide conjugates as potential antisense agents," FEBS Letters. 456:59-62.
International Preliminary Report on Patentability corresponding to International Patent Application No. PCT/US2004/013660, dated Nov. 4, 2005.
International Preliminary Report on Patentability corresponding to International Patent Application No. PCT/US2008/008168, dated Oct. 12, 2009.
International Preliminary Report on Patentability corresponding to International Patent Application No. PCT/US2005/018213, dated Oct. 23, 2007.
International Search Report with Written Opinion corresponding to International Patent Application No. PCT/US2005/018213, dated Sep. 26, 2007.
International Search Report with Written Opinion corresponding to International Patent Application No. PCT/US2008/008168, dated Mar. 19, 2009.
International Search Report with Written Opinion corresponding to International Patent Application No. PCT/US2004/013660, dated Feb. 21, 2005.
Abes et al. (2006) "Vectorization of morpholino oligomers by the (R-Ahx-R)4 peptide allows efficient splicing correction in the absence of endosomolytic agents," Journal of Controlled Release. 116:304-313.
Abes et al. (2008) "Arginine-rich cell penetrating peptides: Design, structure-activity, and applications to alter pre-mRNA splicing by steric-block oligonucleotides," Journal of Peptide Science. 14:455-460.
Abes et al. (2008) "Delivery of steric block morpholino oligomers by (R-X-R)4 peptides: structure-activity studies," Nucleic Acids Research 36(20):6343-6354.
Alter et al. (2006) "Systemic delivery of morpholino oligonucleotide restores dystrophin expression bodywide and improves dystrophic pathology," Nature Medicine. 12(2):175-177.
Andreasen et al. (2003) "Expression and Functional Importance of Collagen-Binding Integrins, $\alpha 1\beta 1$ and $\alpha 2\ \beta 1$, on Virus-Activated T Cells," The Journal of Immunology. 171:2804-2811.
Arora et al. (2002) "Bioavailability and efficacy of antisense morpholino oligomers targeted to c-myc and cytochrome P-450 3A2 following oral administration in rats," Journal of Pharmaceutical Sciences. 91(4):1009-1018.
Astriab-Fisher et al. (2000) "Antisense Inhibition of P-glycoprotein Expression Using Peptide-Oligonucleotide Conjugates," Biochemical Pharmacology. 60:83-90.
Astriab-Fisher et al. (2002) "Conjugates of Antisense Oligonucleotides with the Tat and Antennapedia Cell-Penetrating Peptides: Effects on Cellular Uptake, Binding to Target Sequences, and Biologic Actions," Pharmaceutical Research. 19(6):744-754.
Blattman et al. (2003) "Therapeutic use of IL-2 to enhance antiviral T-cell responses in vivo," Nature Medicine. 9(5):540-547.
Burrer et al. (2007) "Antiviral Effects of Antisense Morpholino Oligomers in Murine Coronavirus Infection Models," Journal of Virology. 81(11):5637-5648.
Carlson et al. (2009) "In vitro-differentiated TH17 cells mediate lethal acute graft-versus-host disease with severe cutaneous and pulmonary pathologic manifestations," Blood. 113(6):1365-1374.
Chen et al. (2003) "A Concise Method for the Preparation of Peptide and Arginine-Rich Peptide—Conjugated Antisense Oligonucleotide," Bioconjugate Chem. 14:532-538.
Dapie et al. (2003) "Biophysical and biological properties of quadruplex oligodeoxyribonucleotides," Nucleic Acids Research. 31(8):2097-2107.
Derossi et al. (1998) "Trojan peptides: the penetratin system for intracellular delivery," Trends in Cell Biology. 8(2):84-87.
Devi (2002) "Prostate cancer: Status of current treatments and emerging antisense-based therapies," Current Opinion in Molecular Therapeutics. 4(2):138-148.
Devi et al. (2002) "Inhibition of human chorionic gonadotropin beta-subunit modulates the mitogenic effect of c-myc in human prostate cancer cells," The Prostate. 53:200-210.
Egholm et al. (1993) "PNA hybridizes to complementary oligonucleotides obeying the Watson—Crick hydrogen—bonding rules," Nature. 365:566-568.
EMBL Database [Online] (Deshazer), Sequence CH899747.1, Accessible on the Internet at URL: http://www.ebi.ac.uk/sgibin/emblfetch?style+html&id+CH899747, 196 pgs. [Last Accessed May 26, 2007].
Eriksson et al. (2002) "Cell Permeabilization and Uptake of Antisense Peptide-Peptide Nucleic Acid (PNA) into *Escherichia coli*," Journal of Biological Chemistry. 277(9):7144-7147.
Ge et al. (2006) "Inhibition of Multiple Subtypes of Influenza A Virus in Cell Cultures with Morpholino Oligomers," Antimicrobial Agents and Chemotherapy 50(11):3724-3733.
Gebski et al. (2003) "Morpholino antisense oligonucleotide induced dystrophin exon 23 skipping in mdx mouse muscle," Human Molecular Genetics. 12(15):1801-1811.
Genbank Database [Online] (Jan. 31, 2009) "Predicted Protein [Nematostella Vectensis]," Accession No. XP_0011635778.1. Accessible on the Internet at URL: http://www.ncbi.nlm.nih.gov/protein/156391881, 1 pg. [Last Accessed Dec. 9, 2014].
Ghosh et al. (2000) "Intracellular Delivery Strategies for Antisense Phosphorodiamidate Morpholino Oligomers," Antisense & Nucleic Acid Drug Developmen.t 10:263-274.
Heineke et al. (2010) "Genetic Deletion of Myostatin From the Heart Prevents Skeletal Muscle Atrophy in Heart Failure," Circulation. 121:419-425.
Hudziak et al. (1996) "Resistance of Morpholino Phosphorodiamidate Oligomers to Enzymatic Degradation," Antisense & Nucleic Acid Drug Development. 6:267-272.
Iversen (2001) "Phosphorodiamidate Morpholino Oligomers," In; Antisense Drug Technology. Ed.: Crooke. Marcel Dekker, Inc. New York, New York. pp. 235-238.
Iversen (2001) "Phosphorodiamidate morpholino oligomers: Favorable properties for sequence-specific gene inactivation," Current Opinion in Molecular Therapeutics. 3(3):235-238.
Jearawiriyapaisarn et al. (2008) "Sustained Dystrophin Expression Induced by Peptide-conjugated Morpholino Oligomers in the Muscles of mdx Mice," Mol. Ther. 16(9):1624-1629.
Kang et al. (1998) "Up-Regulation of Luciferase Gene Expression with Antisense Oligonucleotides: Implications and Applications in Functional Assay Development," Biochemistry. 37:6235-6239.
Knapp et al. (2003) "Resistance to chemotherapeutic drugs overcome by c-Myc inhibition in a Lewis lung carcinoma murine model," Anti-Cancer Drugs. 14:39-47.
Kolonin et al. (2006) "Synchronous selection of homing peptides for multiple tissues by in vivo phage display," The FASEB Journal. 20(7):979-981.
Lebleu et al. (2008) "Cell penetrating peptide conjugates of steric block oligonucleotides," Advanced Drug Delivery Reviews. 60:517-529.
Marshall et al. (2007) "Arginine-rich cell-penetrating peptides facilitate delivery of antisense oligomers into murine eukocytes and alter pre-mRNA splicing," Journal of Immunological Methods. 325:114-126.

(56) References Cited

OTHER PUBLICATIONS

Matsui et al. (2003) "Protein Therapy: In Vivo Protein Transduction by Polyarginine (11R) PTD and Subcellular Targeting Delivery," Current Protein and Peptide Science. 4:151-157.

Meade et al. (2007) "Exogenous siRNA delivery using peptide transduction domains/cell penetrating peptides," Advanced Drug Delivery Reviews. 59:134-140.

Mizutani et al. (1994) "Enhancement of sensitivity of urinary bladder tumor cells to cisplatin by c-myc antisense oligonucleotide," Cancer. 74:2546-2554.

Moskophidis et al. (1994) "Resistance of Lymphocytic Choriomeningitis Virus to Alpha/Beta Interferon and to Gamma Interferon," Journal of Virology. 68(3):1951-1955.

Moskophidis et al. (1995) "Role of virus and host variables in virus persistence or immunopathological disease caused by a non-cytolytic virus," Journal of General Virology. 76:381-391.

Moulton et al. (2003) "HIV Tat peptide enhances cellular delivery of antisense morpholino oligomers," Antisense Nucleic Acid Drug Dev. 13(1):31-43.

Moulton et al. (2004) "Cellular Uptake of Antisense Morpholino Oligomers Conjugated to Arginine-Rich Peptides," Bioconjugate Chem. 15:290-299.

Nasevicius et al. (2000) "Effective targeted gene 'knockdown' in zebrafish," Nature Genetics. 26:216-220.

Park et al. (2009) "Peroxisome Proliferator-Activated Receptor γ Agonist Down-Regulates IL-17 Expression in a Murine Model of Allergic Airway Inflammation," The Journal of Immunology. 183:3259-3267.

PUBCHEM Database [Online] "6-Aminocaproic Acid," CID 5460263. Accessible on the Internet at URL: http://pubchem.ncbi.nlm.nih.gov/summary/summary.cgi?cid=5460263&loc=ec_rcs, 3 pgs. [Last Accessed Jun. 3, 2010].

Qin et al. (2000) "In Vivo Evaluation of a Morpholino Antisense Oligomer Directed Against Tumor Necrosis Factor-a," Antisense & Nucleic Acid Drug Development. 10:11-16.

Rangachari et al. (2006) "T-bet negatively regulates autoimmune myocarditis by suppressing local production of interleukin 17," The Journal of Experimental Medicine. 203(8):2009-2019.

Richard et al. (2003) "Cell-penetrating Peptides. A Reevaluation of the Mechanism of Cellular Uptake," Journal of Biological Chemistry. 278(1):585-590.

Ricker et al. (2002) "c-myc antisense oligonucleotide treatment ameliorates murine ARPKD," Kidney International. 61:S125-S131.

Rothbard et al. (2002) "Arginine-Rich Molecular Transporters for Drug Delivery: Role of Backbone Spacing in Cellular Uptake," J. Med. Chem. 45:3612-3618.

Samoylova et al. (1999) "Elucidation of Muscle-Binding Peptides by Phage Display Screening," Muscle & Nerve. 22(4):460-466.

Shafer et al. (2001) "Biological Aspects of DNA/RNA Quadruplexes," Biopolymers. 56(3):209-227.

\* cited by examiner

PMO<sup>apn</sup>

PMO<sup>suc</sup>

SEQUENCE LISTING

```
<160> NUMBER OF SEQ ID NOS: 583

<210> SEQ ID NO 1
<211> LENGTH: 22
<212> TYPE: DNA
<213> ORGANISM: Artificial Sequence
<220> FEATURE:
<223> OTHER INFORMATION: Antisense oligomer

<400> SEQUENCE: 1
cggtccacgt agactaacaa ct                                              22

<210> SEQ ID NO 2
<211> LENGTH: 23
<212> TYPE: DNA
<213> ORGANISM: Artificial Sequence
<220> FEATURE:
<223> OTHER INFORMATION: Antisense oligomer

<400> SEQUENCE: 2
gaagttcaca cagataaact tct                                             23

<210> SEQ ID NO 3
<211> LENGTH: 20
<212> TYPE: DNA
<213> ORGANISM: Artificial Sequence
<220> FEATURE:
<223> OTHER INFORMATION: Antisense oligomer

<400> SEQUENCE: 3
cggttagaag actcatcttt                                                 20

<210> SEQ ID NO 4
```

```
<211> LENGTH: 25
<212> TYPE: DNA
<213> ORGANISM: Artificial Sequence
<220> FEATURE:
<223> OTHER INFORMATION: Antisense oligomer

<400> SEQUENCE: 4
tttcgacatc ggttagaaga ctcat                                           25

<210> SEQ ID NO 5
<211> LENGTH: 22
<212> TYPE: DNA
<213> ORGANISM: Artificial Sequence
<220> FEATURE:
<223> OTHER INFORMATION: Antisense oligomer

<400> SEQUENCE: 5
gagacgccat gatgtggatg tc                                              22

<210> SEQ ID NO 6
<211> LENGTH: 23
<212> TYPE: DNA
<213> ORGANISM: Artificial Sequence
<220> FEATURE:
<223> OTHER INFORMATION: Antisense oligomer

<400> SEQUENCE: 6
gaaacacgga cacccaaagt agt                                             23

<210> SEQ ID NO 7
<211> LENGTH: 22
<212> TYPE: DNA
<213> ORGANISM: Artificial Sequence
<220> FEATURE:
<223> OTHER INFORMATION: Antisense oligomer

<400> SEQUENCE: 7
tcccagcgtc aatatgctgt tt                                              22

<210> SEQ ID NO 8
<211> LENGTH: 20
<212> TYPE: DNA
<213> ORGANISM: Artificial Sequence
<220> FEATURE:
<223> OTHER INFORMATION: Antisense oligomer

<400> SEQUENCE: 8
gcctaggatc cacggtgcgc                                                 20

<210> SEQ ID NO 9
<211> LENGTH: 40
<212> TYPE: DNA
<213> ORGANISM: Artificial Sequence
<220> FEATURE:
<223> OTHER INFORMATION: Antisense oligomer

<400> SEQUENCE: 9
gggacaaaat ggatcccatt attaatggaa attctgctaa                           40

<210> SEQ ID NO 10
<211> LENGTH: 21
<212> TYPE: DNA
<213> ORGANISM: Artificial Sequence
<220> FEATURE:
<223> OTHER INFORMATION: Antisense oligomer

<400> SEQUENCE: 10
```

```
taatgggatc cattttgtcc c                                              21

<210> SEQ ID NO 11
<211> LENGTH: 23
<212> TYPE: DNA
<213> ORGANISM: Artificial Sequence
<220> FEATURE:
<223> OTHER INFORMATION: Antisense oligomer

<400> SEQUENCE: 11
aataatggga tccattttgt ccc                                            23

<210> SEQ ID NO 12
<211> LENGTH: 27
<212> TYPE: DNA
<213> ORGANISM: Artificial Sequence
<220> FEATURE:
<223> OTHER INFORMATION: Antisense oligomer

<400> SEQUENCE: 12
cattaataat gggatccatt ttgtccc                                        27

<210> SEQ ID NO 13
<211> LENGTH: 30
<212> TYPE: DNA
<213> ORGANISM: Artificial Sequence
<220> FEATURE:
<223> OTHER INFORMATION: Antisense oligomer

<400> SEQUENCE: 13
gaatttccat taataatggg atccattttg                                     30

<210> SEQ ID NO 14
<211> LENGTH: 29
<212> TYPE: DNA
<213> ORGANISM: Artificial Sequence
<220> FEATURE:
<223> OTHER INFORMATION: Antisense oligomer

<400> SEQUENCE: 14
cagaatttcc attaataatg ggatccatt                                      29

<210> SEQ ID NO 15
<211> LENGTH: 25
<212> TYPE: DNA
<213> ORGANISM: Artificial Sequence
<220> FEATURE:
<223> OTHER INFORMATION: Antisense oligomer

<400> SEQUENCE: 15
ggccaaacct cggcttacct gaaat                                          25

<210> SEQ ID NO 16
<211> LENGTH: 25
<212> TYPE: DNA
<213> ORGANISM: Artificial Sequence
<220> FEATURE:
<223> OTHER INFORMATION: Antisense oligomer

<400> SEQUENCE: 16
ggccaaacct cggcttacct gaaat                                          25

<210> SEQ ID NO 17
<211> LENGTH: 18
<212> TYPE: DNA
```

```
<213> ORGANISM: Artificial Sequence
<220> FEATURE:
<223> OTHER INFORMATION: Antisense oligomer

<400> SEQUENCE: 17
gctattacct taacccag                                                        18

<210> SEQ ID NO 18
<211> LENGTH: 52
<212> TYPE: DNA
<213> ORGANISM: Artificial Sequence
<220> FEATURE:
<223> OTHER INFORMATION: Antisense oligomer

<400> SEQUENCE: 18
gaaaaaagat tatattgatt ttaaaatcat gcaaaaactg caactctgtg tt                  52

<210> SEQ ID NO 19
<211> LENGTH: 25
<212> TYPE: DNA
<213> ORGANISM: Artificial Sequence
<220> FEATURE:
<223> OTHER INFORMATION: Antisense oligomer

<400> SEQUENCE: 19
catacatttg cagttttgc atcat                                                 25

<210> SEQ ID NO 20
<211> LENGTH: 26
<212> TYPE: DNA
<213> ORGANISM: Artificial Sequence
<220> FEATURE:
<223> OTHER INFORMATION: Antisense oligomer

<400> SEQUENCE: 20
tcatttttaa aaatcagcac aatctt                                               26

<210> SEQ ID NO 21
<211> LENGTH: 26
<212> TYPE: DNA
<213> ORGANISM: Artificial Sequence
<220> FEATURE:
<223> OTHER INFORMATION: Antisense oligomer

<400> SEQUENCE: 21 cagttttgc atcattttta aaaatc                                                26

<210> SEQ ID NO 22
<211> LENGTH: 25
<212> TYPE: DNA
<213> ORGANISM: Artificial Sequence
<220> FEATURE:
<223> OTHER INFORMATION: Antisense oligomer

<400> SEQUENCE: 22
gatctgtcaa atcgcctgca ggtaa                                                25

<210> SEQ ID NO 23
<211> LENGTH: 25
<212> TYPE: DNA
<213> ORGANISM: Artificial Sequence
<220> FEATURE:
<223> OTHER INFORMATION: Antisense oligomer

<400> SEQUENCE: 23
aaactgttca gcttctgtta gccac                                                25
```

```
<210> SEQ ID NO 24
<211> LENGTH: 25
<212> TYPE: DNA
<213> ORGANISM: Artificial Sequence
<220> FEATURE:
<223> OTHER INFORMATION: Antisense oligomer

<400> SEQUENCE: 24
ttgtgtcttt ctgagaaact gttca                                  25

<210> SEQ ID NO 25
<211> LENGTH: 25
<212> TYPE: DNA
<213> ORGANISM: Artificial Sequence
<220> FEATURE:
<223> OTHER INFORMATION: Antisense oligomer

<400> SEQUENCE: 25
ctgacaacag tttgccgctg cccaa                                  25

<210> SEQ ID NO 26
<211> LENGTH: 26
<212> TYPE: DNA
<213> ORGANISM: Artificial Sequence
<220> FEATURE:
<223> OTHER INFORMATION: Antisense oligomer

<400> SEQUENCE: 26
ccaatgccat cctggagttc ctgtaa                                 26

<210> SEQ ID NO 27
<211> LENGTH: 30
<212> TYPE: DNA
<213> ORGANISM: Artificial Sequence
<220> FEATURE:
<223> OTHER INFORMATION: Antisense oligomer

<400> SEQUENCE: 27
cattcaatgt tctgacaaca gtttgccgct                             30

<210> SEQ ID NO 28
<211> LENGTH: 25
<212> TYPE: DNA
<213> ORGANISM: Artificial Sequence
<220> FEATURE:
<223> OTHER INFORMATION: Antisense oligomer

<400> SEQUENCE: 28
cttacaggct ccaatagtgg tcagt                                  25

<210> SEQ ID NO 29
<211> LENGTH: 29
<212> TYPE: DNA
<213> ORGANISM: Artificial Sequence
<220> FEATURE:
<223> OTHER INFORMATION: Antisense oligomer

<400> SEQUENCE: 29
ccactcagag ctcagatctt ctaacttcc                              29

<210> SEQ ID NO 30
<211> LENGTH: 25
<212> TYPE: DNA
<213> ORGANISM: Artificial Sequence
<220> FEATURE:
```

```
<223> OTHER INFORMATION: Antisense oligomer

<400> SEQUENCE: 30
gggatccagt atacttacag gctcc                                        25

<210> SEQ ID NO 31
<211> LENGTH: 30
<212> TYPE: DNA
<213> ORGANISM: Artificial Sequence
<220> FEATURE:
<223> OTHER INFORMATION: Antisense oligomer

<400> SEQUENCE: 31
acatcaagga agatggcatt tctagtttgg                                   30

<210> SEQ ID NO 32
<211> LENGTH: 30
<212> TYPE: DNA
<213> ORGANISM: Artificial Sequence
<220> FEATURE:
<223> OTHER INFORMATION: Antisense oligomer

<400> SEQUENCE: 32
ctccaacatc aaggaagatg gcatttctag                                   30

<210> SEQ ID NO 33
<211> LENGTH: 26
<212> TYPE: DNA
<213> ORGANISM: Artificial Sequence
<220> FEATURE:
<223> OTHER INFORMATION: Antisense oligomer

<400> SEQUENCE: 33
gagcaggtac ctccaacatc aaggaa                                       26

<210> SEQ ID NO 34
<211> LENGTH: 25
<212> TYPE: DNA
<213> ORGANISM: Artificial Sequence
<220> FEATURE:
<223> OTHER INFORMATION: Antisense oligomer

<400> SEQUENCE: 34
ctgaaggtgt tcttgtactt catcc                                        25

<210> SEQ ID NO 35
<211> LENGTH: 30
<212> TYPE: DNA
<213> ORGANISM: Artificial Sequence
<220> FEATURE:
<223> OTHER INFORMATION: Antisense oligomer

<400> SEQUENCE: 35
tgttcttgta cttcatccca ctgattctga                                   30

<210> SEQ ID NO 36
<211> LENGTH: 18
<212> TYPE: DNA
<213> ORGANISM: Artificial Sequence
<220> FEATURE:
<223> OTHER INFORMATION: Antisense oligomer

<400> SEQUENCE: 36
ctttcataat gctggcag                                                18
```

```
<210> SEQ ID NO 37
<211> LENGTH: 14
<212> TYPE: DNA
<213> ORGANISM: Artificial Sequence
<220> FEATURE:
<223> OTHER INFORMATION: Antisense oligomer

<400> SEQUENCE: 37
cataatgctg gcag                                                      14

<210> SEQ ID NO 38
<211> LENGTH: 8
<212> TYPE: DNA
<213> ORGANISM: Artificial Sequence
<220> FEATURE:
<223> OTHER INFORMATION: Antisense oligomer

<400> SEQUENCE: 38 gctggcag                                                              8

<210> SEQ ID NO 39
<211> LENGTH: 9
<212> TYPE: DNA
<213> ORGANISM: Artificial Sequence
<220> FEATURE:
<223> OTHER INFORMATION: Antisense oligomer

<400> SEQUENCE: 39 cagcagcag                                                             9

<210> SEQ ID NO 40
<211> LENGTH: 12
<212> TYPE: DNA
<213> ORGANISM: Artificial Sequence
<220> FEATURE:
<223> OTHER INFORMATION: Antisense oligomer

<400> SEQUENCE: 40
cagcagcagc ag                                                        12

<210> SEQ ID NO 41
<211> LENGTH: 15
<212> TYPE: DNA
<213> ORGANISM: Artificial Sequence
<220> FEATURE:
<223> OTHER INFORMATION: Antisense oligomer

<400> SEQUENCE: 41
cagcagcagc agcag                                                     15

<210> SEQ ID NO 42
<211> LENGTH: 18
<212> TYPE: DNA
<213> ORGANISM: Artificial Sequence
<220> FEATURE:
<223> OTHER INFORMATION: Antisense oligomer

<400> SEQUENCE: 42
cagcagcagc agcagcag                                                  18

<210> SEQ ID NO 43
<211> LENGTH: 9
<212> TYPE: DNA
<213> ORGANISM: Artificial Sequence
<220> FEATURE:
<223> OTHER INFORMATION: Antisense oligomer
```

```
<400> SEQUENCE: 43 agcagcagc                                                              9

<210> SEQ ID NO 44
<211> LENGTH: 12
<212> TYPE: DNA
<213> ORGANISM: Artificial Sequence
<220> FEATURE:
<223> OTHER INFORMATION: Antisense oligomer

<400> SEQUENCE: 44
agcagcagca gc                                                         12

<210> SEQ ID NO 45
<211> LENGTH: 15
<212> TYPE: DNA
<213> ORGANISM: Artificial Sequence
<220> FEATURE:
<223> OTHER INFORMATION: Antisense oligomer

<400> SEQUENCE: 45
agcagcagca gcagc                                                      15

<210> SEQ ID NO 46
<211> LENGTH: 18
<212> TYPE: DNA
<213> ORGANISM: Artificial Sequence
<220> FEATURE:
<223> OTHER INFORMATION: Antisense oligomer

<400> SEQUENCE: 46
agcagcagca gcagcagc                                                   18

<210> SEQ ID NO 47
<211> LENGTH: 9
<212> TYPE: DNA
<213> ORGANISM: Artificial Sequence
<220> FEATURE:
<223> OTHER INFORMATION: Antisense oligomer

<400> SEQUENCE: 47 gcagcagca                                                              9

<210> SEQ ID NO 48
<211> LENGTH: 12
<212> TYPE: DNA
<213> ORGANISM: Artificial Sequence
<220> FEATURE:
<223> OTHER INFORMATION: Antisense oligomer

<400> SEQUENCE: 48
gcagcagcag ca                                                         12

<210> SEQ ID NO 49
<211> LENGTH: 15
<212> TYPE: DNA
<213> ORGANISM: Artificial Sequence
<220> FEATURE:
<223> OTHER INFORMATION: Antisense oligomer

<400> SEQUENCE: 49
gcagcagcag cagca                                                      15

<210> SEQ ID NO 50
<211> LENGTH: 18
```

```
<212> TYPE: DNA
<213> ORGANISM: Artificial Sequence
<220> FEATURE:
<223> OTHER INFORMATION: Antisense oligomer

<400> SEQUENCE: 50
gcagcagcag cagcagca                                          18

<210> SEQ ID NO 51
<211> LENGTH: 25
<212> TYPE: DNA
<213> ORGANISM: Artificial Sequence
<220> FEATURE:
<223> OTHER INFORMATION: Antisense oligomer

<400> SEQUENCE: 51
agcagcagca gcagcagcag cagca                                  25

<210> SEQ ID NO 52
<211> LENGTH: 25
<212> TYPE: DNA
<213> ORGANISM: Artificial Sequence
<220> FEATURE:
<223> OTHER INFORMATION: Antisense oligomer

<400> SEQUENCE: 52
cagcagcagc agcagcagca gcagc                                  25

<210> SEQ ID NO 53
<211> LENGTH: 9
<212> TYPE: DNA
<213> ORGANISM: Artificial Sequence
<220> FEATURE:
<223> OTHER INFORMATION: Antisense oligomer

<400> SEQUENCE: 53 caggcaggc                                                    9

<210> SEQ ID NO 54
<211> LENGTH: 12
<212> TYPE: DNA
<213> ORGANISM: Artificial Sequence
<220> FEATURE:
<223> OTHER INFORMATION: Antisense oligomer

<400> SEQUENCE: 54
caggcaggca gg                                                12

<210> SEQ ID NO 55
<211> LENGTH: 24
<212> TYPE: DNA
<213> ORGANISM: Artificial Sequence
<220> FEATURE:
<223> OTHER INFORMATION: Antisense oligomer

<400> SEQUENCE: 55
caggcaggca ggcaggcagg cagg                                   24

<210> SEQ ID NO 56
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 56
```

Arg Arg Arg Gln Arg Arg Lys Lys Arg
1               5

<210> SEQ ID NO 57
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 57

Arg Lys Lys Arg Arg Gln Arg Arg Arg
1               5

<210> SEQ ID NO 58
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 58

Arg Arg Arg Arg Arg Arg Arg Arg Arg Phe Phe
1               5                   10

<210> SEQ ID NO 59
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 59

Arg Arg Arg Arg Arg Phe Phe Arg Arg Arg Arg
1               5                   10

<210> SEQ ID NO 60
<211> LENGTH: 4
<212> TYPE: PRT
<213> ORGANISM: Artificial Sequence
<220> FEATURE:
<223> OTHER INFORMATION: cell penetrating peptide

<400> SEQUENCE: 60

Arg Arg Arg Arg
1

<210> SEQ ID NO 61
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 61

Arg Arg Arg Arg Arg
1               5

<210> SEQ ID NO 62
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 62

Arg Arg Arg Arg Arg Arg

```
1               5

<210> SEQ ID NO 63
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 63

Arg Arg Arg Arg Arg Arg Arg
1               5

<210> SEQ ID NO 64
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 64

Arg Arg Arg Arg Arg Arg Arg Arg
1               5

<210> SEQ ID NO 65
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 65

Arg Arg Arg Arg Arg Arg Arg Arg Arg
1               5

<210> SEQ ID NO 66
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11
<223> OTHER INFORMATION: Xaa = Acp

<400> SEQUENCE: 66

Arg Xaa Arg Arg Xaa Arg Arg Xaa Arg Arg Xaa Arg
1               5                   10

<210> SEQ ID NO 67
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 14
<223> OTHER INFORMATION: Xaa = Acp

<400> SEQUENCE: 67

Arg Xaa Arg Arg Xaa Arg Arg Xaa Arg Arg Xaa Arg Arg Xaa Arg
1               5                   10                  15

<210> SEQ ID NO 68
<211> LENGTH: 12
<212> TYPE: PRT
```

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8
<223> OTHER INFORMATION: Xaa = Acp
<220> FEATURE:
<221> NAME/KEY: MOD_RES
<222> LOCATION: 5, 11
<223> OTHER INFORMATION: Xaa = bAla

<400> SEQUENCE: 68

Arg Xaa Arg Arg Xaa Arg Arg Xaa Arg Arg Xaa Arg
1               5                   10

<210> SEQ ID NO 69
<211> LENGTH: 15
<212> TYPE: PRT
<213> ORGANISM: Artificial Sequence
<220> FEATURE:
<223> OTHER INFORMATION: cell penetrating peptide

<400> SEQUENCE: 69

Arg Ala Arg Arg Ala Arg Arg Ala Arg Arg Ala Arg Phe Phe Cys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: cell penetrating peptide

<400> SEQUENCE: 70

Arg Gly Arg Arg Gly Arg Arg Gly Arg Arg Gly Arg Phe Phe Cys
1               5                   10                  15

<210> SEQ ID NO 71
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 71

Arg Arg Arg Gln Arg Arg Lys Lys Arg Cys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 72

Arg Arg Arg Arg Arg Arg Arg Arg Arg Phe Phe Cys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 3, 6, 9, 12
```

```
<223> OTHER INFORMATION: Xaa = Acp
<220> FEATURE:
<221> NAME/KEY: MOD_RES
<222> LOCATION: 13
<223> OTHER INFORMATION: Xaa = bAla

<400> SEQUENCE: 73

Arg Arg Xaa Arg Arg Xaa Arg Arg Xaa Arg Arg Xaa Xaa
1               5                   10

<210> SEQ ID NO 74
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 13
<223> OTHER INFORMATION: Xaa = Acp
<220> FEATURE:
<221> NAME/KEY: MOD_RES
<222> LOCATION: 14
<223> OTHER INFORMATION: Xaa = bAla

<400> SEQUENCE: 74

Arg Xaa Arg Arg Xaa Arg Arg Xaa Arg Arg Xaa Arg Xaa Xaa
1               5                   10

<210> SEQ ID NO 75
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1, 4, 7, 10, 13
<223> OTHER INFORMATION: Xaa = Acp
<220> FEATURE:
<221> NAME/KEY: MOD_RES
<222> LOCATION: 14
<223> OTHER INFORMATION: Xaa = bAla

<400> SEQUENCE: 75

Xaa Arg Arg Xaa Arg Arg Xaa Arg Arg Xaa Arg Arg Xaa Xaa
1               5                   10

<210> SEQ ID NO 76
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6, 8, 10, 12
<223> OTHER INFORMATION: Xaa = Acp
<220> FEATURE:
<221> NAME/KEY: MOD_RES
<222> LOCATION: 13
<223> OTHER INFORMATION: Xaa = bAla

<400> SEQUENCE: 76

Arg Xaa Arg Xaa Arg Xaa Arg Xaa Arg Xaa Arg Xaa Xaa
1               5                   10

<210> SEQ ID NO 77
<211> LENGTH: 15
<212> TYPE: PRT
<213> ORGANISM: Artificial Sequence
```

```
<220> FEATURE:
<223> OTHER INFORMATION: cell penetrating peptide
<220> FEATURE:
<221> NAME/KEY: MOD_RES
<222> LOCATION: 2, 4, 6, 8, 10, 12, 14
<223> OTHER INFORMATION: Xaa = Acp
<220> FEATURE:
<221> NAME/KEY: MOD_RES
<222> LOCATION: 15
<223> OTHER INFORMATION: Xaa = bAla

<400> SEQUENCE: 77

Arg Xaa Arg Xaa Arg Xaa Arg Xaa Arg Xaa Arg Xaa Arg Xaa Xaa
1               5                   10                  15

<210> SEQ ID NO 78
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 14, 16
<223> OTHER INFORMATION: Xaa = Acp
<220> FEATURE:
<221> NAME/KEY: MOD_RES
<222> LOCATION: 17
<223> OTHER INFORMATION: Xaa = bAla

<400> SEQUENCE: 78

Arg Xaa Arg Arg Xaa Arg Arg Xaa Arg Arg Xaa Arg Arg Xaa Arg Xaa
1               5                   10                  15

Xaa

<210> SEQ ID NO 79
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 13
<223> OTHER INFORMATION: Xaa = Acp
<220> FEATURE:
<221> NAME/KEY: MOD_RES
<222> LOCATION: 5, 11, 14
<223> OTHER INFORMATION: Xaa = bAla

<400> SEQUENCE: 79

Arg Xaa Arg Arg Xaa Arg Arg Xaa Arg Arg Xaa Arg Xaa Xaa
1               5                   10

<210> SEQ ID NO 80
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 80

Arg Arg Arg Arg Arg Arg Gly
1               5

<210> SEQ ID NO 81
<211> LENGTH: 8
<212> TYPE: PRT
<213> ORGANISM: Artificial Sequence
<220> FEATURE:
```

```
<223> OTHER INFORMATION: cell penetrating peptide

<400> SEQUENCE: 81

Arg Arg Arg Arg Arg Arg Arg Gly
1               5

<210> SEQ ID NO 82
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 82

Arg Arg Arg Arg Arg Arg Arg Arg Gly
1               5

<210> SEQ ID NO 83
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 83

Arg Arg Arg Arg Arg Gly Arg Arg Arg Arg Gly
1               5                   10

<210> SEQ ID NO 84
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 84

Arg Arg Arg Arg Arg Phe Phe Arg Arg Arg Arg Gly
1               5                   10

<210> SEQ ID NO 85
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 85

Arg Lys Lys Arg Arg Gln Arg Arg Arg Gly
1               5                   10

<210> SEQ ID NO 86
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 86

Arg Arg Arg Gln Arg Arg Lys Lys Arg Gly
1               5                   10

<210> SEQ ID NO 87
<211> LENGTH: 12
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: VARIANT
<222> LOCATION: 2, 8
<223> OTHER INFORMATION: Xaa = Ala,  beta-alanine, Val, Leu, Ile, Ser,
      Gly, Thr, Phe, Trp, and 6-aminohexanoic acid

<400> SEQUENCE: 87

Arg Xaa Arg Arg Gly Gly Arg Xaa Arg Arg Gly Gly
1               5                   10

<210> SEQ ID NO 88
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: VARIANT
<222> LOCATION: 2, 6, 8, 12
<223> OTHER INFORMATION: Xaa = Ala,  beta-alanine, Val, Leu, Ile, Ser,
      Gly, Thr, Phe, Trp, and 6-aminohexanoic acid

<400> SEQUENCE: 88

Arg Xaa Arg Arg Arg Xaa Arg Xaa Arg Arg Arg Xaa Gly
1               5                   10

<210> SEQ ID NO 89
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 89

Arg Phe Phe Arg Phe Phe Arg Phe Phe Xaa
1               5                   10

<210> SEQ ID NO 90
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 90

Arg Thr Arg Thr Arg Phe Leu Arg Arg Thr Xaa
1               5                   10

<210> SEQ ID NO 91
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 91

Arg Phe Phe Arg Phe Phe Arg Phe Phe Arg Xaa
1               5                   10
```

```
<210> SEQ ID NO 92
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 92

Lys Thr Arg Thr Lys Phe Leu Lys Lys Thr Xaa
1               5                   10

<210> SEQ ID NO 93
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 93

Lys Phe Phe Lys Phe Phe Lys Phe Phe Xaa
1               5                   10

<210> SEQ ID NO 94
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 94

Lys Phe Phe Lys Phe Phe Lys Phe Phe Lys Xaa
1               5                   10

<210> SEQ ID NO 95
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)...(7)
<223> OTHER INFORMATION: Xaa = glycine or proline

<400> SEQUENCE: 95

Arg Phe Phe Arg Phe Phe Xaa
1               5

<210> SEQ ID NO 96
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
```

```
<223> OTHER INFORMATION: Xaa = glycine or proline

<400> SEQUENCE: 96

Arg Phe Phe Arg Phe Phe Arg Xaa
1               5

<210> SEQ ID NO 97
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(3)
<223> OTHER INFORMATION: Xaa = 6-aminohexanoic acid
<220> FEATURE:
<221> NAME/KEY: MOD_RES
<222> LOCATION: (5)...(6)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 97

Arg Xaa Xaa Arg Xaa Xaa Arg Xaa
1               5

<210> SEQ ID NO 98
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = glycine or proline

<400> SEQUENCE: 98

Arg Xaa Arg Arg Xaa Arg Xaa Arg Arg Xaa Arg Xaa
1               5                   10

<210> SEQ ID NO 99
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)...(12)
<223> OTHER INFORMATION: Xaa = glycine or proline

<400> SEQUENCE: 99
```

Tyr Gly Arg Lys Lys Arg Arg Gln Arg Arg Xaa
1               5                   10

<210> SEQ ID NO 100
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 100

Gly Arg Lys Lys Arg Arg Gln Arg Arg Arg Xaa
1               5                   10

<210> SEQ ID NO 101
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 101

Arg Lys Lys Arg Arg Gln Arg Arg Arg Xaa
1               5                   10

<210> SEQ ID NO 102
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (19)...(19)
<223> OTHER INFORMATION: Xaa = glycine or proline

<400> SEQUENCE: 102

Arg Gln Ile Lys Ile Trp Phe Gln Asn Arg Arg Met Lys Trp Lys Lys
1               5                   10                  15

Gly Gly Xaa

<210> SEQ ID NO 103
<211> LENGTH: 28
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (28)...(28)
<223> OTHER INFORMATION: Xaa = glycine or proline

<400> SEQUENCE: 103

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu Xaa
            20                  25

<210> SEQ ID NO 104
<211> LENGTH: 23

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (23)...(23)
<223> OTHER INFORMATION: Xaa = glycine or proline

<400> SEQUENCE: 104

Tyr Ala Arg Val Arg Arg Arg Gly Pro Arg Gly Tyr Ala Arg Val Arg
1               5                   10                  15

Arg Arg Gly Pro Arg Arg Xaa
            20

<210> SEQ ID NO 105
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)...(12)
<223> OTHER INFORMATION: Xaa = glycine or proline

<400> SEQUENCE: 105

Tyr Ala Arg Val Arg Arg Gly Pro Arg Arg Xaa
1               5                   10

<210> SEQ ID NO 106
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 106

Ala Lys Ala Ala Arg Gln Ala Ala Arg Xaa
1               5                   10

<210> SEQ ID NO 107
<211> LENGTH: 35
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (35)...(35)
<223> OTHER INFORMATION: Xaa = glycine or proline

<400> SEQUENCE: 107

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Pro
            20                  25                  30

Val Glu Xaa
        35

<210> SEQ ID NO 108
<211> LENGTH: 22
<212> TYPE: PRT
<213> ORGANISM: Artificial Sequence
```

```
<220> FEATURE:
<223> OTHER INFORMATION: cell penetrating peptide
<220> FEATURE:
<221> NAME/KEY: MOD_RES
<222> LOCATION: (22)...(22)
<223> OTHER INFORMATION: Xaa = glycine or proline

<400> SEQUENCE: 108

Lys Glu Thr Trp Trp Glu Thr Trp Trp Thr Glu Trp Ser Gln Pro Lys
1               5                   10                  15

Lys Lys Arg Lys Val Xaa
            20

<210> SEQ ID NO 109
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (22)...(22)
<223> OTHER INFORMATION: Xaa = glycine or proline

<400> SEQUENCE: 109

Lys Glu Thr Trp Phe Glu Thr Trp Phe Thr Glu Trp Ser Gln Pro Lys
1               5                   10                  15

Lys Lys Arg Lys Val Xaa
            20

<210> SEQ ID NO 110
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (17)...(17)
<223> OTHER INFORMATION: Xaa = glycine or proline

<400> SEQUENCE: 110

Arg Gln Ile Lys Ile Trp Phe Gln Asn Arg Arg Met Lys Trp Lys Lys
1               5                   10                  15

Xaa

<210> SEQ ID NO 111
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (25)...(25)
<223> OTHER INFORMATION: Xaa = glycine or proline

<400> SEQUENCE: 111

Arg Arg Arg Arg Arg Arg Arg Gln Ile Lys Ile Trp Phe Gln Asn Arg
1               5                   10                  15

Arg Met Lys Trp Lys Lys Gly Gly Xaa
            20                  25

<210> SEQ ID NO 112
<211> LENGTH: 11
<212> TYPE: PRT
<213> ORGANISM: Artificial Sequence
```

```
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 112

Arg Arg Arg Gln Arg Arg Lys Lys Arg Cys Xaa
1               5                   10

<210> SEQ ID NO 113
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 113

Cys Tyr Gly Arg Lys Lys Arg Arg Gln Arg Arg Xaa
1               5                   10

<210> SEQ ID NO 114
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 114

Arg Arg Arg Arg Arg Arg Arg Arg Arg Phe Phe Cys Xaa
1               5                   10

<210> SEQ ID NO 115
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 115

Arg Arg Arg Arg Arg Arg Arg Arg Arg Cys Phe Phe Xaa
1               5                   10

<210> SEQ ID NO 116
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 116

Arg Arg Arg Arg Arg Arg Arg Arg Cys Phe Phe Arg Xaa
1               5                   10
```

```
<210> SEQ ID NO 117
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 117

Arg Arg Arg Arg Arg Arg Cys Phe Phe Arg Arg Arg Xaa
1               5                   10

<210> SEQ ID NO 118
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 118

Arg Arg Arg Arg Arg Phe Cys Phe Arg Arg Arg Arg Xaa
1               5                   10

<210> SEQ ID NO 119
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)...(12)
<223> OTHER INFORMATION: Xaa = glycine or proline

<400> SEQUENCE: 119

Arg Arg Arg Arg Arg Phe Phe Arg Arg Arg Arg Xaa
1               5                   10

<210> SEQ ID NO 120
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 120

Arg Arg Arg Arg Cys Phe Phe Arg Arg Arg Arg Arg Xaa
1               5                   10

<210> SEQ ID NO 121
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
```

<223> OTHER INFORMATION: Xaa = glycine or proline

<400> SEQUENCE: 121

Arg Arg Cys Phe Phe Arg Arg Arg Arg Arg Arg Xaa
1               5                   10

<210> SEQ ID NO 122
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 122

Cys Phe Phe Arg Arg Arg Arg Arg Arg Arg Arg Xaa
1               5                   10

<210> SEQ ID NO 123
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 123

Cys Arg Arg Arg Arg Arg Arg Arg Arg Arg Phe Phe Xaa
1               5                   10

<210> SEQ ID NO 124
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)...(12)
<223> OTHER INFORMATION: Xaa = glycine or proline

<400> SEQUENCE: 124

Phe Phe Arg Arg Arg Arg Arg Arg Arg Arg Arg Xaa
1               5                   10

<210> SEQ ID NO 125
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (15)...(15)
<223> OTHER INFORMATION: Xaa = glycine or proline

<400> SEQUENCE: 125

Arg Arg Arg Arg Arg Phe Phe Cys Phe Phe Arg Arg Arg Arg Xaa
1               5                   10                  15

<210> SEQ ID NO 126
<211> LENGTH: 12
<212> TYPE: PRT

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)...(12)
<223> OTHER INFORMATION: Xaa = glycine or proline

<400> SEQUENCE: 126

Arg Arg Arg Arg Arg Arg Arg Arg Arg Ile Ile Xaa
1               5                   10

<210> SEQ ID NO 127
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)...(12)
<223> OTHER INFORMATION: Xaa = glycine or proline

<400> SEQUENCE: 127

Arg Arg Arg Arg Arg Arg Arg Arg Phe Phe Phe Xaa
1               5                   10

<210> SEQ ID NO 128
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (14)...(14)
<223> OTHER INFORMATION: Xaa = glycine or proline

<400> SEQUENCE: 128

Arg Arg Arg Arg Arg Arg Arg Arg Arg Phe Phe Phe Phe Xaa
1               5                   10

<210> SEQ ID NO 129
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 129

Arg Arg Arg Arg Arg Arg Arg Arg Phe Phe Xaa
1               5                   10

<210> SEQ ID NO 130
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)...(9)
<223> OTHER INFORMATION: Xaa = glycine or proline

<400> SEQUENCE: 130

Arg Arg Arg Arg Arg Arg Phe Phe Xaa
```

<210> SEQ ID NO 131
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 131

Arg Arg Arg Arg Arg Phe Phe Xaa
1               5

<210> SEQ ID NO 132
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (3)...(3)
<223> OTHER INFORMATION: Xaa = 6-aminohexanoic acid
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (9)...(9)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 132

Arg Arg Xaa Arg Arg Xaa Arg Arg Xaa Arg Arg Xaa
1               5                   10

<210> SEQ ID NO 133
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = glycine or proline

<400> SEQUENCE: 133

Arg Xaa Arg Arg Xaa Arg Arg Xaa Arg Arg Xaa Arg Xaa 1               5                    10

<210> SEQ ID NO 134
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)...(1)
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = glycine or proline

<400> SEQUENCE: 134

Xaa Arg Arg Xaa Arg Arg Xaa Arg Arg Xaa Arg Arg Xaa
1               5                   10

<210> SEQ ID NO 135
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = 6-aminohexanoic acid
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 135

Arg Xaa Arg Xaa Arg Xaa Arg Xaa Arg Xaa Arg Xaa
1               5                   10

<210> SEQ ID NO 136
<211> LENGTH: 10
<212> TYPE: PRT
<213> ORGANISM: Artificial Sequence
<220> FEATURE:
<223> OTHER INFORMATION: cell penetrating peptide

```
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = glycine or proline

<400> SEQUENCE: 136

Arg Xaa Arg Arg Xaa Arg Arg Xaa Arg Xaa
1               5                   10

<210> SEQ ID NO 137
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 137

Arg Xaa Arg Arg Xaa Arg Arg Xaa
1               5

<210> SEQ ID NO 138
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = glycine or proline

<400> SEQUENCE: 138

Arg Xaa Arg Arg Xaa Arg Xaa
1               5

<210> SEQ ID NO 139
<211> LENGTH: 12
<212> TYPE: PRT
<213> ORGANISM: Artificial Sequence
<220> FEATURE:
<223> OTHER INFORMATION: cell penetrating peptide
```

<220> FEATURE:
<221> NAME/KEY: MOD_RES
<222> LOCATION: (3)...(3)
<223> OTHER INFORMATION: Xaa = 6-aminohexanoic acid
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (9)...(9)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 139

Arg Lys Xaa Arg Lys Xaa Arg Lys Xaa Arg Lys Xaa
1               5                   10

<210> SEQ ID NO 140
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (3)...(3)
<223> OTHER INFORMATION: Xaa = 6-aminohexanoic acid
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (9)...(9)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 140

Arg His Xaa Arg His Xaa Arg His Xaa Arg His Xaa
1               5                   10

<210> SEQ ID NO 141
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 141

Arg Arg Arg Arg Arg Arg Arg Arg Cys Phe Phe Arg Xaa
1               5                   10

<210> SEQ ID NO 142
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (3)...(3)
<223> OTHER INFORMATION: Xaa = 6-aminohexanoic acid

```
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (9)...(9)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 142

Arg Arg Xaa Arg Arg Xaa Arg Arg Xaa Arg Arg Xaa
1               5                   10

<210> SEQ ID NO 143
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = glycine or proline

<400> SEQUENCE: 143

Arg Xaa Arg Arg Xaa Arg Arg Xaa Arg Arg Xaa Arg Xaa
1               5                   10

<210> SEQ ID NO 144
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1, 4, 7, 10
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = glycine or proline

<400> SEQUENCE: 144

Xaa Arg Arg Xaa Arg Arg Xaa Arg Arg Xaa Arg Arg Xaa
1               5                   10

<210> SEQ ID NO 145
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6, 8, 10
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 145

Arg Xaa Arg Xaa Arg Xaa Arg Xaa Arg Xaa Arg Xaa
```

<210> SEQ ID NO 146
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6, 8, 10, 12
<223> OTHER INFORMATION: Xaa = 6-aminohexanoic acid
<220> FEATURE:
<221> NAME/KEY: MOD_RES
<222> LOCATION: (14)...(14)
<223> OTHER INFORMATION: Xaa = glycine or proline

<400> SEQUENCE: 146

Arg Xaa Arg Xaa Arg Xaa Arg Xaa Arg Xaa Arg Xaa Arg Xaa
1               5                   10

<210> SEQ ID NO 147
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 14
<223> OTHER INFORMATION: Xaa = 6-aminohexanoic acid
<220> FEATURE:
<221> NAME/KEY: MOD_RES
<222> LOCATION: (16)...(16)
<223> OTHER INFORMATION: Xaa = glycine or proline

<400> SEQUENCE: 147

Arg Xaa Arg Arg Xaa Arg Arg Xaa Arg Arg Xaa Arg Arg Xaa Arg Xaa
1               5                   10                  15

<210> SEQ ID NO 148
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8
<223> OTHER INFORMATION: Xaa = 6-aminohexanoic acid
<220> FEATURE:
<221> NAME/KEY: MOD_RES
<222> LOCATION: 5, 11
<223> OTHER INFORMATION: Xaa = beta-alanine
<220> FEATURE:
<221> NAME/KEY: MOD_RES
<222> LOCATION: (13)...(13)
<223> OTHER INFORMATION: Xaa = glycine or proline

<400> SEQUENCE: 148

Arg Xaa Arg Arg Xaa Arg Arg Xaa Arg Arg Xaa Arg Xaa
1               5                   10

<210> SEQ ID NO 149
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8

```
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = beta-alanine
<220> FEATURE:
<221> NAME/KEY: MOD_RES
<222> LOCATION: (13)...(13)
<223> OTHER INFORMATION: Xaa = glycine or proline

<400> SEQUENCE: 149

Arg Xaa Arg Arg Xaa Arg Arg Xaa Arg Arg Xaa Arg Xaa
1               5                   10

<210> SEQ ID NO 150
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6, 8, 10, 14
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = 6-aminohexanoic acid
<220> FEATURE:
<221> NAME/KEY: MOD_RES
<222> LOCATION: (16)...(16)
<223> OTHER INFORMATION: Xaa = glycine or proline

<400> SEQUENCE: 150

Arg Xaa Arg Xaa Arg Xaa Arg Xaa Arg Xaa Arg Xaa Arg Xaa Arg Xaa
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6, 10, 12, 14
<223> OTHER INFORMATION: Xaa =beta-alanine
<220> FEATURE:
<221> NAME/KEY: MOD_RES
<222> LOCATION: (8)...(8)
<223> OTHER INFORMATION: Xaa = 6-aminohexanoic acid
<220> FEATURE:
<221> NAME/KEY: MOD_RES
<222> LOCATION: (16)...(16)
<223> OTHER INFORMATION: Xaa = glycine or proline

<400> SEQUENCE: 151

Arg Xaa Arg Xaa Arg Xaa Arg Xaa Arg Xaa Arg Xaa Arg Xaa Arg Xaa
1               5                   10                  15

<210> SEQ ID NO 152
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1, 9
<223> OTHER INFORMATION: Xaa = 6-aminohexanoic acid
<220> FEATURE:
<221> NAME/KEY: MOD_RES
<222> LOCATION: 3, 5, 7, 11, 13, 15
```

<223> OTHER INFORMATION: Xaa = beta-alanine
<220> FEATURE:
<221> NAME/KEY: MOD_RES
<222> LOCATION: (17)...(17)
<223> OTHER INFORMATION: Xaa = glycine or proline

<400> SEQUENCE: 152

Xaa Arg Xaa Arg Xaa Arg Xaa Arg Xaa Arg Xaa Arg Xaa Arg Xaa Arg
1               5                   10                  15

Xaa

<210> SEQ ID NO 153
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 4, 8, 12
<223> OTHER INFORMATION: Xaa = 6-aminohexanoic acid
<220> FEATURE:
<221> NAME/KEY: MOD_RES
<222> LOCATION: 2, 6, 10, 14
<223> OTHER INFORMATION: Xaa = beta-alanine
<220> FEATURE:
<221> NAME/KEY: MOD_RES
<222> LOCATION: (16)...(16)
<223> OTHER INFORMATION: Xaa = glycine or proline

<400> SEQUENCE: 153

Arg Xaa Arg Xaa Arg Xaa Arg Xaa Arg Xaa Arg Xaa Arg Xaa Arg Xaa
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 10, 12, 14
<223> OTHER INFORMATION: Xaa = 6-aminohexanoic acid
<220> FEATURE:
<221> NAME/KEY: MOD_RES
<222> LOCATION: 2, 4, 6, 8
<223> OTHER INFORMATION: Xaa = beta-alanine
<220> FEATURE:
<221> NAME/KEY: MOD_RES
<222> LOCATION: (16)...(16)
<223> OTHER INFORMATION: Xaa = glycine or proline

<400> SEQUENCE: 154

Arg Xaa Arg Xaa Arg Xaa Arg Xaa Arg Xaa Arg Xaa Arg Xaa Arg Xaa
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8
<223> OTHER INFORMATION: Xaa = 6-aminohexanoic acid
<220> FEATURE:
<221> NAME/KEY: MOD_RES
<222> LOCATION: 4, 6, 10, 12, 14
<223> OTHER INFORMATION: Xaa = beta-alanine
<220> FEATURE:

```
<221> NAME/KEY: MOD_RES
<222> LOCATION: (16)...(16)
<223> OTHER INFORMATION: Xaa = glycine or proline

<400> SEQUENCE: 155

Arg Xaa Arg Xaa Arg Xaa Arg Xaa Arg Xaa Arg Xaa Arg Xaa Arg Xaa
 1               5                  10                  15

<210> SEQ ID NO 156
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6, 8, 10, 12, 14
<223> OTHER INFORMATION: Xaa = beta-alanine
<220> FEATURE:
<221> NAME/KEY: MOD_RES
<222> LOCATION: (16)...(16)
<223> OTHER INFORMATION: Xaa = glycine or proline

<400> SEQUENCE: 156

Arg Xaa Arg Xaa Arg Xaa Arg Xaa Arg Xaa Arg Xaa Arg Xaa Arg Xaa
 1               5                  10                  15

<210> SEQ ID NO 157
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = glycine or proline

<400> SEQUENCE: 157

Arg Arg Arg Arg Xaa
 1               5

<210> SEQ ID NO 158
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)...(6)
<223> OTHER INFORMATION: Xaa = glycine or proline

<400> SEQUENCE: 158

Arg Arg Arg Arg Arg Xaa
 1               5

<210> SEQ ID NO 159
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)...(7)
<223> OTHER INFORMATION: Xaa = glycine or proline

<400> SEQUENCE: 159

Arg Arg Arg Arg Arg Arg Xaa
```

```
<210> SEQ ID NO 160
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 160

Arg Arg Arg Arg Arg Arg Arg Xaa
1               5

<210> SEQ ID NO 161
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)...(9)
<223> OTHER INFORMATION: Xaa = glycine or proline

<400> SEQUENCE: 161

Arg Arg Arg Arg Arg Arg Arg Arg Xaa
1               5

<210> SEQ ID NO 162
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 162

Arg Arg Arg Arg Arg Gly Arg Arg Arg Arg Xaa
1               5                   10

<210> SEQ ID NO 163
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)...(12)
<223> OTHER INFORMATION: Xaa = glycine or proline

<400> SEQUENCE: 163

Arg Arg Arg Arg Arg Phe Phe Arg Arg Arg Arg Xaa
1               5                   10

<210> SEQ ID NO 164
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

```
<222> LOCATION: (10)...(10)
<223> OTHER INFORMATION: Xaa = glycine or proline

<400> SEQUENCE: 164

Arg Lys Lys Arg Arg Gln Arg Arg Arg Xaa
1               5                   10

<210> SEQ ID NO 165
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 165

Arg Arg Arg Gln Arg Arg Lys Lys Arg Xaa
1               5                   10

<210> SEQ ID NO 166
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = glycine or proline

<400> SEQUENCE: 166

Arg Xaa Arg Arg Xaa Arg Xaa
1               5

<210> SEQ ID NO 167
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5
<223> OTHER INFORMATION: Xaa = beta-alanine
<220> FEATURE:
<221> NAME/KEY: MOD_RES
<222> LOCATION: (7)...(7)
<223> OTHER INFORMATION: Xaa = glycine or proline

<400> SEQUENCE: 167

Arg Xaa Arg Arg Xaa Arg Xaa
1               5

<210> SEQ ID NO 168
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
```

```
<221> NAME/KEY: MOD_RES
<222> LOCATION: (5)...(5)
<223> OTHER INFORMATION: Xaa = beta-alanine
<220> FEATURE:
<221> NAME/KEY: MOD_RES
<222> LOCATION: (7)...(7)
<223> OTHER INFORMATION: Xaa = glycine or proline

<400> SEQUENCE: 168

Arg Xaa Arg Arg Xaa Arg Xaa
1               5

<210> SEQ ID NO 169
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = glycine or proline

<400> SEQUENCE: 169

Arg Xaa Arg Arg Xaa Arg Xaa
1               5

<210> SEQ ID NO 170
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = NH-(CHRe)n-C(O)-wherein n is 2 to 7 and
     each Re is independently, at each occurrence, hydrogen
     or methyl
<220> FEATURE:
<221> NAME/KEY: MOD_RES
<222> LOCATION: (8)...(8)
<223> OTHER INFORMATION: Xaa - glycine or proline

<400> SEQUENCE: 170

Arg Xaa Arg Xaa Arg Xaa Arg Xaa
1               5

<210> SEQ ID NO 171
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = beta-alanine
<220> FEATURE:
<221> NAME/KEY: MOD_RES
<222> LOCATION: (4)...(4)
```

-continued

```
<223> OTHER INFORMATION: Xaa = NH-(CHRe)n-C(O)-wherein n is 2 to 7 and
      each Re is independently, at each occurrence, hydrogen
      or methyl
<220> FEATURE:
<221> NAME/KEY: MOD_RES
<222> LOCATION: (8)...(8)
<223> OTHER INFORMATION: Xaa = glycine or proline

<400> SEQUENCE: 171

Arg Xaa Arg Xaa Arg Xaa Arg Xaa
1               5

<210> SEQ ID NO 172
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = NH-(CHRe)n-C(O)-wherein n is 2 to 7 and
      each Re is independently, at each occurrence, hydrogen
      or methyl
<220> FEATURE:
<221> NAME/KEY: MOD_RES
<222> LOCATION: (6)...(6)
<223> OTHER INFORMATION: Xaa = beta-alanine
<220> FEATURE:
<221> NAME/KEY: MOD_RES
<222> LOCATION: (8)...(8)
<223> OTHER INFORMATION: Xaa = glycine or proline

<400> SEQUENCE: 172

Arg Xaa Arg Xaa Arg Xaa Arg Xaa
1               5

<210> SEQ ID NO 173
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = NH-(CHRe)n-C(O)-wherein n is 2 to 7 and
      each Re is independently, at each occurrence, hydrogen
      or methyl
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 173

Arg Xaa Arg Xaa Arg Xaa Arg Xaa
1               5

<210> SEQ ID NO 174
<211> LENGTH: 12
<212> TYPE: PRT
```

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 174

Arg Xaa Arg Ile Leu Phe Gln Tyr Arg Xaa Arg Xaa
 1               5                  10

<210> SEQ ID NO 175
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = glycine or proline

<400> SEQUENCE: 175

Arg Xaa Arg Ile Leu Phe Gln Tyr Arg Xaa Arg Xaa
 1               5                  10

<210> SEQ ID NO 176
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = glycine or proline

<400> SEQUENCE: 176

Arg Xaa Arg Ile Leu Phe Gln Tyr Arg Xaa Arg Xaa
 1               5                  10

<210> SEQ ID NO 177
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: (10)...(10)
<223> OTHER INFORMATION: Xaa = 6-aminohexanoic acid
<220> FEATURE:
```

```
<221> NAME/KEY: MOD_RES
<222> LOCATION: (12)...(12)
<223> OTHER INFORMATION: Xaa = glycine or proline

<400> SEQUENCE: 177

Arg Xaa Arg Ile Leu Phe Gln Tyr Arg Xaa Arg Xaa
1               5                   10

<210> SEQ ID NO 178
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa - 6-aminohexanoic acid
<220> FEATURE:
<221> NAME/KEY: MOD_RES
<222> LOCATION: (10)...(10)
<223> OTHER INFORMATION: Xaa = glycine or proline

<400> SEQUENCE: 178

Arg Xaa Arg Arg Xaa Arg Arg Xaa Arg Xaa
1               5                   10

<210> SEQ ID NO 179
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = beta-alanine
<220> FEATURE:
<221> NAME/KEY: MOD_RES
<222> LOCATION: (10)...(10)
<223> OTHER INFORMATION: Xaa = glycine or proline

<400> SEQUENCE: 179

Arg Xaa Arg Arg Xaa Arg Arg Xaa Arg Xaa
1               5                   10

<210> SEQ ID NO 180
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8
<223> OTHER INFORMATION: Xaa = 6-aminohexanoic acid
<220> FEATURE:
<221> NAME/KEY: MOD_RES
<222> LOCATION: (5)...(5)
<223> OTHER INFORMATION: Xaa = beta-alanine
<220> FEATURE:
<221> NAME/KEY: MOD_RES
<222> LOCATION: (10)...(10)
<223> OTHER INFORMATION: Xaa = glycine or proline

<400> SEQUENCE: 180

Arg Xaa Arg Arg Xaa Arg Arg Xaa Arg Xaa
1               5                   10

<210> SEQ ID NO 181
<211> LENGTH: 10
```

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: 5, 8
<223> OTHER INFORMATION: Xaa = beta-alanine
<220> FEATURE:
<221> NAME/KEY: MOD_RES
<222> LOCATION: (10)...(10)
<223> OTHER INFORMATION: Xaa = glycine or proline

<400> SEQUENCE: 181

Arg Xaa Arg Arg Xaa Arg Arg Xaa Arg Xaa
1               5                   10

<210> SEQ ID NO 182
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = beta-alanine
<220> FEATURE:
<221> NAME/KEY: MOD_RES
<222> LOCATION: (10)...(10)
<223> OTHER INFORMATION: Xaa = glycine or proline

<400> SEQUENCE: 182

Arg Xaa Arg Arg Xaa Arg Arg Xaa Arg Xaa
1               5                   10

<210> SEQ ID NO 183
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8
<223> OTHER INFORMATION: Xaa = beta-alanine
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = glycine or proline

<400> SEQUENCE: 183

Arg Xaa Arg Arg Xaa Arg Arg Xaa Arg Xaa
1               5                   10

<210> SEQ ID NO 184
<211> LENGTH: 10
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: 5, 8
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = glycine or proline

<400> SEQUENCE: 184

Arg Xaa Arg Arg Xaa Arg Arg Xaa Arg Xaa
1               5                   10

<210> SEQ ID NO 185
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5
<223> OTHER INFORMATION: Xaa = beta-alanine
<220> FEATURE:
<221> NAME/KEY: MOD_RES
<222> LOCATION: (8)...(8)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = glycine or proline

<400> SEQUENCE: 185

Arg Xaa Arg Arg Xaa Arg Arg Xaa Arg Xaa
1               5                   10

<210> SEQ ID NO 186
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6, 9
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = glycine or proline
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl

<400> SEQUENCE: 186

Arg Xaa Arg Xaa Arg Xaa Arg Arg Xaa Arg Xaa
1               5                   10

<210> SEQ ID NO 187
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

<222> LOCATION: 2, 5, 9
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (11)...(11)
<223> OTHER INFORMATION: Xaa = glycine or proline

<400> SEQUENCE: 187

Arg Xaa Arg Arg Xaa Arg Xaa Arg Xaa Arg Xaa
1               5                   10

<210> SEQ ID NO 188
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10, 13
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 188

Arg Xaa Arg Ile Leu Phe Gln Tyr Arg Xaa Arg Arg Xaa Arg Xaa
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 189

Arg Xaa Arg Arg Xaa Arg Ile Leu Phe Gln Tyr Arg Xaa Arg Xaa
1               5                   10                  15

<210> SEQ ID NO 190
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6, 10
<223> OTHER INFORMATION: Xaa = 6-aminohexanoic acid
<220> FEATURE:
<221> NAME/KEY: MOD_RES
<222> LOCATION: 4, 8
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES

```
<222> LOCATION: (12)...(12)
<223> OTHER INFORMATION: Xaa = glycine or proline

<400> SEQUENCE: 190

Arg Xaa Arg Xaa Arg Xaa Arg Xaa Arg Xaa Arg Xaa
1               5                   10

<210> SEQ ID NO 191
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10, 18
<223> OTHER INFORMATION: Xaa = 6-aminohexanoic acid
<220> FEATURE:
<221> NAME/KEY: MOD_RES
<222> LOCATION: (20)...(20)
<223> OTHER INFORMATION: Xaa = glycine or proline

<400> SEQUENCE: 191

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 192
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10, 14
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
<223> OTHER INFORMATION: Xaa = glycine or proline

<400> SEQUENCE: 192

Arg Xaa Arg Ile Leu Phe Gln Tyr Arg Xaa Arg Xaa Arg Xaa Arg Xaa
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6, 14
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
```

```
<223> OTHER INFORMATION: Xaa = glycine or proline

<400> SEQUENCE: 193

Arg Xaa Arg Xaa Arg Xaa Arg Ile Leu Phe Gln Tyr Arg Xaa Arg Xaa
1               5                   10                  15

<210> SEQ ID NO 194
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6, 9
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (11)...(11)
<223> OTHER INFORMATION: Xaa = glycine or proline

<400> SEQUENCE: 194

Arg Xaa Arg Xaa Arg Xaa Arg Arg Xaa Arg Xaa
1               5                   10

<210> SEQ ID NO 195
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 9
<223> OTHER INFORMATION: Xaa = beta-alanine
<220> FEATURE:
<221> NAME/KEY: MOD_RES
<222> LOCATION: (7)...(7)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (11)...(11)
<223> OTHER INFORMATION: Xaa = glycine or proline

<400> SEQUENCE: 195

Arg Xaa Arg Arg Xaa Arg Xaa Arg Xaa Arg Xaa
1               5                   10

<210> SEQ ID NO 196
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10, 13
<223> OTHER INFORMATION: Xaa = beta-alanine
<220> FEATURE:
<221> NAME/KEY: MOD_RES
<222> LOCATION: (15)...(15)
<223> OTHER INFORMATION: Xaa = glycine or proline

<400> SEQUENCE: 196
```

```
Arg Xaa Arg Ile Leu Phe Gln Tyr Arg Xaa Arg Arg Xaa Arg Xaa
1               5                   10                  15
```

<210> SEQ ID NO 197
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13
<223> OTHER INFORMATION: Xaa = beta-alanine
<220> FEATURE:
<221> NAME/KEY: MOD_RES
<222> LOCATION: (15)...(15)
<223> OTHER INFORMATION: Xaa = glycine or proline

<400> SEQUENCE: 197

```
Arg Xaa Arg Arg Asx Arg Ile Leu Phe Gln Tyr Arg Xaa Arg Xaa
1               5                   10                  15
```

<210> SEQ ID NO 198
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6, 10
<223> OTHER INFORMATION: Xaa = beta-alanine
<220> FEATURE:
<221> NAME/KEY: MOD_RES
<222> LOCATION: (8)...(8)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (12)...(12)
<223> OTHER INFORMATION: Xaa = glycine or proline

<400> SEQUENCE: 198

```
Arg Xaa Arg Tyr Arg Xaa Arg Xaa Arg Xaa Arg Xaa
1               5                   10
```

<210> SEQ ID NO 199
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10, 18
<223> OTHER INFORMATION: Xaa = beta-alanine
<220> FEATURE:
<221> NAME/KEY: MOD_RES
<222> LOCATION: (20)...(20)
<223> OTHER INFORMATION: Xaa = glycine or proline

<400> SEQUENCE: 199

```
Arg Xaa Arg Ile Leu Phe Gln Tyr Arg Xaa Arg Ile Leu Phe Gln Tyr
1               5                   10                  15

Arg Xaa Arg Xaa
                20
```

<210> SEQ ID NO 200
<211> LENGTH: 16
<212> TYPE: PRT

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6, 14
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
<223> OTHER INFORMATION: Xaa = glycine or alanine

<400> SEQUENCE: 200

Arg Xaa Arg Xaa Arg Xaa Arg Ile Leu Phe Gln Tyr Arg Xaa Arg Xaa
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10, 14
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
<223> OTHER INFORMATION: Xaa = glycine or proline

<400> SEQUENCE: 201

Arg Xaa Arg Ile Leu Phe Gln Tyr Arg Xaa Arg Xaa Arg Xaa Arg Xaa
1               5                   10                  15

<210> SEQ ID NO 202
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 9
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (6)...(6)
<223> OTHER INFORMATION: Xaa = beta-alanine
<220> FEATURE:
<221> NAME/KEY: MOD_RES
<222> LOCATION: (11)...(11)
<223> OTHER INFORMATION: Xaa = glycine or proline

<400> SEQUENCE: 202

Arg Xaa Arg Xaa Arg Xaa Arg Arg Xaa Arg Xaa
```

<210> SEQ ID NO 203
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 9
<223> OTHER INFORMATION: Xaa = 6-aminohexanoic acid
<220> FEATURE:
<221> NAME/KEY: MOD_RES
<222> LOCATION: (5)...(5)
<223> OTHER INFORMATION: Xaa = beta-alanine
<220> FEATURE:
<221> NAME/KEY: MOD_RES
<222> LOCATION: (7)...(7)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (11)...(11)
<223> OTHER INFORMATION: Xaa = glycine or proline

<400> SEQUENCE: 203

Arg Xaa Arg Arg Xaa Arg Xaa Arg Xaa Arg Xaa
1               5                   10

<210> SEQ ID NO 204
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 13
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = beta-alanine
<220> FEATURE:
<221> NAME/KEY: MOD_RES
<222> LOCATION: (15)...(15)
<223> OTHER INFORMATION: Xaa = glycine or proline

<400> SEQUENCE: 204

Arg Xaa Arg Ile Leu Phe Gln Tyr Arg Xaa Arg Arg Xaa Arg Xaa
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = beta-alanine
<220> FEATURE:
<221> NAME/KEY: MOD_RES
<222> LOCATION: 2, 13
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 205

Arg Xaa Arg Arg Xaa Arg Ile Leu Phe Gln Tyr Arg Xaa Arg Xaa
1               5                   10                  15

<210> SEQ ID NO 206
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = 6-aminohexanoic acid
<220> FEATURE:
<221> NAME/KEY: MOD_RES
<222> LOCATION: 4, 8
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (6)...(6)
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = glycine or proline

<400> SEQUENCE: 206

Arg Xaa Arg Xaa Arg Xaa Arg Xaa Arg Xaa Arg Xaa
1               5                   10

<210> SEQ ID NO 207
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 18
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = beta-alanine
<220> FEATURE:
<221> NAME/KEY: MOD_RES
<222> LOCATION: (20)...(20)
<223> OTHER INFORMATION: Xaa = glycine or proline

<400> SEQUENCE: 207

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 208
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 14
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,

```
      hydrogen or methyl
<220> FEATURE:
<221> NAME/KEY: MOD_RES
<222> LOCATION: (6)...(6)
<223> OTHER INFORMATION: Xaa = beta-alanine
<220> FEATURE:
<221> NAME/KEY: MOD_RES
<222> LOCATION: (16)...(16)
<223> OTHER INFORMATION: Xaa = glycine or proline

<400> SEQUENCE: 208

Arg Xaa Arg Xaa Arg Xaa Arg Ile Leu Phe Gln Tyr Arg Xaa Arg Xaa
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 14
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
<223> OTHER INFORMATION: Xaa = glycine or proline

<400> SEQUENCE: 209

Arg Xaa Arg Ile Leu Phe Gln Tyr Arg Xaa Arg Xaa Arg Xaa Arg Xaa
1               5                   10                  15

<210> SEQ ID NO 210
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: 6, 9
<223> OTHER INFORMATION: Xaa = beta-alanine
<220> FEATURE:
<221> NAME/KEY: MOD_RES
<222> LOCATION: (11)...(11)
<223> OTHER INFORMATION: Xaa = glycine or proline

<400> SEQUENCE: 210

Arg Xaa Arg Xaa Arg Xaa Arg Arg Xaa Arg Xaa
1               5                   10

<210> SEQ ID NO 211
```

```
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: 5, 9
<223> OTHER INFORMATION: Xaa = beta-alanine
<220> FEATURE:
<221> NAME/KEY: MOD_RES
<222> LOCATION: (7)...(7)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (11)...(11)
<223> OTHER INFORMATION: Xaa = glycine or proline

<400> SEQUENCE: 211

Arg Xaa Arg Arg Xaa Arg Xaa Arg Xaa Arg Xaa
1               5                   10

<210> SEQ ID NO 212
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: 10, 13
<223> OTHER INFORMATION: Xaa = beta-alanine
<220> FEATURE:
<221> NAME/KEY: MOD_RES
<222> LOCATION: (15)...(15)
<223> OTHER INFORMATION: Xaa = glycine or proline

<400> SEQUENCE: 212

Arg Xaa Arg Ile Leu Phe Gln Tyr Arg Xaa Arg Arg Xaa Arg Xaa
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: 5, 13
<223> OTHER INFORMATION: Xaa = beta-alanine
<220> FEATURE:
<221> NAME/KEY: MOD_RES
<222> LOCATION: (15)...(15)
<223> OTHER INFORMATION: Xaa = glycine or proline

<400> SEQUENCE: 213

Arg Xaa Arg Arg Xaa Arg Ile Leu Phe Gln Tyr Arg Xaa Arg Xaa
1               5                   10                  15
```

```
<210> SEQ ID NO 214
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: 4, 8
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: 6, 10
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = glycine or proline

<400> SEQUENCE: 214

Arg Xaa Arg Xaa Arg Xaa Arg Xaa Arg Xaa Arg Xaa
1               5                   10

<210> SEQ ID NO 215
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: 10, 18
<223> OTHER INFORMATION: Xaa = beta-alanine
<220> FEATURE:
<221> NAME/KEY: MOD_RES
<222> LOCATION: (20)...(20)
<223> OTHER INFORMATION: Xaa = glycine or proline

<400> SEQUENCE: 215

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 216
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: 6, 14
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
```

```
      hydrogen or methyl
<220> FEATURE:
<221> NAME/KEY: MOD_RES
<222> LOCATION: (16)...(16)
<223> OTHER INFORMATION: Xaa = glycine or proline

<400> SEQUENCE: 216

Arg Xaa Arg Xaa Arg Xaa Arg Ile Leu Phe Gln Tyr Arg Xaa Arg Xaa
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: 10, 14
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
<223> OTHER INFORMATION: Xaa = glycine or proline

<400> SEQUENCE: 217

Arg Xaa Arg Ile Leu Phe Gln Tyr Arg Xaa Arg Xaa Arg Xaa Arg Xaa
1               5                   10                  15

<210> SEQ ID NO 218
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (9)...(9)
<223> OTHER INFORMATION: Xaa = beta-alanine
<220> FEATURE:
<221> NAME/KEY: MOD_RES
<222> LOCATION: (11)...(11)
<223> OTHER INFORMATION: Xaa = glycine or proline

<400> SEQUENCE: 218

Arg Xaa Arg Xaa Arg Xaa Arg Arg Xaa Arg Xaa
1               5                   10

<210> SEQ ID NO 219
<211> LENGTH: 11
<212> TYPE: PRT
<213> ORGANISM: Artificial Sequence
<220> FEATURE:
```

```
<223> OTHER INFORMATION: cell penetrating peptide
<220> FEATURE:
<221> NAME/KEY: MOD_RES
<222> LOCATION: 2, 5
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (9)...(9)
<223> OTHER INFORMATION: Xaa = beta-alanine
<220> FEATURE:
<221> NAME/KEY: MOD_RES
<222> LOCATION: (11)...(11)
<223> OTHER INFORMATION: Xaa = glycine or proline

<400> SEQUENCE: 219

Arg Xaa Arg Arg Xaa Arg Xaa Arg Xaa Arg Xaa
1               5                   10

<210> SEQ ID NO 220
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = beta-alanine
<220> FEATURE:
<221> NAME/KEY: MOD_RES
<222> LOCATION: (15)...(15)
<223> OTHER INFORMATION: Xaa = glycine or alanine

<400> SEQUENCE: 220

Arg Xaa Arg Ile Leu Phe Gln Tyr Arg Xaa Arg Arg Xaa Arg Xaa
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = beta-alanine
<220> FEATURE:
<221> NAME/KEY: MOD_RES
<222> LOCATION: (15)...(15)
<223> OTHER INFORMATION: Xaa = glycine or proline

<400> SEQUENCE: 221

Arg Xaa Arg Arg Xaa Arg Leu Leu Phe Gln Tyr Arg Xaa Arg Xaa
1               5                   10                  15

<210> SEQ ID NO 222
<211> LENGTH: 12
<212> TYPE: PRT
```

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = 6-aminohexanoic acid
<220> FEATURE:
<221> NAME/KEY: MOD_RES
<222> LOCATION: 4, 8
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (10)...(10)
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = glycine or proline

<400> SEQUENCE: 222

Arg Xaa Arg Xaa Arg Xaa Arg Xaa Arg Xaa Arg Xaa
1               5                   10

<210> SEQ ID NO 223
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = 6-aminohexanoic acid
<220> FEATURE:
<221> NAME/KEY: MOD_RES
<222> LOCATION: (18)...(18)
<223> OTHER INFORMATION: Xaa = beta-alanine
<220> FEATURE:
<221> NAME/KEY: MOD_RES
<222> LOCATION: (20)...(20)
<223> OTHER INFORMATION: Xaa = glycine or proline

<400> SEQUENCE: 223

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 224
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (14)...(4)
<223> OTHER INFORMATION: Xaa = beta-alanine
<220> FEATURE:
<221> NAME/KEY: MOD_RES
<222> LOCATION: (16)...(16)
```

```
<223> OTHER INFORMATION: Xaa = glycine or proline

<400> SEQUENCE: 224

Arg Xaa Arg Xaa Arg Xaa Arg Ile Leu Phe Gln Tyr Arg Xaa Arg Xaa
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (14)...(14)
<223> OTHER INFORMATION: Xaa = beta-alanine
<220> FEATURE:
<221> NAME/KEY: MOD_RES
<222> LOCATION: (16)...(16)
<223> OTHER INFORMATION: Xaa = glycine or proline

<400> SEQUENCE: 225

Arg Xaa Arg Ile Leu Phe Gln Tyr Arg Xaa Arg Xaa Arg Xaa Arg Xaa
1               5                   10                  15

<210> SEQ ID NO 226
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 9
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = glycine or proline

<400> SEQUENCE: 226

Arg Xaa Arg Xaa Arg Xaa Arg Arg Xaa Arg Xaa
1               5                   10

<210> SEQ ID NO 227
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 9
```

<223> OTHER INFORMATION: Xaa = beta-alanine
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = -NH-(CHRe)n-C(O)-wherein n is 2 to 7 and
each Re is independently, at each occurrence,
hydrogen or methyl
<220> FEATURE:
<221> NAME/KEY: MOD_RES
<222> LOCATION: (11)...(11)
<223> OTHER INFORMATION: Xaa = glycine or proline

<400> SEQUENCE: 227

Arg Xaa Arg Arg Xaa Arg Xaa Arg Xaa Arg Xaa
1               5                   10

<210> SEQ ID NO 228
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 13
<223> OTHER INFORMATION: Xaa = beta-alanine
<220> FEATURE:
<221> NAME/KEY: MOD_RES
<222> LOCATION: (10)...(10)
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa - glycine or proline

<400> SEQUENCE: 228

Arg Xaa Arg Ile Leu Phe Gln Tyr Arg Xaa Arg Arg Xaa Arg Xaa
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 13
<223> OTHER INFORMATION: Xaa = beta-alanine
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 229

Arg Xaa Arg Arg Xaa Arg Ile Leu Phe Gln Tyr Arg Xaa Arg Xaa
1               5                   10                  15

<210> SEQ ID NO 230
<211> LENGTH: 12
<212> TYPE: PRT
<213> ORGANISM: Artificial Sequence
<220> FEATURE:
<223> OTHER INFORMATION: cell penetrating peptide
<220> FEATURE:

```
<221> NAME/KEY: MOD_RES
<222> LOCATION: 2, 10
<223> OTHER INFORMATION: Xaa = beta-alanine
<220> FEATURE:
<221> NAME/KEY: MOD_RES
<222> LOCATION: 4, 8
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 230

Arg Xaa Arg Xaa Arg Xaa Arg Xaa Arg Xaa Arg Xaa
1               5                   10

<210> SEQ ID NO 231
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 18
<223> OTHER INFORMATION: Xaa = beta-alanine
<220> FEATURE:
<221> NAME/KEY: MOD_RES
<222> LOCATION: (10)...(10)
<223> OTHER INFORMATION: Xaa = 6-aminohexanoic acid
<220> FEATURE:
<221> NAME/KEY: MOD_RES
<222> LOCATION: (20)...(20)
<223> OTHER INFORMATION: Xaa = glycine or proline

<400> SEQUENCE: 231

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 232
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 14
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (6)...(6)
<223> OTHER INFORMATION: Xaa = 6-aminihexanoic acid
<220> FEATURE:
<221> NAME/KEY: MOD_RES
<222> LOCATION: (16)...(16)
<223> OTHER INFORMATION: Xaa = glycine or proline

<400> SEQUENCE: 232
```

```
Arg Xaa Arg Xaa Arg Xaa Arg Ile Leu Phe Gln Tyr Arg Xaa Arg Xaa
1               5                   10                  15
```

<210> SEQ ID NO 233
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 14
<223> OTHER INFORMATION: Xaa = beta-alanine
<220> FEATURE:
<221> NAME/KEY: MOD_RES
<222> LOCATION: (10)...(10)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
<223> OTHER INFORMATION: Xaa = glycine or proline

<400> SEQUENCE: 233

```
Arg Xaa Arg Ile Leu Phe Gln Tyr Arg Xaa Arg Xaa Arg Xaa Arg Xaa
1               5                   10                  15
```

<210> SEQ ID NO 234
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: 6, 9
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = glycine or proline

<400> SEQUENCE: 234

```
Arg Xaa Arg Xaa Arg Xaa Arg Arg Xaa Arg Xaa
1               5                   10
```

<210> SEQ ID NO 235
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: 5, 9

```
<223> OTHER INFORMATION: Xaa = 6-aminohexanoic acid
<220> FEATURE:
<221> NAME/KEY: MOD_RES
<222> LOCATION: (7)...(7)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (11)...(11)
<223> OTHER INFORMATION: Xaa = glycine or proline

<400> SEQUENCE: 235

Arg Xaa Arg Arg Xaa Arg Xaa Arg Xaa Arg Xaa
1               5                   10

<210> SEQ ID NO 236
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: 10, 13
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 236

Arg Xaa Arg Ile Leu Phe Gln Tyr Arg Xaa Arg Arg Xaa Arg Xaa
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: 5, 13
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 237

Arg Xaa Arg Arg Xaa Arg Ile Leu Phe Gln Tyr Arg Xaa Arg Xaa
1               5                   10                  15

<210> SEQ ID NO 238
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
```

```
<221> NAME/KEY: MOD_RES
<222> LOCATION: 6, 10
<223> OTHER INFORMATION: Xaa = 6-aminohexanoic acid
<220> FEATURE:
<221> NAME/KEY: MOD_RES
<222> LOCATION: 4, 8
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (12)...(12)
<223> OTHER INFORMATION: Xaa = glycine or proline

<400> SEQUENCE: 238

Arg Xaa Arg Xaa Arg Xaa Arg Xaa Arg Xaa Arg Xaa
1               5                   10

<210> SEQ ID NO 239
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: 10, 18
<223> OTHER INFORMATION: Xaa = 6-aminohexanoic acid
<220> FEATURE:
<221> NAME/KEY: MOD_RES
<222> LOCATION: (20)...(20)
<223> OTHER INFORMATION: Xaa = glycine or proline

<400> SEQUENCE: 239

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 240
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: 6, 14
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
<223> OTHER INFORMATION: Xaa = glycine or proline

<400> SEQUENCE: 240

Arg Xaa Arg Xaa Arg Xaa Arg Ile Leu Phe Gln Tyr Arg Xaa Arg Xaa
1               5                   10                  15
```

```
<210> SEQ ID NO 241
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = beta-alanine
<220> FEATURE:
<221> NAME/KEY: MOD_RES
<222> LOCATION: 10, 14
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (16)...(16)
<223> OTHER INFORMATION: Xaa = glycine or proline

<400> SEQUENCE: 241

Arg Xaa Arg Ile Leu Phe Gln Tyr Arg Xaa Arg Xaa Arg Xaa Arg Xaa
1               5                   10                  15

<210> SEQ ID NO 242
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (9)...(9)
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = glycine or proline

<400> SEQUENCE: 242

Arg Xaa Arg Xaa Arg Xaa Arg Arg Xaa Arg Xaa
1               5                   10

<210> SEQ ID NO 243
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5
<223> OTHER INFORMATION: Xaa = beta-alanine
<220> FEATURE:
<221> NAME/KEY: MOD_RES
<222> LOCATION: (7)...(7)
<223> OTHER INFORMATION: Xaa = -NH-(CHRe)n-C(O)-wherein n is 2 to 7 and
      each Re is independently, at each occurrence,
      hydrogen or methyl
<220> FEATURE:
```

```
<221> NAME/KEY: MOD_RES
<222> LOCATION: (9)...(9)
<223> OTHER INFORMATION: Xaa = 6-aminohexanoic acid
<220> FEATURE:
<221> NAME/KEY: MOD_RES
<222> LOCATION: (11)...(11)
<223> OTHER INFORMATION: Xaa = glycine or proline

<400> SEQUENCE: 243

Arg Xaa Arg Arg Xaa Arg Xaa Arg Xaa Arg Xaa
1               5                   10

<210> SEQ ID NO 244
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = beta-alanine
<220> FEATURE:
<221> NAME/KEY: MOD_RES
<222> LOCATION: (13)...(13)
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 244

Arg Xaa Arg Ile Leu Phe Gln Tyr Arg Xaa Arg Arg Xaa Arg Xaa
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5
<223> OTHER INFORMATION: Xaa = beta-alanine
<220> FEATURE:
<221> NAME/KEY: MOD_RES
<222> LOCATION: (13)...(13)
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 245

Arg Xaa Arg Arg Xaa Arg Ile Leu Phe Gln Tyr Arg Xaa Arg Xaa
1               5                   10                  15

<210> SEQ ID NO 246
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = beta-alanine
<220> FEATURE:
<221> NAME/KEY: MOD_RES
<222> LOCATION: 4, 8
<223> OTHER INFORMATION: Xaa = -NH-(CHRe)n-C(O)-wherein n is 2 to 7 and
      each Re is independently, at each occurrence,
```

```
            hydrogen or methyl
<220> FEATURE:
<221> NAME/KEY: MOD_RES
<222> LOCATION: (10)...(10)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = glycine or proline

<400> SEQUENCE: 246

Arg Xaa Arg Xaa Arg Xaa Arg Xaa Arg Xaa Arg Xaa
1               5                   10

<210> SEQ ID NO 247
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = beta-alanine
<220> FEATURE:
<221> NAME/KEY: MOD_RES
<222> LOCATION: (18)...(18)
<223> OTHER INFORMATION: Xaa = 6-aminohexanoic acid
<220> FEATURE:
<221> NAME/KEY: MOD_RES
<222> LOCATION: (20)...(20)
<223> OTHER INFORMATION: Xaa = glycine or proline

<400> SEQUENCE: 247

Arg Xaa Arg Ile Leu Phe Gln Tyr Arg Xaa Arg Ile Leu Phe Gln Tyr
1               5                   10                  15

Arg Xaa Arg Xaa
            20

<210> SEQ ID NO 248
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = beta-alanine
<220> FEATURE:
<221> NAME/KEY: MOD_RES
<222> LOCATION: (4)...(4)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (14)...(14)
<223> OTHER INFORMATION: Xaa = 6-aminohexanoic acid
<220> FEATURE:
<221> NAME/KEY: MOD_RES
<222> LOCATION: (16)...(16)
<223> OTHER INFORMATION: Xaa = glycine or proline

<400> SEQUENCE: 248

Arg Xaa Arg Xaa Arg Xaa Arg Ile Leu Phe Gln Tyr Arg Xaa Arg Xaa
1               5                   10                  15

<210> SEQ ID NO 249
<211> LENGTH: 16
<212> TYPE: PRT
<213> ORGANISM: Artificial Sequence
```

```
<220> FEATURE:
<223> OTHER INFORMATION: cell penetrating peptide
<220> FEATURE:
<221> NAME/KEY: MOD_RES
<222> LOCATION: 2, 10
<223> OTHER INFORMATION: Xaa = beta-alanine
<220> FEATURE:
<221> NAME/KEY: MOD_RES
<222> LOCATION: (12)...(12)
<223> OTHER INFORMATION: Xaa = -NH-(CHRe)n-C(O)-wherein n is 2 to 7 and
      each Re is independently, at each occurrence,
      hydrogen or methyl
<220> FEATURE:
<221> NAME/KEY: MOD_RES
<222> LOCATION: (14)...(14)
<223> OTHER INFORMATION: Xaa = 6-aminohexanoic acid
<220> FEATURE:
<221> NAME/KEY: MOD_RES
<222> LOCATION: (16)...(16)
<223> OTHER INFORMATION: Xaa = glycine or proline

<400> SEQUENCE: 249

Arg Xaa Arg Ile Leu Phe Gln Tyr Arg Xaa Arg Xaa Arg Xaa Arg Xaa
1               5                   10                  15

<210> SEQ ID NO 250
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = glycine or proline

<400> SEQUENCE: 250

Arg Xaa Arg Arg Xaa Arg Arg Xaa Arg Arg Xaa Arg Xaa
1               5                   10

<210> SEQ ID NO 251
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 20
<223> OTHER INFORMATION: Xaa = 6-aminohexanoic acid
<220> FEATURE:
<221> NAME/KEY: MOD_RES
<222> LOCATION: 5, 18
<223> OTHER INFORMATION: Xaa = beta-alanine
<220> FEATURE:
<221> NAME/KEY: MOD_RES
<222> LOCATION: (22)...(22)
<223> OTHER INFORMATION: Xaa = glycine or proline

<400> SEQUENCE: 251

Arg Xaa Arg Arg Xaa Arg Arg Xaa Arg Ile Leu Phe Gln Tyr Arg Xaa
1               5                   10                  15

Arg Xaa Arg Xaa Arg Xaa
            20

<210> SEQ ID NO 252
<211> LENGTH: 13
<212> TYPE: PRT
```

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8
<223> OTHER INFORMATION: Xaa = 6-aminohexanoic acid
<220> FEATURE:
<221> NAME/KEY: MOD_RES
<222> LOCATION: 5, 11
<223> OTHER INFORMATION: Xaa = beta-alanine
<220> FEATURE:
<221> NAME/KEY: MOD_RES
<222> LOCATION: (13)...(13)
<223> OTHER INFORMATION: Xaa = glycine or proline

<400> SEQUENCE: 252

Arg Xaa Arg Arg Xaa Arg Arg Xaa Arg Arg Xaa Arg Xaa
1               5                   10

<210> SEQ ID NO 253
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 253

Tyr Gly Arg Lys Lys Arg Arg Gln Arg Arg Pro Xaa
1               5                   10

<210> SEQ ID NO 254
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 13, 22
<223> OTHER INFORMATION: Xaa = 6-aminohexanoic acid
<220> FEATURE:
<221> NAME/KEY: MOD_RES
<222> LOCATION: (14)...(14)
<223> OTHER INFORMATION: Xaa = beta-alanine
<220> FEATURE:
<221> NAME/KEY: MOD_RES
<222> LOCATION: (24)...(24)
<223> OTHER INFORMATION: Xaa = glycine or proline

<400> SEQUENCE: 254

Arg Xaa Arg Arg Xaa Arg Arg Xaa Arg Arg Xaa Arg Xaa Xaa Ala Ser
1               5                   10                  15

Ser Leu Asn Ile Ala Xaa Cys Xaa
                20

<210> SEQ ID NO 255
<211> LENGTH: 32
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 20, 30
<223> OTHER INFORMATION: Xaa = 6-aminohexanoic acid
<220> FEATURE:
<221> NAME/KEY: MOD_RES
```

```
<222> LOCATION: 5, 18, 22
<223> OTHER INFORMATION: Xaa = beta-alanine
<220> FEATURE:
<221> NAME/KEY: MOD_RES
<222> LOCATION: (32)...(32)
<223> OTHER INFORMATION: Xaa = glycine or proline

<400> SEQUENCE: 255

Arg Xaa Arg Arg Xaa Arg Arg Xaa Arg Ile Leu Phe Gln Tyr Arg Xaa
1               5                   10                  15
Arg Xaa Arg Xaa Arg Xaa Ala Ser Ser Leu Asn Ile Ala Xaa Cys Xaa
            20                  25                  30

<210> SEQ ID NO 256
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 20, 24
<223> OTHER INFORMATION: Xaa = beta-alanine
<220> FEATURE:
<221> NAME/KEY: MOD_RES
<222> LOCATION: 2, 8, 18, 22
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 256

Arg Xaa Arg Arg Xaa Arg Arg Xaa Arg Ala Ser Ser Leu Asn Ile Ala
1               5                   10                  15
Arg Xaa Arg Xaa Arg Xaa Arg Xaa Cys Xaa
            20                  25

<210> SEQ ID NO 257
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 13
<223> OTHER INFORMATION: Xaa = 6-aminohexanoic acid
<220> FEATURE:
<221> NAME/KEY: MOD_RES
<222> LOCATION: 5, 11, 14
<223> OTHER INFORMATION: Xaa = beta-alanine
<220> FEATURE:
<221> NAME/KEY: MOD_RES
<222> LOCATION: (22)...(22)
<223> OTHER INFORMATION: Xaa = glycine or proline

<400> SEQUENCE: 257

Arg Xaa Arg Arg Xaa Arg Arg Xaa Arg Arg Xaa Arg Xaa Xaa Ala Ser
1               5                   10                  15
Ser Leu Asn Ile Ala Xaa
            20

<210> SEQ ID NO 258
<211> LENGTH: 13
<212> TYPE: PRT
<213> ORGANISM: Artificial Sequence
<220> FEATURE:
<223> OTHER INFORMATION: cell penetrating peptide
<220> FEATURE:
```

-continued

```
<221> NAME/KEY: MOD_RES
<222> LOCATION: (13)...(13)
<223> OTHER INFORMATION: Xaa = glycine or proline

<400> SEQUENCE: 258

Thr His Arg Pro Pro Met Trp Ser Pro Val Trp Pro Xaa
1               5                   10

<210> SEQ ID NO 259
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (12)...(12)
<223> OTHER INFORMATION: Xaa = glycine or proline

<400> SEQUENCE: 259

His Arg Pro Pro Met Trp Ser Pro Val Trp Pro Xaa
1               5                   10

<210> SEQ ID NO 260
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 260

Thr His Arg Pro Pro Met Trp Ser Pro Val Xaa
1               5                   10

<210> SEQ ID NO 261
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 261

Thr His Arg Pro Pro Met Trp Ser Pro Xaa
1               5                   10

<210> SEQ ID NO 262
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 262

Thr His Arg Pro Pro Met Trp Ser Pro Val Phe Pro Xaa
1               5                   10

<210> SEQ ID NO 263
```

```
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 263

Thr His Arg Pro Pro Met Trp Ser Pro Val Tyr Pro Xaa
 1               5                  10

<210> SEQ ID NO 264
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 264

Thr His Arg Pro Pro Met Trp Ser Pro Ala Trp Pro Xaa
 1               5                  10

<210> SEQ ID NO 265
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 265

Thr His Arg Pro Pro Met Trp Ser Pro Leu Trp Pro Xaa
 1               5                  10

<210> SEQ ID NO 266
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 266

Thr His Arg Pro Pro Met Trp Ser Pro Ile Trp Pro Xaa
 1               5                  10

<210> SEQ ID NO 267
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (14)...(14)
<223> OTHER INFORMATION: Xaa = glycine or proline

<400> SEQUENCE: 267
```

Thr His Arg Pro Pro Met Trp Thr Pro Val Val Trp Pro Xaa
1               5                   10

<210> SEQ ID NO 268
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 268

Thr His Arg Pro Pro Met Phe Ser Pro Val Trp Pro Xaa
1               5                   10

<210> SEQ ID NO 269
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)...(9)
<223> OTHER INFORMATION: Xaa = glycine or proline

<400> SEQUENCE: 269

Thr His Arg Pro Pro Met Trp Ser Xaa
1               5

<210> SEQ ID NO 270
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 270

His Arg Pro Pro Met Trp Ser Pro Val Trp Xaa
1               5                   10

<210> SEQ ID NO 271
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 271

Thr His Arg Pro Pro Met Tyr Ser Pro Val Trp Pro Xaa
1               5                   10

<210> SEQ ID NO 272
<211> LENGTH: 13
<212> TYPE: PRT
<213> ORGANISM: Artificial Sequence
<220> FEATURE:
<223> OTHER INFORMATION: cell penetrating peptide

```
<220> FEATURE:
<221> NAME/KEY: MOD_RES
<222> LOCATION: (13)...(13)
<223> OTHER INFORMATION: Xaa = glycine or proline
<220> FEATURE:
<221> NAME/KEY: MOD_RES
<222> LOCATION: (6)...(6)
<223> OTHER INFORMATION: Xaa = norleucine

<400> SEQUENCE: 272

Thr His Arg Pro Pro Xaa Trp Ser Pro Val Trp Pro Xaa
 1               5                  10

<210> SEQ ID NO 273
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 273

Thr His Lys Pro Pro Met Trp Ser Pro Val Trp Pro Xaa
 1               5                  10

<210> SEQ ID NO 274
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
<223> OTHER INFORMATION: Xaa = glycine or proline

<400> SEQUENCE: 274

Ser His Arg Pro Pro Met Trp Ser Pro Val Trp Pro Xaa
 1               5                  10

<210> SEQ ID NO 275
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 275

Ser Thr Phe Thr His Pro Arg Xaa
 1               5

<210> SEQ ID NO 276
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 276
```

Tyr Asp Ile Asp Asn Arg Arg Xaa
1               5

<210> SEQ ID NO 277
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 277

Ala Tyr Lys Pro Val Gly Arg Xaa
1               5

<210> SEQ ID NO 278
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 278

His Ala Ile Tyr Pro Arg His Xaa
1               5

<210> SEQ ID NO 279
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 279

His Thr Pro Asn Ser Thr His Xaa
1               5

<210> SEQ ID NO 280
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 280

Ala Ser Ser Pro Val His Arg Xaa
1               5

<210> SEQ ID NO 281
<211> LENGTH: 8
<212> TYPE: PRT
<213> ORGANISM: Artificial Sequence
<220> FEATURE:
<223> OTHER INFORMATION: cell penetrating peptide
<220> FEATURE:

```
<221> NAME/KEY: MOD_RES
<222> LOCATION: (8)...(8)
<223> OTHER INFORMATION: Xaa = glycine or proline

<400> SEQUENCE: 281

Ser Ser Leu Pro Leu Arg Lys Xaa
1               5

<210> SEQ ID NO 282
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = glycine or proline

<400> SEQUENCE: 282

Lys Lys Arg Ser Xaa
1               5

<210> SEQ ID NO 283
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = glycine or proline

<400> SEQUENCE: 283

Lys Arg Ser Lys Xaa
1               5

<210> SEQ ID NO 284
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)...(6)
<223> OTHER INFORMATION: Xaa = glycine or proline

<400> SEQUENCE: 284

Lys Lys Arg Ser Lys Xaa
1               5

<210> SEQ ID NO 285
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = glycine or proline

<400> SEQUENCE: 285

Lys Ser Arg Lys Xaa
1               5

<210> SEQ ID NO 286
```

```
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = glycine or proline

<400> SEQUENCE: 286

Ser Arg Lys Arg Xaa
1               5

<210> SEQ ID NO 287
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = glycine or proline

<400> SEQUENCE: 287

Arg Lys Arg Lys Xaa
1               5

<210> SEQ ID NO 288
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)...(6)
<223> OTHER INFORMATION: Xaa = glycine or proline

<400> SEQUENCE: 288

Lys Ser Arg Lys Arg Xaa
1               5

<210> SEQ ID NO 289
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 289

Gln His Pro Pro Trp Arg Val Xaa
1               5

<210> SEQ ID NO 290
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 290
```

```
Thr His Pro Pro Thr Thr His Xaa
1               5

<210> SEQ ID NO 291
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 291

Tyr Lys His Thr Pro Thr Thr Xaa
1               5

<210> SEQ ID NO 292
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 292

Gln Gly Met His Arg Gly Thr Xaa
1               5

<210> SEQ ID NO 293
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)...(6)
<223> OTHER INFORMATION: Xaa = glycine or proline

<400> SEQUENCE: 293

Ser Arg Lys Arg Lys Xaa
1               5

<210> SEQ ID NO 294
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)...(7)
<223> OTHER INFORMATION: Xaa = glycine or proline

<400> SEQUENCE: 294

Lys Ser Arg Lys Arg Lys Xaa
1               5

<210> SEQ ID NO 295
<211> LENGTH: 8
<212> TYPE: PRT
<213> ORGANISM: Artificial Sequence
<220> FEATURE:
<223> OTHER INFORMATION: cell penetrating peptide
```

```
<220> FEATURE:
<221> NAME/KEY: MOD_RES
<222> LOCATION: (8)...(8)
<223> OTHER INFORMATION: Xaa = glycine or proline

<400> SEQUENCE: 295

Pro Lys Lys Lys Arg Lys Val Xaa
1               5

<210> SEQ ID NO 296
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 296

Gly Lys Lys Arg Ser Lys Val Xaa
1               5

<210> SEQ ID NO 297
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 297

Lys Ser Arg Lys Arg Lys Leu Xaa
1               5

<210> SEQ ID NO 298
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 298

His Ser Pro Ser Lys Ile Pro Xaa
1               5

<210> SEQ ID NO 299
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 299

His Met Ala Thr Phe His Tyr Xaa
1               5
```

```
<210> SEQ ID NO 300
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 300

Ala Gln Pro Asn Lys Phe Lys Xaa
1               5

<210> SEQ ID NO 301
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 301

Asn Leu Thr Arg Leu His Thr Xaa
1               5

<210> SEQ ID NO 302
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = glycine or proline

<400> SEQUENCE: 302

Lys Lys Lys Arg Xaa
1               5

<210> SEQ ID NO 303
<211> LENGTH: 5
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = glycine or proline

<400> SEQUENCE: 303

Lys Lys Arg Lys Xaa
1               5

<210> SEQ ID NO 304
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (6)...(6)
<223> OTHER INFORMATION: Xaa = glycine or proline
```

```
<400> SEQUENCE: 304

Lys Lys Lys Arg Lys Xaa
1               5

<210> SEQ ID NO 305
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (25)...(25)
<223> OTHER INFORMATION: Xaa = glycine or proline

<400> SEQUENCE: 305

Arg Arg Arg Arg Arg Arg Gln Ile Lys Ile Trp Phe Gln Asn Arg Arg
1               5                   10                  15

Met Lys Trp Lys Lys Gly Gly Cys Xaa
            20                  25

<210> SEQ ID NO 306
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (26)...(26)
<223> OTHER INFORMATION: Xaa = glycine or proline

<400> SEQUENCE: 306

Arg Arg Arg Arg Arg Arg Arg Gln Ile Lys Ile Trp Phe Gln Asn Arg
1               5                   10                  15

Arg Met Lys Trp Lys Lys Gly Gly Cys Xaa
            20                  25

<210> SEQ ID NO 307
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (20)...(20)
<223> OTHER INFORMATION: Xaa = glycine or proline

<400> SEQUENCE: 307

Arg Gln Ile Lys Ile Trp Phe Gln Asn Arg Arg Met Lys Trp Lys Lys
1               5                   10                  15

Gly Gly Cys Xaa
            20

<210> SEQ ID NO 308
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (24)...(24)
<223> OTHER INFORMATION: Xaa = glycine or proline

<400> SEQUENCE: 308
```

```
Arg Arg Arg Arg Arg Arg Arg Gln Ile Lys Ile Trp Phe Gln Asn Arg
1               5                   10                  15

Arg Met Lys Trp Lys Lys Cys Xaa
                20
```

<210> SEQ ID NO 309
<211> LENGTH: 29
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (29)...(29)
<223> OTHER INFORMATION: Xaa = glycine or proline

<400> SEQUENCE: 309

```
Arg Xaa Arg Arg Xaa Arg Arg Xaa Arg Arg Gln Ile Lys Ile Trp Phe
1               5                   10                  15

Gln Asn Arg Arg Met Lys Trp Lys Lys Gly Gly Cys Xaa
                20                  25
```

<210> SEQ ID NO 310
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 17, 19, 21, 23
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 310

```
Arg Arg Arg Arg Arg Arg Arg Gln Ile Lys Ile Leu Phe Gln Asn Arg
1               5                   10                  15

Xaa Arg Xaa Arg Xaa Arg Xaa Cys Xaa
                20                  25
```

<210> SEQ ID NO 311
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11
<223> OTHER INFORMATION: Xaa = 6-aminohexanoic acid
<220> FEATURE:
<221> NAME/KEY: MOD_RES
<222> LOCATION: (14)...(14)
<223> OTHER INFORMATION: Xaa = glycine or proline

<400> SEQUENCE: 311

```
Arg Xaa Arg Arg Xaa Arg Arg Xaa Arg Arg Xaa Arg Cys Xaa
1               5                   10
```

<210> SEQ ID NO 312
<211> LENGTH: 15
<212> TYPE: PRT

<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 13
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 312

Arg Xaa Arg Arg Xaa Arg Arg Xaa Arg Xaa Arg Xaa Cys Xaa
1               5                   10                  15

<210> SEQ ID NO 313
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8,
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 313

Arg Xaa Arg Arg Xaa Arg Arg Xaa Arg Ile Lys Ile Leu Phe Gln Asn
1               5                   10                  15

Arg Arg Met Lys Trp Lys Lys Gly Gly Cys Xaa
            20                  25

<210> SEQ ID NO 314
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 314

Arg Xaa Arg Arg Xaa Arg Arg Xaa Arg Ile Lys Ile Leu Phe Gln Asn
1               5                   10                  15

Arg Arg Met Lys Trp Lys Lys Cys Xaa
            20                  25

<210> SEQ ID NO 315
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (24)...(24)

```
<223> OTHER INFORMATION: Xaa = glycine or proline

<400> SEQUENCE: 315

Arg Xaa Arg Arg Xaa Arg Arg Xaa Arg Ile Lys Ile Leu Phe Gln Asn
1               5                   10                  15

Arg Met Lys Trp Lys Lys Cys Xaa
            20

<210> SEQ ID NO 316
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 316

Arg Xaa Arg Arg Xaa Arg Arg Xaa Arg Ile Lys Ile Leu Phe Gln Asn
1               5                   10                  15

Xaa Arg Met Lys Trp Lys Lys Cys Xaa
            20                  25

<210> SEQ ID NO 317
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 317

Arg Xaa Arg Arg Xaa Arg Arg Xaa Arg Ile Lys Ile Leu Phe Gln Asn
1               5                   10                  15

His Arg Met Lys Trp Lys Lys Cys Xaa
            20                  25

<210> SEQ ID NO 318
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 318

Arg Xaa Arg Arg Xaa Arg Arg Xaa Arg Ile Lys Ile Leu Phe Gln Asn
1               5                   10                  15
```

Xaa Arg Met Lys Trp Lys Lys Cys Xaa
            20                  25

<210> SEQ ID NO 319
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 319

Arg Xaa Arg Arg Xaa Arg Arg Xaa Arg Ile Lys Ile Leu Phe Gln Asn
1               5                   10                  15

Xaa Arg Met Lys Trp Lys Lys Cys Xaa
            20                  25

<210> SEQ ID NO 320
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 320

Arg Xaa Arg Arg Xaa Arg Arg Xaa Arg Ile Lys Ile Leu Phe Gln Asn
1               5                   10                  15

Xaa Arg Met Lys Trp Lys Ala Cys Xaa
            20                  25

<210> SEQ ID NO 321
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 321

Arg Xaa Arg Arg Xaa Arg Arg Xaa Arg Ile Lys Ile Leu Phe Gln Asn
1               5                   10                  15

Xaa Arg Met Lys Trp His Lys Ala Cys Xaa
            20                  25

<210> SEQ ID NO 322
<211> LENGTH: 25
<212> TYPE: PRT

```
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 322

Arg Xaa Arg Arg Xaa Arg Arg Xaa Arg Ile Lys Ile Leu Phe Gln Asn
1               5                   10                  15

Xaa Arg Met Lys Trp His Arg Cys Xaa
            20                  25

<210> SEQ ID NO 323
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6, 8
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 323

Arg Xaa Arg Xaa Arg Xaa Arg Xaa Arg Ile Lys Ile Leu Phe Gln Asn
1               5                   10                  15

Arg Arg Met Lys Trp Lys Lys Cys Xaa
            20                  25

<210> SEQ ID NO 324
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (25)...(25)
<223> OTHER INFORMATION: Xaa = glycine or proline

<400> SEQUENCE: 324

Arg Ala Arg Ala Arg Ala Arg Ala Arg Ile Lys Ile Leu Phe Gln Asn
1               5                   10                  15

Arg Arg Met Lys Trp Lys Lys Cys Xaa
            20                  25

<210> SEQ ID NO 325
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline
```

<400> SEQUENCE: 325

Arg Xaa Arg Arg Xaa Arg Arg Xaa Arg Ile Xaa Ile Leu Phe Gln Asn
1               5                   10                  15

Xaa Arg Met Lys Trp His Lys Ala Cys Xaa
            20                  25

<210> SEQ ID NO 326
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 326

Arg Xaa Arg Arg Xaa Arg Arg Xaa Arg Ile His Ile Leu Phe Gln Asn
1               5                   10                  15

Xaa Arg Met Lys Trp His Lys Ala Cys Xaa
            20                  25

<210> SEQ ID NO 327
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 327

Arg Xaa Arg Arg Xaa Arg Arg Xaa Arg Ile Arg Ile Leu Phe Gln Asn
1               5                   10                  15

Xaa Arg Met Lys Trp His Lys Ala Cys Xaa
            20                  25

<210> SEQ ID NO 328
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 328

Arg Xaa Arg Arg Xaa Arg Arg Xaa Arg Ile Xaa Ile Leu Phe Gln Tyr
1               5                   10                  15

Xaa Arg Met Lys Trp His Lys Ala Cys Xaa

```
            20                  25

<210> SEQ ID NO 329
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 18
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 329

Arg Xaa Arg Arg Xaa Arg Arg Xaa Arg Leu Tyr Ser Pro Leu Ser Phe
1               5                   10                  15

Gln Xaa Arg Met Lys Trp His Lys Ala Cys Xaa
            20                  25

<210> SEQ ID NO 330
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 330

Arg Xaa Arg Arg Xaa Arg Arg Xaa Arg Ile Ser Ile Leu Phe Gln Tyr
1               5                   10                  15

Xaa Arg Met Lys Trp His Lys Ala Cys Xaa
            20                  25

<210> SEQ ID NO 331
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 331

Arg Xaa Arg Arg Xaa Arg Arg Xaa Arg Ile Leu Phe Gln Tyr Xaa Arg
1               5                   10                  15

Met Lys Trp His Lys Ala Cys Xaa
            20

<210> SEQ ID NO 332
<211> LENGTH: 23
<212> TYPE: PRT
<213> ORGANISM: Artificial Sequence
```

```
<220> FEATURE:
<223> OTHER INFORMATION: cell penetrating peptide
<220> FEATURE:
<221> NAME/KEY: MOD_RES
<222> LOCATION: 2, 5, 8, 14
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 332

Arg Xaa Arg Arg Xaa Arg Ile Xaa Ile Leu Phe Gln Tyr Xaa Arg Met
1               5                   10                  15

Lys Trp His Lys Ala Cys Xaa
            20

<210> SEQ ID NO 333
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 333

Arg Xaa Arg Arg Ala Arg Arg Xaa Arg Ile His Ile Leu Phe Gln Tyr
1               5                   10                  15

Xaa Arg Met Lys Trp His Lys Ala Cys Xaa
            20                  25

<210> SEQ ID NO 334
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 334

Arg Ala Arg Arg Xaa Arg Arg Ala Arg Ile His Ile Leu Phe Gln Tyr
1               5                   10                  15

Xaa Arg Met Lys Trp His Lys Ala Cys Xaa
            20                  25

<210> SEQ ID NO 335
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
```

```
<221> NAME/KEY: MOD_RES
<222> LOCATION: (26)...(26)
<223> OTHER INFORMATION: Xaa = glycine or proline

<400> SEQUENCE: 335

Arg Xaa Arg Arg Xaa Arg Arg Xaa Arg Ile His Ile Leu Phe Gln Tyr
1               5                   10                  15

Xaa Arg Met Lys Trp His Lys Ala Cys Xaa
            20                  25

<210> SEQ ID NO 336
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 336

Arg Xaa Arg Arg Xaa Arg Arg Xaa Arg Ile Xaa Ile Leu Phe Gln Asn
1               5                   10                  15

Xaa Arg Met Lys Trp His Lys Ala Cys Xaa
            20                  25

<210> SEQ ID NO 337
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 337

Arg Xaa Arg Arg Xaa Arg Arg Xaa Arg Ile His Ile Leu Phe Gln Asn
1               5                   10                  15

Xaa Arg Met Lys Trp His Lys Ala Cys Xaa
            20                  25

<210> SEQ ID NO 338
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8,
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 338

Arg Xaa Arg Arg Xaa Arg Arg Xaa Arg Ile Lys Ile Leu Phe Gln Asn
```

```
                1               5                  10                 15
Arg Arg Met Lys Trp His Lys Xaa
                20

<210> SEQ ID NO 339
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 339

Arg Xaa Arg Arg Xaa Arg Arg Xaa Arg Ile Lys Ile Leu Phe Gln Asn
1               5                  10                 15

Xaa Arg Met Lys Trp His Lys Xaa
                20

<210> SEQ ID NO 340
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 340

Arg Xaa Arg Arg Xaa Arg Arg Xaa Arg Ile Xaa Ile Leu Phe Gln Asn
1               5                  10                 15

Arg Arg Met Lys Trp His Lys Xaa
                20

<210> SEQ ID NO 341
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 341

Arg Xaa Arg Arg Xaa Arg Arg Xaa Arg Ile Xaa Ile Leu Phe Gln Asn
1               5                  10                 15

Xaa Arg Met Lys Trp His Lys Xaa
                20

<210> SEQ ID NO 342
```

```
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 342

Arg Xaa Arg Arg Xaa Arg Arg Xaa Arg Ile His Ile Leu Phe Gln Asn
1               5                   10                  15

Arg Arg Met Lys Trp His Lys Xaa
            20

<210> SEQ ID NO 343
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 343

Arg Xaa Arg Arg Xaa Arg Arg Xaa Arg Ile His Ile Leu Phe Gln Asn
1               5                   10                  15

Xaa Arg Met Lys Trp His Lys Xaa
            20

<210> SEQ ID NO 344
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 344

Arg Xaa Arg Arg Xaa Arg Arg Xaa Arg Ile Arg Ile Leu Phe Gln Asn
1               5                   10                  15

Arg Arg Met Lys Trp His Lys Xaa
            20

<210> SEQ ID NO 345
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

```
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 345

Arg Xaa Arg Arg Xaa Arg Arg Xaa Arg Ile Arg Ile Leu Phe Gln Asn
1               5                   10                  15

Xaa Arg Met Lys Trp His Lys Xaa
            20

<210> SEQ ID NO 346
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 346

Arg Xaa Arg Arg Xaa Arg Arg Xaa Arg Ile Ile Leu Phe Gln Asn Arg
1               5                   10                  15

Arg Met Lys Trp His Lys Xaa
            20

<210> SEQ ID NO 347
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 347

Arg Xaa Arg Arg Xaa Arg Arg Xaa Arg Ile Ile Leu Phe Gln Asn Xaa
1               5                   10                  15

Arg Met Lys Trp His Lys Xaa
            20

<210> SEQ ID NO 348
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline
```

-continued

```
<400> SEQUENCE: 348

Arg Xaa Arg Arg Xaa Arg Arg Xaa Arg Lys Ile Leu Phe Gln Asn Arg
1               5                   10                  15

Arg Met Lys Trp His Lys Xaa
            20

<210> SEQ ID NO 349
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 349

Arg Xaa Arg Arg Xaa Arg Arg Xaa Arg Lys Ile Leu Phe Gln Asn Xaa
1               5                   10                  15

Arg Met Lys Trp His Lys Xaa
            20

<210> SEQ ID NO 350
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 10
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 350

Arg Xaa Arg Arg Xaa Arg Arg Xaa Arg Xaa Ile Leu Phe Gln Asn Arg
1               5                   10                  15

Arg Met Lys Trp His Lys Xaa
            20

<210> SEQ ID NO 351
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 10, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 351

Arg Xaa Arg Arg Xaa Arg Arg Xaa Arg Xaa Ile Leu Phe Gln Asn Xaa
1               5                   10                  15

Arg Met Lys Trp His Lys Xaa
            20
```

```
<210> SEQ ID NO 352
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 352

Arg Xaa Arg Arg Xaa Arg Arg Xaa Arg His Ile Leu Phe Gln Asn Arg
1               5                   10                  15

Arg Met Lys Trp His Lys Xaa
            20

<210> SEQ ID NO 353
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 353

Arg Xaa Arg Arg Xaa Arg Arg Xaa Arg His Ile Leu Phe Gln Asn Xaa
1               5                   10                  15

Arg Met Lys Trp His Lys Xaa
            20

<210> SEQ ID NO 354
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 354

Arg Xaa Arg Arg Xaa Arg Arg Xaa Arg Ile Leu Phe Gln Asn Arg
1               5                   10                  15

Arg Met Lys Trp His Lys Xaa
            20

<210> SEQ ID NO 355
<211> LENGTH: 23
<212> TYPE: PRT
<213> ORGANISM: Artificial Sequence
<220> FEATURE:
```

```
<223> OTHER INFORMATION: cell penetrating peptide
<220> FEATURE:
<221> NAME/KEY: MOD_RES
<222> LOCATION: 2, 5, 8, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 355

Arg Xaa Arg Arg Xaa Arg Arg Xaa Arg Arg Ile Leu Phe Gln Asn Xaa
1               5                   10                  15

Arg Met Lys Trp His Lys Xaa
            20

<210> SEQ ID NO 356
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 356

Arg Xaa Arg Arg Xaa Arg Arg Xaa Arg Ile Leu Phe Gln Asn Arg Arg
1               5                   10                  15

Met Lys Trp His Lys Xaa
            20

<210> SEQ ID NO 357
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 357

Arg Xaa Arg Arg Xaa Arg Arg Xaa Arg Ile Leu Phe Gln Asn Xaa Arg
1               5                   10                  15

Met Lys Trp His Lys Xaa
            20

<210> SEQ ID NO 358
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
```

```
<222> LOCATION: (24)...(24)
<223> OTHER INFORMATION: Xaa = glycine or proline

<400> SEQUENCE: 358

Arg Xaa Arg Arg Xaa Arg Arg Xaa Arg Ile Lys Ile Leu Phe Gln Tyr
1               5                   10                  15

Arg Arg Met Lys Trp His Lys Xaa
            20

<210> SEQ ID NO 359
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 359

Arg Xaa Arg Arg Xaa Arg Arg Xaa Arg Ile Lys Ile Leu Phe Gln Tyr
1               5                   10                  15

Xaa Arg Met Lys Trp His Lys Xaa
            20

<210> SEQ ID NO 360
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 360

Arg Xaa Arg Arg Xaa Arg Arg Xaa Arg Ile Xaa Ile Leu Phe Gln Tyr
1               5                   10                  15

Arg Arg Met Lys Trp His Lys Xaa
            20

<210> SEQ ID NO 361
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 361

Arg Xaa Arg Arg Xaa Arg Arg Xaa Arg Ile Xaa Ile Leu Phe Gln Tyr
1               5                   10                  15
```

Xaa Arg Met Lys Trp His Lys Xaa
            20

<210> SEQ ID NO 362
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 362

Arg Xaa Arg Arg Xaa Arg Arg Xaa Arg Ile His Ile Leu Phe Gln Tyr
1               5                   10                  15

Arg Arg Met Lys Trp His Lys Xaa
            20

<210> SEQ ID NO 363
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 363

Arg Xaa Arg Arg Xaa Arg Arg Xaa Arg Ile His Ile Leu Phe Gln Tyr
1               5                   10                  15

Xaa Arg Met Lys Trp His Lys Xaa
            20

<210> SEQ ID NO 364
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 364

Arg Xaa Arg Arg Xaa Arg Arg Xaa Arg Ile Arg Ile Leu Phe Gln Tyr
1               5                   10                  15

Arg Arg Met Lys Trp His Lys Xaa
            20

<210> SEQ ID NO 365
<211> LENGTH: 24

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 365

Arg Xaa Arg Arg Xaa Arg Arg Xaa Arg Ile Arg Ile Leu Phe Gln Tyr
1               5                   10                  15

Xaa Arg Met Lys Trp His Lys Xaa
            20

<210> SEQ ID NO 366
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa - glycine or proline

<400> SEQUENCE: 366

Arg Xaa Arg Arg Xaa Arg Arg Xaa Arg Ile Ile Leu Phe Gln Tyr Arg
1               5                   10                  15

Arg Met Lys Trp His Lys Xaa
            20

<210> SEQ ID NO 367
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 367

Arg Xaa Arg Arg Xaa Arg Arg Xaa Arg Ile Ile Leu Phe Gln Tyr Xaa
1               5                   10                  15

Arg Met Lys Trp His Lys Xaa
            20

<210> SEQ ID NO 368
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
```

-continued

<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 368

Arg Xaa Arg Arg Xaa Arg Arg Xaa Arg Lys Ile Leu Phe Gln Tyr Arg
1               5                   10                  15

Arg Met Lys Trp His Lys Xaa
            20

<210> SEQ ID NO 369
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 369

Arg Xaa Arg Arg Xaa Arg Arg Xaa Arg Lys Ile Leu Phe Gln Tyr Xaa
1               5                   10                  15

Arg Met Lys Trp His Lys Xaa
            20

<210> SEQ ID NO 370
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 10
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 370

Arg Xaa Arg Arg Xaa Arg Arg Xaa Arg Xaa Ile Leu Phe Gln Tyr Arg
1               5                   10                  15

Arg Met Lys Trp His Lys Xaa
            20

<210> SEQ ID NO 371
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8,10, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 371

```
Arg Xaa Arg Arg Xaa Arg Arg Xaa Arg Xaa Ile Leu Phe Gln Tyr Xaa
1               5                   10                  15

Arg Met Lys Trp His Lys Xaa
            20
```

<210> SEQ ID NO 372
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 372

```
Arg Xaa Arg Arg Xaa Arg Arg Xaa Arg His Ile Leu Phe Gln Tyr Arg
1               5                   10                  15

Arg Met Lys Trp His Lys Xaa
            20
```

<210> SEQ ID NO 373
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 373

```
Arg Xaa Arg Arg Xaa Arg Arg Xaa Arg His Ile Leu Phe Gln Tyr Xaa
1               5                   10                  15

Arg Met Lys Trp His Lys Xaa
            20
```

<210> SEQ ID NO 374
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 374

```
Arg Xaa Arg Arg Xaa Arg Arg Xaa Arg Ile Leu Phe Gln Tyr Arg
1               5                   10                  15

Arg Met Lys Trp His Lys Xaa
            20
```

<210> SEQ ID NO 375
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 16
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 375

Arg Xaa Arg Arg Xaa Arg Arg Xaa Arg Arg Ile Leu Phe Gln Tyr Xaa
1               5                   10                  15

Arg Met Lys Trp His Lys Xaa
            20

<210> SEQ ID NO 376
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 376

Arg Xaa Arg Arg Xaa Arg Arg Xaa Arg Ile Leu Phe Gln Tyr Arg Arg
1               5                   10                  15

Met Lys Trp His Lys Xaa
            20

<210> SEQ ID NO 377
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 377

Arg Xaa Arg Arg Xaa Arg Arg Xaa Arg Ile Leu Phe Gln Tyr Xaa Arg
1               5                   10                  15

Met Lys Trp His Lys Xaa
            20

<210> SEQ ID NO 378
<211> LENGTH: 10
<212> TYPE: PRT
<213> ORGANISM: Artificial Sequence
<220> FEATURE:
<223> OTHER INFORMATION: cell penetrating peptide

```
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = glycine or proline

<400> SEQUENCE: 378

Arg Xaa Arg Arg Xaa Arg Arg Xaa Arg Xaa
1               5                   10

<210> SEQ ID NO 379
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8,11
<223> OTHER INFORMATION: Xaa = 6-aminohexanoic acid
<220> FEATURE:
<221> NAME/KEY: MOD_RES
<222> LOCATION: (13)...(13)
<223> OTHER INFORMATION: Xaa = glycine or proline

<400> SEQUENCE: 379

Arg Xaa Arg Arg Xaa Arg Arg Xaa Arg Arg Xaa Arg Xaa
1               5                   10

<210> SEQ ID NO 380
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)...(7)
<223> OTHER INFORMATION: Xaa = glycine or proline

<400> SEQUENCE: 380

Arg Ala Arg Arg Ala Arg Xaa
1               5

<210> SEQ ID NO 381
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 381

Arg Ala Arg Arg Ala Arg Arg Ala Arg Xaa
1               5                   10

<210> SEQ ID NO 382
<211> LENGTH: 13
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (13)...(13)
```

<223> OTHER INFORMATION: Xaa = glycine or proline

<400> SEQUENCE: 382

Arg Ala Arg Arg Ala Arg Arg Ala Arg Arg Ala Arg Xaa
1               5                   10

<210> SEQ ID NO 383
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (9)...(9)
<223> OTHER INFORMATION: Xaa = glycine or proline

<400> SEQUENCE: 383

Arg Xaa Arg Arg Xaa Arg Ile Xaa Xaa
1               5

<210> SEQ ID NO 384
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = glycine or proline

<400> SEQUENCE: 384

Arg Xaa Arg Arg Ala Arg Arg Xaa Arg Xaa
1               5                   10

<210> SEQ ID NO 385
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (5)...(5)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = glycine or proline

<400> SEQUENCE: 385

Arg Ala Arg Arg Xaa Arg Arg Ala Arg Xaa
1               5                   10

<210> SEQ ID NO 386
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES

```
<222> LOCATION: (6)...(6)
<223> OTHER INFORMATION: Xaa = glycine or proline

<400> SEQUENCE: 386

Arg Arg Arg Arg Arg Xaa
1               5

<210> SEQ ID NO 387
<211> LENGTH: 7
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (7)...(7)
<223> OTHER INFORMATION: Xaa = glycine or proline

<400> SEQUENCE: 387

Arg Arg Arg Arg Arg Arg Xaa
1               5

<210> SEQ ID NO 388
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 388

Arg Arg Arg Arg Arg Arg Arg Xaa
1               5

<210> SEQ ID NO 389
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11
<223> OTHER INFORMATION: Xaa = 6-aminohexanoic acid
<220> FEATURE:
<221> NAME/KEY: MOD_RES
<222> LOCATION: (14)...(14)
<223> OTHER INFORMATION: Xaa = glycine or proline

<400> SEQUENCE: 389

Arg Xaa Arg Arg Xaa Arg Arg Xaa Arg Arg Xaa Arg Cys Xaa
1               5                   10

<210> SEQ ID NO 390
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 13
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline
```

-continued

<400> SEQUENCE: 390

Arg Xaa Arg Arg Xaa Arg Arg Xaa Arg Xaa Arg Xaa Cys Xaa
1               5                   10                  15

<210> SEQ ID NO 391
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 391

Arg Xaa Arg Arg Xaa Arg Arg Xaa Arg Ile Lys Ile Leu Phe Gln Asn
1               5                   10                  15

Arg Arg Met Lys Trp Lys Lys Gly Gly Cys Xaa
            20                  25

<210> SEQ ID NO 392
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 392

Arg Xaa Arg Arg Xaa Arg Arg Xaa Arg Ile Lys Ile Leu Phe Gln Asn
1               5                   10                  15

Arg Arg Met Lys Trp Lys Lys Cys Xaa
            20                  25

<210> SEQ ID NO 393
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 393

Arg Xaa Arg Arg Xaa Arg Arg Xaa Arg Ile Lys Ile Leu Phe Gln Asn
1               5                   10                  15

Arg Met Lys Trp Lys Lys Cys Xaa
            20

<210> SEQ ID NO 394

<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 394

Arg Xaa Arg Arg Xaa Arg Arg Xaa Arg Ile Lys Ile Leu Phe Gln Asn
1               5                   10                  15

Xaa Arg Met Lys Trp Lys Lys Cys Xaa
            20                  25

<210> SEQ ID NO 395
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 395

Arg Xaa Arg Arg Xaa Arg Arg Xaa Arg Ile Lys Ile Leu Phe Gln Asn
1               5                   10                  15

His Arg Met Lys Trp Lys Lys Cys Xaa
            20                  25

<210> SEQ ID NO 396
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 396

Arg Xaa Arg Arg Xaa Arg Arg Xaa Arg Ile Lys Ile Leu Phe Gln Asn
1               5                   10                  15

Xaa Arg Met Lys Trp Lys Lys Cys Xaa
            20                  25

<210> SEQ ID NO 397
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES

```
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 397

Arg Xaa Arg Arg Xaa Arg Arg Xaa Arg Ile Lys Ile Leu Phe Gln Asn
1               5                   10                  15

Xaa Arg Met Lys Trp Lys Lys Cys Xaa
            20                  25

<210> SEQ ID NO 398
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 398

Arg Xaa Arg Arg Xaa Arg Arg Xaa Arg Ile Lys Ile Leu Phe Gln Asn
1               5                   10                  15

Xaa Arg Met Lys Trp Lys Ala Cys Xaa
            20                  25

<210> SEQ ID NO 399
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 399

Arg Xaa Arg Arg Xaa Arg Arg Xaa Arg Ile Lys Ile Leu Phe Gln Asn
1               5                   10                  15

Xaa Arg Met Lys Trp His Lys Ala Cys Xaa
            20                  25

<210> SEQ ID NO 400
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline
```

<400> SEQUENCE: 400

Arg Xaa Arg Arg Xaa Arg Arg Xaa Arg Ile Lys Ile Leu Phe Gln Asn
1               5                   10                  15

Xaa Arg Met Lys Trp His Arg Cys Xaa
            20                  25

<210> SEQ ID NO 401
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6, 8
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 401

Arg Xaa Arg Xaa Arg Xaa Arg Xaa Arg Ile Lys Ile Leu Phe Gln Asn
1               5                   10                  15

Arg Arg Met Lys Trp Lys Lys Cys Xaa
            20                  25

<210> SEQ ID NO 402
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (25)...(25)
<223> OTHER INFORMATION: Xaa = glycine or proline

<400> SEQUENCE: 402

Arg Ala Arg Ala Arg Ala Arg Ala Arg Ile Lys Ile Leu Phe Gln Asn
1               5                   10                  15

Arg Arg Met Lys Trp Lys Lys Cys Xaa
            20                  25

<210> SEQ ID NO 403
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 403

Arg Xaa Arg Arg Xaa Arg Arg Xaa Arg Ile Xaa Ile Leu Phe Gln Asn
1               5                   10                  15

Xaa Arg Met Lys Trp His Lys Ala Cys Xaa
            20                  25

<210> SEQ ID NO 404
<211> LENGTH: 26

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 404

Arg Xaa Arg Arg Xaa Arg Arg Xaa Arg Ile His Ile Leu Phe Gln Asn
1               5                   10                  15

Xaa Arg Met Lys Trp His Lys Ala Cys Xaa
            20                  25

<210> SEQ ID NO 405
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 405

Arg Xaa Arg Arg Xaa Arg Arg Xaa Arg Ile Arg Ile Leu Phe Gln Asn
1               5                   10                  15

Xaa Arg Met Lys Trp His Lys Ala Cys Xaa
            20                  25

<210> SEQ ID NO 406
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 406

Arg Xaa Arg Arg Xaa Arg Arg Xaa Arg Ile Xaa Ile Leu Phe Gln Tyr
1               5                   10                  15

Xaa Arg Met Lys Trp His Lys Ala Cys Xaa
            20                  25

<210> SEQ ID NO 407
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 18
```

<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 407

Arg Xaa Arg Arg Xaa Arg Arg Xaa Arg Leu Tyr Ser Pro Leu Ser Phe
1               5                  10                  15

Gln Xaa Arg Met Lys Trp His Lys Ala Cys Xaa
            20                  25

<210> SEQ ID NO 408
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 408

Arg Arg Met Lys Trp His Lys Xaa
1               5

<210> SEQ ID NO 409
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)...(1)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 409

Xaa Arg Met Lys Trp His Lys Xaa
1               5

<210> SEQ ID NO 410
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 410

Xaa Xaa Xaa Xaa Xaa Xaa Xaa Xaa Xaa Xaa Xaa Xaa Xaa Xaa Ile Leu
1               5                  10                  15

Phe Gln Xaa Xaa Arg Met Lys Trp His Lys Xaa
            20                  25

<210> SEQ ID NO 411
<211> LENGTH: 27

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 411

Xaa Xaa Xaa Xaa Xaa Xaa Xaa Xaa Xaa Xaa Xaa Xaa Xaa Xaa Ile Leu
1               5                   10                  15

Phe Gln Xaa Xaa Arg Met Lys Trp His Lys Xaa
            20                  25

<210> SEQ ID NO 412
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (26)...(26)
<223> OTHER INFORMATION: Xaa = glycine or proline

<400> SEQUENCE: 412

Arg Arg Arg Arg Arg Arg Arg Gln Ile Lys Ile Leu Phe Gln Asn Pro
1               5                   10                  15

Lys Lys Lys Arg Lys Val Gly Gly Cys Xaa
            20                  25

<210> SEQ ID NO 413
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (17)...(17)
<223> OTHER INFORMATION: Xaa = glycine or proline

<400> SEQUENCE: 413

His His Phe Phe Arg Arg Arg Arg Arg Arg Arg Arg Arg Phe Phe Cys
1               5                   10                  15

Xaa

<210> SEQ ID NO 414
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (19)...(19)
<223> OTHER INFORMATION: Xaa = glycine or proline

<400> SEQUENCE: 414

His His His His His His Arg Arg Arg Arg Arg Arg Arg Arg Phe
1               5                   10                  15

Phe Cys Xaa
```

```
<210> SEQ ID NO 415
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (21)...(21)
<223> OTHER INFORMATION: Xaa = glycine or proline

<400> SEQUENCE: 415

His His His His His His Phe Phe Arg Arg Arg Arg Arg Arg Arg
1               5                   10                  15

Arg Phe Phe Cys Xaa
            20

<210> SEQ ID NO 416
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (20)...(20)
<223> OTHER INFORMATION: Xaa = glycine or proline
<220> FEATURE:
<221> NAME/KEY: MOD_RES
<222> LOCATION: 6, 7
<223> OTHER INFORMATION: Xaa = 6-aminohexanoic acid

<400> SEQUENCE: 416

His His His His His Xaa Xaa Arg Arg Arg Arg Arg Arg Arg Arg
1               5                   10                  15

Phe Phe Cys Xaa
            20

<210> SEQ ID NO 417
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (23)...(23)
<223> OTHER INFORMATION: Xaa = glycine or proline
<220> FEATURE:
<221> NAME/KEY: MOD_RES
<222> LOCATION: 7, 8
<223> OTHER INFORMATION: Xaa = 6-aminohexanoic acid

<400> SEQUENCE: 417

His His His His His His Xaa Xaa Phe Phe Arg Arg Arg Arg Arg
1               5                   10                  15

Arg Arg Arg Phe Phe Cys Xaa
            20

<210> SEQ ID NO 418
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 4, 16
<223> OTHER INFORMATION: Xaa = 6-aminohexanoic acid
```

```
<220> FEATURE:
<221> NAME/KEY: MOD_RES
<222> LOCATION: (21)...(21)
<223> OTHER INFORMATION: Xaa = glycine or proline

<400> SEQUENCE: 418

His His His Xaa Arg Arg Arg Arg Arg Arg Arg Arg Phe Phe Xaa
1               5                   10                  15

His His His Cys Xaa
            20

<210> SEQ ID NO 419
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)...(1)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 419

Xaa Arg Met Lys Trp His Lys Xaa
1               5

<210> SEQ ID NO 420
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (1)...(1)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 420

Xaa Arg Trp Lys Trp His Lys Xaa
1               5

<210> SEQ ID NO 421
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 6
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 421

Arg Xaa Arg Ala Arg Xaa Arg Xaa
1               5

<210> SEQ ID NO 422
<211> LENGTH: 8
```

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 4, 6
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 422

Arg Xaa Arg Xaa Arg Xaa Arg Xaa
1               5

<210> SEQ ID NO 423
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (4)...(4)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = glycine or proline

<400> SEQUENCE: 423

Arg Ala Arg Xaa Arg Ala Arg Xaa
1               5

<210> SEQ ID NO 424
<211> LENGTH: 6
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (6)...(6)
<223> OTHER INFORMATION: Xaa = glycine or proline

<400> SEQUENCE: 424

Arg Xaa Arg Ala Arg Xaa
1               5

<210> SEQ ID NO 425
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 425

Xaa Xaa Xaa Xaa Xaa Xaa Xaa Xaa Xaa Xaa Xaa Xaa Xaa Xaa Ile Leu
```

```
1               5                   10                  15
Phe Gln Xaa Xaa His Met Lys Trp His Lys Xaa
            20                  25

<210> SEQ ID NO 426
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 426

Xaa Xaa Xaa Xaa Xaa Xaa Xaa Xaa Xaa Xaa Xaa Xaa Xaa Xaa Ile Leu
1               5                   10                  15

Phe Gln Xaa Xaa Arg Trp Lys Trp His Lys Xaa
            20                  25

<210> SEQ ID NO 427
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 427

Xaa Xaa Xaa Xaa Xaa Xaa Xaa Xaa Xaa Xaa Xaa Xaa Xaa Xaa Ile Leu
1               5                   10                  15

Phe Gln Xaa Xaa His Trp Lys Trp His Lys Xaa
            20                  25

<210> SEQ ID NO 428
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 428

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg Xaa
            20                  25

<210> SEQ ID NO 429
```

```
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 23, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 429

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Xaa Arg Xaa Arg Xaa
            20                  25

<210> SEQ ID NO 430
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 24
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 430

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Arg Xaa Arg Xaa
            20                  25

<210> SEQ ID NO 431
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 23
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 431

Xaa Xaa Xaa Xaa Xaa Xaa Xaa Xaa Xaa Xaa Xaa Xaa Xaa Xaa Ile Leu
1               5                   10                  15

Phe Gln Xaa Arg Ala Arg Xaa Arg Ala Arg Xaa
            20                  25

<210> SEQ ID NO 432
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

<222> LOCATION: 1-14, 19, 21, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 432

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg Xaa
            20                  25

<210> SEQ ID NO 433
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 433

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa
            20                  25

<210> SEQ ID NO 434
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 434

Xaa Xaa Xaa Xaa Xaa Xaa Xaa Xaa Xaa Xaa Xaa Xaa Xaa Xaa Ile Leu
1               5                   10                  15

Ile Gln Xaa Xaa Arg Met Lys Trp His Lys Xaa
            20                  25

<210> SEQ ID NO 435
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

```
<400> SEQUENCE: 435

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Met Lys Trp His Lys Xaa
            20                  25

<210> SEQ ID NO 436
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 436

Xaa Xaa Xaa Xaa Xaa Xaa Xaa Xaa Xaa Xaa Xaa Xaa Xaa Xaa Ile Leu
1               5                   10                  15

Ile Gln Xaa Xaa Arg Trp Lys Trp His Lys Xaa
            20                  25

<210> SEQ ID NO 437
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 437

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Trp Lys Trp His Lys Xaa
            20                  25

<210> SEQ ID NO 438
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19,21, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 438

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg Xaa
            20                  25
```

```
<210> SEQ ID NO 439
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 23, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 439

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Xaa Arg Xaa Arg Xaa
            20                  25

<210> SEQ ID NO 440
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 24
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 440

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Arg Xaa Arg Xaa
            20                  25

<210> SEQ ID NO 441
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 23
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 441

Xaa Xaa Xaa Xaa Xaa Xaa Xaa Xaa Xaa Xaa Xaa Xaa Xaa Xaa Ile Leu
1               5                   10                  15

Ile Gln Xaa Arg Ala Arg Xaa Arg Ala Arg Xaa
            20                  25

<210> SEQ ID NO 442
<211> LENGTH: 27
<212> TYPE: PRT
<213> ORGANISM: Artificial Sequence
<220> FEATURE:
```

<223> OTHER INFORMATION: cell penetrating peptide
<220> FEATURE:
<221> NAME/KEY: MOD_RES
<222> LOCATION: 1-14, 19, 21, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 442

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg Xaa
            20                  25

<210> SEQ ID NO 443
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 443

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa
            20                  25

<210> SEQ ID NO 444
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 444

Xaa Xaa Xaa Xaa Xaa Xaa Xaa Xaa Xaa Xaa Xaa Xaa Xaa Xaa Ile Leu
1               5                   10                  15

Phe Gln Xaa Xaa His Met Lys Trp His Lys Xaa
            20                  25

<210> SEQ ID NO 445
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 445

Xaa Xaa Xaa Xaa Xaa Xaa Xaa Xaa Xaa Xaa Xaa Xaa Xaa Xaa Ile Leu
1               5                   10                  15

Phe Gln Xaa Xaa Arg Trp Lys Trp His Lys Xaa
            20                  25

<210> SEQ ID NO 446
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 446

Xaa Xaa Xaa Xaa Xaa Xaa Xaa Xaa Xaa Xaa Xaa Xaa Xaa Xaa Ile Leu
1               5                   10                  15

Phe Gln Xaa Xaa His Trp Lys Trp His Lys Xaa
            20                  25

<210> SEQ ID NO 447
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 447

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg Xaa
            20                  25

<210> SEQ ID NO 448
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 23, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 448

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Xaa Arg Xaa Arg Xaa
            20                  25

<210> SEQ ID NO 449
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19,21, 24
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 449

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Arg Xaa Arg Xaa
            20                  25

<210> SEQ ID NO 450
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 23
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 450

Xaa Xaa Xaa Xaa Xaa Xaa Xaa Xaa Xaa Xaa Xaa Xaa Xaa Xaa Ile Leu
1               5                   10                  15

Phe Gln Xaa Arg Ala Arg Xaa Arg Ala Arg Xaa
            20                  25

<210> SEQ ID NO 451
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 451

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg Xaa
            20                  25

<210> SEQ ID NO 452
<211> LENGTH: 25

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 452

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa
            20                  25

<210> SEQ ID NO 453
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 453

Xaa Xaa Xaa Xaa Xaa Xaa Xaa Xaa Xaa Xaa Xaa Xaa Xaa Xaa Ile Leu
1               5                   10                  15

Ile Gln Xaa Xaa Arg Met Lys Trp His Lys Xaa
            20                  25

<210> SEQ ID NO 454
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 454

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Met Lys Trp His Lys Xaa
            20                  25

<210> SEQ ID NO 455
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
```

```
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 455

Xaa Xaa Xaa Xaa Xaa Xaa Xaa Xaa Xaa Xaa Xaa Xaa Xaa Xaa Ile Leu
1               5                   10                  15

Ile Gln Xaa Xaa Arg Trp Lys Trp His Lys Xaa
            20                  25

<210> SEQ ID NO 456
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19-20
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 456

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Trp Lys Trp His Lys Xaa
            20                  25

<210> SEQ ID NO 457
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 457

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg Xaa
            20                  25

<210> SEQ ID NO 458
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 23, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 458
```

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Xaa Arg Xaa Arg Xaa
            20                  25

<210> SEQ ID NO 459
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 24
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 459

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Arg Xaa Arg Xaa
            20                  25

<210> SEQ ID NO 460
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 23
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 460

Xaa Xaa Xaa Xaa Xaa Xaa Xaa Xaa Xaa Xaa Xaa Xaa Xaa Xaa Ile Leu
1               5                   10                  15

Ile Gln Xaa Arg Ala Arg Xaa Arg Ala Arg Xaa
            20                  25

<210> SEQ ID NO 461
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21, 25
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 461

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg Xaa
            20                  25

<210> SEQ ID NO 462
<211> LENGTH: 25
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 1-14, 19, 21
<223> OTHER INFORMATION: Xaa = 6-aminohexanoic acid
<220> FEATURE:
<221> NAME/KEY: MOD_RES
<222> LOCATION: (25)...(25)
<223> OTHER INFORMATION: Xaa = glycine or proline

<400> SEQUENCE: 462

Xaa Xaa Xaa Xaa Xaa Xaa Xaa Xaa Xaa Xaa Xaa Xaa Xaa Xaa Ile Leu
1               5                   10                  15
Ile Gln Xaa Arg Xaa Arg Ala Arg Xaa
            20                  25

<210> SEQ ID NO 463
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 13
<223> OTHER INFORMATION: Xaa = 6-aminohexanoic acid
<220> FEATURE:
<221> NAME/KEY: MOD_RES
<222> LOCATION: (15)...(15)
<223> OTHER INFORMATION: Xaa = glycine or proline

<400> SEQUENCE: 463

Arg Xaa Arg Arg Ala Arg Arg Xaa Arg Ala Arg Xaa Ala Xaa
1               5                   10                  15

<210> SEQ ID NO 464
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 464

Arg Xaa Arg Arg Ala Arg Arg Xaa Arg Ile Leu Phe Gln Tyr Xaa His
1               5                   10                  15
Met Lys Trp His Lys Ala Cys Xaa
            20

<210> SEQ ID NO 465
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15

```
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 465

Arg Xaa Arg Arg Ala Arg Arg Xaa Arg Ile Leu Phe Gln Tyr Xaa Arg
1               5                   10                  15

Met Lys Trp His Lys Ala Cys Xaa
            20

<210> SEQ ID NO 466
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 466

Arg Xaa Arg Arg Ala Arg Arg Xaa Arg Ile Leu Phe Gln Tyr Xaa Arg
1               5                   10                  15

Trp Lys Trp His Lys Ala Cys Xaa
            20

<210> SEQ ID NO 467
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11
<223> OTHER INFORMATION: Xaa = 6-aminohexanoic acid
<220> FEATURE:
<221> NAME/KEY: MOD_RES
<222> LOCATION: (14)...(14)
<223> OTHER INFORMATION: Xaa = glycine or proline

<400> SEQUENCE: 467

Arg Xaa Arg Arg Xaa Arg Arg Xaa Arg Arg Xaa Arg Cys Xaa
1               5                   10

<210> SEQ ID NO 468
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 468

Arg Xaa Arg Arg Xaa Arg Arg Xaa Arg Ile Xaa Ile Leu Phe Gln Asn
1               5                   10                  15
```

```
Xaa Arg Met Lys Trp His Lys Ala Cys Xaa
            20                  25

<210> SEQ ID NO 469
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 469

Arg Xaa Arg Arg Xaa Arg Arg Xaa Arg Ile His Ile Leu Phe Gln Asn
1               5                   10                  15

Xaa Arg Met Lys Trp His Lys Ala Cys Xaa
            20                  25

<210> SEQ ID NO 470
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 11, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 470

Arg Xaa Arg Arg Xaa Arg Arg Xaa Arg Ile Xaa Ile Leu Phe Gln Tyr
1               5                   10                  15

Xaa Arg Met Lys Trp His Lys Ala Cys Xaa
            20                  25

<210> SEQ ID NO 471
<211> LENGTH: 27
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 18
<223> OTHER INFORMATION: Xaa = 6-aminohexanoic acid
<220> FEATURE:
<221> NAME/KEY: MOD_RES
<222> LOCATION: (27)...(27)
<223> OTHER INFORMATION: Xaa = glycine or proline

<400> SEQUENCE: 471

Arg Xaa Arg Arg Xaa Arg Arg Xaa Arg Leu Tyr Ser Pro Leu Ser Phe
1               5                   10                  15

Gln Xaa Arg Met Lys Trp His Lys Ala Cys Xaa
                20                  25

<210> SEQ ID NO 472
<211> LENGTH: 24
```

```
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 472

Arg Xaa Arg Arg Xaa Arg Arg Xaa Arg Ile Leu Phe Gln Tyr Xaa Arg
1               5                  10                  15

Met Lys Trp His Lys Ala Cys Xaa
            20

<210> SEQ ID NO 473
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 8, 14
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 473

Arg Xaa Arg Arg Xaa Arg Ile Xaa Ile Leu Phe Gln Tyr Xaa Arg Met
1               5                  10                  15

Lys Trp His Lys Ala Cys Xaa
            20

<210> SEQ ID NO 474
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 474

Arg Ala Arg Arg Xaa Arg Arg Ala Arg Ile Leu Phe Gln Tyr Xaa Arg
1               5                  10                  15

Met Lys Trp His Lys Ala Cys Xaa
            20

<210> SEQ ID NO 475
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
```

```
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 475

Arg Xaa Arg Arg Ala Arg Arg Xaa Arg Ile Leu Phe Gln Tyr Xaa Arg
1               5                   10                  15

Met Lys Trp His Lys Ala Cys Xaa
            20

<210> SEQ ID NO 476
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 476

Arg Ala Arg Arg Xaa Arg Arg Ala Arg Ile Leu Phe Gln Tyr Xaa Arg
1               5                   10                  15

Met Lys Trp His Lys Ala Cys Xaa
            20

<210> SEQ ID NO 477
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 477

Arg Xaa Arg Arg Ala Arg Arg Xaa Arg Ile Leu Phe Gln Tyr Xaa Arg
1               5                   10                  15

Met Lys Trp His Lys Ala Cys Xaa
            20

<210> SEQ ID NO 478
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 478
```

Arg Xaa Arg Arg Ala Arg Arg Xaa Arg Ile Leu Phe Gln Tyr Xaa His
1               5                   10                  15

Met Lys Trp His Lys Ala Cys Xaa
            20

<210> SEQ ID NO 479
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 479

Arg Xaa Arg Arg Ala Arg Arg Xaa Arg Ile Leu Phe Gln Tyr Xaa Arg
1               5                   10                  15

Met Lys Trp His Lys Ala Cys Xaa
            20

<210> SEQ ID NO 480
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 480

Arg Xaa Arg Arg Ala Arg Arg Xaa Arg Ile Leu Phe Gln Tyr Xaa Arg
1               5                   10                  15

Trp Lys Trp His Lys Ala Cys Xaa
            20

<210> SEQ ID NO 481
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 481

Arg Xaa Arg Arg Ala Arg Arg Xaa Arg Ile Leu Phe Gln Tyr Xaa His
1               5                   10                  15

Trp Lys Trp His Lys Ala Cys Xaa
            20

```
<210> SEQ ID NO 482
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 20
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 482

Arg Xaa Arg Arg Ala Arg Arg Xaa Arg Ile Leu Phe Gln Tyr Arg Xaa
1               5                   10                  15

Arg Ala Arg Xaa Arg Ala Cys Xaa
            20

<210> SEQ ID NO 483
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 18, 20
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 483

Arg Xaa Arg Arg Ala Arg Arg Xaa Arg Ile Leu Phe Gln Tyr Arg Xaa
1               5                   10                  15

Arg Xaa Arg Xaa Arg Ala Cys Xaa
            20

<210> SEQ ID NO 484
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 484

Arg Xaa Arg Arg Ala Arg Arg Xaa Arg Ile Leu Ile Gln Tyr Xaa Arg
1               5                   10                  15

Met Lys Trp His Lys Ala Cys Xaa
            20

<210> SEQ ID NO 485
<211> LENGTH: 19
<212> TYPE: PRT
<213> ORGANISM: Artificial Sequence
<220> FEATURE:
<223> OTHER INFORMATION: cell penetrating peptide
```

-continued

```
<220> FEATURE:
<221> NAME/KEY: MOD_RES
<222> LOCATION: 2, 5, 13, 16
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 485

Arg Xaa Arg Arg Xaa Arg Ile Leu Phe Gln Tyr Arg Xaa Arg Arg Xaa
1               5                   10                  15

Arg Cys Xaa

<210> SEQ ID NO 486
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 20
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 486

Arg Xaa Arg Arg Ala Arg Arg Xaa Arg Ile Leu Phe Gln Tyr Arg Xaa
1               5                   10                  15

Arg Ala Arg Xaa Arg Ala Cys Xaa
            20

<210> SEQ ID NO 487
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 18, 20
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 487

Arg Xaa Arg Arg Ala Arg Arg Xaa Arg Ile Leu Phe Gln Tyr Arg Xaa
1               5                   10                  15

Arg Xaa Arg Xaa Arg Ala Cys Xaa
            20

<210> SEQ ID NO 488
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline
```

```
<400> SEQUENCE: 488

Arg Xaa Arg Arg Ala Arg Arg Xaa Arg Ile Leu Ile Gln Tyr Xaa Arg
1               5                   10                  15

Met Lys Trp His Lys Ala Cys Xaa
            20

<210> SEQ ID NO 489
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13, 16
<223> OTHER INFORMATION: Xaa = 6-aminohexanoic acid
<220> FEATURE:
<221> NAME/KEY: MOD_RES
<222> LOCATION: (21)...(21)
<223> OTHER INFORMATION: Xaa = glycine or proline

<400> SEQUENCE: 489

Arg Xaa Arg Arg Xaa Arg Ile Leu Phe Gln Tyr Arg Xaa Arg Arg Xaa
1               5                   10                  15

Arg Cys Tyr Ser Xaa
            20

<210> SEQ ID NO 490
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 18
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 490

Arg Ala Arg Arg Xaa Arg Arg Ala Arg Ile Leu Phe Gln Tyr Arg Ala
1               5                   10                  15

Arg Xaa Arg Ala Arg Ala Cys Xaa
            20

<210> SEQ ID NO 491
<211> LENGTH: 24
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 20
<223> OTHER INFORMATION: Xaa = 6-aminohexanoic acid
<220> FEATURE:
<221> NAME/KEY: MOD_RES
<222> LOCATION: (24)...(24)
<223> OTHER INFORMATION: Xaa = glycine or proline

<400> SEQUENCE: 491

Arg Ala Arg Arg Xaa Arg Arg Ala Arg Ile Leu Phe Gln Tyr Arg Xaa
1               5                   10                  15

Arg Ala Arg Xaa Arg Ala Cys Xaa
```

20

<210> SEQ ID NO 492
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 19
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 492

Arg Ala Arg Arg Xaa Arg Arg Ala Arg Ile Leu Phe Gln Tyr Arg Xaa
1               5                   10                  15

Arg Arg Xaa Arg Ala Cys Xaa
            20

<210> SEQ ID NO 493
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 20
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 493

Arg Ala Arg Arg Xaa Arg Arg Ala Arg Ile Leu Phe Gln Tyr Arg Xaa
1               5                   10                  15

Arg Ala Arg Xaa Ala Cys Xaa
            20

<210> SEQ ID NO 494
<211> LENGTH: 23
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 19
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 494

Arg Xaa Arg Arg Ala Arg Arg Xaa Arg Ile Leu Phe Gln Tyr Arg Xaa
1               5                   10                  15

Arg Arg Xaa Arg Ala Cys Xaa
            20

<210> SEQ ID NO 495
<211> LENGTH: 23
<212> TYPE: PRT
<213> ORGANISM: Artificial Sequence

```
<220> FEATURE:
<223> OTHER INFORMATION: cell penetrating peptide
<220> FEATURE:
<221> NAME/KEY: MOD_RES
<222> LOCATION: 2, 8, 16, 20
<223> OTHER INFORMATION: Xaa = 6-aminohexanoic acid
<220> FEATURE:
<221> NAME/KEY: MOD_RES
<222> LOCATION: (23)...(23)
<223> OTHER INFORMATION: Xaa = glycine or proline

<400> SEQUENCE: 495

Arg Xaa Arg Arg Ala Arg Arg Xaa Arg Ile Leu Phe Gln Tyr Arg Xaa
1               5                   10                  15

Arg Ala Arg Xaa Ala Cys Xaa
            20

<210> SEQ ID NO 496
<211> LENGTH: 26
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 17
<223> OTHER INFORMATION: Xaa = 6-aminohexanoic acid
<220> FEATURE:
<221> NAME/KEY: MOD_RES
<222> LOCATION: (26)...(26)
<223> OTHER INFORMATION: Xaa = glycine or proline

<400> SEQUENCE: 496

Arg Xaa Arg Arg Ala Arg Arg Xaa Arg Ile His Ile Leu Phe Gln Asn
1               5                   10                  15

Xaa Arg Met Lys Trp His Lys Ala Cys Xaa
            20                  25

<210> SEQ ID NO 497
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 13
<223> OTHER INFORMATION: Xaa = 6-aminohexanoic acid
<220> FEATURE:
<221> NAME/KEY: MOD_RES
<222> LOCATION: (16)...(16)
<223> OTHER INFORMATION: Xaa = glycine or proline

<400> SEQUENCE: 497

Arg Xaa Arg Arg Ala Arg Arg Xaa Arg Arg Ala Arg Xaa Ala Cys Xaa
1               5                   10                  15

<210> SEQ ID NO 498
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline
```

```
<400> SEQUENCE: 498

Arg Xaa Arg Arg Ala Arg Arg Xaa Arg Ile Leu Phe Gln Tyr Xaa His
1               5                   10                  15

Met Lys Trp His Lys Xaa
            20

<210> SEQ ID NO 499
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 499

Arg Xaa Arg Arg Ala Arg Arg Xaa Arg Ile Leu Phe Gln Tyr Xaa Arg
1               5                   10                  15

Met Lys Trp His Lys Xaa
            20

<210> SEQ ID NO 500
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 500

Arg Xaa Arg Arg Ala Arg Arg Xaa Arg Ile Leu Phe Gln Tyr Xaa Arg
1               5                   10                  15

Trp Lys Trp His Lys Xaa
            20

<210> SEQ ID NO 501
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 501

Arg Xaa Arg Arg Ala Arg Arg Xaa Arg Ile Leu Phe Gln Tyr Xaa Arg
1               5                   10                  15

Met Lys Trp His Lys Xaa
```

20

<210> SEQ ID NO 502
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 20
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 502

Arg Xaa Arg Arg Ala Arg Arg Xaa Arg Ile Leu Phe Gln Tyr Arg Xaa
1               5                   10                  15

Arg Ala Arg Xaa Arg Xaa
            20

<210> SEQ ID NO 503
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 18, 20
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 503

Arg Xaa Arg Arg Ala Arg Arg Xaa Arg Ile Leu Phe Gln Tyr Arg Xaa
1               5                   10                  15

Arg Xaa Arg Xaa Arg Xaa
            20

<210> SEQ ID NO 504
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 19
<223> OTHER INFORMATION: Xaa = 6-aminohexanoic acid
<220> FEATURE:
<221> NAME/KEY: MOD_RES
<222> LOCATION: (21)...(21)
<223> OTHER INFORMATION: Xaa = glycine or proline

<400> SEQUENCE: 504

Arg Xaa Arg Arg Ala Arg Arg Xaa Arg Ile Leu Phe Gln Tyr Arg Xaa
1               5                   10                  15

Arg Arg Xaa Arg Xaa
            20

<210> SEQ ID NO 505
<211> LENGTH: 22
<212> TYPE: PRT
<213> ORGANISM: Artificial Sequence

```
<220> FEATURE:
<223> OTHER INFORMATION: cell penetrating peptide
<220> FEATURE:
<221> NAME/KEY: MOD_RES
<222> LOCATION: 2, 8, 18
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 505

Arg Xaa Arg Arg Ala Arg Arg Xaa Arg Ile Leu Phe Gln Tyr Arg Ala
1               5                   10                  15

Arg Xaa Arg Ala Arg Xaa
            20

<210> SEQ ID NO 506
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16
<223> OTHER INFORMATION: Xaa = 6-aminohexanoic acid
<220> FEATURE:
<221> NAME/KEY: MOD_RES
<222> LOCATION: (20)...(20)
<223> OTHER INFORMATION: Xaa = glycine or proline

<400> SEQUENCE: 506

Arg Xaa Arg Arg Ala Arg Arg Xaa Arg Ile Leu Phe Gln Tyr Arg Xaa
1               5                   10                  15

Arg Ala Arg Xaa
            20

<210> SEQ ID NO 507
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 507

Arg Xaa Arg Arg Ala Arg Arg Xaa Arg Ile Leu Ile Gln Tyr Xaa His
1               5                   10                  15

Met Lys Trp His Lys Xaa
            20

<210> SEQ ID NO 508
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
```

```
<221> NAME/KEY: MOD_RES
<222> LOCATION: (22)...(22)
<223> OTHER INFORMATION: Xaa = glycine or proline

<400> SEQUENCE: 508

Arg Xaa Arg Arg Ala Arg Arg Xaa Arg Ile Leu Ile Gln Tyr Xaa Arg
1               5                   10                  15

Met Lys Trp His Lys Xaa
            20

<210> SEQ ID NO 509
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 509

Arg Xaa Arg Arg Ala Arg Arg Xaa Arg Ile Leu Ile Gln Tyr Xaa Arg
1               5                   10                  15

Trp Lys Trp His Lys Xaa
            20

<210> SEQ ID NO 510
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 510

Arg Xaa Arg Arg Ala Arg Arg Xaa Arg Ile Leu Ile Gln Tyr Xaa Arg
1               5                   10                  15

Met Lys Trp His Lys Xaa
            20

<210> SEQ ID NO 511
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 20
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 511

Arg Xaa Arg Arg Ala Arg Arg Xaa Arg Ile Leu Ile Gln Tyr Arg Xaa
```

-continued

```
1               5                   10                  15

Arg Ala Arg Xaa Arg Xaa
            20

<210> SEQ ID NO 512
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 18, 20
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 512

Arg Xaa Arg Arg Ala Arg Arg Xaa Arg Ile Leu Ile Gln Tyr Arg Xaa
1               5                   10                  15

Arg Xaa Arg Xaa Arg Xaa
            20

<210> SEQ ID NO 513
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16, 19
<223> OTHER INFORMATION: Xaa = 6-aminohexanoic acid
<220> FEATURE:
<221> NAME/KEY: MOD_RES
<222> LOCATION: (21)...(21)
<223> OTHER INFORMATION: Xaa = glycine or proline

<400> SEQUENCE: 513

Arg Xaa Arg Arg Ala Arg Arg Xaa Arg Ile Leu Ile Gln Tyr Arg Xaa
1               5                   10                  15

Arg Arg Xaa Arg Xaa
            20

<210> SEQ ID NO 514
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 18
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 514

Arg Xaa Arg Arg Ala Arg Arg Xaa Arg Ile Leu Ile Gln Tyr Arg Ala
1               5                   10                  15

Arg Xaa Arg Ala Arg Xaa
            20

<210> SEQ ID NO 515
```

```
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 8, 16
<223> OTHER INFORMATION: Xaa = 6-aminohexanoic acid
<220> FEATURE:
<221> NAME/KEY: MOD_RES
<222> LOCATION: (20)...(20)
<223> OTHER INFORMATION: Xaa = glycine or proline

<400> SEQUENCE: 515

Arg Xaa Arg Arg Ala Arg Arg Xaa Arg Ile Leu Ile Gln Tyr Arg Xaa
1               5                   10                  15

Arg Ala Arg Xaa
            20

<210> SEQ ID NO 516
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 516

Arg Ala Arg Arg Xaa Arg Arg Ala Arg Ile Leu Phe Gln Tyr Xaa His
1               5                   10                  15

Met Lys Trp His Lys Xaa
            20

<210> SEQ ID NO 517
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 517

Arg Ala Arg Arg Xaa Arg Arg Ala Arg Ile Leu Phe Gln Tyr Xaa Arg
1               5                   10                  15

Met Lys Trp His Lys Xaa
            20

<210> SEQ ID NO 518
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
```

-continued

```
<222> LOCATION: 5, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 518

Arg Ala Arg Arg Xaa Arg Arg Ala Arg Ile Leu Phe Gln Tyr Xaa Arg
1               5                   10                  15

Trp Lys Trp His Lys Xaa
            20

<210> SEQ ID NO 519
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 519

Arg Ala Arg Arg Xaa Arg Arg Ala Arg Ile Leu Phe Gln Tyr Xaa Arg
1               5                   10                  15

Met Lys Trp His Lys Xaa
            20

<210> SEQ ID NO 520
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 20
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 520

Arg Ala Arg Arg Xaa Arg Arg Ala Arg Ile Leu Phe Gln Tyr Arg Xaa
1               5                   10                  15

Arg Ala Arg Xaa Arg Xaa
            20

<210> SEQ ID NO 521
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 18, 20
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline
```

```
<400> SEQUENCE: 521

Arg Ala Arg Arg Xaa Arg Arg Ala Arg Ile Leu Phe Gln Tyr Arg Xaa
1               5                   10                  15

Arg Xaa Arg Xaa Arg Xaa
            20

<210> SEQ ID NO 522
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 19
<223> OTHER INFORMATION: Xaa = 6-aminohexanoic acid
<220> FEATURE:
<221> NAME/KEY: MOD_RES
<222> LOCATION: (21)...(21)
<223> OTHER INFORMATION: Xaa = glycine or proline

<400> SEQUENCE: 522

Arg Ala Arg Arg Xaa Arg Arg Ala Arg Ile Leu Phe Gln Tyr Arg Xaa
1               5                   10                  15

Arg Arg Xaa Arg Xaa
            20

<210> SEQ ID NO 523
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 18
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 523

Arg Ala Arg Arg Xaa Arg Arg Ala Arg Ile Leu Phe Gln Tyr Arg Ala
1               5                   10                  15

Arg Xaa Arg Ala Arg Xaa
            20

<210> SEQ ID NO 524
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16
<223> OTHER INFORMATION: Xaa = 6-aminohexanoic acid
<220> FEATURE:
<221> NAME/KEY: MOD_RES
<222> LOCATION: (20)...(20)
<223> OTHER INFORMATION: Xaa = glycine or proline

<400> SEQUENCE: 524

Arg Ala Arg Arg Xaa Arg Arg Ala Arg Ile Leu Phe Gln Tyr Arg Xaa
1               5                   10                  15

Arg Ala Arg Xaa
            20
```

```
<210> SEQ ID NO 525
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 525

Arg Ala Arg Arg Xaa Arg Arg Ala Arg Ile Leu Ile Gln Tyr Xaa His
1               5                   10                  15

Met Lys Trp His Lys Xaa
            20

<210> SEQ ID NO 526
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 526

Arg Ala Arg Arg Xaa Arg Arg Ala Arg Ile Leu Ile Gln Tyr Xaa Arg
1               5                   10                  15

Met Lys Trp His Lys Xaa
            20

<210> SEQ ID NO 527
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 527

Arg Ala Arg Arg Xaa Arg Arg Ala Arg Ile Leu Ile Gln Tyr Xaa Arg
1               5                   10                  15

Trp Lys Trp His Lys Xaa
            20

<210> SEQ ID NO 528
<211> LENGTH: 22
<212> TYPE: PRT
<213> ORGANISM: Artificial Sequence
<220> FEATURE:
```

<223> OTHER INFORMATION: cell penetrating peptide
<220> FEATURE:
<221> NAME/KEY: MOD_RES
<222> LOCATION: 5, 15
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 528

Arg Ala Arg Arg Xaa Arg Arg Ala Arg Ile Leu Ile Gln Tyr Xaa Arg
1               5                   10                  15

Met Lys Trp His Lys Xaa
            20

<210> SEQ ID NO 529
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 20
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 529

Arg Ala Arg Arg Xaa Arg Arg Ala Arg Ile Leu Ile Gln Tyr Arg Xaa
1               5                   10                  15

Arg Ala Arg Xaa Arg Xaa
            20

<210> SEQ ID NO 530
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 18, 20
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 530

Arg Ala Arg Arg Xaa Arg Arg Ala Arg Ile Leu Ile Gln Tyr Arg Xaa
1               5                   10                  15

Arg Xaa Arg Xaa Arg Xaa
            20

<210> SEQ ID NO 531
<211> LENGTH: 21
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16, 19
<223> OTHER INFORMATION: Xaa = 6-aminohexanoic acid
<220> FEATURE:
<221> NAME/KEY: MOD_RES

```
<222> LOCATION: (21)...(21)
<223> OTHER INFORMATION: Xaa = glycine or proline

<400> SEQUENCE: 531

Arg Ala Arg Arg Xaa Arg Arg Ala Arg Ile Leu Ile Gln Tyr Arg Xaa
1               5                   10                  15
Arg Arg Xaa Arg Xaa
            20

<210> SEQ ID NO 532
<211> LENGTH: 22
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 18
<223> OTHER INFORMATION: Xaa = 6-aminohexanoic acid
<220> FEATURE:
<221> NAME/KEY: MOD_RES
<222> LOCATION: (22)...(22)
<223> OTHER INFORMATION: Xaa = glycine or proline

<400> SEQUENCE: 532

Arg Ala Arg Arg Xaa Arg Arg Ala Arg Ile Leu Ile Gln Tyr Arg Ala
1               5                   10                  15
Arg Xaa Arg Ala Arg Xaa
            20

<210> SEQ ID NO 533
<211> LENGTH: 20
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 5, 16
<223> OTHER INFORMATION: Xaa = 6-aminohexanoic acid
<220> FEATURE:
<221> NAME/KEY: MOD_RES
<222> LOCATION: (20)...(20)
<223> OTHER INFORMATION: Xaa = glycine or proline

<400> SEQUENCE: 533

Arg Ala Arg Arg Xaa Arg Arg Ala Arg Ile Leu Ile Gln Tyr Arg Xaa
1               5                   10                  15
Arg Ala Arg Xaa
            20

<210> SEQ ID NO 534
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 12
<223> OTHER INFORMATION: Xaa = glycine or proline

<400> SEQUENCE: 534

Arg Xaa Arg Arg Xaa Arg Ile Leu Phe Gln Tyr Xaa His Met Lys Trp
1               5                   10                  15
His Lys Xaa
```

```
<210> SEQ ID NO 535
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 12
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 535

Arg Xaa Arg Arg Xaa Arg Ile Leu Phe Gln Tyr Xaa Arg Met Lys Trp
1               5                   10                  15

His Lys Xaa

<210> SEQ ID NO 536
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 12
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 536

Arg Xaa Arg Arg Xaa Arg Ile Leu Phe Gln Tyr Xaa Arg Trp Lys Trp
1               5                   10                  15

His Lys Xaa

<210> SEQ ID NO 537
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 12
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 537

Arg Xaa Arg Arg Xaa Arg Ile Leu Phe Gln Tyr Xaa Arg Met Lys Trp
1               5                   10                  15

His Lys Xaa

<210> SEQ ID NO 538
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13, 17
<223> OTHER INFORMATION: Xaa = 6-aminohexanoic acid
```

```
<220> FEATURE:
<221> NAME/KEY: MOD_RES
<222> LOCATION: (19)...(19)
<223> OTHER INFORMATION: Xaa = glycine or proline

<400> SEQUENCE: 538

Arg Xaa Arg Arg Xaa Arg Ile Leu Phe Gln Tyr Arg Xaa Arg Ala Arg
1               5                   10                  15

Xaa Arg Xaa

<210> SEQ ID NO 539
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13, 15, 17
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 539

Arg Xaa Arg Arg Xaa Arg Ile Leu Phe Gln Tyr Arg Xaa Arg Xaa Arg
1               5                   10                  15

Xaa Arg Xaa

<210> SEQ ID NO 540
<211> LENGTH: 18
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13, 16
<223> OTHER INFORMATION: Xaa = 6-aminohexanoic acid
<220> FEATURE:
<221> NAME/KEY: MOD_RES
<222> LOCATION: (18)...(18)
<223> OTHER INFORMATION: Xaa = glycine or proline

<400> SEQUENCE: 540

Arg Xaa Arg Arg Xaa Arg Ile Leu Phe Gln Tyr Arg Xaa Arg Arg Xaa
1               5                   10                  15

Arg Xaa

<210> SEQ ID NO 541
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 15
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 541

Arg Xaa Arg Arg Xaa Arg Ile Leu Phe Gln Tyr Arg Ala Arg Xaa Arg
1               5                   10                  15
```

Ala Arg Xaa

<210> SEQ ID NO 542
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13
<223> OTHER INFORMATION: Xaa = 6-aminohexanoic acid
<220> FEATURE:
<221> NAME/KEY: MOD_RES
<222> LOCATION: (17)...(17)
<223> OTHER INFORMATION: Xaa = glycine or proline

<400> SEQUENCE: 542

Arg Xaa Arg Arg Xaa Arg Ile Leu Phe Gln Tyr Arg Xaa Arg Ala Arg
1               5                   10                  15

Xaa

<210> SEQ ID NO 543
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 12
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 543

Arg Xaa Arg Arg Xaa Arg Ile Leu Ile Gln Tyr Xaa His Met Lys Trp
1               5                   10                  15

His Lys Xaa

<210> SEQ ID NO 544
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 12
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 544

Arg Xaa Arg Arg Xaa Arg Ile Leu Ile Gln Tyr Xaa Arg Met Lys Trp
1               5                   10                  15

His Lys Xaa

<210> SEQ ID NO 545
<211> LENGTH: 19
<212> TYPE: PRT
<213> ORGANISM: Artificial Sequence
<220> FEATURE:
<223> OTHER INFORMATION: cell penetrating peptide
<220> FEATURE:

```
<221> NAME/KEY: MOD_RES
<222> LOCATION: 2, 5,12
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 545

Arg Xaa Arg Arg Xaa Arg Ile Leu Ile Gln Tyr Xaa Arg Trp Lys Trp
1               5                   10                  15

His Lys Xaa

<210> SEQ ID NO 546
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 12
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 546

Arg Xaa Arg Arg Xaa Arg Ile Leu Ile Gln Tyr Xaa Arg Met Lys Trp
1               5                   10                  15

His Lys Xaa

<210> SEQ ID NO 547
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13, 17
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 547

Arg Xaa Arg Arg Xaa Arg Ile Leu Ile Gln Tyr Arg Xaa Arg Ala Arg
1               5                   10                  15

Xaa Arg Xaa

<210> SEQ ID NO 548
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13, 15, 17
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 548
```

-continued

Arg Xaa Arg Arg Xaa Arg Ile Leu Ile Gln Tyr Arg Xaa Arg Xaa
1               5                   10                  15

Xaa Arg Xaa

<210> SEQ ID NO 549
<211> LENGTH: 18
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13, 16
<223> OTHER INFORMATION: Xaa = 6-aminohexanoic acid
<220> FEATURE:
<221> NAME/KEY: MOD_RES
<222> LOCATION: (18)...(18)
<223> OTHER INFORMATION: Xaa = glycine or proline

<400> SEQUENCE: 549

Arg Xaa Arg Arg Xaa Arg Ile Leu Ile Gln Tyr Arg Xaa Arg Arg Xaa
1               5                   10                  15

Arg Xaa

<210> SEQ ID NO 550
<211> LENGTH: 19
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 15
<223> OTHER INFORMATION: Xaa = 6-aminohexanoic acid
<220> FEATURE:
<221> NAME/KEY: MOD_RES
<222> LOCATION: (19)...(19)
<223> OTHER INFORMATION: Xaa = glycine or proline

<400> SEQUENCE: 550

Arg Xaa Arg Arg Xaa Arg Ile Leu Ile Gln Tyr Arg Ala Arg Xaa Arg
1               5                   10                  15

Ala Arg Xaa

<210> SEQ ID NO 551
<211> LENGTH: 17
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: 2, 5, 13
<223> OTHER INFORMATION: Xaa = 6-aminohexanoic acid
<220> FEATURE:
<221> NAME/KEY: MOD_RES
<222> LOCATION: (17)...(17)
<223> OTHER INFORMATION: Xaa = glycine or proline

<400> SEQUENCE: 551

Arg Xaa Arg Arg Xaa Arg Ile Leu Ile Gln Tyr Arg Xaa Arg Ala Arg
1               5                   10                  15

Xaa

<210> SEQ ID NO 552
<211> LENGTH: 18
<212> TYPE: PRT
<213> ORGANISM: Artificial Sequence

```
<220> FEATURE:
<223> OTHER INFORMATION: cell penetrating peptide
<220> FEATURE:
<221> NAME/KEY: MOD_RES
<222> LOCATION: (4)...(14)
<223> OTHER INFORMATION: Xaa = 6-aminohexanoic acid
<220> FEATURE:
<221> NAME/KEY: MOD_RES
<222> LOCATION: (18)...(18)
<223> OTHER INFORMATION: Xaa - glycine or proline

<400> SEQUENCE: 552

Pro Arg Pro Xaa Xaa Xaa Xaa Xaa Xaa Xaa Xaa Xaa Xaa Xaa Pro Arg
1               5                   10                  15

Gly Xaa

<210> SEQ ID NO 553
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)...(9)
<223> OTHER INFORMATION: Xaa = glycine or proline

<400> SEQUENCE: 553

Arg Arg Arg Arg Arg Arg Arg Arg Xaa
1               5

<210> SEQ ID NO 554
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 554

Arg Arg Met Lys Trp Lys Lys Xaa
1               5

<210> SEQ ID NO 555
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 555

Pro Lys Lys Lys Arg Lys Val Xaa
1               5

<210> SEQ ID NO 556
<211> LENGTH: 33
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (33)...(33)
```

```
<223> OTHER INFORMATION: Xaa = glycine or proline

<400> SEQUENCE: 556

Cys Lys Asp Glu Pro Gln Arg Arg Ser Ala Arg Leu Ser Ala Lys Pro
1               5                   10                  15

Ala Pro Pro Lys Pro Glu Pro Lys Pro Lys Ala Pro Ala Lys Lys
            20                  25                  30

Xaa

<210> SEQ ID NO 557
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 557

Arg Lys Lys Arg Arg Gln Arg Arg Arg Xaa
1               5                   10

<210> SEQ ID NO 558
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)...(9)
<223> OTHER INFORMATION: Xaa = glycine or proline

<400> SEQUENCE: 558

Arg Lys Lys Arg Arg Gln Arg Arg Xaa
1               5

<210> SEQ ID NO 559
<211> LENGTH: 8
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (8)...(8)
<223> OTHER INFORMATION: Xaa = glycine or proline

<400> SEQUENCE: 559

Arg Lys Lys Arg Arg Gln Arg Xaa
1               5

<210> SEQ ID NO 560
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)...(9)
<223> OTHER INFORMATION: Xaa = glycine or proline

<400> SEQUENCE: 560

Lys Lys Arg Arg Gln Arg Arg Arg Xaa
1               5
```

```
<210> SEQ ID NO 561
<211> LENGTH: 9
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (9)...(9)
<223> OTHER INFORMATION: Xaa = glycine or proline

<400> SEQUENCE: 561

Lys Lys Arg Arg Gln Arg Arg Arg Xaa
1               5

<210> SEQ ID NO 562
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xa = glycine or proline

<400> SEQUENCE: 562

Ala Lys Lys Arg Arg Gln Arg Arg Arg Xaa
1               5                   10

<210> SEQ ID NO 563
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 563

Arg Ala Lys Arg Arg Gln Arg Arg Arg Xaa
1               5                   10

<210> SEQ ID NO 564
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
<223> OTHER INFORMATION: Xaa = glycine or proline

<400> SEQUENCE: 564

Arg Lys Ala Arg Arg Gln Arg Arg Arg Xaa
1               5                   10

<210> SEQ ID NO 565
<211> LENGTH: 10
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (10)...(10)
```

<223> OTHER INFORMATION: Xaa = glycine or proline

<400> SEQUENCE: 565

Arg Lys Lys Ala Arg Gln Arg Arg Arg Xaa
1               5                   10

<210> SEQ ID NO 566
<211> LENGTH: 11
<212> TYPE: PRT
<213> ORGANISM: Artificial Sequence
<220> FEATURE:
<223> OTHER INFORMATION: cell penetrating peptide
<220> FEATURE:
<221> NAME/KEY: MOD_RES
<222> LOCATION: (11)...(11)
<223> OTHER INFORMATION: Xaa = glycine or proline

<400> SEQUENCE: 566

Cys Arg Trp Arg Trp Lys Cys Cys Lys Lys Xaa
1               5                   10

<210> SEQ ID NO 567
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 567
cggtccacgt agactaacaa ct                                              22

<210> SEQ ID NO 568
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 568
gaagttcaca cagataaact tct                                             23

<210> SEQ ID NO 569
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 569
tttcgacatc ggttagaaga ctcat                                           25

<210> SEQ ID NO 570
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 570
tttcgacatc ggttagaaga ctcat                                           25

<210> SEQ ID NO 571
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 571
gagacgccat gatgtggatg tc                                          22

<210> SEQ ID NO 572
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 572
gaaacacgga cacccaaagt agt                                         23

<210> SEQ ID NO 573
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 573
tcccagcgtc aatatgctgt tt                                          22

<210> SEQ ID NO 574
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 574
gcctaggatc cacggtgcgc                                             20

<210> SEQ ID NO 575
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 575
gggacaaaat ggatcccatt attaatggaa attctgctaa                       40

<210> SEQ ID NO 576
<211> LENGTH: 5
<212> TYPE: PRT
<213> ORGANISM: Artificial Sequence
<220> FEATURE:
<223> OTHER INFORMATION: carrier peptide

<400> SEQUENCE: 576

Ile Leu Phe Gln Tyr
1               5

<210> SEQ ID NO 577
<211> LENGTH: 4
<212> TYPE: PRT
<213> ORGANISM: Artificial Sequence
<220> FEATURE:
<223> OTHER INFORMATION: carrier peptide

<400> SEQUENCE: 577

Ile Leu Phe Gln
1

```
<210> SEQ ID NO 578
<211> LENGTH: 4
<212> TYPE: PRT
<213> ORGANISM: Artificial Sequence
<220> FEATURE:
<223> OTHER INFORMATION: carrier peptide

<400> SEQUENCE: 578

Ile Trp Phe Gln
1

<210> SEQ ID NO 579
<211> LENGTH: 4
<212> TYPE: PRT
<213> ORGANISM: Artificial Sequence
<220> FEATURE:
<223> OTHER INFORMATION: carrier peptide

<400> SEQUENCE: 579

Ile Leu Ile Gln
1

<210> SEQ ID NO 580
<211> LENGTH: 5
<212> TYPE: PRT
<213> ORGANISM: Artificial Sequence
<220> FEATURE:
<223> OTHER INFORMATION: carrier peptide

<400> SEQUENCE: 580

Pro Pro Met Trp Ser
1               5

<210> SEQ ID NO 581
<211> LENGTH: 5
<212> TYPE: PRT
<213> ORGANISM: Artificial Sequence
<220> FEATURE:
<223> OTHER INFORMATION: carrier peptide

<400> SEQUENCE: 581

Pro Pro Met Trp Thr
1               5

<210> SEQ ID NO 582
<211> LENGTH: 5
<212> TYPE: PRT
<213> ORGANISM: Artificial Sequence
<220> FEATURE:
<223> OTHER INFORMATION: carrier peptide

<400> SEQUENCE: 582

Pro Pro Met Phe Ser
1               5

<210> SEQ ID NO 583
<211> LENGTH: 5
<212> TYPE: PRT
<213> ORGANISM: Artificial Sequence
<220> FEATURE:
<223> OTHER INFORMATION: carrier peptide

<400> SEQUENCE: 583

Pro Pro Met Tyr Ser
1               5
```

PEPTIDE OLIGONUCLEOTIDE CONJUGATES

CROSS-REFERENCE TO RELATED APPLICATIONS

This application is a Continuation of U.S. application Ser. No. 14/851,434 filed Sep. 11, 2015, which is a Divisional of U.S. application Ser. No. 13/299,310 filed Nov. 17, 2011, now issued as U.S. Pat. No. 9,161,948, which is a Continuation-in-part of U.S. patent application Ser. No. 13/101,942 filed on May 5, 2011, now abandoned, and a Continuation-in-part of U.S. patent application Ser. No. 13/107,528 filed on May 13, 2011, now issued as U.S. Pat. No. 9,238,042. These applications are incorporated herein by reference in their entireties.

STATEMENT REGARDING SEQUENCE LISTING

This application contains a Sequence Listing in computer readable format. The Sequence Listing is provided as a file entitled 120178_495C2_SEQUENCE_LISTING.txt created Nov. 29, 2017 which is 232,122 bytes in size. The information in the computer readable form of the Sequence Listing is incorporated herein by reference in its entirety.

BACKGROUND

Technical Field

The present invention is generally related to oligonucleotide compounds (oligomers) useful as antisense compounds, and more particularly to oligomer compounds conjugated to cell-penetrating peptides, and the use of such oligomer compounds in antisense applications.

Description of the Related Art

The practical utility of many drugs having potentially useful biological activity is often stymied by difficulty in delivering such drugs to their targets. Compounds to be delivered into cells must generally be delivered from a largely aqueous extracellular environment and then penetrate a lipophilic cell membrane to gain entry to the cell. Unless the substance is actively transported by a specific transport mechanism, many molecules, particularly large molecules, are either too lipophilic for practical solubilization or are too hydrophilic to penetrate the membrane.

A segment of the HIV Tat protein consisting of amino acid residues 49-57 (Tat 49 57, having the sequence RKKRRQRRR (SEQ ID NO: 57)) has been used to deliver biologically active peptides and proteins to cells (e.g. Barsoum et al., 1994, PCT Pubn. No. WO 94/04686). Tat (49 60) has been used to enhance delivery of phosphorothioate oligonucleotides (Astriab-Fisher, Sergueev et al. 2000; Astriab-Fisher, Sergueev et al. 2002). Reverse Tat, or rTat (57-49) (RRRQRRKKR) (SEQ ID NO: 56), has been reported to deliver fluorescein into cells with enhanced efficacy compared to Tat (49 57) (Wender, Mitchell et al. 2000; Rothbard, Kreider et al. 2002). Rothbard and Wender have also disclosed other arginine-rich transport polymers (PCT Pubn. No. WO 01/62297; U.S. Pat. No. 6,306,993; US Patent Appn. Pubn. No. 2003/0032593).

Oligonucleotides are one class of potentially useful drug compounds whose delivery has often been an impediment to therapeutic use. Phosphorodiamidate-linked morpholino oligomers (PMOs; see e.g. Summerton and Weller, 1997) have been found more promising in this regard than charged oligonucleotide analogs such as phosphorothioates. The PMOs are water-soluble, uncharged or substantially uncharged antisense molecules that inhibit gene expression by preventing binding or progression of splicing or translational machinery components. PMOs have also been to shown to inhibit or block viral replication (Stein, Skilling et al. 2001; McCaffrey, Meuse et al. 2003). They are highly resistant to enzymatic digestion (Hudziak, Barofsky et al. 1996). PMOs have demonstrated high antisense specificity and efficacy in vitro in cell-free and cell culture models (Stein, Foster et al. 1997; Summerton and Weller 1997), and in vivo in zebrafish, frog and sea urchin embryos (Heasman, Kofron et al. 2000; Nasevicius and Ekker 2000), as well as in adult animal models, such as rats, mice, rabbits, dogs, and pigs (see e.g. Arora and Iversen 2000; Qin, Taylor et al. 2000; Iversen 2001; Kipshidze, Keane et al. 2001; Devi 2002; Devi, Oldenkamp et al. 2002; Kipshidze, Kim et al. 2002; Ricker, Mata et al. 2002).

Antisense PMO oligomers have been shown to be taken up into cells and to be more consistently effective in vivo, with fewer nonspecific effects, than other widely used antisense oligonucleotides (see e.g. P. Iversen, "Phosphoramidite Morpholino Oligomers", in Antisense Drug Technology, S. T. Crooke, ed., Marcel Dekker, Inc., New York, 2001). Conjugation of PMOs to arginine rich peptides has been shown to increase their cellular uptake (see e.g., U.S. Pat. No. 7,468,418); however, the toxicity of the conjugates has slowed their development as viable drug candidates.

Although significant progress has been made, there remains a need in the art for oligonucleotide conjugates with improved antisense or antigene performance. Such improved antisense or antigene performance includes; lower toxicity, stronger affinity for DNA and RNA without compromising sequence selectivity; improved pharmacokinetics and tissue distribution; improved cellular delivery and reliable and controllable in vivo distribution.

BRIEF SUMMARY

Compounds of the present invention address these issues and provide improvements over existing antisense molecules in the art. By linking a cell-penetrating peptide to a substantially uncharged nucleic acid analogue via a glycine or proline amino acid, the present inventors have addressed the toxicity issues associated with other peptide oligomer conjugates. Furthermore, modification of the intersubunit linkages and/or conjugation of terminal moieties to the 5' and/or 3' terminus of an oligonucleotide analogue, for example a morpholino oligonucleotide, may also improve the properties of the conjugates. For example, in certain embodiments the disclosed conjugates have decreased toxicity and/or enhanced cell delivery, potency, and/or tissue distribution compared to other oligonucleotide analogues and/or can be more effectively delivered to the target organs. These superior properties give rise to favorable therapeutic indices, reduced clinical dosing, and lower cost of goods.

Accordingly, in one embodiment the present disclosure provides a conjugate comprising:

(a) a carrier peptide comprising amino acid subunits; and
(b) a nucleic acid analogue comprising a substantially uncharged backbone and a targeting base sequence for sequence-specific binding to a target nucleic acid;

wherein:

two or more of the amino acid subunits are positively charged amino acids, the carrier peptide comprises a glycine (G) or proline (P) amino acid at a carboxy terminus of the carrier peptide, and the carrier peptide is covalently attached to the nucleic acid analogue. A composition comprising the above conjugate and a pharmaceutically acceptable vehicle are also provided.

In another embodiment, the present disclosure provides a method of inhibiting production of a protein, the method comprising exposing a nucleic acid encoding the protein to a conjugate of the present disclosure.

Another aspect of the present disclosure includes a method for enhancing the transport of a nucleic acid analogue into a cell, the method comprising conjugating the carrier peptide of claim 1 to a nucleic acid analogue, and wherein the transport of the nucleic acid analogue into the cell is enhanced relative to the nucleic acid analogue in unconjugated form.

In another embodiment, the disclosure is directed to a method of treating a disease in a subject, the method comprising administering a therapeutically effective amount of a disclosed conjugate to the subject. Methods of making the conjugates, methods for their use and carrier peptides useful for conjugating to nucleic acid analogues are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

I. Definitions

Figure 1A:
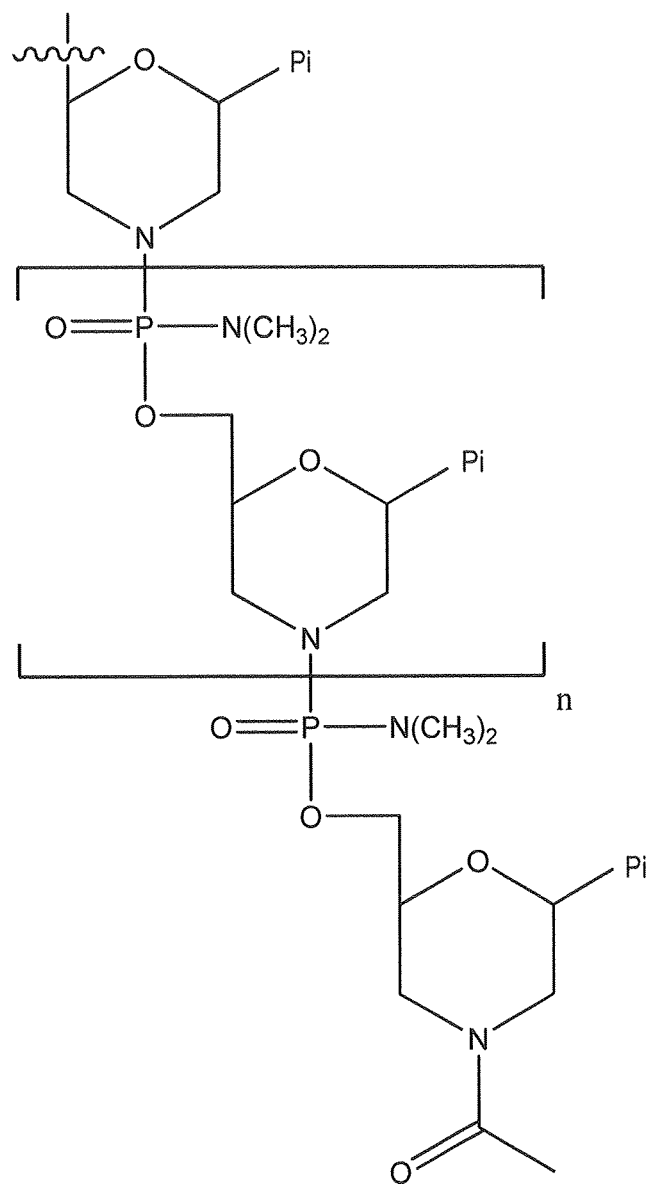
FIG. 1A shows an exemplary morpholino oligomer structure comprising a phosphorodiamidate linkage.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH$_2$ radical.

"Cyano" or "nitrile" refers to the —CN radical.

"Hydroxy" or "hydroxyl" refers to the —OH radical.

"Imino" refers to the =NH substituent.

"Guanidinyl" refers to the —NHC(=NH)NH$_2$ substituent.

"Amidinyl" refers to the —C(=NH)NH$_2$ substituent.

"Nitro" refers to the —NO$_2$ radical.

"Oxo" refers to the =O substituent.

"Thioxo" refers to the =S substituent.

"Cholate" refers to the following structure:

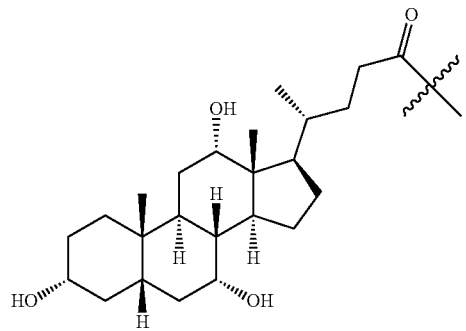

"Deoxycholate" refers to the following structure:

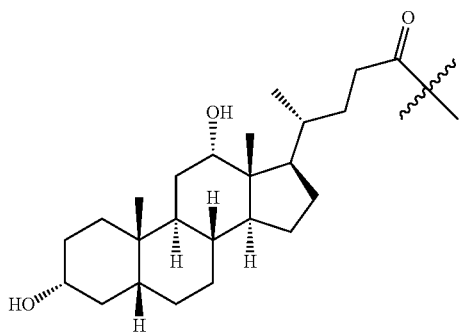

"Alkyl" refers to a straight or branched hydrocarbon chain radical which is saturated or unsaturated (i.e., contains one or more double and/or triple bonds), having from one to thirty carbon atoms, and which is attached to the rest of the molecule by a single bond. Alkyls comprising any number of carbon atoms from 1 to 30 are included. An alkyl comprising up to 30 carbon atoms is refered to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarily. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, but-2-ynyl, but-3-ynyl, pentynyl, hexynyl, and the like. Unless stated otherwise specifically in the specification, an alkyl group may be optionally substituted as described below.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

"Alkoxyalkyl" refers to a radical of the formula —$R_bOR_a$ where $R_a$ is an alkyl radical as defined and where $R_b$ is an alkylene radical as defined. Unless stated otherwise specifically in the specification, an alkoxyalkyl group may be optionally substituted as described below.

"Alkylcarbonyl" refers to a radical of the formula —C(=O)$R_a$ where $R_a$ is an alkyl radical as defined above. Unless stated otherwise specifically in the specification, an alkylcarbonyl group may be optionally substituted as described below.

"Alkyloxycarbonyl" refers to a radical of the formula —C(=O)$OR_a$ where $R_a$ is an alkyl radical as defined. Unless stated otherwise specifically in the specification, an alkyloxycarbonyl group may be optionally substituted as described below.

"Alkylamino" refers to a radical of the formula —NH$R_a$ or —$NR_aR_a$ where each $R_a$ is, independently, an alkyl radical as defined above. Unless stated otherwise specifically in the specification, an alkylamino group may be optionally substituted as described below.

"Amidyl" refers to a radical of the formula —N(H)C(=O) $R_a$ where $R_a$ is an alkyl or aryl radical as defined herein. Unless stated otherwise specifically in the specification, an amidyl group may be optionally substituted as described below.

"Amidinylalkyl" refers a radical of the formula —$R_b$—C(=NH)NH$_2$ where $R_b$ is an alkylene radical as defined above. Unless stated otherwise specifically in the specification, an amidinylalkyl group may be optionally substituted as described below.

"Amidinylalkylcarbonyl" refers a radical of the formula —C(=O)$R_b$—C(=NH)NH$_2$ where $R_b$ is an alkylene radical as defined above. Unless stated otherwise specifically in the specification, an amidinylalkylcarbonyl group may be optionally substituted as described below.

"Aminoalkyl" refers to a radical of the formula —$R_b$—$NR_aR_a$ where $R_b$ is an alkylene radical as defined above, and each $R_a$ is independently a hydrogen or an alkyl radical.

"Thioalkyl" refers to a radical of the formula —$SR_a$ where $R_a$ is an alkyl radical as defined above. Unless stated otherwise specifically in the specification, a thioalkyl group may be optionally substituted.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$-$R_c$ where $R_b$ is an alkylene chain as defined above and $R_c$ is one or more aryl radicals as defined above, for example, benzyl, diphenylmethyl, trityl and the like. Unless stated otherwise specifically in the specification, an aralkyl group may be optionally substituted.

"Arylcarbonyl" refers to a radical of the formula —C(=O)$R_c$ where $R_c$ is one or more aryl radicals as defined above, for example, phenyl. Unless stated otherwise specifically in the specification, an arylcarbonyl group may be optionally substituted.

"Aryloxycarbonyl" refers to a radical of the formula —C(=O)$OR_c$ where $R_c$ is one or more aryl radicals as defined above, for example, phenyl. Unless stated otherwise specifically in the specification, an aryloxycarbonyl group may be optionally substituted.

"Aralkylcarbonyl" refers to a radical of the formula —C(=O)$R_b$—$R_c$ where $R_b$ is an alkylene chain as defined above and $R_c$ is one or more aryl radicals as defined above, for example, phenyl. Unless stated otherwise specifically in the specification, an aralkylcarbonyl group may be optionally substituted.

"Aralkyloxycarbonyl" refers to a radical of the formula —C(=O)O$R_b$—$R_c$ where $R_b$ is an alkylene chain as defined above and $R_c$ is one or more aryl radicals as defined above, for example, phenyl. Unless stated otherwise specifically in the specification, an aralkyloxycarbonyl group may be optionally substituted.

"Aryloxy" refers to a radical of the formula —O$R_c$ where $R_c$ is one or more aryl radicals as defined above, for example, phenyl. Unless stated otherwise specifically in the specification, an arylcarbonyl group may be optionally substituted.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms and from three to eight carbon atoms, Monocyclic cycicoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted.

"Cycloalkylalkyl" refers to a radical of the formula —$R_b R_d$ where $R_b$ is an alkylene chain as defined above and $R_d$ is a cycloalkyl radical as defined above. Unless stated otherwise specifically in the specification, a cycloalkylalkyl group may be optionally substituted.

"Cycloalkylcarbonyl" refers to a radical of the formula —C(=O)$R_d$ where $R_d$ is a cycloalkyl radical as defined above. Unless stated otherwise specifically in the specification, a cycloalkylcarbonyl group may be optionally substituted.

"Cycloalkyloxycarbonyl" refers to a radical of the formula —C(=O)O$R_d$ where $R_d$ is a cycloalkyl radical as defined above. Unless stated otherwise specifically in the specification, a cycloalkyloxycarbonyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Guanidinylalkyl" refers a radical of the formula —$R_b$—NHC(=NH)$NH_2$ where $R_b$ is an alkylene radical as defined above. Unless stated otherwise specifically in the specification, a guanidinylalkyl group may be optionally substituted as described below.

"Guanidinylalkylcarbonyl" refers a radical of the formula —C(=O)$R_b$—NHC(=NH)$NH_2$ where $R_b$ is an alkylene radical as defined above. Unless stated otherwise specifically in the specification, a guanidinylalkylcarbonyl group may be optionally substituted as described below.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl", "heterocycle" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (i.e., alkyl, alkylene, alkoxy, alkoxyalkyl, alkylcarbonyl, alkyloxycarbonyl,alkylamino, amidyl, amidinylalkyl, amidinylalkylcarbonyl, aminoalkyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cyclo alkyloxycarbonyl, guanidinylalkyl, guanidinylalkylcarbonyl, haloalkyl, heterocyclyl and/or heteroaryl), may be further functionalized wherein at least one hydrogen atom is replaced by a bond to a non-hydrogen atom substituent. Unless stated specifically in the specification, a substituted group may include one or more substituents selected from: oxo, —$CO_2H$, nitrile, nitro, —$CONH_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cyclo alkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_B$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$CH_2SO_2R_g$, —$CH_2SO_2NR_gR_h$, —SH, —$SR_g$ or —$SSR_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarly, an alkyl group may be substituted with one or more internal sulfur atoms to form a thioether, disulfide, etc. Amidyl moieties may be substituted with up to 2 halo atoms, while other groups above may be substituted with one or more halo atoms. Any of the above groups may also be substituted with amino, monoalklyamino, guanidinyl or amidynyl. Optional substitutents for any of the above groups also include arylphosphoryl, for example —$R_aP(Ar)_3$ wherein $R_a$ is an alkylene and Ar is aryl moiety, for example phenyl.

The terms "antisense oligomer" or "antisense compound" are used interchangeably and refer to a sequence of subunits, each having a base carried on a backbone subunit composed of ribose or other pentose sugar or morpholino group, and where the backbone groups are linked by intersubunit linkages that allow the bases in the compound to hybridize to a target sequence in a nucleic acid (typically an RNA) by Watson-Crick base pairing, to form a nucleic acid:oligomer heteroduplex within the target sequence. The oligomer may have exact sequence complementarity to the target sequence or near complementarity. Such antisense oligomers are designed to block or inhibit translation of the mRNA containing the target sequence, and may be said to be "directed to" a sequence with which it hybridizes.

A "morpholino oligomer" or "PMO" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. An exemplary"morpholino" oligomer comprises morpholino subunit structures linked together by (thio)phosphoramidate or (thio)phosphorodiamidate linkages, joining the morpholino nitrogen of one subunit to the 5' exocyclic carbon of an adjacent subunit, each subunit comprising a purine or pyrimidine base-pairing moiety effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication number WO/2009/064471 all of which are incorporated herein by reference in their entirety. Representative PMOs include PMOs wherein the intersubunit linkages are linkage (A1).

"PMO+" refers to phosphorodiamidate morpholino oligomers comprising any number of (1-piperazino)phosphinylideneoxy, (1-(4-(ω-guanidino-alkanoyl))-piperazino) phosphinylideneoxy linkages (A2 and A3) that have been described previously (see e.g., PCT publication WO/2008/036127 which is incorporated herein by reference in its entirety.

"PMO-X" refers to phosphorodiamidate morpholino oligomers disclosed herein comprising at least one (B) linkage or at least one of the disclosed terminal modifications.

Figures 1B, 1C:
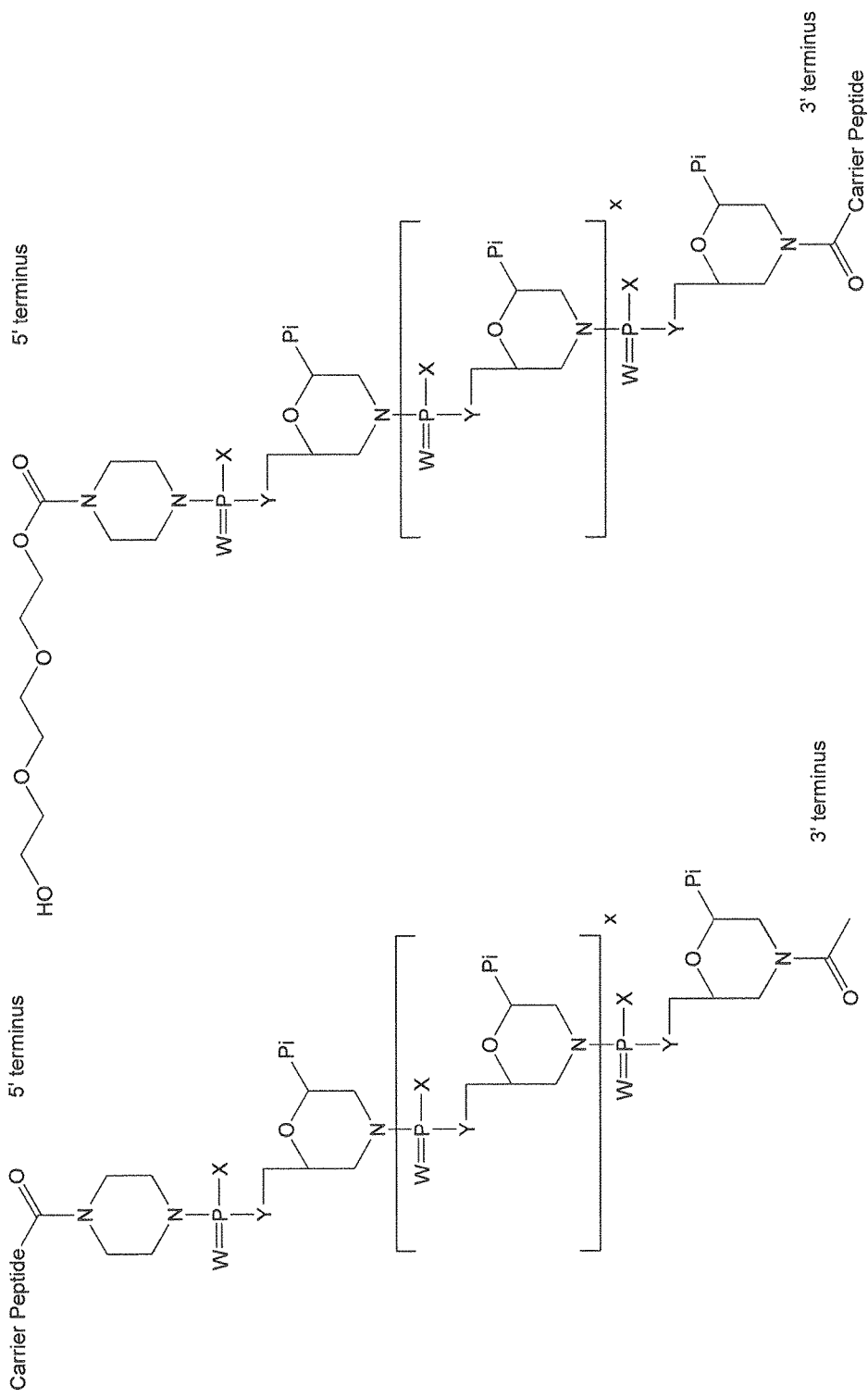
FIG. 1B shows a morpholino oligomer conjugated to a carrier peptide at the 5' end.
FIG. 1C shows a morpholino oligomer conjugated to a carrier peptide at the 3' end.
Figure 1D:
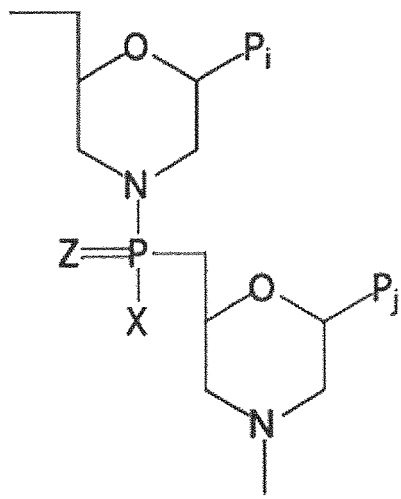
FIGS. 1D-G show the repeating subunit segment of exemplary morpholino oligonucleotides, designated 1D through 1G.
Figure 1E:
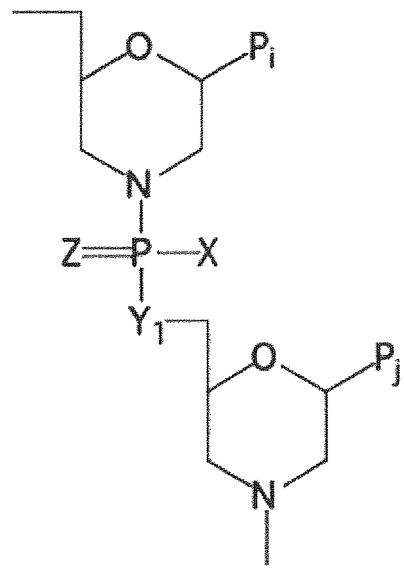
Figure 1F:
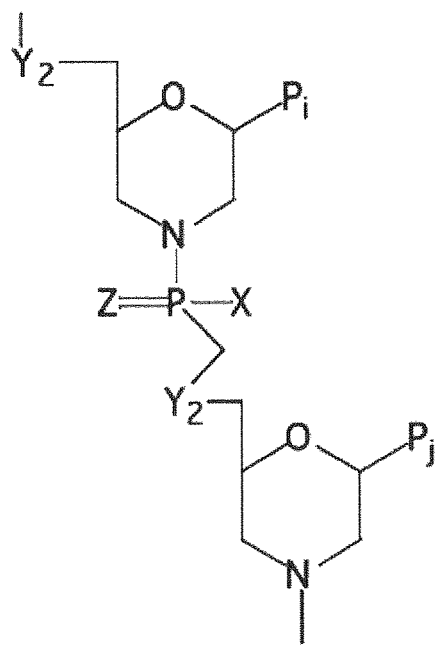
Figure 1G:
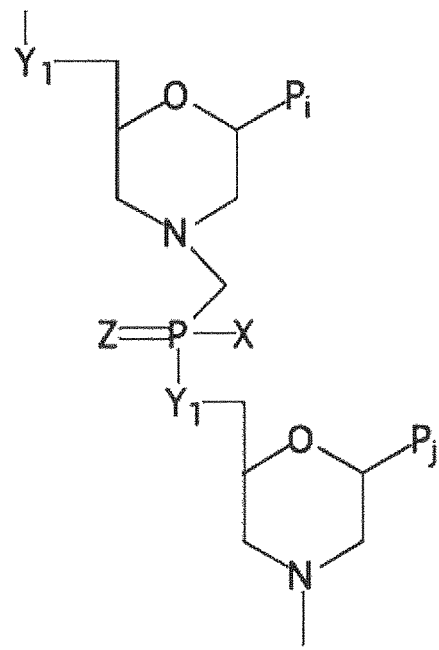
Figure 2:
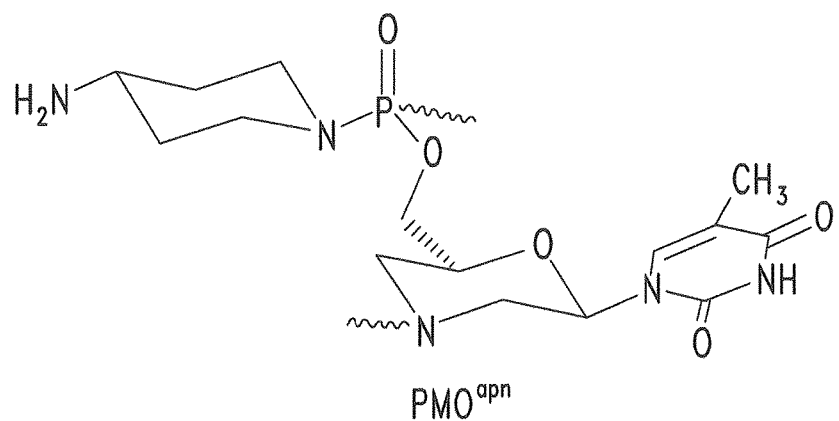
FIG. 2 depicts exemplary intersubunit linkages linked to a morpholino-T moiety.
Figure 2:
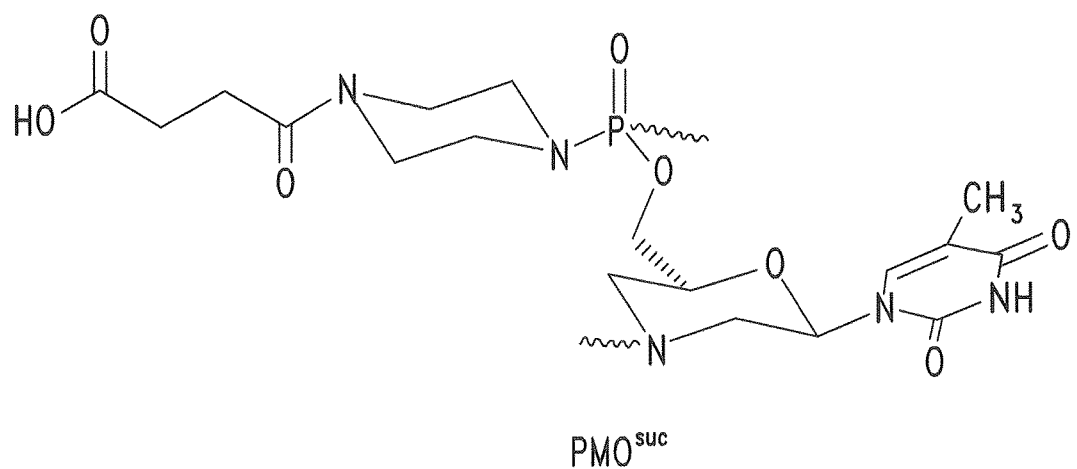

A "phosphoramidate" group comprises phosphorus having three attached oxygen atoms and one attached nitrogen atom, while a "phosphorodiamidate" group (see e.g., FIGS. 1D-E) comprises phosphorus having two attached oxygen atoms and two attached nitrogen atoms. In the uncharged or the modified intersubunit linkages of the oligomers described herein and U.S. Patent Application No. 61/349,783 and Ser. No. 11/801,885, one nitrogen is always pendant to the backbone chain. The second nitrogen, in a phosphorodiamidate linkage, is typically the ring nitrogen in a morpholino ring structure.

"Thiophosphoramidate" or "thiophosphorodiamidate" linkages are phosphoramidate or phosphorodiamidate linkages, respectively, wherein one oxygen atom, typically the oxygen pendant to the backbone, is replaced with sulfur.

"Intersubunit linkage" refers to the linkage connecting two morpholino subunits, for example structure (I).

"Charged", "uncharged", "cationic" and "anionic" as used herein refer to the predominant state of a chemical moiety at near-neutral pH, e.g., about 6 to 8. For example, the term may refer to the predominant state of the chemical moiety at physiological pH, that is, about 7.4.

"Lower alkyl" refers to an alkyl radical of one to six carbon atoms, as exemplified by methyl, ethyl, n-butyl, i-butyl, t-butyl, isoamyl, n-pentyl, and isopentyl. In certain embodiments, a "lower alkyl" group has one to four carbon atoms. In other embodiments a "lower alkyl" group has one to two carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and/or relatively non-polar groups such as methyl, ethyl, methoxy, ethoxy, or fluoro.

An oligonucleotide or antisense oligomer "specifically hybridizes" to a target polynucleotide if the oligomer hybridizes to the target under physiological conditions, with a Tm greater than 37° C., greater than 45° C., preferably at least 50° C., and typically 60° C.-80° C. or higher. The "Tm" of an oligomer is the temperature at which 50% hybridizes to a complementary polynucleotide. Tm is determined under standard conditions in physiological saline, as described, for example, in Miyada et al., *Methods Enzymol.* 154:94-107 (1987). Such hybridization may occur with "near" or "substantial" complementary of the antisense oligomer to the target sequence, as well as with exact complementarity.

Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

A first sequence is an "antisense sequence" with respect to a second sequence if a polynucleotide whose sequence is the first sequence specifically binds to, or specifically hybridizes with, the second polynucleotide sequence under physiological conditions.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence.

The "backbone" of an oligonucleotide analog (e.g., an uncharged oligonucleotide analogue) refers to the structure supporting the base-pairing moieties; e.g., for a morpholino oligomer, as described herein, the "backbone" includes morpholino ring structures connected by intersubunit linkages (e.g., phosphorus-containing linkages). A "substantially uncharged backbone" refers to the backbone of an oligonuceltoide analogue wherein less than 50% of the intersubunit linkages are charged at near-neutral pH. For example, a substantially uncharged backbone may comprise less than 50%, less than 40%, less than 30%, less than 20%, less than 10%, less than 5% or even 0% intersubunit linkages which are charged at near neutral pH. In some embodiments, the substantially uncharged backbone comprises at most one charged (at physiological pH) intersubunit linkage for every four uncharged (at physiological pH) linkages, at most one for every eight or at most one for every sixteen uncharged linkages. In some embodiments, the nucleic acid analogs described herein are fully uncharged.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." Preferably, the oligonucleotide analog compounds employed in the presently described methods have at most one mismatch with the target sequence per every 10 nucleotides, and preferably at most one mismatch out of 20. Alternatively, the antisense oligomers employed have at least 80%, at least 90% sequence homology or at least 95% sequence homology, with the exemplary targeting sequences as designated herein. For purposes of complementary binding to an RNA target, and as discussed below, a guanine base may be complementary to either a cytosineor uracil RNA base.

A "heteroduplex" refers to a duplex between an oligonculeotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane.

The terms "modulating expression" and/or "antisense activity" refer to the ability of an antisense oligomer to either enhance or, more typically, reduce the expression of a given protein, by interfering with the expression or translation of RNA. In the case of reduced protein expression, the antisense oligomer may directly block expression of a given gene, or contribute to the accelerated breakdown of the RNA transcribed from that gene. Morpholino oligomers as described herein are believed to act via the former (steric blocking) mechanism. Preferred antisense targets for steric blocking oligomers include the ATG start codon region, splice sites, regions closely adjacent to splice sites, and 5'-untranslated region of mRNA, although other regions have been successfully targeted using morpholino oligomers.

An "amino acid subunit" is generally an α-amino acid residue (—CO—CHR—NH—); but may also be a β- or other amino acid residue (e.g. —CO—CH$_2$CHR—NH—), where R is an amino acid side chain.

The term "naturally occurring amino acid" refers to an amino acid present in proteins found in nature. The term "non-natural amino acids" refers to those amino acids not present in proteins found in nature; examples include beta-alanine β-Ala) and 6-aminohexanoic acid (Ahx).

An "effective amount" or "therapeutically effective amount" refers to an amount of antisense oligomer administered to a mammalian subject, either as a single dose or as part of a series of doses, which is effective to produce a desired therapeutic effect, typically by inhibiting translation of a selected target nucleic acid sequence.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

II. Carrier Peptides

A. Properties of the Carrier Peptide

As noted above, the present disclosure is directed to conjugates of carrier peptides and nucleic acid analogues. The carrier peptides are generally effective to enhance cell penetration of the nucleic acid analogues. Furthermore, Applicants have surprisingly discovered that including a glycine (G) or proline (P) amino acid subunit between the nucleic acid analogue and the remainder of the carrier peptide (e.g., at the carboxy or amino terminus of the carrier peptide) reduces the toxicity of the conjugate, while the efficacy remains the same or is improved relative to conjugates with different linkages between the carrierpeptide and nucleic acid analogue. Thus the presently disclosed conjugates have a better therapeutic window and are more promising drug candidates than other peptide-oligomer conjugates.

In addition to reduced toxicity, the presence of a glycine or proline amino acid subunit between the nucleic acid analogue and the carrier peptide is believed to provide additional advantages. For example, glycine is inexpensive and is easily coupled to the nucleic acid analogue (or optional linker) without any possibility of racemization. Similarily, proline is easily coupled without racemization and also provides carrier peptides which are not helix formers. The hydrophobicity of proline may also confer certain advantages with respect to interaction of the carrier peptide with the lipid bilayer of cells, and carrier peptides comprising multiple prolines (for example in certain embodiments) may resist G-tetraplex formation. Finally, in certain embodiments, when the proline moiety is adjacent to an arginine amino acid subunit, the proline moiety confers metabolic to the conjugates since the argine-proline amide bond is not cleavable by common endopeptidases.

As noted above, conjugates comprising carrier peptides linked to nucleic acid analogues via a glycine or proline amino acid subunit have lower toxicity and similar efficacy compared to other known conjugates. Experiments performed in support of the present application show that kidney toxicity markers are much lower with the presently disclosed conjugates compared to other conjugates (see e.g., kidney injury marker (KIM) and blood urea nitrogen (BUN) data described inExample 30). While not wishing to be bound by theory, the present inventors believe the reduced toxicity of the disclosed conjugates may be related to the absence of unnatural amino acids such as aminohexanoic acid or β-alanine in the portion of the peptide which is attached to the nucleic acid analogue (e.g., the carboxy terminus). Since these unnatural amino acids are not cleaved in vivo, it is believed that toxic concentrations of the uncleaved peptides may accumulate and cause toxic effects.

The glycine or proline moiety may be at either the amino or carboxy terminus of the carrier peptide, and in some instances, the carrier peptide may be linked to the nucleic acid analogue directly via the glycine or proline subunit or the carrier peptide may be linked to the nucleic acid analogue via an optional linker.

In one embodiment, the present disclosure is directed to a conjugate comprising:
 (a) a carrier peptide comprising amino acid subunits; and
 (b) a nucleic acid analogue comprising a substantially uncharged backbone and a targeting base sequence for sequence-specific binding to a target nucleic acid;
wherein:
 two or more of the amino acid subunits are positively charged amino acids, the carrier peptide comprises a glycine (G) or proline (P) amino acid subunit at a carboxy terminus of the carrier peptide and the carrier peptide is covalently attached to the nucleic acid analogue. In some embodiments, no more than seven contiguous amino acid subunits are arginine, for example 6 or fewer contiguous amino acid subunits are arginine. In some embodiments, the carrier peptide comprises a glycine amino acid subunit at the carboxy terminus. In other embodiments, the carrier peptide comprises a proline amino acid subunit at the carboxy terminus. In still other embodiments, the carrier peptide comprises a single glycine or proline at the carboxy terminus (i.e., does not comprise a glycine or proline dimmer or trimer, etc. at the carboxy terminus).

In certain embodiments, the carrier peptide, when conjugated to an antisense oligomer having a substantially uncharged backbone, is effective to enhance the binding of the antisense oligomer to its target sequence, relative to the antisense oligomer in unconjugated form, as evidenced by:
 (i) a decrease in expression of an encoded protein, relative to that provided by the unconjugated oligomer, when binding of the antisense oligomer to its target sequence is effective to block a translation start codon for the encoded protein, or
 (ii) an increase in expression of an encoded protein, relative to that provided by the unconjugated oligomer, when binding of the antisense oligomer to its target sequence is effective to block an aberrant splice site in a pre-mRNA which encodes said protein when correctly spliced. Assays suitable for measurement of these effects are described further below. In one embodiment, conjugation of the peptide provides this activity in a cell-free translation assay, as described herein. In some embodiments, activity is enhanced by a factor of at least two, a factor of at least five or a factor of at least ten.

Alternatively or in addition, the carrier peptide is effective to enhance the transport of the nucleic acid analog into a cell, relative to the analog in unconjugated form. In certain embodiments, transport is enhanced by a factor of at least two, a factor of at least two, a factor of at least five or a factor of at least ten.

In other embodiments, the carrier peptide is effective to decrease the toxicity (i.e., increase maximum tolerated dose) of the conjugate, relative to a conjugate comprising a carrier peptide lacking the terminal glycine or proline amino subunits. In certain embodiments, toxicity is decreased by a factor of at least two, a factor of at least two, a factor of at least five or a factor of at least ten.

A further benefit of the peptide transport moiety is its expected ability to stabilize a duplex between an antisense oligomer and its target nucleic acid sequence. While not wishing to be bound by theory, this ability to stabilize a duplex may result from the electrostatic interaction between the positively charged transport moiety and the negatively charged nucleic acid.

The length of the carrier peptide is not particularly limited and varies in different embodiments. In some embodiments, the carrier peptide comprises from 4 to 40 amino acid subunits. In other embodiments, the carrier peptide comprises from 6 to 30, from 6 to 20, from 8 to 25 or from 10 to 20 amino acid subunits. In some embodiments, the carrier peptide is straight, while in other embodiments it is branched.

In some embodiments, the carrier peptides are rich in positively charged amino acid subunits, for example arginine amino acid subunits. A carrier peptide is "rich" in positively charged amino acids if at least 10% of the amino acid subunits are positively charged. For example, in some embodiments at least 20%, at least 30%, at least 40%, at least 50%, at least 60%, at least 70%, at least 80% or at least 90% of the amino acid subunits are positively charged. In even other embodiments, all the amino acid subunits, except the glycine or proline amino acid subunit, are positively charged. In still other embodiment, all of the positively charged amino acid subunits are arginine.

In other embodiments, the number of positively charged amino acid subunits in the carrier peptide ranges from 1 to 20, for example from 1 to 10 or from 1 to 6. In certain embodiments, the number of positively charged amino acids in the carrier peptide is 1, 2, 3, 4, 5, 6, 7, 8, 9, 10, 11, 12, 13, 14, 15, 16, 17, 18, 19 or 20.

The positively charged amino acids can be naturally occurring, non-naturally occurring, synthetic, modified or analogues of naturally occurring amino acids. For instance, modified amino acids with a net positive charge may be specifically designed for use in the invention as described in more detail below. A number of different types of modification to amino acids are well known in the art. In certain embodiments, the positively charged amino acids are histidine (H), lysine (K) or arginine (R). In other embodiments, the carrier peptide comprises only natural amino acid subunits (i.e., does not contain unnatural amino acids). In other embodiments, the terminal amino acids may be capped, for example with an acetyl, benzoyl or stearyl moiety, for example on the N-terminal end.

Any number, combination and/or sequence of H, K and/or R may be present in the carrier peptide. In some embodiments, all of the amino acid subunits, except the carboxy terminal glycine or proline, are positively charged amino acids. In other embodiments, at least one of the positively charged amino acids is arginine. For example, in some embodiments, all of the positively charged amino acids are arginine, and in even other embodiments the carrier peptide consists of arginine and the carboxy terminal glycine or proline. In yet other embodiments, the carrier peptide comprises no more than seven contiguous arginines, for example no more than six contiguous arginines.

Other types of positively charged amino acids are also envisioned. For example, in certain embodiments, at least one of the positively charged amino acids is an arginine analog. For example, the arginine analog may be a cationic α-amino acid comprising a side chain of the structure $R^aN=C(NH_2)R^b$, where $R^a$ is H or $R^c$; $R^b$ is $R^c$, $NH_2$, $NHR$, or $N(R^c)_2$, where $R^c$ is lower alkyl or lower alkenyl and optionally comprises oxygen or nitrogen or $R^a$ and $R^b$ may together form a ring; and wherein the side chain is linked to the amino acid via $R^a$ or $R^b$. The carrier peptides may comprise any number of these arginine analogues.

The positively charged amino acids may occur in any sequence within the carrier peptide. For example, in some embodiments the positively charged amino acids may alternate or may be sequential. For example, the carrier peptide may comprise the sequence $(R^d)_m$, wherein $R^d$ is independently, at each occurrence, a positively charged amino acid and m is an integer ranging from 2 to 12, from 2 to 10, from 2 to 8 or from 2 to 6. For example, in certain embodiments, $R^d$ is arginine, and the carrier peptide comprises a sequence selected from $(R)_4$, $(R)_5$, $(R)_6$, $(R)_7$ and $(R)_8$, or selected from $(R)_4$, $(R)_5$, $(R)_6$ and $(R)_7$ for example in specific embodiments the carrier peptide comprises the sequence $(R)_6$, for example $(R)_6G$ or $(R)_6P$.

In other embodiments, the carrier peptide consists of the sequence $(R^d)_m$ and the carboxy terminal glycine or proline, wherein $R^d$ is independently, at each occurrence, a positively charged amino acid and m is an integer ranging from 2 to 12, from 2 to 10, from 2 to 8 or from 2 to 6. In certain embodiments $R^d$ is independently, at each occurrence, arginine, histidine or lysine. For example, in certain embodiments, $R^d$ is arginine, and the carrier peptide consists of a sequence selected from $(R)_4$, $(R)_5$, $(R)_6$, $(R)_7$ and $(R)_8$ and the carboxy terminal glycine or proline. For example in specific embodiments the carrier peptide consists of the sequence $(R)_6G$ or $(R)_6P$.

In some other embodiments, the carrier peptide may comprise one or more hydrophobic amino acid subunits, the hydrophobic amino acid subunits comprising a substituted or unsubstituted alkyl, alkenyl, alkynyl, aryl or aralkyl side chain wherein the alkyl, alkenyl and alkynyl side chain includes at most one heteroatom for every six carbon atoms acid. In some embodiments, the hydrophobic amino acid is phenylalanine (F). For example, the carrier peptide may comprise two or more contingous hydrophobic amino acids such as phenylalanine (F), for example two contiguous phenylalanine moieties. The hydrophobic amino acid(s) may be at any point in the carrier peptide sequence.

In other embodiments, the carrier peptide comprises the sequence $[(R^dY^bR^d)_x(R^dR^dY^b)_y]_z$, or $[(R^dR^dY^b)_y(R^dY^bR^d)_x]_z$ wherein $R^d$ is independently, at each occurrence, a positively charged amino acid, x and y are independently, at each occurrence, 0 or 1, provided that x+y is 1 or 2, z is 1, 2, 3, 4, 5 or 6 and $Y^b$ is

wherein n is 2 to 7 and each $R^e$ is independently, at each occurrence, hydrogen or methyl. In some of these embodiments, $R^d$ is independently, at each occurrence arginine, histidine or lysine. In other embodiments, each $R^d$ is arginine. In other embodiments, n is 5 and $Y^b$ is an aminohexanoic acid moiety. In other embodiments, n is 2 and $Y^b$ is a β-alanine moiety. In yet other embodiments, $R^e$ is hydrogen.

In certain embodiments of the foregoing, x is 1 and y is 0, and the carrier peptide comprises the sequence $(R^dY^bR^d)_z$. In other embodiments, n is 5 and $Y^b$ is an aminohexanoic acid moiety. In other embodiments, n is 2 and $Y^b$ is a β-alanine moiety. In yet other embodiments, $R^e$ is hydrogen.

In still other embodiments of the foregoing, x is 0 and y is 1, and the carrier peptide comprises the sequence $(R^dR^dY^b)_z$. In other embodiments, n is 5 and $Y^b$ is an aminohexanoic acid moiety. In other embodiments, n is 2 and $Y^b$ is a β-alanine moiety. In yet other embodiments, $R^e$ is hydrogen.

In other embodiments, the carrier peptide comprises the sequence $(R^dY^b)_p$, wherein $R^d$ and $Y^b$ are as defined above and p is an integer ranging from 2 to 8. In other embodiments, each $R^d$ is arginine. In other embodiments, n is 5 and $Y^b$ is an aminohexanoic acid moiety. In other embodiments, n is 2 and $Y^b$ is a β-alanine moiety. In yet other embodiments, $R^e$ is hydrogen.

In other embodiments, the carrier peptide comprises the sequence ILFQY (SEQ ID NO: 576). The peptides may comprise the ILFQY (SEQ ID NO: 576) sequence in addition to any of the other sequences disclosed herein. For example the carrier peptide may comprise ILFQY (SEQ ID NO: 576) and $[(R^dY^bR^d)_x(R^dR^dY^b)_y]_z$, $[(R^dR^dY^b)_y(R^dY^bR^d)_x]_z$, $(R^dY^b)_p$ or combinations thereof wherein $R^d$, x, y and $Y^b$ are as defined above. The $[(R^dY^bR^d)_x(R^dR^dY^b)_y]_z$, $[(R^dR^dY^b)_y(R^dY^bR^d)_x]_z$ or $(R^dY^b)_p$ sequence may be on the amino terminus, carboxy terminus or both of the ILFQY (SEQ ID NO: 576) sequence. In certain embodiments, x is 1 and y is 0 and the carrier peptide comprises (R$^d$Y$^b$R$^d$)$_z$ linked to the ILFQY (SEQ ID NO: 576) sequence via an optional Z linker.

In other related embodiments, the carrier peptide comprises the sequence ILFQ (SEQ ID NO: 577), IWFQ (SEQ ID NO: 578) or ILIQ (SEQ ID NO: 579). Other embodiments include carrier peptides which comprise the sequence PPMWS (SEQ ID NO: 580), PPMWT (SEQ ID NO: 581), PPMFS (SEQ ID NO: 582) or PPMYS (SEQ ID NO: 583). The carrier peptide may comprise these sequences in addition to any of the other sequences described herein, for example in addition to the sequences [(R$^d$Y$^b$R$^d$)$_x$(R$^d$R$^d$Y$^b$)$_y$]$_z$, [(R$^d$R$^d$Y$^b$)$_y$(R$^d$Y$^b$R$^d$)$_x$]$_z$ or (R$^d$Y$^b$)$_p$ wherein R$^d$, x, y and Y$^b$ are as defined above.

Some embodiments of the carrier peptide include modifications to naturally occurring amino acid subunits, for example the amino terminal or carboxy terminal amino acid subunit may be modified. Such modifications include capping the free amino or free carboxy with a hydrophobic group. For example, the amino terminus may be capped with an acetyl, benzoyl or stearoyl moiety. For example, any of the pepetide sequences in Table 1 may have such modifications even if not specifically depticted in the table. In these embodiments, the amino terminus of the carrier peptide can be depicted as follows:

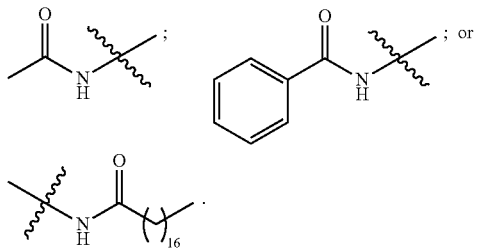

In yet other embodiments, the carrier peptide comprises at least one of alanine, asparagine, cysteine, glutamine, glycine, histidine, lysine, methionine, serine or threonine.

In some of the embodiments disclosed herein, the carrier peptide consists of the noted sequences and the carboxy terminal glycine or proline amino acid subunit.

In some embodiments the carrier peptide does not consist of the following sequences (amino terminal to carboxy terminal): R$_6$G, R$_7$G, R$_8$G, R$_5$GR$_4$G, R$_5$F$_2$R$_4$G, Tat-G, rTat-G, (RXR$_2$G$_2$)$_2$ or (RXR$_3$X)$_2$G. In yet other embodiments, the carrier peptide does not consist of R$_8$G, R$_9$G or R$_9$F$_2$G. In still other embodiments, the carrier peptide does not consist of the following sequences: Tat-G, rTat-G, R$_9$F$_2$G, R$_5$F$_2$R$_4$, R$_4$G, R$_5$G, R$_6$G, R$_7$G, R$_8$G, R$_9$G, (RXR)$_4$G, (RXR)$_5$G, (RXRRBR)$_2$G, (RAR)$_4$F$_2$ or (RGR)$_4$F$_2$. In other embodiments, the carrier peptide does not consist of "Penetratin" or "R$_6$Pen".

In another aspect, the present disclosure provides a peptide-nucleic acid analog conjugate, comprising
a nucleic acid analog having a substantially uncharged backbone and a targeting base sequence, and
covalently linked to the nucleic acid analog, a peptide comprising a carboxy terminal glycine or proiline amino acid subunit and consisting of 8 to 16 additional other subunits selected from R$^d$ subunits, Y subunits, and optional Z subunits, including at least eight R$^d$ subunits, at least two Y subunits, and at most three Z subunits, where >50% of said subunits are R$^d$ subunits, and where (a) each R$^d$ subunit independently represents arginine or an arginine analog, the arginine analog being a cationic α-amino acid comprising a side chain of the structure R$^a$N=C(NH$_2$)R$^b$, where R$^a$ is H or R$^c$; R$^b$ is R$^c$, NH$_2$, NHR, or N(R$^c$)$_2$, where R$^c$ is lower alkyl or lower alkenyl and optionally comprises oxygen or nitrogen or R$^a$ and R$^b$ may together form a ring; and wherein the side chain is linked to the amino acid via R$^a$ or R$^b$;

(b) the at least two Y subunits are Y$^a$ or Y$^b$, wherein:
(i) each Y$^a$ is independently a neutral α-amino acid subunits having side chains independently selected from substituted or unsubstituted alkyl, alkenyl, alkynyl, aryl, and aralkyl, wherein said side chain, when selected from substituted alkyl, alkenyl, and alkynyl, includes at most one heteroatom for every two, preferably every four, and more preferably every six carbon atoms, and wherein said subunits are contiguous or are flanking a linker moiety, and
(ii) Y$^b$ is:

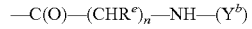

—C(O)—(CHR$^e$)$_n$—NH—(Y$^b$)

wherein n is 2 to 7 and each R$^e$ is independently, at each occurrence, hydrogen or methyl; and (c) Z represents an amino acid subunit selected from alanine, asparagine, cysteine, glutamine, glycine, histidine, lysine, methionine, serine, threonine and amino acids having side chains which are one- or two-carbon homologs of naturally occurring side chains, excluding side chains which are negatively charged at physiological pH (e.g. carboxylate side chains). In some embodiments, the side chains are neutral. In other embodiments, the Z side chains are side chains of naturally occurring amino acids. The optional Z subunits in some embodiments are selected from alanine, glycine, methionine, serine, and threonine. The carrier peptide may include zero, one, two, or three Z subunits, and in some embodiments includes at most two Z subunits.

In selected embodiments, the carrier peptide has exactly two Y subunits of type Y$^a$, which are contiguous or are flanking a cysteine subunit. In some embodiments, the two Y$^a$ subunits are contiguous. In other embodiments, side chains for Y$^a$ subunits include side chains of naturally occurring amino acids and one- or two-carbon homologs thereof, excluding side chains which are charged at physiological pH. Other possible side chains are side chains of naturally occurring amino acids. In further embodiments, the side chain is an aryl or aralkyl side chain; for example, each Y$^a$ may be independently selected from phenylalanine, tyrosine, tryptophan, leucine, isoleucine, and valine.

In selected embodiments, each Y$^a$ is independently selected from phenylalanine and tyrosine; in further embodiments, each Y$^a$ is phenylalanine. This includes, for example, conjugates which consist of arginine subunits, phenylalanine subunits, the glycine or proline amino acid subunit, an optional linker moiety, and the nucleic acid analog. One such conjugate includes a peptide having the formula Arg$_9$Phe$_2$aa, where aa is glycine or proline.

The foregoing carrier peptides may also comprise ILFQY (SEQ ID NO: 576), ILFQ (SEQ ID NO: 577), IWFQ (SEQ ID NO: 578) or ILIQ (SEQ ID NO: 579). Other embodiments include the foregoing carrier peptides which comprise the sequence PPMWS (SEQ ID NO: 580), PPMWT (SEQ ID NO: 581), PPMFS (SEQ ID NO: 582) or PPMYS (SEQ ID NO: 583).

The peptide-oligomer conjugates of the invention are more effective than the unconjugated oligomer in various functions, including: inhibiting expression of targeted mRNA in a protein expression system, including cell free translation systems; inhibiting splicing of targeted pre-mRNA; and inhibiting replication of a virus, by targeting cis-acting elements which control nucleic acid replication or mRNA transcription of the virus.

Also included within the scope of the present invention are conjugates of other pharmacological agents (i.e., not a nucleic acid analog) and the carrier peptide. Specifically, some embodiments provide a conjugate comprising:
   (a) a carrier peptide comprising amino acid subunits; and
   (b) a pharmacological agent;
wherein:
   two or more of the amino acid subunits are positively charged amino acids, the carrier peptide comprises a glycine (G) or proline (P) amino acid subunit at a carboxy terminus of the carrier peptide and the carrier peptide is covalently attached to the pharmacological agent. The carrier peptide in these embodiments may be any of the carrier peptides described herein. Methods for delivering the pharmacological agent by conjugating it to the carrier peptide are also provided.

The pharmacological agent to be delivered is may be a biologically active agent, e.g. a therapeutic or diagnostic agent, although it may be a compound employed for detection, such as a fluorescent compound. Biologically active agents include drug substances selected from biomolecules, e.g. peptides, proteins, saccharides, or nucleic acids, particularly antisense oligonucleotides, or "small molecule" organic or inorganic compounds. A "small molecule" compound may be defined broadly as an organic, inorganic, or organometallic compound which is not a biomolecule as described above. Typically, such compounds have molecular weights of less than 1000, or, in one embodiment, less than 500.

In one embodiment, the pharmacological agent to be delivered does not include single amino acids, dipeptides, or tripeptides. In another embodiment, it does not include short oligopeptides; that is, oligopeptides having fewer than six amino acid subunits. In a further embodiment, it does not include longer oligopeptides; that is, oligopeptides having between seven and 20 amino acid subunits. In a still further embodiment, it does not include polypeptides, having greater than 20 amino acid subunits, or proteins.

The carrier peptide is effective to enhance the transport of the pharmacological agent into a cell relative to the pharmacological agent in unconjugated form and/or with less toxicity, relative to the pharmacological agent conjugated to a corresponding peptide lacking the glycing or proline subunits. In some embodiments, transport is enhanced by a factor of at least two, at least five or at least ten. In other embodiments, toxicity is decreased (i.e., maximum tolerated dose increased) by a factor of at least two, at least five or at least ten.

B. Peptide Linkers

The carrier peptide can be linked to the agent to be delivered (e.g., nuceleic acid analogue, pharmacological agent, etc.) by a variety of methods available to one of skill in the art. In some embodiments, the carrier peptide is linked to the nucleic acid analogue directly without an intervening linker. In this regard, formation of an amide bond between the terminal amino acid and a free amine of free carboxyl on the nucleic acid analogue may be useful for forming the conjugate. In certain embodiments, the carboxy terminal glycine or proline subunit is linked directly to the 3' end of the nucleic acid analogue, for example the carrier peptide may be linked by forming an amide bond between the carboxy terminal glycine or proline moiety and the 3' morpholino ring nitrogen (see e.g., FIG. 1C).

In some embodiments, the nucleic acid analog is conjugated to the carrier peptide via a linker moiety selected from a $Y^a$ or $Y^b$ subunit, a cysteine subunit, and an uncharged, non-amino acid linker moiety. In other embodiments, the nucleic acid analogue is linked to the carrier peptide directly via the glycine or proline moiety at either the 5' or 3' end of the nucleic acid analogue. In some embodiments, the carrier peptide is linked directly via the glycine or proline amino acid subunit to the 3' of the nucleic acid analogue, for example directly linked to the 3' morpholino nitrogen via an amide bond.

In other embodiments, the conjugates comprise a linking moiety between the terminal glycine or proline amino acid subunit. In some of the embodiments, the linker is up to 18 atoms in length comprising bonds selected from alkyl, hydroxyl, alkoxy, alkylamino, amide, ester, carbonyl, carbamate, phosphorodiamidate, phosphoroamidate, phosphorothioate and phosphodiester. In certain embodiments, the linker comprises phosphorodiamidate and piperazine bonds. For example, in some embodiments the linker has the following structure (XXIX):

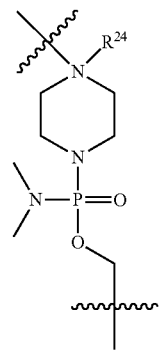

(XXIX)

wherein $R^{24}$ is absent, H or $C_1$-$C_6$ alkyl. In certain embodiments, $R^{24}$ is absent and in other embodiments structure (XXIX) links the 5' end of a nucleic acid analogue (e.g., a morpholino oligomer) to the carrier peptide (see e.g., FIG. 1B).

In some embodiments, the side chain moieties of the $R^d$ subunits are independently selected from guanidyl (HN=C(NH$_2$)NH—), amidinyl (HN=C(NH$_2$)C<), 2-aminodihydropyrimidyl, 2-aminotetrahydropyrimidyl, 2-aminopyridinyl and 2-amino pyrimidinyl.

Multiple carrier peptides can be attached to a single compound if desired; alternatively, multiple compounds can be conjugated to a single transporter. The linker between the carrier peptide and the nucleic acid analogue may also consist of natural or non-natural amino acids (e.g., 6-aminohexanoic acid or β-alanine). The linker may also comprise a direct bond between the carboxy terminus of a transporter peptide and an amine or hydroxy group of the nucleic acid analogue (e.g., at the 3' morpholino nitrogen or 5' OH), formed by condensation promoted by e.g. carbodiimide.

In general, the linker may comprise any nonreactive moiety which does not interfere with transport or function of the conjugate. Linkers can be selected from those which are non-cleavable under normal conditions of use, e.g., containing an ether, thioether, amide, or carbamate bond. In other embodiments, it may be desirable to include a linkage between the carrier peptide and compound (e.g., oligonucleotide analogue, pharmacological agent, etc.) which is cleavable in vivo. Bonds which are cleavable in vivo are known in the art and include, for example, carboxylic acid esters, which are hydrolyzed enzymatically, and disulfides, which are cleaved in the presence of glutathione. It may also be feasible to cleave a photolytically cleavable linkage, such as an ortho-nitrophenyl ether, in vivo by application of radiation of the appropriate wavelength. Exemplary heterobifunctional linking agents which further contain a cleavable disulfide group include N-hydroxysuccinimidyl 3-[(4-azidophenyl)dithio]propionate and others described in Vanin, E. F. and Ji, T. H., Biochemistry 20:6754-6760 (1981).

C. Exemplary Carrier Peptides

A Table of sequences of exemplary carrier peptides and oligonucleotide sequences is provided below in Table 1. In some embodiments, the present disclosure provides a peptide oligomer conjugate, wherein the peptide comprises or consists of any one of the peptide sequences in Table 1. In another embodiment, the the nucleic acid analogue comprises or consists of any of the oligonucleotide sequences in Table 1. In still other embodiments, the present disclosure provides a peptide oligomer conjugate, wherein the peptide comprises or consists of any one of the peptide sequences in Table 1, and the nucleic acid analogue comprises or consists of any of the oligonucleotide sequences in Table 1. In other embodiments, the disclosure provides a peptide comprising or consisting of any one of the sequences in Table 1.

TABLE 1

Exemplary Carrier Peptides and Oligonucleotide Sequences

| Name | Sequence (Amino to Carboxy Terminus or 5' to 3') | SEQ ID NO. |
| --- | --- | --- |
| (RFF)$_3$; CP0407 | RFFRFFRFF-aa | 89 |
| RTR | RTRTRFLRRT-aa | 90 |
| RFFR | RFFRFFRFFR-aa | 91 |
| KTR | KTRTKFLKKT-aa | 92 |
| KFF | KFFKFFKFF-aa | 93 |
| KFFK | KFFKFFKFFK-aa | 94 |
| (RFF)$_2$ | RFFRFF-aa | 95 |
| (RFF)$_2$R | RFFRFFR-aa | 96 |
| RX | RXXRXXR-aa | 97 |
| (RXR)$_4$; P007 | RXRRXRRXRRXR-aa | 98 |
| Tat$_{47-58}$ | YGRKKRRQRRR-aa | 99 |
| Tat$_{48-58}$ | GRKKRRQRRR-aa | 100 |
| Tat$_{49-58}$ | RKKRRQRRR-aa | 101 |
| Penetratin | RQIKIWFQNRRMKWKKGG-aa | 102 |
| Transportan | GWTLNSAGYLLGKINLKALAALAKKIL-aa | 103 |
| 2XHph-1 | YARVRRRGPRGYARVRRRGPRR-aa | 104 |
| Hph-1 | YARVRRRGPRR-aa | 105 |
| Sim-2 | AKAARQAAR-aa | 106 |
| HSV1 VP22 | DAATATRGRSAASRPTERPRAPARSASRPRRPVE-aa | 107 |
| Pep-1 | KETWWETWWTEWSQPKKKRKV-aa | 108 |
| Pep-2 | KETWFETWFTEWSQPKKKRKV-aa | 109 |
| ANTP | RQIKIWFQNRRMKWKK-aa | 110 |
| R$_6$Pen | RRRRRR-RQIKIWFQNRRMKWKKGG-aa | 111 |
| rTat | RRRQRRKKRC-aa | 112 |
| pTat | CYGRKKRRQRRR-aa | 113 |
| R$_9$F$_2$ | RRRRRRRRRFFC-aa | 114 |
| R$_9$CF$_2$ RRRRRRRRRCFF | RRRRRRRRRCFF-aa | 115 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| $R_8CF_2R$ | RRRRRRRRCFFR-aa | 116 |
| $R_6CF_2R_3$ | RRRRRRCFFRRR-aa | 117 |
| $R_5FCFR_4$ | RRRRRFCFRRRR-aa | 118 |
| $R_5F_2R_4$ | RRRRRFFRRRR-aa | 119 |
| $R_4CF_2R_5$ | RRRRCFFRRRRR-aa | 120 |
| $R_2CF_2R_7$ | RRCFFRRRRRRR-aa | 121 |
| $CF_2R_9$ | CFFRRRRRRRRR-aa | 122 |
| $CR_9F_2$ | CRRRRRRRRRFF-aa | 123 |
| $F_2R_9$ | FFRRRRRRRRR-aa | 124 |
| $R_5F_2CF_2R_4$ | RRRRRFFCFFRRRR-aa | 125 |
| $R_9I_2$ | RRRRRRRRRII-aa | 126 |
| $R_8F_3$ | RRRRRRRRFFF-aa | 127 |
| $R_9F_4$ | RRRRRRRRRFFFF-aa | 128 |
| $R_8F_2$ | RRRRRRRRFF-aa | 129 |
| $R_6F_2$ | RRRRRRFF-aa | 130 |
| $R_5F_2$ | RRRRRFF-aa | 131 |
| $(RRX)_3RR$ | RRXRRXRRXRR-aa | 132 |
| $(RXR)_4$ | RXRXRRXRRRXR-aa | 133 |
| $(XRR)_4$ | XRRXRRXRRXRR-aa | 134 |
| $(RX)_5RR$ | RXRXRXRXRXRR-aa | 135 |
| $(RXR)_3$ | RXRRXRRXR-aa | 136 |
| $(RXR)_2R$ | RXRRXRR-aa | 137 |
| $(RXR)_2$ | RXRRXR-aa | 138 |
| $(RKX)_3RK$ | RKXRKXRKXRK-aa | 139 |
| $(RHX)_3RH$ | RHXRHXRHXRH-aa | 140 |
| $R_8CF_2R$ | RRRRRRRRCFFR-aa | 141 |
| $(RRX)_3RR$ | RRXRRXRRXRR-aa | 142 |
| $(RXR)_4$; P007 | RXRRXRRXRRXR-aa | 143 |
| $(XRR)_4$ | XRRXRRXRRXRR-aa | 144 |
| $(RX)_5R$ | RXRXRXRXRXR-aa | 145 |
| $(RX)_7R$ | RXRXRXRXRXRXRXR-aa | 146 |
| $(RXR)_5$ | RXRRXRRXRRXRRXR-aa | 147 |
| $(RXRRBR)_2$; B | RXRRBRRXRRBR-aa | 148 |
| $(RXR)_3RBR$ | RXRRXRRXRRBR-aa | 149 |
| $(RB)_5RXRBR$ | RBRBRBRBRBRXRBR-aa | 150 |
| RBRBRBRXRBRBRBR | RBRBRBRXRBRBRBR-aa | 151 |
| $X(RB)_3RX(RB)_3R-X$ | XRBRBRBRXRBRBRBR-aa | 152 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| (RBRX)$_4$ | RBRXRBRXRBRXRBR-aa | 153 |
| (RB)$_4$(RX)$_3$R | RBRBRBRBRXRXRXR-aa | 154 |
| RX(RB)$_2$RX(RB)$_3$R | RXRBRBRXRBRBRBR-aa | 155 |
| (RB)$_7$R | RBRBRBRBRBRBRBR-aa | 156 |
| R$_4$ | tg-RRRR-aa | 157 |
| R$_5$ | tg-RRRRR-aa | 158 |
| R$_6$ | tg-RRRRRR-aa | 159 |
| R$_7$ | tg-RRRRRRR-aa | 160 |
| R$_8$ | tg-RRRRRRRR-aa | 161 |
| R$_5$GR$_4$ | tg-RRRRRGRRRR-aa | 162 |
| R$_5$F$_2$R$_4$ | tg-RRRRRFFRRRR-aa | 163 |
| Tat | tg-RKKRRQRRR-aa | 164 |
| rTat | tg-RRRQRRKKR-aa | 165 |
|  | RXRRXR-aa | 166 |
|  | RBRRBR-aa | 167 |
|  | RXRRBR-aa | 168 |
|  | RBRRXR-aa | 169 |
|  | RXRY$^b$RXR-aa | 170 |
|  | RBRY$^b$RBR-aa | 171 |
|  | RXRY$^b$RBR-aa | 172 |
|  | RBRY$^b$RXR-aa | 173 |
|  | RXRILFQYRXR-aa | 174 |
|  | RBRILFQYRBR-aa | 175 |
|  | RXRILFQYRBR-aa | 176 |
|  | RBRILFQYRXR-aa | 177 |
|  | RXRRXRRXR-aa | 178 |
|  | RBRRBRRBR-aa | 179 |
|  | RXRRBRRXR-aa | 180 |
|  | RXRRBRRBR-aa | 181 |
|  | RXRRXRRBR-aa | 182 |
|  | RBRRXRRBR-aa | 183 |
|  | RBRRXRRXR-aa | 184 |
|  | RBRRBRRXR-aa | 185 |
|  | RXRY$^b$RXRRXR-aa | 186 |
|  | RXRRXRY$^b$RXR-aa | 187 |
|  | RXRILFQYRXRRXR-aa | 188 |
|  | RXRRXRILFQYRXR-aa | 189 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | RXRY$^b$RXRY$^b$RXR-aa | 190 |
| | RXRILFQYRXRILFQYRXR-aa | 191 |
| | RXRILFQYRXRY$^b$RXR-aa | 192 |
| | RXRY$^b$RXRILFQYRXR-aa | 193 |
| | RBRY$^b$RBRRBR-aa | 194 |
| | RBRRBRY$^b$RBR-aa | 195 |
| | RBRILFQYRBRRBR-aa | 196 |
| | RBRRBRILFQYRBR-aa | 197 |
| | RBRYRBRY$^b$RBR-aa | 198 |
| | RBRILFQYRBRILFQYRBR-aa | 199 |
| | RBRY$^b$RBRILFQYRBR-aa | 200 |
| | RBRILFQYRBRY$^b$RBR-aa | 201 |
| | RXRY$^b$RBRRXR-aa | 202 |
| | RXRRBRY$^b$RXR-aa | 203 |
| | RXRILFQYRBRRXR-aa | 204 |
| | RXRRBRILFQYRXR-aa | 205 |
| | RXRY$^b$RBRY$^b$RXR-aa | 206 |
| | RXRILFQYRBRILFQYRXR-aa | 207 |
| | RXRY$^b$RBRILFQYRXR-aa | 208 |
| | RXRILFQYRBRY$^b$RXR-aa | 209 |
| | RXRY$^b$RBRRBR-aa | 210 |
| | RXRRBRY$^b$RBR-aa | 211 |
| | RXRILFQYRBRRBR-aa | 212 |
| | RXRRBRILFQYRBR-aa | 213 |
| | RXRY$^b$RBRY$^b$RBR-aa | 214 |
| | RXRILFQYRBRILFQYRBR-aa | 215 |
| | RXRY$^b$RBRILFQYRBR-aa | 216 |
| | RXRILFQYRBRY$^b$RBR-aa | 217 |
| | RXRY$^b$RXRRBR-aa | 218 |
| | RXRRXRY$^b$RBR-aa | 219 |
| | RXRILFQYRXRRBR-aa | 220 |
| | RXRRXR1LFQYRBR-aa | 221 |
| | RXRY$^b$RXRY$^b$RBR-aa | 222 |
| | RXRILFQYRXRILFQYRBR-aa | 223 |
| | RXRY$^b$RXRILFQYRBR-aa | 224 |
| | RXRILFQYRXRY$^b$RBR-aa | 225 |
| | RBRY$^b$RXRRBR-aa | 226 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | RBRRXRY$^b$RBR-aa | 227 |
| | RBRILFQYRXRRBR-aa | 228 |
| | RBRRXRILFQYRBR-aa | 229 |
| | RBRY$^b$RXRY$^b$RBR-aa | 230 |
| | RBRILFQYRXRILFQYRBR-aa | 231 |
| | RBRY$^b$RXRILFQYRBR-aa | 232 |
| | RBRILFQYRXRY$^b$RBR-aa | 233 |
| | RBRY$^b$RXRRXR-aa | 234 |
| | RBRRXRY$^b$RXR-aa | 235 |
| | RBRILFQYRXRRXR-aa | 236 |
| | RBRRXRILFQYRXR-aa | 237 |
| | RBRY$^b$RXRY$^b$RXR-aa | 238 |
| | RBRILFQYRXRILFQYRXR-aa | 239 |
| | RBRY$^b$RXRILFQYRXR-aa | 240 |
| | RBRILFQYRXRY$^b$RXR-aa | 241 |
| | RBRY$^b$RBRRXR-aa | 242 |
| | RBRRBRY$^b$RXR-aa | 243 |
| | RBRILFQYRBRRXR-aa | 244 |
| | RBRRBRILFQYRXR-aa | 245 |
| | RBRY$^b$RBRY$^b$RXR-aa | 246 |
| | RBRILFQYRBRILFQYRXR-aa | 247 |
| | RBRY$^b$RBRILFQYRXR-aa | 248 |
| | RBRILFQYRBRY$^b$RXR-aa | 249 |
| | RXRRXRRXRRXR-aa | 250 |
| | RXRRBRRXRILFQYRXRBRXR-aa | 251 |
| | RXRRBRRXRRBR-aa | 252 |
| | YGRKKRRQRRRP-aa | 253 |
| | RXRRXRRXRRXRXBASSLNIAXC-aa | 254 |
| | RXRRBRRXRILFQYRXRBRXRBASSLNIAXC-aa | 255 |
| | RXRRBRRXRASSLNIARXRBRXRBC-aa | 256 |
| | RXRRBRRXRRBRXBASSLNIA-aa | 257 |
| | THRPPMWSPVWP-aa | 258 |
| | HRPPMWSPVWP-aa | 259 |
| | THRPPMWSPV-aa | 260 |
| | THRPPMWSP-aa | 261 |
| | THRPPMWSPVFP-aa | 262 |
| | THRPPMWSPVYP-aa | 263 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | THRPPMWSPAWP-aa | 264 |
| | THRPPMWSPLWP-aa | 265 |
| | THRPPMWSPIWP-aa | 266 |
| | THRPPMWTPVVWP-aa | 267 |
| | THRPPMFSPVWP-aa | 268 |
| | THRPPMWS-aa | 269 |
| | HRPPMWSPVW-aa | 270 |
| | THRPPMYSPVWP-aa | 271 |
| | THRPPnleWSPVWP-aa (nle = norleucine) | 272 |
| | THKPPMWSPVWP-aa | 273 |
| | SHRPPMWSPVWP-aa | 274 |
| | STFTHPR-aa | 275 |
| | YDIDNRR-aa | 276 |
| | AYKPVGR-aa | 277 |
| | HAIYPRH-aa | 278 |
| | HTPNSTH-aa | 279 |
| | ASSPVHR-aa | 280 |
| | SSLPLRK-aa | 281 |
| | KKRS-aa | 282 |
| | KRSK-aa | 283 |
| | KKRSK-aa | 284 |
| | KSRK-aa | 285 |
| | SRKR-aa | 286 |
| | RKRK-aa | 287 |
| | KSRKR-aa | 288 |
| | QHPPWRV-aa | 289 |
| | THPPTTH-aa | 290 |
| | YKHTPTT-aa | 291 |
| | QGMHRGT-aa | 292 |
| | SRKRK-aa | 293 |
| | KSRKRK-aa | 294 |
| | PKKKRKV-aa | 295 |
| | GKKRSKV-aa | 296 |
| | KSRKRKL-aa | 297 |
| | HSPSKIP-aa | 298 |
| | HMATFHY-aa | 299 |
| | AQPNKFK-aa | 300 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | NLTRLHT-aa | 301 |
| | KKKR-aa | 302 |
| | KKRK-aa | 303 |
| | KKKRK-aa | 304 |
| | RRRRRRQIKIWFQNRRMKWKKGGC-aa | 305 |
| | RRRRRRRQIKIWFQNRRMKWKKGGC-aa | 306 |
| | RQIKIWFQNRRMKWKKGGC-aa | 307 |
| | RRRRRRQIKIWFQNRRMKWKKC-aa | 308 |
| | RXRRXRRXRRQIKIWFQNRRMKWKKGGC-aa | 309 |
| | RRRRRRQIKILFQNRXRXRXRXC-aa | 310 |
| | RXRRXRRXRRXRC-aa | 311 |
| | RXRRXRRXRRXRXC-aa | 312 |
| | RXRRXRRXRIKILFQNRRMKWKKGGC-aa | 313 |
| | RXRRXRRXRIKILFQNRRMKWKKC-aa | 314 |
| | RXRRXRRXRIKILFQNRMKWKKC-aa | 315 |
| | RXRRXRRXRIKILFQNXRMKWKKC-aa | 316 |
| | RXRRXRRXRIKILFQNHRMKWKKC-aa | 317 |
| | RXRRXRRXRIKILFQNXRMKWKKC-aa | 318 |
| | RXRRXRRXRIKILFQNXRMKWKKC-aa | 319 |
| | RXRRXRRXRIKILFQNXRMKWKAC-aa | 320 |
| | RXRRXRRXRIKILFQNXRMKWHKAC-aa | 321 |
| | RXRRXRRXRIKILFQNXRMKWHRC-aa | 322 |
| | RXRXRXRXRIKILFQNRRMKWKKC-aa | 323 |
| | RARARARARIKILFQNRRMKWKKC-aa | 324 |
| | RXRRXRRXRIXILFQNXRMKWHKAC-aa | 325 |
| | RXRRXRRXRIHILFQNXRMKWHKAC-aa | 326 |
| | RXRRXRRXRIRILFQNXRMKWHKAC-aa | 327 |
| | RXRRXRRXRIXILFQYXRMKWHKAC-aa | 328 |
| | RXRRXRRXRLYSPLSFQXRMKWHKAC-aa | 329 |
| | RXRRXRRXRISILFQYXRMKWHKAC-aa | 330 |
| | RXRRXRRXRILFQYXRMKWHKAC-aa | 331 |
| | RXRRXRIXILFQYXRMKWHKAC-aa | 332 |
| | RXRRARRXRIHILFQYXRMKWHKAC-aa | 333 |
| | RARRXRRARIHILFQYXRMKWHKAC-aa | 334 |
| | RXRRXRRXRIHILFQYXRMKWHKAC-aa | 335 |
| | RXRRXRRXRIXILFQNXRMKWHKAC-aa | 336 |
| | RXRRXRRXRIHILFQNXRMKWHKAC-aa | 337 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | RXRRXRRXRIKILFQNRRMKWHK-aa | 338 |
| | RXRRXRRXRIKILFQNXRMKWHK-aa | 339 |
| | RXRRXRRXRIXILFQNRRMKWHK-aa | 340 |
| | RXRRXRRXRIXILFQNXRMKWHK-aa | 341 |
| | RXRRXRRXRIHILFQNRRMKWHK-aa | 342 |
| | RXRRXRRXRIHILFQNXRMKWHK-aa | 343 |
| | RXRRXRRXRIRILFQNRRMKWHK-aa | 344 |
| | RXRRXRRXRIRILFQNXRMKWHK-aa | 345 |
| | RXRRXRRXRIILFQNRRMKWHK-aa | 346 |
| | RXRRXRRXRIILFQNXRMKWHK-aa | 347 |
| | RXRRXRRXRKILFQNRRMKWHK-aa | 348 |
| | RXRRXRRXRKILFQNXRMKWHK-aa | 349 |
| | RXRRXRRXRXILFQNRRMKWHK-aa | 350 |
| | RXRRXRRXRXILFQNXRMKWHK-aa | 351 |
| | RXRRXRRXRHILFQNRRMKWHK-aa | 352 |
| | RXRRXRRXRHILFQNXRMKWHK-aa | 353 |
| | RXRRXRRXRRILFQNRRMKWHK-aa | 354 |
| | RXRRXRRXRRILFQNXRMKWHK-aa | 355 |
| | RXRRXRRXRILFQNRRMKWHK-aa | 356 |
| | RXRRXRRXRILFQNXRMKWHK-aa | 357 |
| | RXRRXRRXRIKILFQYRRMKWHK-aa | 358 |
| | RXRRXRRXRIKILFQYXRMKWHK-aa | 359 |
| | RXRRXRRXRIXILFQYRRMKWHK-aa | 360 |
| | RXRRXRRXRIXILFQYXRMKWHK-aa | 361 |
| | RXRRXRRXRIHILFQYRRMKWHK-aa | 362 |
| | RXRRXRRXRIHILFQYXRMKWHK-aa | 363 |
| | RXRRXRRXRIRILFQYRRMKWHK-aa | 364 |
| | RXRRXRRXRIRILFQYXRMKWHK-aa | 365 |
| | RXRRXRRXRIILFQYRRMKWHK-aa | 366 |
| | RXRRXRRXRIILFQYXRMKWHK-aa | 367 |
| | RXRRXRRXRKILFQYRRMKWHK-aa | 368 |
| | RXRRXRRXRKILFQYXRMKWHK-aa | 369 |
| | RXRRXRRXRXILFQYRRMKWHK-aa | 370 |
| | RXRRXRRXRXILFQYXRMKWHK-aa | 371 |
| | RXRRXRRXRHILFQYRRMKWHK-aa | 372 |
| | RXRRXRRXRHILFQYXRMKWHK-aa | 373 |
| | RXRRXRRXRRILFQYRRMKWHK-aa | 374 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | RXRRXRRXRRILFQYXRMKWHK-aa | 375 |
| | RXRRXRRXRILFQYRRMKWHK-aa | 376 |
| | RXRRXRRXRILFQYXRMKWHK-aa | 377 |
| | RXRRXRRXR-aa | 378 |
| | RXRRXRRXRRXR-aa | 379 |
| | RARRAR-aa | 380 |
| | RARRARRAR-aa | 381 |
| | RARRARRARRAR-aa | 382 |
| | RXRRXRI-aa | 383 |
| | RXRRARRXR-aa | 384 |
| | RARRXRRAR-aa | 385 |
| | RRRRR-aa | 386 |
| | RRRRRR-aa | 387 |
| | RRRRRRR-aa | 388 |
| | RXRRXRRXRRXRC-aa | 389 |
| | RXRRXRRXRRXRXC-aa | 390 |
| | RXRRXRRXRIKILFQNRRMKWKKGGC-aa | 391 |
| | RXRRXRRXRIKILFQNRRMKWKKC-aa | 392 |
| | RXRRXRRXRIKILFQNRMKWKKC-aa | 393 |
| | RXRRXRRXRIKILFQNXRMKWKKC-aa | 394 |
| | RXRRXRRXRIKILFQNHRMKWKKC-aa | 395 |
| | RXRRXRRXRIKILFQNXRMKWKKC-aa | 396 |
| | RXRRXRRXRIKILFQNXRMKWKKC-aa | 397 |
| | RXRRXRRXRIKILFQNXRMKWAC-aa | 398 |
| | RXRRXRRXRIKILFQNXRMKWHKAC-aa | 399 |
| | RXRRXRRXRIKILFQNXRMKWHRC-aa | 400 |
| | RXRXRXRXRIKILFQNRRMKWKKC-aa | 401 |
| | RARARARARIKILFQNRRMKWKKC-aa | 402 |
| | RXRRXRRXRIXILFQNXRMKWHKAC-aa | 403 |
| | RXRRXRRXRIHILFQNXRMKWHKAC-aa | 404 |
| | RXRRXRRXRIRILFQNXRMKWHKAC-aa | 405 |
| | RXRRXRRXRIXILFQYXRMKWHKAC-aa | 406 |
| | RXRRXRRXRLYSPLSFQXRMKWHKAC-aa | 407 |
| | RRMKWHK-aa | 408 |
| | XRMKWHK-aa | 409 |
| | XXXXXXXXXXXXXILFQXXRMKWHK-aa | 410 |
| | XXXXXXXXXXXXXXILFQXXRMKWHK-aa | 411 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | RRRRRRRQIKILFQNPKKKRKVGGC-aa | 412 |
| | HHFFRRRRRRRRRRFFC-aa | 413 |
| | HHHHHHRRRRRRRRRRFFC-aa | 414 |
| | HHHHHHFFRRRRRRRRRRFFC-aa | 415 |
| | HHHHHXXRRRRRRRRRRFFC-aa | 416 |
| | HHHHHHXXFFRRRRRRRRRRFFC-aa | 417 |
| | HHHXRRRRRRRRRRFFXHHHC-aa | 418 |
| | XRMKWHK-aa | 419 |
| | XRWKWHK-aa | 420 |
| | RXRARXR-aa | 421 |
| | RXRXRXR-aa | 422 |
| | RARXRAR-aa | 423 |
| | RXRAR-aa | 424 |
| | XXXXXXXXXXXXXXILFQXXHMKWHK-aa | 425 |
| | XXXXXXXXXXXXXXILFQXXRWKWHK-aa | 426 |
| | XXXXXXXXXXXXXXILFQXXHWKWHK-aa | 427 |
| | XXXXXXXXXXXXXXILFQXRXRARXR-aa | 428 |
| | XXXXXXXXXXXXXXILFQXRXRXRXR-aa | 429 |
| | XXXXXXXXXXXXXXILFQXRXRRXR-aa | 430 |
| | XXXXXXXXXXXXXXILFQXRARXRAR-aa | 431 |
| | XXXXXXXXXXXXXXILFQXRXRARXR-aa | 432 |
| | XXXXXXXXXXXXXXILFQXRXRAR-aa | 433 |
| | XXXXXXXXXXXXXXILIQXXRMKWHK-aa | 434 |
| | XXXXXXXXXXXXXXILIQXXHMKWHK-aa | 435 |
| | XXXXXXXXXXXXXXILIQXXRWKWHK-aa | 436 |
| | XXXXXXXXXXXXXXILIQXXHWKWHK-aa | 437 |
| | XXXXXXXXXXXXXXILIQXRXRARXR-aa | 438 |
| | XXXXXXXXXXXXXXILIQXRXRXRXR-aa | 439 |
| | XXXXXXXXXXXXXXILIQXRXRRXR-aa | 440 |
| | XXXXXXXXXXXXXXILIQXRARXRAR-aa | 441 |
| | XXXXXXXXXXXXXXILIQXRXRARXR-aa | 442 |
| | XXXXXXXXXXXXXXILIQXRXRAR-aa | 443 |
| | XXXXXXXXXXXXXXILFQXXHMKWHK-aa | 444 |
| | XXXXXXXXXXXXXXILFQXXRWKWHK-aa | 445 |
| | XXXXXXXXXXXXXXILFQXXHWKWHK-aa | 446 |
| | XXXXXXXXXXXXXXILFQXRXRARXR-aa | 447 |
| | XXXXXXXXXXXXXXILFQXRXRXRXR-aa | 448 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | XXXXXXXXXXXXXXILFQXRXRRXR-aa | 449 |
| | XXXXXXXXXXXXXXILFQXRARXRAR-aa | 450 |
| | XXXXXXXXXXXXXXILFQXRARXR-aa | 451 |
| | XXXXXXXXXXXXXXILFQXRXRAR-aa | 452 |
| | XXXXXXXXXXXXXXILIQXXRMKWHK-aa | 453 |
| | XXXXXXXXXXXXXXILIQXXHMKWHK-aa | 454 |
| | XXXXXXXXXXXXXXILIQXXRWKWHK-aa | 455 |
| | XXXXXXXXXXXXXXILIQXXHWKWHK-aa | 456 |
| | XXXXXXXXXXXXXXILIQXRXRARXR-aa | 457 |
| | XXXXXXXXXXXXXXILIQXRXRXRXR-aa | 458 |
| | XXXXXXXXXXXXXXILIQXRXRRXR-aa | 459 |
| | XXXXXXXXXXXXXXILIQXRARXRAR-aa | 460 |
| | XXXXXXXXXXXXXXILIQXRXRARXR-aa | 461 |
| | XXXXXXXXXXXXXXILIQXRXRAR-aa | 462 |
| | RXRRARRXRRARXA-aa | 463 |
| | RXRRARRXRILFQYXHMKWHKAC-aa | 464 |
| | RXRRARRXRILFQYXRMKWHKAC-aa | 465 |
| | RXRRARRXRILFQYXRWKWHKAC-aa | 466 |
| | RXRRXRRXRRXRC-aa | 467 |
| | RXRRXRRXRIXILFQNXRMKWHKAC-aa | 468 |
| | RXRRXRRXRIHILFQNXRMKWHKAC-aa | 469 |
| | RXRRXRRXRIXILFQYXRMKWHKAC-aa | 470 |
| | RXRRXRRXRLYSPLSFQXRMKWHKAC-aa | 471 |
| | RXRRXRRXRILFQYXRMKWHKAC-aa | 472 |
| | RXRRXRIXILFQYXRMKWHKAC-aa | 473 |
| | RARRXRRARILFQYXRMKWHKAC-aa | 474 |
| | RXRRARRXRILFQYXRMKWHKAC-aa | 475 |
| | RARRXRRARILFQYXRMKWHKAC-aa | 476 |
| | RXRRARRXRILFQYXRMKWHKAC-aa | 477 |
| | RXRRARRXRILFQYXHMKWHKAC-aa | 478 |
| | RXRRARRXRILFQYXRMKWHKAC-aa | 479 |
| | RXRRARRXRILFQYXRWKWHKAC-aa | 480 |
| | RXRRARRXRILFQYXHWKWHKAC-aa | 481 |
| | RXRRARRXRILFQYRXRARXRAC-aa | 482 |
| | RXRRARRXRILFQYRXRXRXRAC-aa | 483 |
| | RXRRARRXRILIQYXRMKWHKAC-aa | 484 |
| | RXRRXRILFQYRXRRXRC-aa | 485 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | RXRRARRXRILFQYRXRARXRAC-aa | 486 |
| | RXRRARRXRILFQYRXRXRXRAC-aa | 487 |
| | RXRRARRXRILIQYXRMKWHKAC-aa | 488 |
| | RXRRXRILFQYRXRRXRCYS-aa | 489 |
| | RARRXRRARILFQYRARXRARAC-aa | 490 |
| | RARRXRRARILFQYRXRARXRAC-aa | 491 |
| | RARRXRRARILFQYRXRRXRAC-aa | 492 |
| | RARRXRRARILFQYRXRARXAC-aa | 493 |
| | RXRRARRXRILFQYRXRRXRAC-aa | 494 |
| | RXRRARRXRILFQYRXRARXAC-aa | 495 |
| | RXRRARRXRIHILFQNXRMKWHKAC-aa | 496 |
| | RXRRARRXRRARXAC-aa | 497 |
| | RXRRARRXRILFQYXHMKWHK-aa | 498 |
| | RXRRARRXRILFQYXRMKWHK-aa | 499 |
| | RXRRARRXRILFQYXRWKWHK-aa | 500 |
| | RXRRARRXRILFQYXRMKWHK-aa | 501 |
| | RXRRARRXRILFQYRXRARXR-aa | 502 |
| | RXRRARRXRILFQYRXRXRXR-aa | 503 |
| | RXRRARRXRILFQYRXRRXR-aa | 504 |
| | RXRRARRXRILFQYRARXRAR-aa | 505 |
| | RXRRARRXRILFQYRXRAR-aa | 506 |
| | RXRRARRXRILIQYXHMKWHK-aa | 507 |
| | RXRRARRXRILIQYXRMKWHK-aa | 508 |
| | RXRRARRXRILIQYXRWKWHK-aa | 509 |
| | RXRRARRXRILIQYXRMKWHK-aa | 510 |
| | RXRRARRXRILIQYRXRARXR-aa | 511 |
| | RXRRARRXRILIQYRXRXRXR-aa | 512 |
| | RXRRARRXRILIQYRXRRXR-aa | 513 |
| | RXRRARRXRILIQYRARXRAR-aa | 514 |
| | RXRRARRXRILIQYRXRAR-aa | 515 |
| | RARRXRRARILFQYXHMKWHK-aa | 516 |
| | RARRXRRARILFQYXRMKWHK-aa | 517 |
| | RARRXRRARILFQYXRWKWHK-aa | 518 |
| | RARRXRRARILFQYXRMKWHK-aa | 519 |
| | RARRXRRARILFQYRXRARXR-aa | 520 |
| | RARRXRRARILFQYRXRXRXR-aa | 521 |
| | RARRXRRARILFQYRXRRXR-aa | 522 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | RARRXRRARILFQYRARXRAR-aa | 523 |
| | RARRXRRARILFQYRXRAR-aa | 524 |
| | RARRXRRARILIQYXHMKWHK-aa | 525 |
| | RARRXRRARILIQYXRMKWHK-aa | 526 |
| | RARRXRRARILIQYXRWKWHK-aa | 527 |
| | RARRXRRARILIQYXRMKWHK-aa | 528 |
| | RARRXRRARILIQYRXRARXR-aa | 529 |
| | RARRXRRARILIQYRXRXRXR-aa | 530 |
| | RARRXRRARILIQYRXRRXR-aa | 531 |
| | RARRXRRARILIQYRARXRAR-aa | 532 |
| | RARRXRRARILIQYRXRAR-aa | 533 |
| | RXRRXRILFQYXHMKWHK-aa | 534 |
| | RXRRXRILFQYXRMKWHK-aa | 535 |
| | RXRRXRILFQYXRWKWHK-aa | 536 |
| | RXRRXRILFQYXRMKWHK-aa | 537 |
| | RXRRXRILFQYRXRARXR-aa | 538 |
| | RXRRXRILFQYRXRXRXR-aa | 539 |
| | RXRRXRILFQYRXRRXR-aa | 540 |
| | RXRRXRILFQYRARXRAR-aa | 541 |
| | RXRRXRILFQYRXRAR-aa | 542 |
| | RXRRXRILIQYXHMKWHK-aa | 543 |
| | RXRRXRILIQYXRMKWHK-aa | 544 |
| | RXRRXRILIQYXRWKWHK-aa | 545 |
| | RXRRXRILIQYXRMKWHK-aa | 546 |
| | RXRRXRILIQYRXRARXR-aa | 547 |
| | RXRRXRILIQYRXRXRXR-aa | 548 |
| | RXRRXRILIQYRXRRXR-aa | 549 |
| | RXRRXRILIQYRARXRAR-aa | 550 |
| | RXRRXRILIQYRXRAR-aa | 551 |
| | PRPXXXXXXXXXXXPRG-aa | 552 |
| | RRRRRRRR-aa | 553 |
| | RRMKWKK-aa | 554 |
| | PKKKRKV-aa | 555 |
| | CKDEPQRRSARLSAKPAPPKPEPKPKKAPAKK-aa | 556 |
| | RKKRRQRRR-aa | 557 |
| | RKKRRQRR-aa | 558 |
| | RKKRRQR-aa | 559 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| | KKRRQRRR-aa | 560 |
| | KKRRQRRR-aa | 561 |
| | AKKRRQRRR-aa | 562 |
| | RAKRRQRRR-aa | 563 |
| | RKARRQRRR-aa | 564 |
| | RKKARQRRR-aa | 565 |
| | CRWRWKCCKK-aa | 566 |
| Dengue | CGGTCCACGTAGACTAACAACT | 1 |
| JEV | GAAGTTCACACAGATAAACTTCT | 2 |
| M1/M2AUG.20.22 | CGGTTAGAAGACTCATCTTT | 3 |
| M1/M2AUG.25.26 | TTTCGACATCGGTTAGAAGACTCAT | 4 |
| NP-AUG | GAGACGCCATGATGTGGATGTC | 5 |
| Picornavirus | GAAACACGGACACCCAAAGTAGT | 6 |
| Dengue 3'-CS | TCCCAGCGTCAATATGCTGTTT | 7 |
| Arenaviruses | GCCTAGGATCCACGGTGCGC | 8 |
| RSV-L target | GGGACAAAATGGATCCCATTATTAATGGAAATTCTGCTAA | 9 |
| RSV-AUG-2 | TAATGGGATCCATTTTGTCCC | 10 |
| RSV-AUG3 | AATAATGGGATCCATTTTGTCCC | 11 |
| RSV-AUG4 | CATTAATAATGGGATCCATTTTGTCCC | 12 |
| RSV-AUG5 | GAATTTCCATTAATAATGGGATCCATTTTG | 13 |
| RSV-AUG6 | CAGAATTTCCATTAATAATGGGATCCATT | 14 |
| M23D | GGCCAAACCTCGGCTTACCTGAAAT | 15 |
| AVI-5225 | GGCCAAACCTCGGCTTACCTGAAAT-RXRRBRRXRRBRXB | 16 |
| eGFP654 | GCTATTACCTTAACCCAG | 17 |
| huMSTN target | GAAAAAAGATTATATTGATTTTAAAATCATGCAAAAACTGCAACTCTGTGTT | 18 |
| muMSTN25-104 | CATACATTTGCAGTTTTTGCATCAT | 19 |
| muMSTN25-183 | TCATTTTTAAAAATCAGCACAATCTT | 20 |
| muMSTN25-194 | CAGTTTTTGCATCATTTTTAAAAATC | 21 |
| Exon44-A | GATCTGTCAAATCGCCTGCAGGTAA | 22 |
| Exon44-B | AAACTGTTCAGCTTCTGTTAGCCAC | 23 |
| Exon44-C | TTGTGTCTTTCTGAGAAACTGTTCA | 24 |
| Exon45-A | CTGACAACAGTTTGCCGCTGCCCAA | 25 |
| Exon45-B | CCAATGCCATCCTGGAGTTCCTGTAA | 26 |
| Exon45-C | CATTCAATGTTCTGACAACAGTTTGCCGCT | 27 |
| Exon50-A | CTTACAGGCTCCAATAGTGGTCAGT | 28 |

TABLE 1-continued

Exemplary Carrier Peptides and Oligonucleotide Sequences

| Name | Sequence (Amino to Carboxy Terminus or 5' to 3') | SEQ ID NO. |
|---|---|---|
| Exon50-B | CCACTCAGAGCTCAGATCTTCTAACTTCC | 29 |
| Exon50-C | GGGATCCAGTATACTTACAGGCTCC | 30 |
| Exon51-A | ACATCAAGGAAGATGGCATTTCTAGTTTGG | 31 |
| Exon51-B | CTCCAACATCAAGGAAGATGGCATTTCTAG | 32 |
| Exon51-C | GAGCAGGTACCTCCAACATCAAGGAA | 33 |
| Exon53-A | CTGAAGGTGTTCTTGTACTTCATCC | 34 |
| Exon53-B | TGTTCTTGTACTTCATCCCACTGATTCTGA | 35 |
| SMN2-A | CTTTCATAATGCTGGCAG | 36 |
| SMN2-B | CATAATGCTGGCAG | 37 |
| SMN2-C | GCTGGCAG | 38 |
| CAG 9 mer | CAG CAG CAG | 39 |
| CAG 12 mer | CAG CAG CAG CAG | 40 |
| CAG 15 mer | CAG CAG CAG CAG CAG | 41 |
| CAG 18 mer | CAG CAG CAG CAG CAG CAG | 42 |
| AGC 9 mer | AGC AGC AGC | 43 |
| AGC 12 mer | AGC AGC AGC AGC | 44 |
| AGC 15 mer | AGC AGC AGC AGC AGC | 45 |
| AGC 18 mer | AGC AGC AGC AGC AGC AGC | 46 |
| GCA 9 mer | GCA GCA GCA | 47 |
| GCA 12 mer | GCA GCA GCA GCA | 48 |
| GCA 15 mer | GCA GCA GCA GCA GCA | 49 |
| GCA 18 mer | GCA GCA GCA GCA GCA GCA | 50 |
| AGC 25 mer | AGC AGC AGC AGC AGC AGC AGC AGC A | 51 |
| CAG 25 mer | CAG CAG CAG CAG CAG CAG CAG CAG C | 52 |
| CAGG 9 mer | CAG GCA GGC | 53 |
| CAGG 12 mer | CAG GCA GGC AGG | 54 |
| CAGG 24 mer | CAG GCA GGC AGG CAG GCA GGC AGG | 55 | aa = glycine or proline; B = β-alanine; X = 6-aminohexanoic acid; tg = unmodifed amino terminus, or the amino terminal capped with an acetyl, benzoyl or stearoyl group (i.e, an acetyl amide, benzoyl amide or stearoyl amide) and $Y^b$ is: $-C(O)-(CHR^e)_n-NH-$ wherein n is 2 to 7 and each $R^e$ is independently, at each occurrence, hydrogen or methyl. For simplicity, not all sequences are noted with a terminal tg group; however, each of the above sequences may comprise an unmodifed amino terminus or an amino terminus capped with an acetyl, benzoyl or stearoyl group

III. Antisense Oligomers

Nucleic acid analogs included in the conjugates of the invention are substantially uncharged synthetic oligomers capable of base-specific binding to a target sequence of a polynucleotide, e.g. antisense oligonucleotide analogs. Such analogs include, for example, methylphosphonates, peptide nucleic acids, substantially uncharged N3'→P5' phosphoramidates, and morpholino oligomers.

The base sequence of the nucleic acid analog, provided by base pairing groups supported by the analog backbone, can be any sequence, where the supported base pairing groups include standard or modified A, T, C, G and U bases or the non-standard inosine (I) and 7-deaza-G bases.

In some embodiments, the nucleic acid analog is a morpholino oligomer, i.e. an oligonucleotide analog composed of morpholino subunit structures of the form shown in FIG. 1, where (i) the structures are linked together by phosphorus-containing linkages, one to three atoms long, preferably two atoms long, joining the morpholino nitrogen of one subunit to the 5' exocyclic carbon of an adjacent subunit, and (ii) Pi and Pj are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are described further below and detailed in U.S. Pat. Nos. 5,698,685, 5,217,866, 5,142, 047, 5,034,506, 5,166,315, 5,521,063, and 5,506,337, all of which are incorporated herein by reference.

Desirable chemical properties of the morpholino-based oligomers include the ability to selectively hybridize with a complementary-base target nucleic acid, including target RNA, with high Tm, even with oligomers as short as 8-14 bases, the ability to be actively transported into mammalian cells, and the ability of an oligomer:RNA heteroduplex to resist RNAse degradation.

In a preferred embodiment, the morpholino oligomer is about 8-40 subunits in length. More typically, the oligomer is about 8-20, about 8-16, about 10-30, or about 12-25 subunits in length. For some applications, such as antibacterial, short oligomers, e.g. from about 8-12 subunits in length, can be especially advantageous, particularly when attached to a peptide transporter as disclosed herein.

A. Oligomers with Modified Intersubunit Linkages

One embodiment of the present disclosure is directed to peptide-oligomer conjugates comprising nucleic acid analogues (e.g., morpholino oligomers) comprising modified intersubunit linkages. In some embodiments, the conjugates have higher affinity for DNA and RNA than do the corresponding unmodified oligomers and demonstrate improved cell delivery, potency, and/or tissue distribution properties compared to oligomers having other intersubunit linkages. In one embodiment, the conjugates comprise one or more intersubunit linkages of type (A) as defined below. In other embodiments, the conjugates comprise at least one intersubunit linkage of type (B) as defined below. In still other embodiments, the conjugates comprise intersubunit linkages of type (A) and type (B). In yet other embodiments, the conjugates comprise a morpholino oligomer as described in more detail below. The structural features and properties of the various linkage types and oligomers are described in more detail in the following discussion.

1. Linkage (A)

Applicants have found that enhancement of antisense activity, biodistribution and/or other desirable properties can be optimized by preparing oligomers having various intersubunit linkages. For example, the oligomers may optionally comprise one or more intersubunit linkages of type (A), and in certain embodiments the oligomers comprise at least one linkage of type (A), for example each linkage may be of type (A). In some other embodiments each linkage of type (A) has the same structure. Linkages of type (A) may include linkages disclosed in co-owned U.S. Pat. No. 7,943,762 which is hereby incorporated by reference in its entirety. Linkage (A) has the following structure (I), wherein 3' and 5' indicate the point of attachment to the 3' and 5' ends, respectively, of the morpholino ring (i.e., structure (i) discussed below):

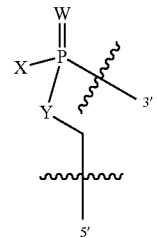

or a salt or isomer thereof, wherein:
W is, at each occurrence, independently S or O;
X is, at each occurrence, independently —N(CH$_3$)$_2$, —NR$^1$R$^2$, —OR$^3$ or;

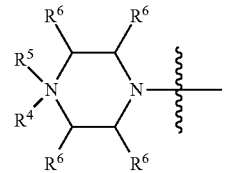

Y is, at each occurrence, independently O or —NR$^2$,
R$^1$ is, at each occurrence, independently hydrogen or methyl;
R$^2$ is, at each occurrence, independently hydrogen or -LNR$^4$R$^5$R$^7$;
R$^3$ is, at each occurrence, independently hydrogen or C$_1$-C$_6$ alkyl;
R$^4$ is, at each occurrence, independently hydrogen, methyl, —C(=NH)NH$_2$, —Z-L-NHC(=NH)NH$_2$ or —[C(=O)CHR'NH]$_m$H, where Z is —C(=O)— or a direct bond, R' is a side chain of a naturally occurring amino acid or a one- or two-carbon homolog thereof, and m is 1 to 6;
R$^5$ is, at each occurrence, independently hydrogen, methyl or an electron pair;
R$^6$ is, at each occurrence, independently hydrogen or methyl;
R$^7$ is, at each occurrence, independently hydrogen C$_1$-C$_6$ alkyl or C$_1$-C$_6$ alkoxyalkyl; and
L is an optional linker up to 18 atoms in length comprising alkyl, alkoxy or alkylamino groups, or combinations thereof.

In some examples, the oligomer comprises at least one linkage of type (A). In some other embodiments, the oligomer includes at least two consecutive linkages of type (A). In further embodiments, at least 5% of the linkages in the oligomer are type (A); for example in some embodiments, 5%-95%, 10% to 90%, 10% to 50%, or 10% to 35% of the linkages may be linkage type (A). In some specific embodiments, at least one type (A) linkage is —N(CH$_3$)$_2$. In other embodiments, each linkage of type (A) is —N(CH$_3$)$_2$, and in even other embodiments each linkage in the oligomer is —N(CH$_3$)$_2$. In other embodiments, at least one type (A) linkage is piperizin-1-yl, for example unsubstituted piperazin-1-yl (e.g., A2 or A3). In other embodiments, each linkage of type (A) is piperizin-1-yl, for example unsubstituted piperazin-1-yl.

In some embodiments, W is, at each occurrence, independently S or O, and in certain embodiments W is O.

In some embodiments, X is, at each occurrence, independently —N(CH$_3$)$_2$, —NR$^1$R$^2$, —OR$^3$. In some embodiments X is —N(CH$_3$)$_2$. In other aspects X is —NR$^1$R$^2$, and in other examples X is —OR$^3$.

In some embodiments, $R^1$ is, at each occurrence, independently hydrogen or methyl. In some embodiments, $R^1$ is hydrogen. In other embodiments X is methyl.

In some embodiments, $R^2$ is, at each occurrence, hydrogen. In other embodiments $R^2$ is, at each occurrence, $-LNR^4R^5R^7$. In some embodiments, $R^3$ is, at each occurrence, independently hydrogen or $C_1$-$C_6$ alkyl. In other embodiments, $R^3$ is methyl. In yet other embodiments, $R^3$ is ethyl. In some other embodiments, $R^3$ is n-propyl or isopropyl. In some other embodiments, $R^3$ is $C_4$ alkyl. In other embodiments, $R^3$ is $C_5$ alkyl. In some embodiments, $R^3$ is $C_6$ alkyl.

In certain embodiments, $R^4$ is, at each occurrence, independently hydrogen. In other embodiments, $R^4$ is methyl. In yet other embodiments, $R^4$ is $-C(=NH)NH_2$, and in other embodiments, $R^4$ is $-Z$-L-$NHC(=NH)NH_2$. In still other embodiments, $R^4$ is $-[C(=O)CHR'NH]_mH$. Z is $-C(=O)-$ in one embodiment and Z is a direct bond in another embodiment. R' is a side chain of a naturally occurring amino acid. In some embodiments R' is a one- or two-carbon homolog of a side chain of a naturally occurring amino acid.

m is and integer from 1 to 6. m may be 1. m may be 2 m may be 3 m may be 4 m may be 5 m may be 6

In some embodiments, $R^5$ is, at each occurrence, independently hydrogen, methyl or an electron pair. In some embodiments, $R^5$ is hydrogen. In other embodiments, $R^5$ is methyl. In yet other embodiments, $R^5$ is an electron pair.

In some embodiments, $R^6$ is, at each occurrence, independently hydrogen or methyl. In some embodiments, $R^6$ is hydrogen. In other embodiments, $R^6$ is methyl.

In other embodiments, $R^7$ is, at each occurrence, independently hydrogen $C_1$-$C_6$ alkyl or $C_2$-$C_6$ alkoxyalkyl. In some embodiments R7 is hydrogen. In other embodiments, $R^7$ is $C_1$-$C_6$ alkyl. In yet other embodiments, $R^7$ is $C_2$-$C_6$ alkoxyalkyl. In some embodiments, $R^7$ is methyl. In other embodiments, $R^7$ is ethyl. In yet other embodiments, $R^7$ is n-propyl or isopropyl. In some other embodiments, $R^7$ is $C_4$ alkyl. In some embodiments, $R^7$ is $C_5$ alkyl. In some embodiments, $R^7$ is $C_6$ alkyl. In yet other embodiments, $R^7$ is $C_2$ alkoxyalkyl. In yet other embodiments, $R^7$ is $C_3$ alkoxyalkyl. In yet other embodiments, $R^7$ is $C_4$ alkoxyalkyl. In some embodiments, $R^7$ is $C_5$ alkoxyalkyl. In other embodiments, $R^7$ is $C_6$ alkoxyalkyl.

The linker group L, as noted above, contains bonds in its backbone selected from alkyl (e.g. $-CH_2-CH_2-$), alkoxy (e.g., $-C-O-C-$), and alkylamino (e.g. $-CH_2-NH-$), with the proviso that the terminal atoms in L (e.g., those adjacent to carbonyl or nitrogen) are carbon atoms. Although branched linkages (e.g. $-CH_2-CHCH_3-$) are possible, the linker is generally unbranched. In one embodiment, the linker is a hydrocarbon linker. Such a linker may have the structure $(CH_2)_n-$, where n is 1-12, preferably 2-8, and more preferably 2-6.

Oligomers having any number of linkage type (A) are provided. In some embodiments, the oligomer contains no linkages of type (A). In certain embodiments, 5, 10, 20, 30, 40, 50, 60, 70, 80 or 90 percent of the linkages are linkage (A). In selected embodiments, 10 to 80, 20 to 80, 20 to 60, 20 to 50, 20 to 40, or 20 to 35 percent of the linkages are linkage (A). In still other embodiments, each linkage is type (A).

2. Linkage (B)

In some embodiments, the oligomers comprise at least one linkage of type (B). For example the oligomers may comprise 1, 2, 3, 4, 5, 6 or more linkages of type (B). The type (B) linkages may be adjacent or may be interspersed throughout the oligomer. Linkage type (B) has the following structure (I):

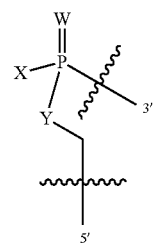

(I)

or a salt or isomer thereof, wherein:

W is, at each occurrence, independently S or O;

X is, at each occurrence, independently $-NR^8R^9$ or $-OR^3$; and

Y is, at each occurrence, independently 0 or $-NR^{10}$.

$R^3$ is, at each occurrence, independently hydrogen or $C_1$-$C_6$ alkyl;

$R^8$ is, at each occurrence, independently hydrogen or $C_2$-$C_{12}$ alkyl;

$R^9$ is, at each occurrence, independently hydrogen, $C_1$-$C_{12}$ alkyl, $C_1$-$C_{12}$ aralkyl or aryl;

$R^{10}$ is, at each occurrence, independently hydrogen, $C_1$-$C_{12}$ alkyl or -$LNR^4R^5R^7$;

wherein $R^8$ and $R^9$ may join to form a 5-18 membered mono or bicyclic heterocycle or $R^8$, $R^9$ or $R^3$ may join with $R^{10}$ to form a 5-7 membered heterocycle, and wherein when X is 4-piperazino, X has the following structure (III):

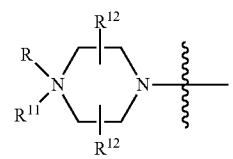

(III)

wherein:

$R^{11}$ is, at each occurrence, independently $C_2$-$C_{12}$ alkyl, $C_1$-$C_{12}$ aminoalkyl, $C_1$-$C_{12}$ alkylcarbonyl, aryl, heteroaryl or heterocyclyl;

R is, at each occurrence, independently an electron pair, hydrogen or $C_1$-$C_{12}$ alkyl; and $R^{12}$ is, at each occurrence, independently, hydrogen, $C_1$-$C_{12}$ alkyl, $C_1$-$C_{12}$ aminoalkyl, $-NH_2$, $-CONH_2$, $-NR^{13}R^{14}$, $-NR^{13}R^{14}R^{15}$, $C_1$-$C_{12}$ alkylcarbonyl, oxo, $-CN$, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, $-SR^{13}$ or $C_1$-$C_{12}$ alkoxy, wherein $R^{13}$, $R^{14}$ and $R^{15}$ are, at each occurrence, independently $C_1$-$C_{12}$ alkyl.

In some examples, the oligomer comprises one linkage of type (B). In some other embodiments, the oligomer comprises two inkages of type (B). In some other embodiments, the oligomer comprises three linkages of type (B). In some other embodiments, the oligomer comprises four linkages of type (B). In still other embodiments, the linkages of type (B) are consecutive (i.e., the type (B) linkages are adjacent to each other). In further embodiments, at least 5% of the linkages in the oligomer are type (B); for example in some embodiments, 5%-95%, 10% to 90%, 10% to 50%, or 10% to 35% of the linkages may be linkage type (B).

In other embodiments, $R^3$ is, at each occurrence, independently hydrogen or $C_1$-$C_6$ alkyl. In yet other embodiments, $R^3$ may be methyl. In some embodiments, $R^3$ may be ethyl. In some other embodiments, $R^3$ may be n-propyl or isopropyl. In yet other embodiments, $R^3$ may be $C_4$ alkyl. In some embodiments, $R^3$ may be $C_5$ alkyl. In some embodiments, $R^3$ may be $C_6$ alkyl.

In some embodiments, $R^8$ is, at each occurrence, independently hydrogen or $C_2$-$C_{12}$ alkyl. In some embodiments, $R^8$ is hydrogen. In yet other embodiments, $R^8$ is ethyl. In some other embodiments, $R^8$ is n-propyl or isopropyl. In some embodiments, $R^8$ is $C_4$ alkyl. In yet other embodiments, $R^8$ is $C_5$ alkyl. In other embodiments, $R^8$ is $C_6$ alkyl. In some embodiments, $R^8$ is $C_7$ alkyl. In yet other embodiments, $R^8$ is $C_8$ alkyl. In other embodiments, $R^8$ is $C_9$ alkyl. In yet other embodiments, $R^8$ is $C_{10}$ alkyl. In some other embodiments, $R^8$ is $C_{11}$ alkyl. In yet other embodiments, $R^8$ is $C_{12}$ alkyl. In some other embodiments, $R^8$ is $C_2$-$C_{12}$ alkyl and the $C_2$-$C_{12}$ alkyl includes one or more double bonds (e.g., alkene), triple bonds (e.g., alkyne) or both. In some embodiments, $R^8$ is unsubstituted $C_2$-$C_{12}$ alkyl.

In some embodiments, $R^9$ is, at each occurrence, independently hydrogen, $C_1$-$C_{12}$ alkyl, $C_1$-$C_{12}$ aralkyl or aryl. In some embodiments, $R^9$ is hydrogen. In yet other embodiments, $R^9$ is $C_1$-$C_{12}$ alkyl. In other embodiments, $R^9$ is methyl. In yet other embodiments, $R^9$ is ethyl. In some other embodiments, $R^9$ is n-propyl or isopropyl. In some embodiments, $R^9$ is $C_4$ alkyl. In some embodiments, $R^9$ is $C_5$ alkyl. In yet other embodiments, $R^9$ is $C_6$ alkyl. In some other embodiments, $R^9$ is $C_7$ alkyl. In some embodiments, $R^9$ is $C_8$ alkyl. In some embodiments, $R^9$ is $C_9$ alkyl. In some other embodiments, $R^9$ is $C_{10}$ alkyl. In some other embodiments, $R^9$ is $C_{11}$ alkyl. In yet other embodiments, $R^9$ is $C_{12}$ alkyl.

In some other embodiments, $R^9$ is $C_1$-$C_{12}$ aralkyl. For example, n some embodiments $R^9$ is benzyl and the benzyl may be optionally substituted on either the phenyl ring or the benzylic carbon. Substituents in this regards include alkyl and alkoxy groups, for example methyl or methoxy. In some embodiments, the benzyl group is substituted with methyl at the benzylic carbon. For example, in some embodiments, $R^9$ has the following structure (XIV):

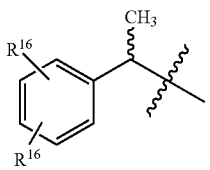

(XIV)

In other embodiments, $R^9$ is aryl. For example, in some embodiments $R^9$ is phenyl, and the phenyl may be optionally substituted. Substituents in this regard substitutents include alkyl and alkoxy groups, for example methyl or methoxy. In other embodiments, $R^9$ is phenyl and the phenyl comprises a crown ether moiety, for example a 12-18 membered crown ether. In one embodiment the crown ether is 18 membered and may further comprise and additional phenyl moiety. For example, in one embodiment $R^9$ has one of the following structures (XV) or XVI):

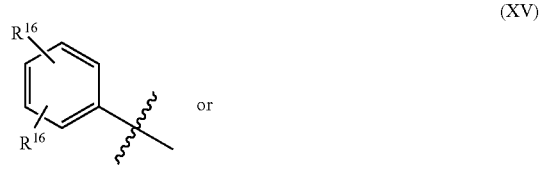

(XV)

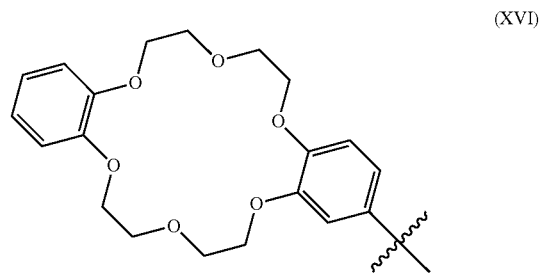

(XVI)

In some embodiments, $R^{10}$ is, at each occurrence, independently hydrogen, $C_1$-$C_{12}$ alkyl or -$LNR^4R^5R^7$, wherein $R^4$, $R^5$ and $R^7$ are as defined above with respect to linkage (A). In other embodiments, $R^{10}$ is hydrogen. In other embodiments, $R^{10}$ is $C_1$-$C_{12}$ alkyl, and in other embodiments $R^{10}$ is -$LNR^4R^5R^7$. In some embodiments, $R^{10}$ is methyl. In yet other embodiments, $R^{10}$ is ethyl. In some embodiments, $R^{10}$ is $C_3$ alkyl. In some embodiments, $R^{10}$ is $C_4$ alkyl. In yet other embodiments, $R^{10}$ is $C_5$ alkyl. In some other embodiments, $R^{10}$ is $C_6$ alkyl. In other embodiments, $R^{10}$ is $C_7$ alkyl. In yet other embodiments, $R^{10}$ is $C_8$ alkyl. In some embodiments, $R^{10}$ is $C_9$ alkyl. In other embodiments, $R^{10}$ is $C_{10}$ alkyl. In yet other embodiments, $R^{10}$ is $C_{11}$ alkyl. In some other embodiments, $R^{10}$ is $C_{12}$ alkyl.

In some embodiments, $R^8$ and $R^9$ join to form a 5-18 membered mono or bicyclic heterocycle. In some embodiments the heterocycle is a 5 or 6 membered monocyclic heterocycle. For example, in some embodiments linkage (B) has the following structure (IV):

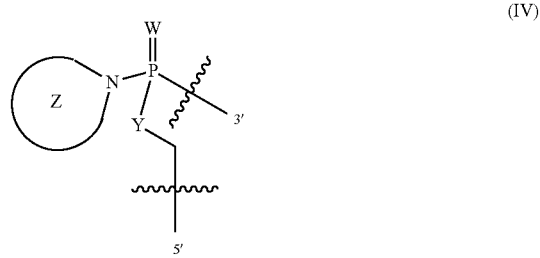

(IV)

wherein Z represents a 5 or 6 membered monocyclic heterocycle.

In other embodiments, heterocycle is bicyclic, for example a 12-membered bicyclic heterocycle. The heterocycle may be piperizinyl. The heterocycle may be morpholino. The heterocycle may be piperidinyl. The heterocycle may be decahydroisoquinoline. Representative heterocycles include the following:

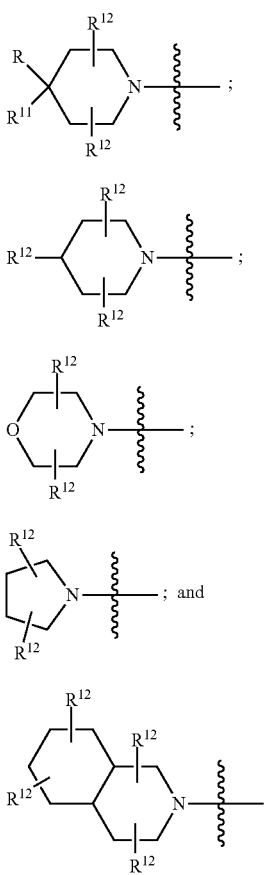

In some embodiments, $R^{11}$ is, at each occurrence, independently $C_2$-$C_{12}$ alkyl, $C_1$-$C_{12}$ aminoalkyl, aryl, heteroaryl or heterocyclyl.

In some embodiments, $R^{11}$ is $C_2$-$C_{12}$ alkyl. In some embodiments, $R^{11}$ is ethyl. In other embodiments, $R^{11}$ is $C_3$ alkyl. In yet other embodiments, $R^{11}$ is isopropyl. In some other embodiments, $R^{11}$ is $C_4$ alkyl. In other embodiments, $R^{11}$ is $C_5$ alkyl. In some embodiments, $R^{11}$ is $C_6$ alkyl. In other embodiments, $R^{11}$ is $C_7$ alkyl. In some embodiments, $R^{11}$ is $C_8$ alkyl. In other embodiments, $R^{11}$ is $C_9$ alkyl. In yet other embodiments, $R^{11}$ is $C_{10}$ alkyl. In some other embodiments, $R^{11}$ is $C_{11}$ alkyl. In some embodiments, $R^{11}$ is $C_{12}$ alkyl.

In other embodiments, $R^{11}$ is $C_1$-$C_{12}$ aminoalkyl. In some embodiments, $R^{11}$ is methylamino. In some embodiments, $R^{11}$ is ethylamino. In other embodiments, $R^{11}$ is $C_3$ aminoalkyl. In yet other embodiments, $R^{11}$ is $C_4$ aminoalkyl. In some other embodiments, $R^{11}$ is $C_5$ aminoalkyl. In other embodiments, $R^{11}$ is $C_6$ aminoalkyl. In yet other embodiments, $R^{11}$ is $C_7$ aminoalkyl. In some embodiments, $R^{11}$ is $C_8$ aminoalkyl. In other embodiments, $R^{11}$ is $C_9$ aminoalkyl. In yet other embodiments, $R^{11}$ is $C_{10}$ aminoalkyl. In some other embodiments, $R^{11}$ is $C_{11}$ aminoalkyl. In other embodiments, $R^{11}$ is $C_{12}$ aminoalkyl.

In other embodiments, $R^{11}$ is $C_1$-$C_{12}$ alkylcarbonyl. In yet other embodiments, $R^{11}$ is $C_1$ alkylcarbonyl. In other embodiments, $R^{11}$ is $C_2$ alkylcarbonyl. In some embodiments, $R^{11}$ is $C_3$ alkylcarbonyl. In yet other embodiments, $R^{11}$ is $C_4$ alkylcarbonyl. In some embodiments, $R^{11}$ is $C_5$ alkylcarbonyl. In some other embodiments, $R^{11}$ is $C_6$ alkylcarbonyl. In other embodiments, $R^{11}$ is $C_7$ alkylcarbonyl. In yet other embodiments, $R^{11}$ is $C_8$ alkylcarbonyl. In some embodiments, $R^{11}$ is $C_9$ alkylcarbonyl. In yet other embodiments, $R^{11}$ is $C_{10}$ alkylcarbonyl. In some other embodiments, $R^{11}$ is $C_{11}$ alkylcarbonyl. In some embodiments, $R^{11}$ is $C_{12}$ alkylcarbonyl. In yet other embodiments, $R^{11}$ is —C(=O)(CH$_2$)$_n$CO$_2$H, where n is 1 to 6. For example, in some embodiments, n is 1. In other embodiments, n is 2. In yet other embodiments, n is 3. In some other embodiments, n is 4. In yet other embodiments, n is 5. In other embodiments, n is 6.

In other embodiments, $R^{11}$ is aryl. For example, in some embodiments, $R^{11}$ is phenyl. In some embodiments, the phenyl is substituted, for example with a nitro group.

In other embodiments, $R^{11}$ is heteroaryl. For example, in some embodiments, $R^{11}$ is pyridinyl. In other embodiments, $R^{11}$ is pyrimidinyl.

In other embodiments, $R^{11}$ is heterocyclyl. For example, in some embodiments, $R^{11}$ is piperidinyl, for example piperidin-4-yl.

In some embodiments, $R^{11}$ is ethyl, isopropyl, piperidinyl, pyrimidinyl, cholate, deoxycholate, or —C(=O)(CH$_2$)$_n$CO$_2$H, where n is 1 to 6.

In some embodiments, R is an electron pair. In other embodiments, R is hydrogen, and in other embodiments R is $C_1$-$C_{12}$ alkyl. In some embodiments, R is methyl. In some embodiments, R is ethyl. In other embodiments, R is $C_3$ alkyl. In yet other embodiments, R is isopropyl. In some other embodiments, R is $C_4$ alkyl. In yet other embodiments, R is $C_5$ alkyl. In some embodiments, R is $C_6$ alkyl. In other embodiments, R is $C_7$ alkyl. In yet other embodiments, R is $C_8$ alkyl. In other embodiments, R is $C_9$ alkyl. In some embodiments, R is $C_{10}$ alkyl. In yet other embodiments, R is $C_{11}$ alkyl. In some embodiments, R is $C_{12}$ alkyl.

In some embodiments, $R^{12}$ is, at each occurrence, independently, hydrogen, $C_1$-$C_{12}$ alkyl, $C_1$-$C_{12}$ aminoalkyl, —NH$_2$, —CONH$_2$, —NR$^{13}$R$^{14}$, —NR$^{13}$R$^{14}$R$^{15}$, oxo, —CN, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, —SR$^{13}$ or $C_1$-$C_{12}$ alkoxy, wherein $R^{13}$, $R^{14}$ and $R^{15}$ are, at each occurrence, independently $C_1$-$C_{12}$ alkyl.

In some embodiments, $R^{12}$ is hydrogen. In some embodiments, $R^{12}$ is $C_1$-$C_{12}$ alkyl. In some embodiments, $R^{12}$ is $C_1$-$C_{12}$ aminoalkyl. In some embodiments, $R^{12}$ is —NH$_2$. In some embodiments, $R^{12}$ is —CONH$_2$. In some embodiments, $R^{12}$ is —NR$^{13}$R$^{14}$. In some embodiments, $R^{12}$ is —NR$^{13}$R$^{14}$R$^{15}$. In some embodiments, $R^{12}$ is $C_1$-$C_{12}$ alkylcarbonyl. In some embodiments, $R^{12}$ is oxo. In some embodiments, $R^{12}$ is —CN. In some embodiments, $R^{12}$ is trifluoromethyl. In some embodiments, $R^{12}$ is amidyl. In some embodiments, $R^{12}$ is amidinyl. In some embodiments, $R^{12}$ is amidinylalkyl. In some embodiments, $R^{12}$ is amidinylalkylcarbonyl. In some embodiments, $R^{12}$ is guanidinyl, for example mono methylguanidynyl or dimethylguanidinyl. In some embodiments, $R^{12}$ is guanidinylalkyl. In some embodiments, $R^{12}$ is amidinylalkylcarbonyl. In some embodiments, $R^{12}$ is cholate. In some embodiments, $R^{12}$ is deoxycholate. In some embodiments, $R^{12}$ is aryl. In some embodiments, $R^{12}$ is heteroaryl. In some embodiments, $R^{12}$ is heterocycle. In some embodiments, $R^{12}$ is —SR$^{13}$. In some embodiments, $R^{12}$ is $C_1$-$C_{12}$ alkoxy. In some embodiments, $R^{12}$ is dimethyl amine.

In other embodiments, $R^{12}$ is methyl. In yet other embodiments, $R^{12}$ is ethyl. In some embodiments, $R^{12}$ is $C_3$ alkyl. In some embodiments, $R^{12}$ is isopropyl. In some embodiments, $R^{12}$ is $C_4$ alkyl. In other embodiments, $R^{12}$ is $C_5$ alkyl. In yet other embodiments, $R^{12}$ is $C_6$ alkyl. In some other embodiments, $R^{12}$ is $C_7$ alkyl. In some embodiments, $R^{12}$ is $C_8$ alkyl. In yet other embodiments, $R^{12}$ is $C_9$ alkyl. In some embodiments, $R^{12}$ is $C_{10}$ alkyl. In yet other embodiments, $R^{12}$ is $C_{11}$ alkyl. In other embodiments, $R^{12}$ is $C_{12}$ alkyl. In yet other embodiments, the alkyl moiety is substituted with one or more oxygen atom to form an ether moiety, for example a methoxymethyl moiety.

In some embodiments, $R^{12}$ is methylamino. In other embodiments, $R^{12}$ is ethylamino. In yet other embodiments, $R^{12}$ is $C_3$ aminoalkyl. In some embodiments, $R^{12}$ is $C_4$ aminoalkyl. In yet other embodiments, $R^{12}$ is $C_5$ aminoalkyl. In some other embodiments, $R^{12}$ is $C_6$ aminoalkyl. In some embodiments, $R^{12}$ is $C_7$ aminoalkyl. In some embodiments, $R^{12}$ is $C_8$ aminoalkyl. In yet other embodiments, $R^{12}$ is $C_9$ aminoalkyl. In some other embodiments, $R^{12}$ is $C_{10}$ aminoalkyl. In yet other embodiments, $R^{12}$ is $C_{11}$ aminoalkyl. In other embodiments, $R^{12}$ is $C_{12}$ aminoalkyl. In some embodiments, the amino alkyl is a dimethylamino alkyl.

In yet other embodiments, $R^{12}$ is acetyl. In some other embodiments, $R^{12}$ is $C_2$ alkylcarbonyl. In some embodiments, $R^{12}$ is $C_3$ alkylcarbonyl. In yet other embodiments, $R^{12}$ is $C_4$ alkylcarbonyl. In some embodiments, $R^{12}$ is $C_5$ alkylcarbonyl. In yet other embodiments, $R^{12}$ is $C_6$ alkylcarbonyl. In some embodiments, $R^{12}$ is $C_7$ alkylcarbonyl. In some embodiments, $R^{12}$ is $C_8$ alkylcarbonyl. In yet other embodiments, $R^{12}$ is $C_9$ alkylcarbonyl. In some other embodiments, $R^{12}$ is $C_{10}$ alkylcarbonyl. In some embodiments, $R^{12}$ is $C_{11}$ alkylcarbonyl. In other embodiments, $R^{12}$ is $C_{12}$ alkylcarbonyl. The alkylcarbonyl is substituted with a carboxy moiety, for example the alkylcarbonyl is substituted to form a succinic acid moiety (i.e., a 3-carboxyalkylcarbonyl). In other embodiments, the alkylcarbonyl is substituted with a terminal —SH group.

In some embodiments, $R^{12}$ is amidyl. In some embodiments, the amidyl comprises an alkyl moiety which is further substituted, for example with —SH, carbamate, or combinations thereof. In other embodiments, the amidyl is substituted with an aryl moiety, for example phenyl. In certain embodiments, $R^{12}$ may have the following structure (IX):

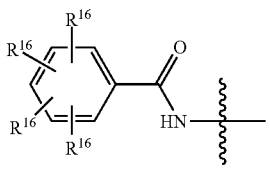

(IX)

wherein $R^{16}$ is, at each occurrence, independently hydrogen, $C_1$-$C_{12}$ alkyl, $C_1$-$C_{12}$ alkoxy, —CN, aryl or heteroaryl.

In some embodiments, $R^{12}$ is methoxy. In other embodiments, $R^{12}$ is ethoxy. In yet other embodiments, $R^{12}$ is $C_3$ alkoxy. In some embodiments, $R^{12}$ is $C_4$ alkoxy. In some embodiments, $R^{12}$ is $C_5$ alkoxy. In some other embodiments, $R^{12}$ is $C_6$ alkoxy. In other embodiments, $R^{12}$ is $C_7$ alkoxy. In some other embodiments, $R^{12}$ is $C_8$ alkoxy. In some embodiments, $R^{12}$ is $C_9$ alkoxy. In other embodiments, $R^{12}$ is $C_{10}$ alkoxy. In some embodiments, $R^{12}$ is $C_{11}$ alkoxy. In yet other embodiments, $R^{12}$ is $C_{12}$ alkoxy.

In certain embodiments, $R^{12}$ is pyrrolidinyl, for example pyrrolidin-1-yl. In other embodiments, $R^{12}$ is piperidinyl, for example piperidin-1-yl or piperidin-4-yl. In other embodiment, $R^{12}$ is morpholino, for example morpholin-4-yl. In other embodiments, $R^{12}$ is phenyl, and in even further embodiments, the phenyl is substituted, for example with a nitro group. In still other embodiments, $R^{12}$ is pyrimidinyl, for example pyrimidin-2-yl.

In other embodiments, $R^{13}$, $R^{14}$ and $R^{15}$ are, at each occurrence, independently $C_1$-$C_{12}$ alkyl. In some embodiments, $R^{13}$, $R^{14}$ or $R^{15}$ is methyl. In yet other embodiments, $R^{13}$, $R^{14}$ or $R^{15}$ is ethyl. In other embodiments, $R^{13}$, $R^{14}$ or $R^{15}$ is $C_3$ alkyl. In yet other embodiments, $R^{13}$, $R^{14}$ or $R^{15}$ is isopropyl. In other embodiments, $R^{13}$, $R^{14}$ or $R^{15}$ is $C_4$ alkyl. In some embodiments, $R^{13}$, $R^{14}$ or $R^{15}$ is $C_5$ alkyl. In some other embodiments, $R^{13}$, $R^{14}$ or $R^{15}$ is $C_6$ alkyl. In other embodiments, $R^{13}$, $R^{14}$ or leis $C_7$ alkyl. In yet other embodiments, $R^{13}$, $R^{14}$ or $R^{15}$ is $C_8$ alkyl. In other embodiments, $R^{13}$, $R^{14}$ or $R^{15}$ is $C_9$ alkyl. In some embodiments, $R^{13}$, $R^{14}$ or $R^{15}$ is $C_{10}$ alkyl. In some embodiments, $R^{13}$, $R^{14}$ or $R^{15}$ is $C_{11}$ alkyl. In yet other embodiments, $R^{13}$, $R^{14}$ or $R^{15}$ is $C_{12}$ alkyl.

As noted above, in some embodiments, $R^{12}$ is amidyl substituted with an aryl moiety. In this regard, each occurrence of $R^{16}$ may be the same or differerent. In certain of these embodiments, $R^{16}$ is hydrogen. In other embodiments, $R^{16}$ is —CN. In other embodiments, $R^{16}$ is heteroaryl, for example tretrazolyl. In certain other embodiments, $R^{16}$ is methoxy. In other embodiments, $R^{16}$ is aryl, and the aryl is optionally substituted. Optional substituents in this regard include: $C_1$-$C_{12}$ alkyl, $C_1$-$C_{12}$ alkoxy, for example methoxy; trifluoromethoxy; halo, for example chloro; and trifluoromethyl.

In other embodiments, $R^{16}$ is methyl. In yet other embodiments, $R^{16}$ is ethyl. In some embodiments, $R^{16}$ is $C_3$ alkyl. In some other embodiments, $R^{16}$ is isopropyl. In yet other embodiments, $R^{16}$ is $C_4$ alkyl. In other embodiments, $R^{16}$ is $C_5$ alkyl. In yet other embodiments, $R^{16}$ is $C_6$ alkyl. In some other embodiments, $R^{16}$ is $C_7$ alkyl. In some embodiments, $R^{16}$ is $C_8$ alkyl. In yet other embodiments, $R^{16}$ is $C_9$ alkyl. In some other embodiments, $R^{16}$ is $C_{10}$ alkyl. In other embodiments, $R^{16}$ is $C_{11}$ alkyl. In some other embodiments, $R^{16}$ is $C_{12}$ alkyl.

In some embodiments, $R^{16}$ is methoxy. In some embodiments, $R^{16}$ is ethoxy. In yet other embodiments, $R^{16}$ is $C_3$ alkoxy. In some other embodiments, $R^{16}$ is $C_4$ alkoxy. In other embodiments, $R^{16}$ is $C_5$ alkoxy. In some other embodiments, $R^{16}$ is $C_6$ alkoxy. In yet other embodiments, leis $C_7$ alkoxy. In some other embodiments, $R^{16}$ is $C_8$ alkoxy. In yet other embodiments, $R^{16}$ is $C_9$ alkoxy. In some other embodiments, $R^{16}$ is $C_{10}$ alkoxy. In some embodiments, $R^{16}$ is $C_{11}$ alkoxy. In some other embodiments, $R^{16}$ is $C_{12}$ alkoxy.

In some other embodiments, $R^8$ and $R^9$ join to form a 12-18 membered crown ether. For example, in some embodiments, the crown ether s 18 membered, and in other embodiments the crown ether is 15 membered. In certain embodiments, $R^8$ and $R^9$ join to form a heterocycle having one of the following structures (X) or (XI):

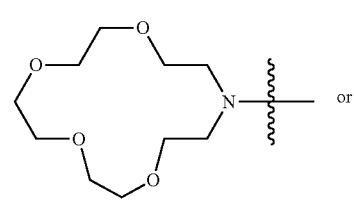

(X)

or

-continued

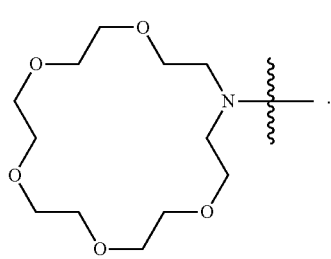
(XI)

In some embodiments, $R^8$, $R^9$ or $R^3$ join with $R^{10}$ to form a 5-7 membered heterocycle. For example, in some embodiments, $R^3$ joins with $R^{10}$ to form a 5-7 membered heterocycle. In some embodiments, the heterocycle is 5-membered. In other embodiments, the heterocycle is 6-membered. In other embodiments, the heterocycle is 7-memebered. In some embodiments, the heterocycle is represented by the following structure (XII):

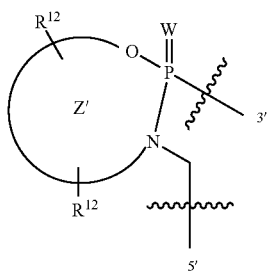
(XII)

wherein Z' represents a 5-7 membered heterocycle. In certain embodiments of structure (XI), $R^{12}$ is hydrogen at each occurrence. For example, linkage (B) may have one of the following structures (B1). (B2) or (B3):

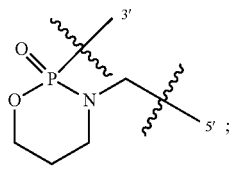
(B1)

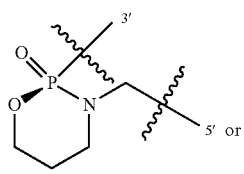
(B2)

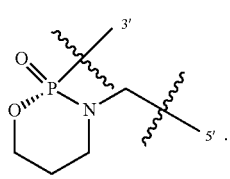
(B3)

In certain other embodiments, $R^{12}$ is $C_1$-$C_{12}$ alkylcarbonyl or amidyl which is further substituted with an arylphosphoryl moiety, for example a triphenyl phosporyl moiety. Examples of linkages having this structure include B56 and B55.

In certain embodiment, linkage (B) does not have any of the the structures A1-A5. Table 2 shows representative linkages of type (A) and (B).

TABLE 2

| | Representative Intersubunit Linkages | |
|---|---|---|
| No. | Name | Structure |
| A1 | PMO | |
| A2 | PMO⁺ (unprotonated form depicted) | |

TABLE 2-continued

Representative Intersubunit Linkages

| No. | Name | Structure |
|---|---|---|
| A3 | PMO⁺ (+) | 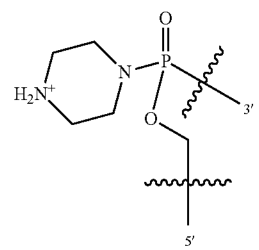 [SMILES: *COP(*)(=O)N1CC[NH2+]CC1] |
| A4 | PMO^mepip (m+) | 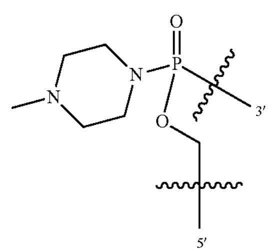 [SMILES: *COP(*)(=O)N1CCN(C)CC1] |
| A5 | PMO^GUX | 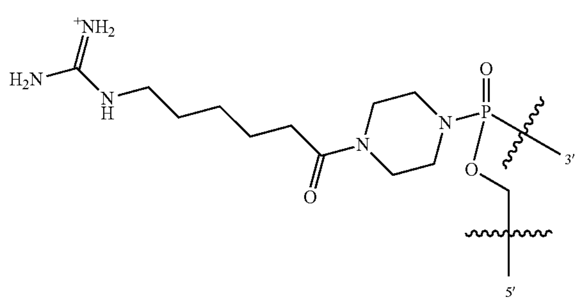 [SMILES: *COP(*)(=O)N1CCN(C(=O)CCCCCNC(N)=[NH2+])CC1] |
| B1 | PMO^cp | 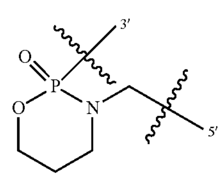 [SMILES: *CN1CCCOP1(*)=O] |
| B2 | PMO^cps | 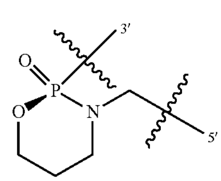 [SMILES: *CN1CCCO[P@]1(*)=O] |
| B3 | PMO^cpr | 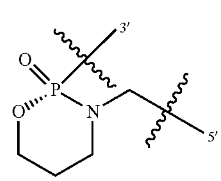 |

TABLE 2-continued

Representative Intersubunit Linkages

| No. | Name | Structure |
|---|---|---|
| B4 | PMO$^{Shc}$ | 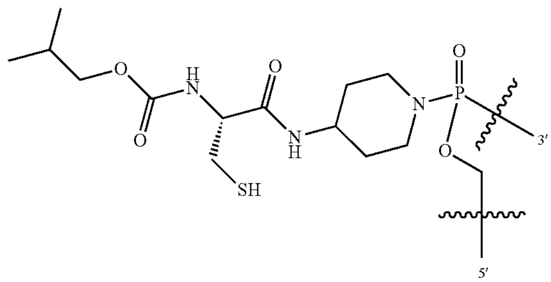 [SMILES: *COP(*)(=O)N1CCC(NC(=O)[C@H](CS)NC(=O)OCC(C)C)CC1] |
| B5 | PMO$^{morpholino}$ (m) | 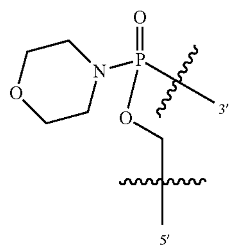 [SMILES: *COP(*)(=O)N1CCOCC1] |
| B6 | PMO$^{tri}$ (t) | 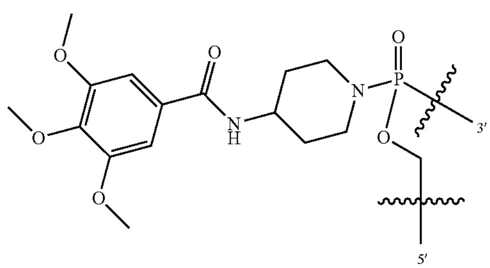 [SMILES: *COP(*)(=O)N1CCC(NC(=O)c2cc(OC)c(OC)c(OC)c2)CC1] |
| B7 | PMO$^{hex}$ (h) | 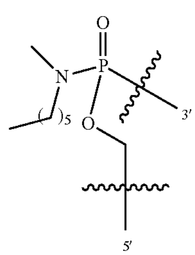 |
| B8 | PMO$^{dodec}$ | 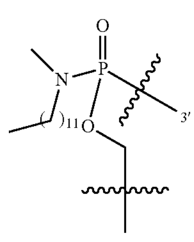 |

TABLE 2-continued
Representative Intersubunit Linkages
| No. | Name | Structure |
|---|---|---|
| B9 | PMO$^{dihex}$ | 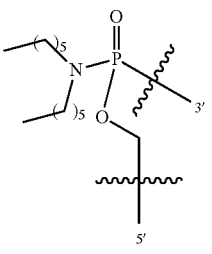 |
| B10 | PMO$^{apn}$ (a) | 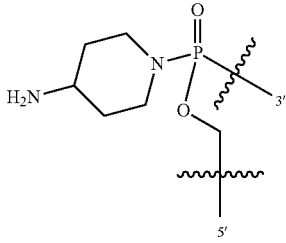 [SMILES: *COP(*)(=O)N1CCC(N)CC1] |
| B11 | PMO$^{pyr}$ (p) | 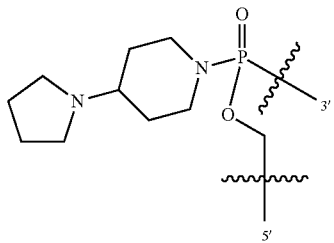 [SMILES: *COP(*)(=O)N1CCC(N2CCCC2)CC1] |
| B12 | PMO$^{pyr}$ (HCl Salt) | 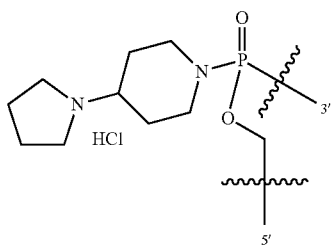 [SMILES: *COP(*)(=O)N1CCC(N2CCCC2)CC1 ; Cl] |
| B13 | PMO$^{rba}$ | 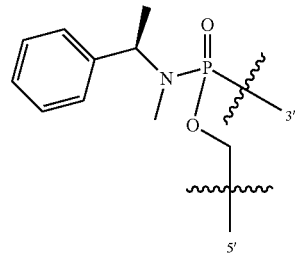 [SMILES: *COP(*)(=O)N(C)[C@H](C)c1ccccc1] |

TABLE 2-continued

Representative Intersubunit Linkages

| No. | Name | Structure |
|---|---|---|
| B14 | PMO$^{sba}$ | 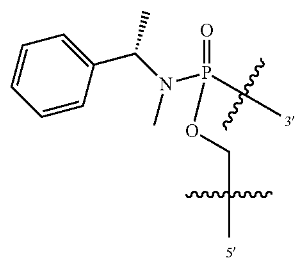 [SMILES: *COP(*)(=O)N(C)[C@@H](C)c1ccccc1] |
| B15 | PMO$^{dimethylapn}$ | 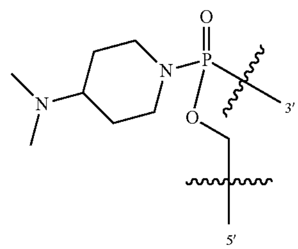 [SMILES: *COP(*)(=O)N1CCC(N(C)C)CC1] |
| B16 | PMO$^{etpip}$ | 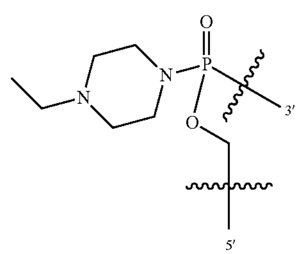 [SMILES: *COP(*)(=O)N1CCN(CC)CC1] |
| B17 | PMO$^{iprpip}$ | 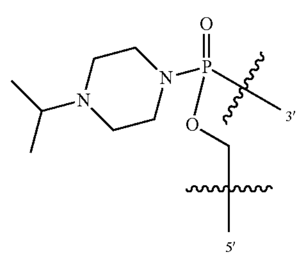 [SMILES: *COP(*)(=O)N1CCN(C(C)C)CC1] |
| B18 | PMO$^{pyrQMe}$ | 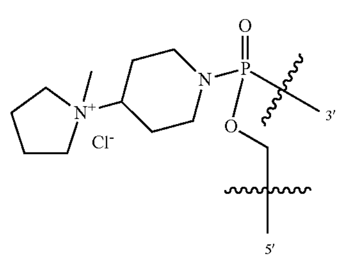 [SMILES: *COP(*)(=O)N1CCC([N+]2(C)CCCC2)CC1 ; [Cl-]] |

TABLE 2-continued
Representative Intersubunit Linkages
| No. | Name | Structure |
|---|---|---|
| B19 | PMO$^{cb}$ | 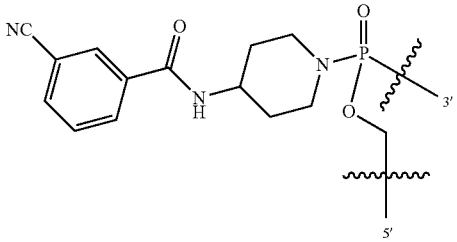 [SMILES: *COP(*)(=O)N1CCC(NC(=O)c2cccc(C#N)c2)CC1] |
| B20 | PMO$^{ma}$ | 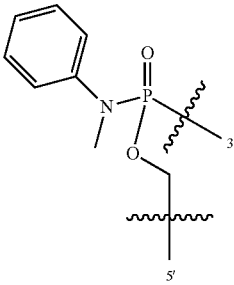 |
| B21 | PMO$^{bu}$ | 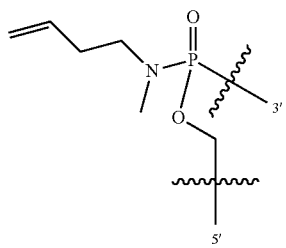 [SMILES: *COP(*)(=O)N(C)CCC=C] |
| B22 | PMO$^{bi}$ | 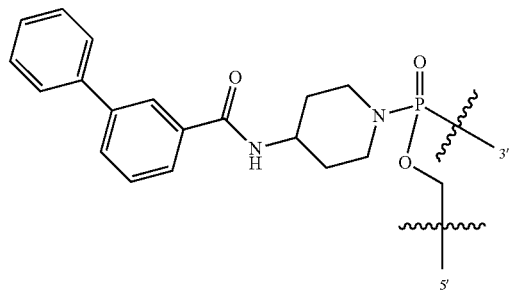 [SMILES: *COP(*)(=O)N1CCC(NC(=O)c2cccc(-c3ccccc3)c2)CC1] |
| B23 | PMO$^{pip}$ | 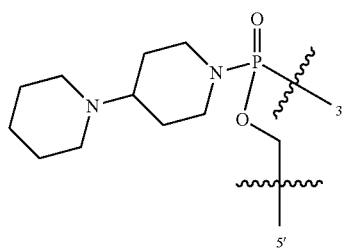 |

TABLE 2-continued

Representative Intersubunit Linkages

| No. | Name | Structure |
|---|---|---|
| B24 | PMO$^{odmb}$ | 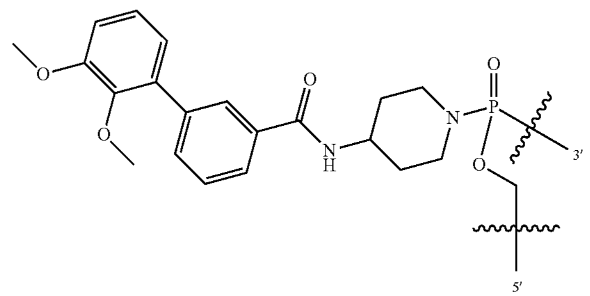 [SMILES: *COP(*)(=O)N1CCC(NC(=O)c2cccc(-c3cccc(OC)c3OC)c2)CC1] |
| B25 | PMO$^{tfb}$ | 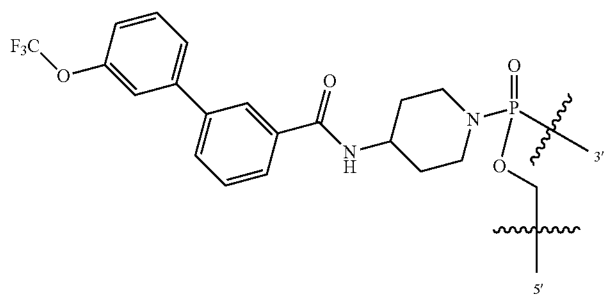 [SMILES: *COP(*)(=O)N1CCC(NC(=O)c2cccc(-c3cccc(OC(F)(F)F)c3)c2)CC1] |
| B26 | PMO$^{ctfb}$ | 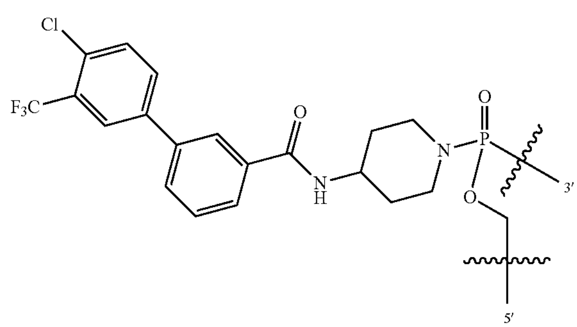 [SMILES: *COP(*)(=O)N1CCC(NC(=O)c2cccc(-c3ccc(Cl)c(C(F)(F)F)c3)c2)CC1] |
| B27 | PMO$^{ptfb}$ | 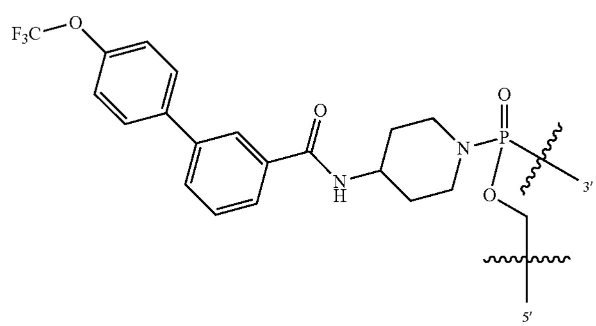 [SMILES: *COP(*)(=O)N1CCC(NC(=O)c2cccc(-c3ccc(OC(F)(F)F)cc3)c2)CC1] |

TABLE 2-continued

Representative Intersubunit Linkages

| No. | Name | Structure |
|-----|------|-----------|
| B28 | PMO$^{dcb}$ | 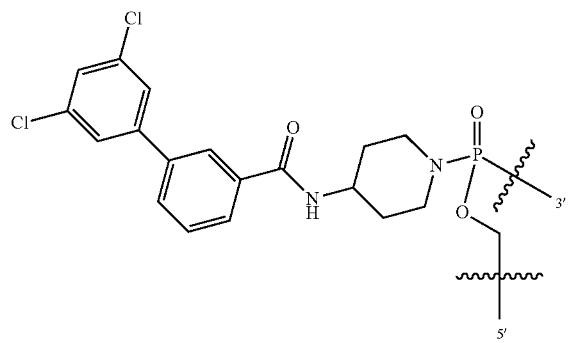 [SMILES: *COP(*)(=O)N1CCC(NC(=O)c2cccc(-c3cc(Cl)cc(Cl)c3)c2)CC1] |
| B29 | PMO$^{dmb}$ | 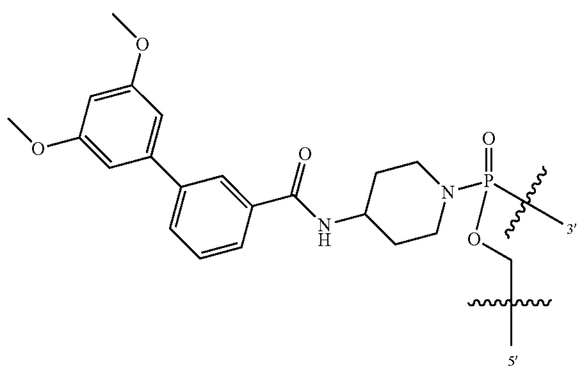 [SMILES: *COP(*)(=O)N1CCC(NC(=O)c2cccc(-c3cc(OC)cc(OC)c3)c2)CC1] |
| B30 | PMO$^{hy}$ | 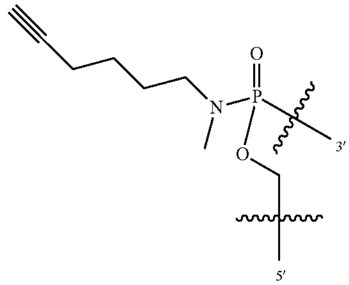 [SMILES: *COP(*)(=O)N(C)CCCCC#C] |
| B31 | PMO$^{6ce}$ | 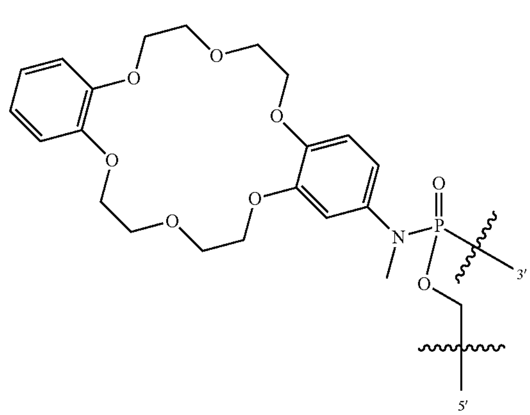 [SMILES: *COP(*)(=O)N(C)c1ccc2c(c1)OCCOCCOc1ccccc1OCCOCCO2] |

TABLE 2-continued

Representative Intersubunit Linkages

| No. | Name | Structure |
|---|---|---|
| B32 | PMO[b] | 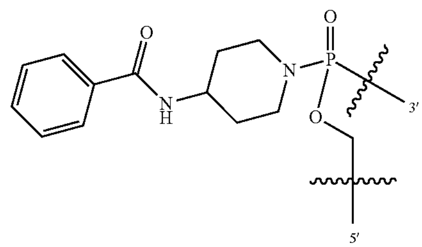 [SMILES: *COP(*)(=O)N1CCC(NC(=O)c2ccccc2)CC1] |
| B33 | PMO[q] | 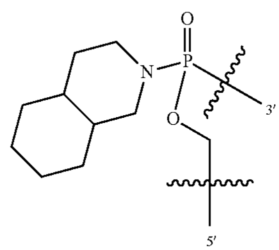 [SMILES: *COP(*)(=O)N1CCC2CCCCC2C1] |
| B34 | PMO[npp] | 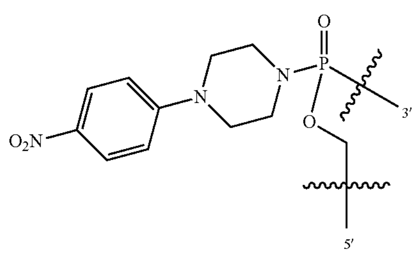 [SMILES: *COP(*)(=O)N1CCN(c2ccc([N+](=O)[O-])cc2)CC1] |
| B35 | PMO[o] | 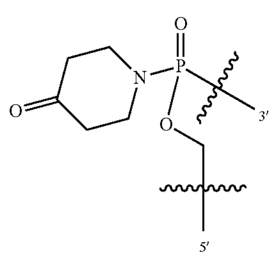 [SMILES: *COP(*)(=O)N1CCC(=O)CC1] |
| B36 | PMO[4ce] | 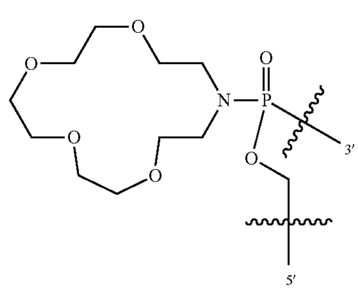 [SMILES: *COP(*)(=O)N1CCOCCOCCOCCOCC1] |

TABLE 2-continued

Representative Intersubunit Linkages

| No. | Name | Structure |
|---|---|---|
| B37 | PMO$^{5ce}$ | 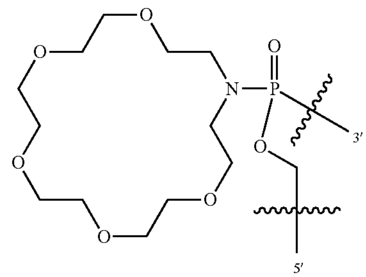 [SMILES: *COP(*)(=O)N1CCOCCOCCOCCOCCOCC1] |
| B38 | PMO$^{f3p}$ | 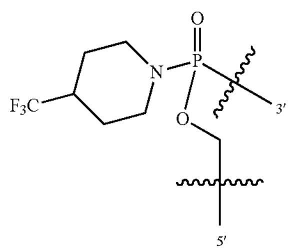 [SMILES: *COP(*)(=O)N1CCC(C(F)(F)F)CC1] |
| B39 | PMO$^{cyp}$ | 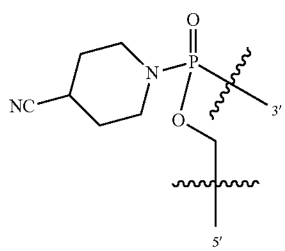 [SMILES: *COP(*)(=O)N1CCC(C#N)CC1] |
| B40 | PMO$^{mop}$ | 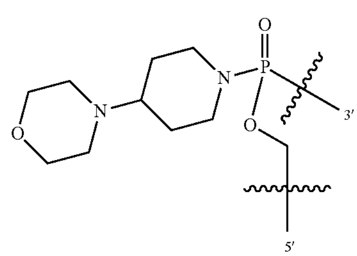 [SMILES: *COP(*)(=O)N1CCC(N2CCOCC2)CC1] |
| B41 | PMO$^{pp}$ | 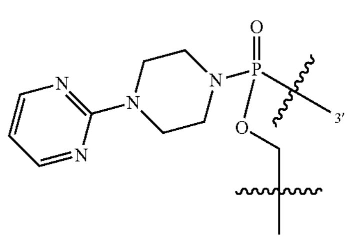 |

TABLE 2-continued

Representative Intersubunit Linkages

| No. | Name | Structure |
|---|---|---|
| B42 | PMO$^{dmepip}$ | 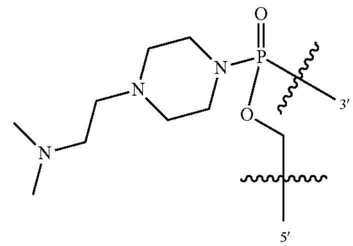 [SMILES: *COP(*)(=O)N1CCN(CCN(C)C)CC1] |
| B43 | PMO$^{NPpip}$ | 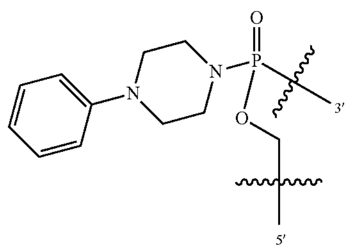 [SMILES: *COP(*)(=O)N1CCN(c2ccccc2)CC1] |
| B44 | PMO$^{bipip}$ | 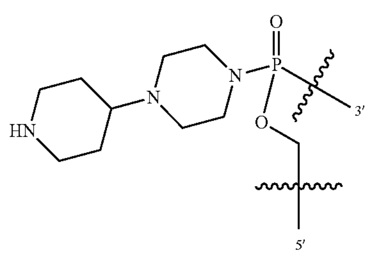 [SMILES: *COP(*)(=O)N1CCN(C2CCNCC2)CC1] |
| B45 | PMO$^{suc}$ | 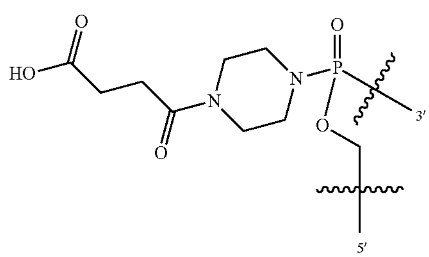 [SMILES: *COP(*)(=O)N1CCN(C(=O)CCC(=O)O)CC1] |
| 46 | PMO$^{glutaric}$ | 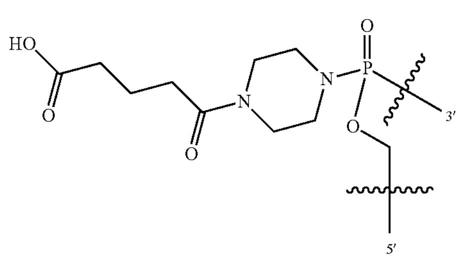 [SMILES: *COP(*)(=O)N1CCN(C(=O)CCCC(=O)O)CC1] |

TABLE 2-continued
Representative Intersubunit Linkages
| No. | Name | Structure |
|---|---|---|
| B47 | PMO<sup>tet</sup> | 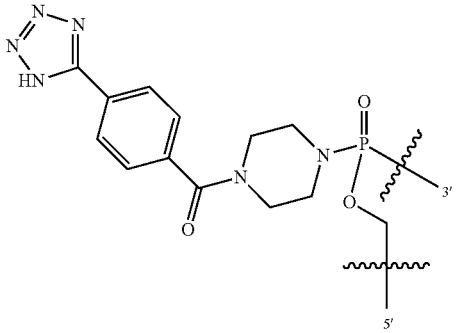 [SMILES: *COP(*)(=O)N1CCN(C(=O)c2ccc(-c3nnn[nH]3)cc2)CC1] |
| B48 | PMO<sup>thiol</sup> (SH) | 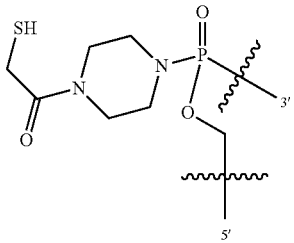 [SMILES: *COP(*)(=O)N1CCN(C(=O)CS)CC1] |
| B49 | PMO<sup>pros</sup> | 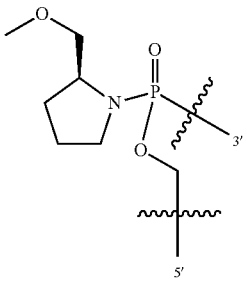 [SMILES: *COP(*)(=O)N1CCC[C@H]1COC] |
| B50 | PMO<sup>pror</sup> | 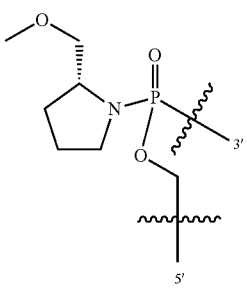 [SMILES: *COP(*)(=O)N1CCC[C@@H]1COC] |
| B51 | PMO<sup>tme</sup> | 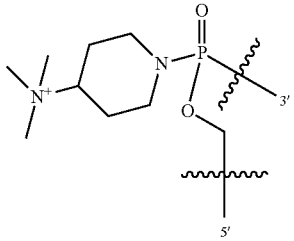 [SMILES: *COP(*)(=O)N1CCC([N+](C)(C)C)CC1] |

TABLE 2-continued
Representative Intersubunit Linkages
| No. | Name | Structure |
|---|---|---|
| B52 | PMO$^{ca}$ | 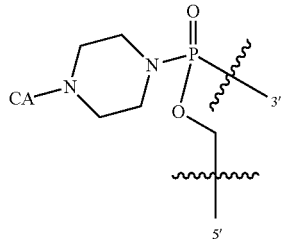<br>CA = Cholate |
| B53 | PMO$^{dca}$ | 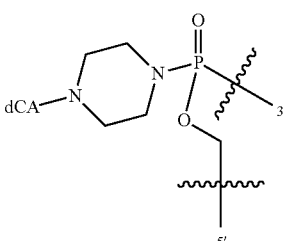<br>dCA = Deoxycholate |
| B54 | PMO$^{guan}$ (g) | 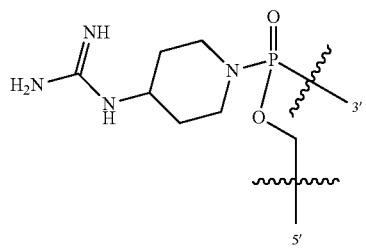 [SMILES: *COP(*)(=O)N1CCC(NC(=N)N)CC1] |
| B55 | PMO$^{+phos}$ | 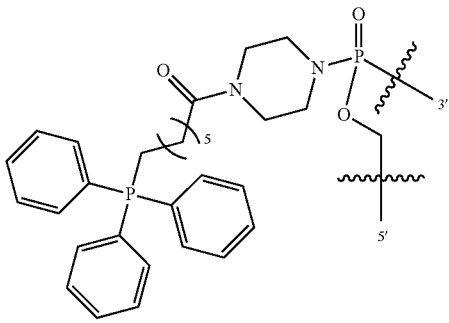 |
| B56 | PMO$^{apnphos}$ | 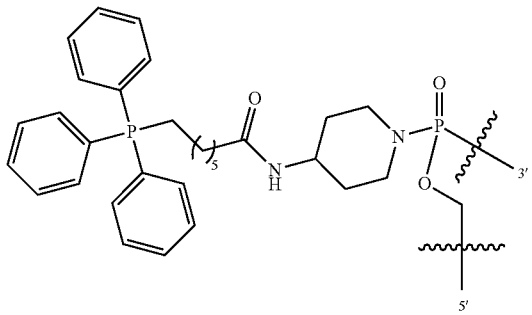 |

In the sequences and discussion that follows, the above names for the linkages are often used. For example, a base comprising a PMO$^{apn}$ linkage is illustrated as $^{apn}$B, where B is a base. Other linkages are designated similarily. In addition, abbreviated designations may be used, for example, the abbreviated designations in parenthses above may be used (e.g., $^a$B, refers to $^{apn}$B). Other readily identifiable abbreviations may also be used.

B. Oligomers with Modified Terminal Groups

In addition to the carrier peptide, the conjugate may also comprise an oligomer comprising modified terminal groups. Applicants have found that modification of the 3' and/or 5' end of the oligomer with various chemical moieties provides beneficial therapeutic properties (e.g., enhanced cell delivery, potency, and/or tissue distribution, etc.) to the conjugates. In various embodiments, the modified terminal groups comprise a hydrophobic moiety, while in other embodiments the modified terminal groups comprise a hydrophilic moiety. The modified terminal groups may be present with or without the linkages described above. For example, in some embodiments, the oligomers to which the carrier peptide is conjugated comprise one or more modified terminal groups and linkages of type (A), for example linkages wherein X is —N(CH$_3$)$_2$. In other embodiments, the oligomers comprise one or more modified terminal group and linkages of type (B), for example linkages wherein X is 4-aminopiperidin-1-yl (i.e., APN). In yet other embodiments, the oligomers comprise one or more modified terminal group and a mixture of linkages (A) and (B). For example, the oligomers may comprise one or more modified terminal group (e.g., trityl or triphenyl acetyl) and linkages wherein X is —N(CH$_3$)$_2$ and linkages wherein X is 4-aminopiperidin-1-yl. Other combinations of modified terminal groups and modified linkages also provide favorable therapeutic properties to the oligomers.

In one embodiment, the oligomers comprising terminal modifications have the following structure (XVII):

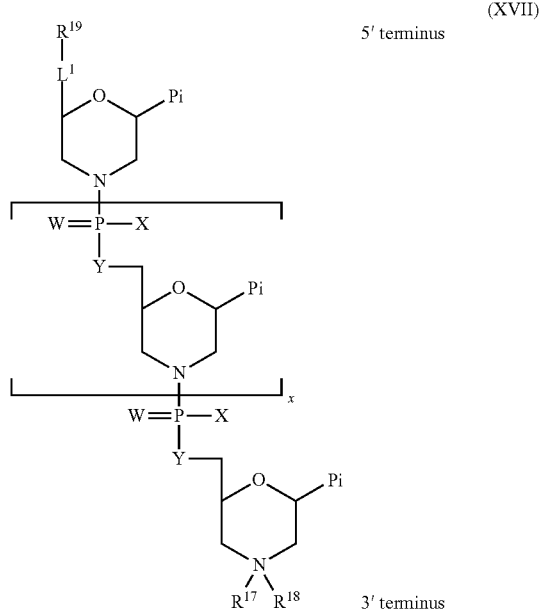

(XVII)

or a salt or isomer thereof, wherein X, W and Y are as defined above for any of linkages (A) and (B) and:

$R^{17}$ is, at each occurrence, independently absent, hydrogen or $C_1$-$C_6$ alkyl;

$R^{18}$ and $R^{19}$ are, at each occurrence, independently absent, hydrogen, the carrier peptide, a natural or non-natural amino acid, $C_2$-$C_{30}$ alkylcarbonyl, —C(=O)OR$^{21}$ or $R^{20}$;

$R^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)(R$^{22}$)$_2$;

Pi is independently, at each occurrence, a base-pairing moiety;

$L^1$ is an optional linker up to 18 atoms in length comprising bonds selected from alkyl, hydroxyl, alkoxy, alkylamino, amide, ester, disulfide, carbonyl, carbamate, phosphorodiamidate, phosphoroamidate, phosphorothioate, piperazine and phosphodiester; and x is an integer of 0 or greater; and wherein at least one of $R^{18}$ or $R^{19}$ is $R^{20}$; and wherein at least one of $R^{18}$ or $R^{19}$ is $R^{20}$ and provided that both of $R^{17}$ and $R^{18}$ are not absent.

The oligomers with modified terminal groups may comprise any number of linkages of types (A) and (B). For example, the oligomers may comprise only linkage type (A). For example, X in each linkage may be —N(CH$_3$)$_2$. Alternatively, the oligomers may only comprise linkage (B). In certain embodiments, the oligomers comprise a mixture of linkages (A) and (B), for example from 1 to 4 linkages of type (B) and the remainder of the linkages being of type (A). Linkages in this regard include, but are not limited to, linkages wherein X is aminopiperidinyl for type (B) and dimethyl amino for type (A).

In some embodiments, $R^{17}$ is absent. In some embodiments, $R^{17}$ is hydrogen. In some embodiments, $R^{17}$ is $C_1$-$C_6$ alkyl. In some embodiments, $R^{17}$ is methyl. In yet other embodiments, $R^{17}$ is ethyl. In some embodiments, $R^{17}$ is $C_3$ alkyl. In some other embodiments, $R^{17}$ is isopropyl. In other embodiments, $R^{17}$ is $C_4$ alkyl. In yet other embodiments, $R^{17}$ is $C_5$ alkyl. In some other embodiments, $R^{17}$ is $C_6$ alkyl.

In other embodiments, $R^{18}$ is absent. In some embodiments, $R^{18}$ is hydrogen. In some embodiments, $R^{18}$ is the carrier peptide. In some embodiments, $R^{18}$ is a natural or non-natural amino acid, for example trimethylglycine. In some embodiments, $R^{18}$ is $R^{20}$.

In other embodiments, $R^{19}$ is absent. In some embodiments, $R^{19}$ is hydrogen. In some embodiments, $R^{19}$ is the carrier peptide. In some embodiments, $R^{19}$ is a natural or non-natural amino acid, for example trimethylglycine. In some embodiments, $R^{19}$ is —C(=O)OR$^{17}$, for example $R^{19}$ may have the following structure:

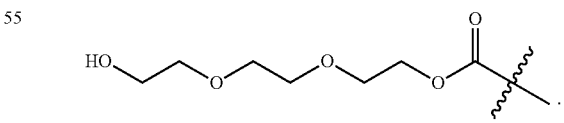

In other embodiments $R^{18}$ or $R^{19}$ is $C_2$-$C_{30}$ alkylcarbonyl, for example —C(=O)(CH$_2$)$_n$CO$_2$H, where n is 1 to 6, for example 2. In other examples, $R^{18}$ or $R^{19}$ is acetyl.

In some embodiments, $R^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_3$-$C_{30}$ alkylcarbonyl, $C_3$-$C_8$ cycloalkylcarbonyl, $C_3$-$C_8$ cycloalkylalkylcarbonyl, $C_6$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, —C(=O)OR$^{21}$, or —P(=O)(R$^{22}$)$_2$, wherein R$^{21}$ is $C_1$-$C_{30}$ alkyl comprising one or more oxygen or hydroxyl moieties or combinations thereof and each R$^{22}$ is $C^6$-$C^{12}$ aryloxy.

In certain other embodiments, R$^{19}$ is —C(=O)OR$^{21}$ and R$^{18}$ is hydrogen, guanidinyl, heterocyclyl, $C_1$-$C_{30}$ alkyl, $C_3$-$C_8$ cycloalkyl; $C_6$-$C_{30}$ aryl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)(R$^{22}$)$_2$, wherein each R$^{22}$ is $C^6$-$C^{12}$ aryloxy.

In other embodiments, R$^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)(R$^{22}$)$_2$. While in other examples, R$^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)(R$^{22}$)$_2$.

In some embodiments R$^{20}$ is guanidinyl, for example mono methylguanidynyl or dimethylguanidinyl. In other embodiments, R$^{20}$ is heterocyclyl. For example, in some embodiments, R$^{20}$ is piperidin-4-yl. In some embodiments, the piperidin-4-yl is substituted with trityl or Boc groups. In other embodiments, R$^{20}$ is $C_3$-$C_8$ cycloalkyl. In other embodiments, R$^{20}$ is $C_6$-$C_{30}$ aryl.

In some embodiments, R$^{20}$ is $C_7$-$C_{30}$ arylcarbonyl. For example, In some embodiments, R$^{20}$ has the following structure (XVIII):

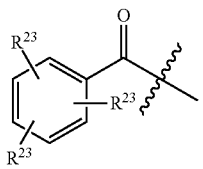

(XVIII)

wherein R$^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one R$^{23}$ may join with another R$^{23}$ to form a heterocyclyl ring. In some embodiments, at least one R$^{23}$ is hydrogen, for example, in some embodiments, each R$^{23}$ is hydrogen. In other embodiments, at least one R$^{23}$ is $C_1$-$C_{30}$ alkoxy, for example in some embodiments, each R$^{23}$ is methoxy. In other embodiments, at least one R$^{23}$ is heteroaryl, for example in some embodiments, at least one R$^{23}$ has one of the following structures (XVIIIa) of (XVIIIb):

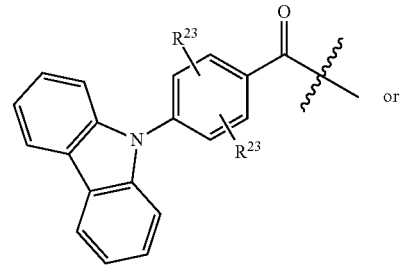

(XVIIIa)

or

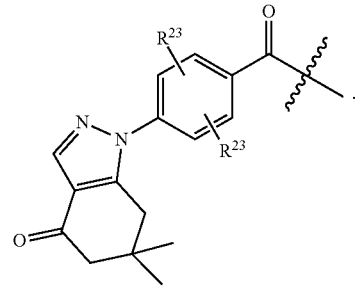

(XVIIIb)

In still other embodiments, one R$^{23}$ joins with another R$^{23}$ to form a heterocyclyl ring. For example, in one embodiment, R$^{20}$ is 5-carboxyfluorescein.

In other embodiments, R$^{20}$ is $C_7$-$C_{30}$ aralkylcarbonyl. For example, in various embodiments, R$^{20}$ has one of the following structures (XIX), (XX) or (XXI):

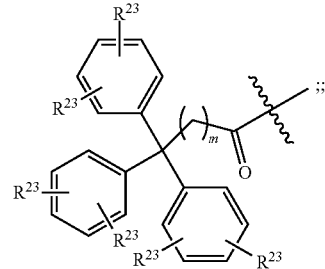

(XIX)

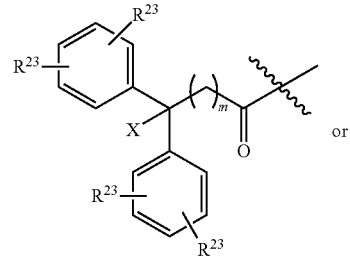

(XX)

or

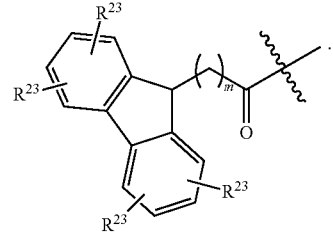

(XXI)

wherein R[23] is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, wherein one R[23] may join with another R[23] to form a heterocyclyl ring, X is —OH or halo and m is an integer from 0 to 6. In some specific embodiments, m is 0. In other embodiments, m is 1, while in other embodiments, m is 2. In other embodiments, at least one R[23] is hydrogen, for example in some embodiments each R[23] is hydrogen. In some embodiments, X is hydrogen. In other embodiments, X is —OH. In other embodiments, X is Cl. In other embodiments, at least one R[23] is $C_1$-$C_{30}$ alkoxy, for example methoxy.

In still other embodiments, R[20] is $C_7$-$C_{30}$ aralkyl, for example trityl. In other embodiments, R[20] is methoxy trityl. In some embodiments, R[20] has the following structure (XXII):

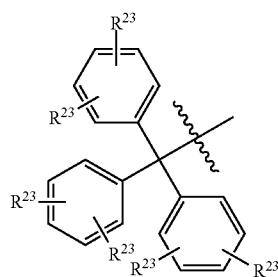

(XXII)

wherein R[23] is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one R[23] may join with another R[23] to form a heterocyclyl ring. For example, in some embodiments each R[23] is hydrogen. In other embodiments, at least one R[23] is $C_1$-$C_{30}$ alkoxy, for example methoxy.

In yet other embodiments, R[20] is $C_7$-$C_{30}$ aralkyl and R[20] has the following structure (XXIII)

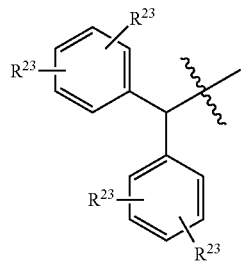

(XXIII)

In some embodiments, at least one R[23] is halo, for example chloro. In some other embodiments, one R[23] is chloro in the para position.

In other embodiments, R[20] is $C_1$-$C_{30}$ alkyl. For example, In some embodiments, R[20] is a $C_4$-$C_{20}$ alkyl and optionally comprises one or more double bonds. For example, In some embodiments, R[20] is a $C_{4-10}$ alkyl comprising a triple bond, for example a terminal triple bond. In some embodiments, R[20] is hexyn-6-yl. In some embodiments, R[20] has one of the following structures (XXIV), (XXV), (XXVI) or (XXVII):

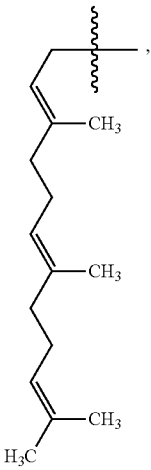

(XXIV)

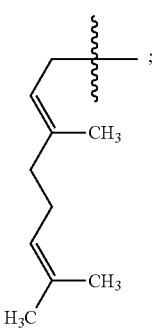

(XXV)

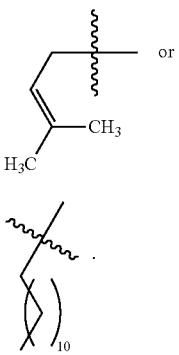

(XXVI)

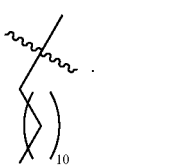

(XXVII)

In still other embodiments, R[20] is a $C_3$-$C_{30}$ alkylcarbonyl, for example a $C_3$-$C_{10}$ alkyl carbonyl. In some embodiments, R[20] is —C(=O)(CH$_2$)$_p$SH or —C(=O)(CH$_2$)$_p$SSHet, wherein p is an integer from 1 to 6 and Het is a heteroaryl. For example, p may be 1 or p may be 2. In other example Het is pyridinyl, for example pyridin-2-yl. In other embodiments, the $C_3$-$C_{30}$ alkylcarbonyl is substituted with a further oligomer, for example in some embodiments the oligomer comprises a $C_3$-$C_{30}$ alkyl carbonyl at the 3' position which links the oligomer to the 3' position of another oligomer. Such terminal modifications are included within the scope of the present disclosure.

In other embodiments, R[20] is a $C_3$-$C_{30}$ alkyl carbonyl which is futher substituted with an arylphosphoryl moiety, for example triphenyl phosphoryl. Examples of such R[20] groups include structure 33 in Table 3.

In other examples, R[20] is $C_3$-$C_8$ cycloalkylcarbonyl, for example $C_5$-$C_7$ alkyl carbonyl. In these embodiments, R$_{20}$ has the following structure (XXVIII):

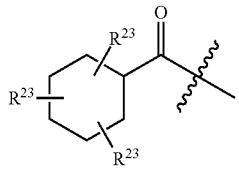

(XXVIII)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one $R^{23}$ may join with another $R^{23}$ to form a heterocyclyl ring. In some embodiments, $R^{23}$ is heterocyclylalkyl, for example in some embodiments $R^{23}$ has the following structure:

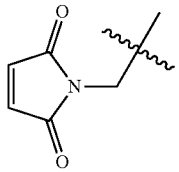 [SMILES: *CN1C(=O)C=CC1=O]

In some other embodiments, $R^{20}$ is $C_3$-$C_8$ cycloalkylalkylcarbonyl. In other embodiments, $R^{20}$ is $C_2$-$C_{30}$ alkyloxycarbonyl. In other embodiments, $R^{20}$ is $C_3$-$C_8$ cycloalkyloxycarbonyl. In other embodiments, $R^{20}$ is $C_7$-$C_{30}$ aryloxycarbonyl. In other embodiments, $R_{20}$ is $C_8$-$C_{30}$ aralkyloxycarbonyl. In other embodiments, $R^{20}$ is —P(=O)($R^{22}$)$_2$, wherein each $R^{22}$ is $C^6$-$C^{12}$ aryloxy, for example in some embodiments $R^{20}$ has the following structure (C24):

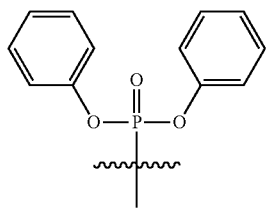

(C24)

In other embodiments, $R^{20}$ comprises one or more halo atoms. For example, in some embodiments $R^{20}$ comprises a perfluoro analogue of any of the above $R^{20}$ moieties. In other embodiments, $R^{20}$ is p-trifluoromethylphenyl, trifluoromethyltrityl, perfluoropentyl or pentafluorophenyl.

In some embodiments the 3' terminus comprises a modification and in other embodiments the 5' terminus comprises a modification. In other embodiments both the 3' and 5' termini comprise modifications. Accordingly, in some embodiments, $R^{18}$ is absent and $R^{19}$ is $R^{20}$. In other embodiments, $R^{19}$ is absent and $R^{18}$ is $R^{20}$. In yet other embodiments, $R^{18}$ and $R^{19}$ are each $R^{20}$.

In some embodiments, the oligomer comprises a cell-penetrating peptide in addition to a 3' or 5' modification. Accordingly, in some embodiments $R^{19}$ is a cell-penetrating peptide and $R^{18}$ is $R^{20}$. In other embodiments, $R^{18}$ is a cell-penetrating peptide and $R^{19}$ is $R^{20}$. In further embodiments of the foregoing, the cell-penetrating peptide is an arginine-rich peptide.

In some embodiments, the linker $L^1$ which links the 5' terminal group (i.e., $R^{19}$) to the oligomer may be present or absent. The linker comprises any number of functional groups and lengths provided the linker retains its ability to link the 5' terminal group to the oligomer and provided that the linker does not interfere with the oligomer's ability to bind to a target sequence in a sequence specific manner. In one embodiment, L comprises phosphorodiamidate and piperazine bonds. For example, in some embodiments L has the following structure (XXIX):

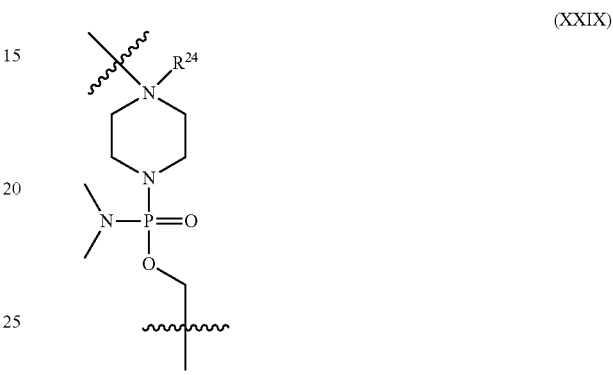

(XXIX)

wherein $R^{24}$ is absent, hydrogen or $C_1$-$C_6$ alkyl. In some embodiments, $R^{24}$ is absent. In some embodiments, $R^{24}$ is hydrogen. In some embodiments, $R^{24}$ is $C_1$-$C_6$ alkyl. In some embodiments, $R^{24}$ is methyl. In other embodiments, $R^{24}$ is ethyl. In yet other embodiments, $R^{24}$ is $C_3$ alkyl. In some other embodiments, $R^{24}$ is isopropyl. In yet other embodiments, $R^{24}$ is $C_4$ alkyl. In some embodiments, $R^{24}$ is $C_5$ alkyl. In yet other embodiments, $R^{24}$ is $C_6$ alkyl.

In yet other embodiments, $R^{20}$ is $C_3$-$C_{30}$ alkylcarbonyl, and $R^{20}$ has the following structure (XXX):

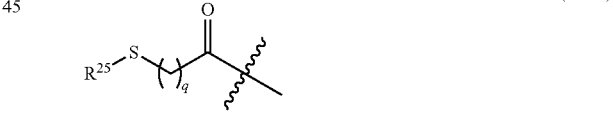

(XXX)

wherein $R^{25}$ is hydrogen or —$SR^{26}$, wherein $R^{26}$ is hydrogen, $C_1$-$C_{30}$ alkyl, heterocyclyl, aryl or heteroaryl, and q is an integer from 0 to 6.

In further embodiments of any of the above, $R^{23}$ is, at each occurrence, independently hydrogen, halo, $C_1$-$C_{30}$ alkyl, $C_1$-$C_{30}$ alkoxy, aryl, heteroaryl, heterocyclyl or heterocyclalkyl.

In some other embodiments, only the 3' terminus of the oligomer is conjugated to one of the groups noted above. In some other embodiments, only the 5' terminus of the oligomer is conjugated to one of the groups noted above. In other embodiments, both the 3' and 5' termini comprise one of the groups noted above. The terminal group may be selected from any one of the groups noted above or any of the specific groups illustrated in Table 3.

TABLE 3

Representative Terminal Groups

| No. | Name | Structure |
|---|---|---|
| C1 | Trimethoxybenzoyl | 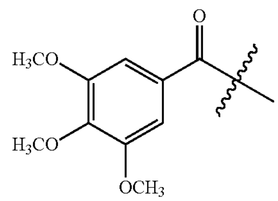 [SMILES: *C(=O)c1cc(OC)c(OC)c(OC)c1] |
| C2 | 9-fluorene-carboxyl | 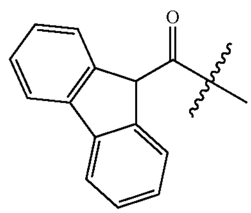 [SMILES: *C(=O)C1c2ccccc2-c2ccccc21] |
| C3 | 4-carbazolylbenzoyl | 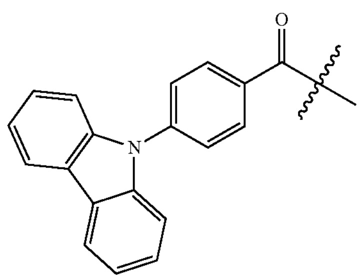 [SMILES: *C(=O)c1ccc(-n2c3ccccc3c3ccccc32)cc1] |
| C4 | 4-indazolylonebenzoyl | 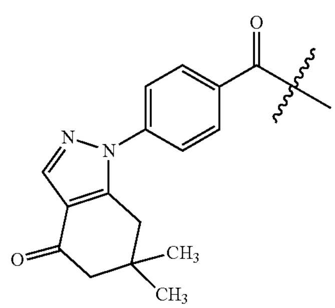 [SMILES: *C(=O)c1ccc(-n2ncc3c2CC(C)(C)CC3=O)cc1] |
| C5 | Farnesyl | 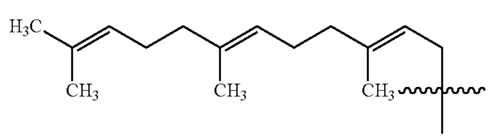 [SMILES: *C/C=C(\C)CC/C=C(\C)CCC=C(C)C] |
| C6 | Geranyl | 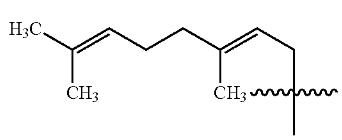 [SMILES: *C/C=C(\C)CCC=C(C)C] |
| C7 | Prenyl | 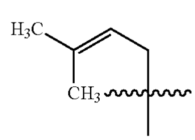 [SMILES: *CC=C(C)C] |

TABLE 3-continued

Representative Terminal Groups

| No. | Name | Structure |
|---|---|---|
| C8 | Diphenylacetyl | 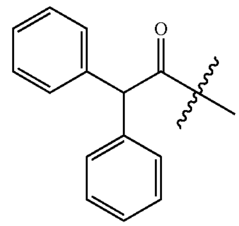 [SMILES: *C(=O)C(c1ccccc1)c1ccccc1] |
| C9 | Chlorodiphenylacetyl | 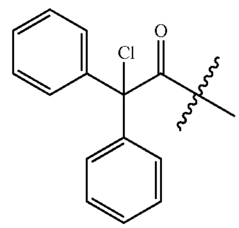 [SMILES: *C(=O)C(Cl)(c1ccccc1)c1ccccc1] |
| C10 | Hydroxydiphenylacetyl | 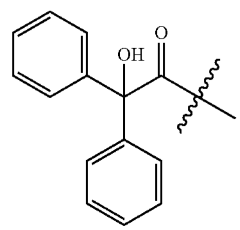 [SMILES: *C(=O)C(O)(c1ccccc1)c1ccccc1] |
| C11 | Triphenylpropionyl | 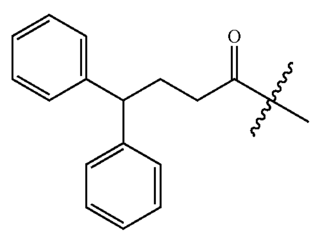 [SMILES: *C(=O)CCC(c1ccccc1)c1ccccc1] |
| C12 | Triphenylpropyl | 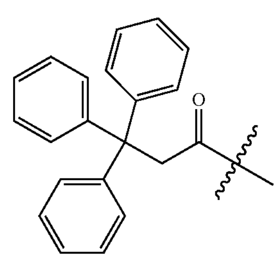 [SMILES: *C(=O)CC(c1ccccc1)(c1ccccc1)c1ccccc1] |
| C13 | Triphenylacetyl | 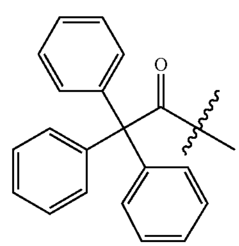 [SMILES: *C(=O)C(c1ccccc1)(c1ccccc1)c1ccccc1] |

TABLE 3-continued
Representative Terminal Groups
| No. | Name | Structure |
|---|---|---|
| C14 | Trityl (Tr) | 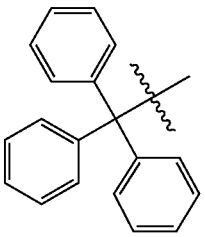 [SMILES: *C(c1ccccc1)(c1ccccc1)c1ccccc1] |
| C15 | Methoxytrityl (MeOTr) | 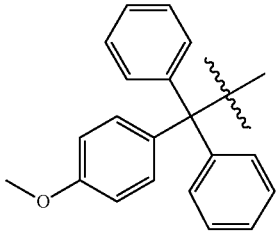 [SMILES: *C(c1ccccc1)(c1ccccc1)c1ccc(OC)cc1] |
| C16 | Methylsuccinimidyl-cyclohexoyl | 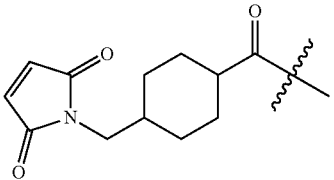 [SMILES: *C(=O)C1CCC(CN2C(=O)C=CC2=O)CC1] |
| C17 | Thioacetyl | 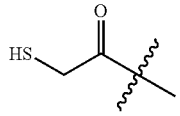 |
| C18 | COCH$_2$CH$_2$SSPy | 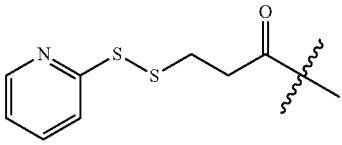 [SMILES: *C(=O)CCSSc1ccccn1] |
| C19 | Guanidinyl | 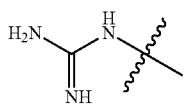 |
| C20 | Trimethylglycine | 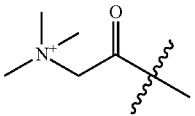 [SMILES: *C(=O)C[N+](C)(C)C] |
| C21 | Lauroyl | 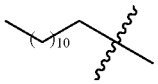 |
| C22 | Triethyleneglycoloyl (EG3) | 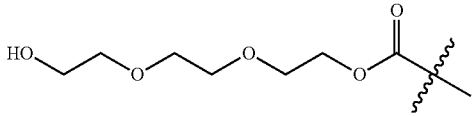 [SMILES: *C(=O)OCCOCCOCCO] |

TABLE 3-continued

| | Representative Terminal Groups | |
|---|---|---|
| No. | Name | Structure |
| C23 | Succinicacetyl | |
| C24 | Diphenylphosphoryl | |
| C25 | Piperidin-4-yl | |
| C26 | Tritylpiperidin-4-yl | |
| C27 | Boc-Piperidin-4-yl | |
| C28 | Hexyn-6-yl | |
| C29 | 5-carboxyfluorescein | |

TABLE 3-continued

Representative Terminal Groups

| No. | Name | Structure |
|---|---|---|
| C30 | Benzhydryl | 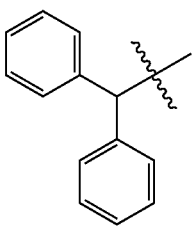 [SMILES: *C(c1ccccc1)c1ccccc1] |
| C31 | p-Chlorobenzhydryl | 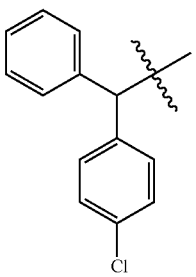 [SMILES: *C(c1ccccc1)c1ccc(Cl)cc1] |
| C32 | Piperazinyl (pip) | 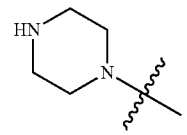 |
| C33 | Triphenylphos | 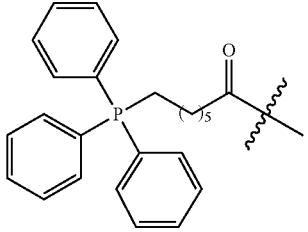 |
| C34 | Dimerized | 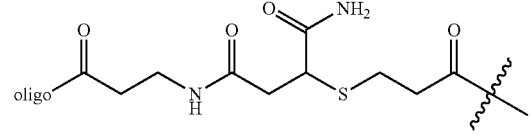 Oligo = a further oligomer |

C. Properties of the Conjugates

As noted above, the present disclosure is directed to conjugates of carrier peptides and oligonucleotide analogues (i.e., oligomers). The oligomers may comprise various modifications which impart desirable properties (e.g., increased antisense activity) to the oligomers. In certain embodiments, the oligomer comprises a backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligomer can bind in a sequence-specific manner to a target nucleic acid. The morpholino ring structures may have the following structure (i):

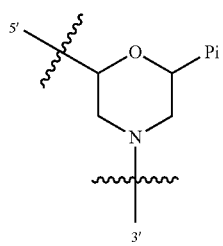

(i)

wherein Pi is, at each occurrence, independently a base-pairing moiety.

Each morpholino ring structure supports a base pairing moiety (Pi), to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine. Analog bases that confer improved binding affinity to the oligomer can also be utilized. Exemplary analogs in this regard include C5-propynyl-modified pyrimidines, 9-(aminoethoxy)phenoxazine (G-clamp) and the like.

As noted above, the oligomer may be modified, in accordance with an aspect of the invention, to include one or more (B) linkages, e.g. up to about 1 per every 2-5 uncharged linkages, typically 3-5 per every 10 uncharged linkages. Certain embodiments also include one or more linkages of type (B). In some embodiments, optimal improvement in antisense activity is seen where up to about half of the backbone linkages are type (B). Some, but not maximum enhancement is typically seen with a small number e.g., 10-20% of (B) linkages.

In one embodiment, the linkage types (A) and (B) are interspersed along the backbone. In some embodiments, the oligomer does not have a strictly alternating pattern of (A) and (B) linkages along its entire length. In addition to the carrier peptide, the oligomers may optionally comprise a 5' and/or 3' modification as described above.

Also considered are oligomers having blocks of (A) linkages and blocks of (B) linkages; for example, a central block of (A) linkages may be flanked by blocks of (B) linkages, or vice versa. In one embodiment, the oligomer has approximately equal-length 5', 3; and center regions, and the percentage of (B) or (A) linkages in the center region is greater than about 50%, o greater than about 70%. Oligomers for use in antisense applications generally range in length from about 10 to about 40 subunits, more preferably about 15 to 25 subunits. For example, an oligomer of the invention having 19-20 subunits, a useful length for an antisense oligomer, may ideally have two to seven, e.g. four to six, or three to five, (B) linkages, and the remainder (A) linkages. An oligomer having 14-15 subunits may ideally have two to five, e.g. 3 or 4, (B) linkages and the remainder (A) linkages.

The morpholino subunits may also be linked by non-phosphorus-based intersubunit linkages, as described further below.

Other oligonucleotide analog linkages which are uncharged in their unmodified state but which could also bear a pendant amine substituent can also be used. For example, a 5'nitrogen atom on a morpholino ring could be employed in a sulfamide linkage (or a urea linkage, where phosphorus is replaced with carbon or sulfur, respectively).

In some embodiments for antisense applications, the oligomer may be 100% complementary to the nucleic acid target sequence, or it may include mismatches, e.g., to accommodate variants, as long as a heteroduplex formed between the oligomer and nucleic acid target sequence is sufficiently stable to withstand the action of cellular nucleases and other modes of degradation which may occur in vivo. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the nucleic acid target sequence, it is effective to stably and specifically bind to the target sequence, such that a biological activity of the nucleic acid target, e.g., expression of encoded protein(s), is modulated.

The stability of the duplex formed between an oligomer and the target sequence is a function of the binding $T_m$ and the susceptibility of the duplex to cellular enzymatic cleavage. The $T_m$ of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol.* Vol. 154 pp. 94-107.

In some embodiments, each antisense oligomer has a binding $T_m$, with respect to a complementary-sequence RNA, of greater than body temperature or in other embodiments greater than 50° C. In other embodiments $T_m$'s are in the range 60-80° C. or greater. According to well known principles, the $T_m$ of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high $T_m$ (50° C. or greater) at a length of 20 bases or less are generally preferred over those requiring greater than 20 bases for high $T_m$ values. For some applications, longer oligomers, for example longer than 20 bases may have certain advantages. For example, in certain embodiments longer oligomers may find particular utility for use in exon skippin or splice modulation.

The targeting sequence bases may be normal DNA bases or analogues thereof, e.g., uracil and inosine that are capable of Watson-Crick base pairing to target-sequence RNA bases.

The oligomers may also incorporate guanine bases in place of adenine when the target nucleotide is a uracil residue. This is useful when the target sequence varies across different viral species and the variation at any given nucleotide residue is either cytosine or uracil. By utilizing guanine in the targeting oligomer at the position of variability, the well-known ability of guanine to base pair with uracil (termed C/U:G base pairing) can be exploited. By incorporating guanine at these locations, a single oligomer can effectively target a wider range of RNA target variability.

The compounds (e.g., oligomers, intersubunit linkages, terminal groups) may exist in different isomeric forms, for example structural isomers (e.g., tautomers). With regard to stereoisomers, the compounds may have chiral centers and may occur as racemates, enantiomerically enriched mixtures, individual enantiomers, mixture or diastereomers or individual diastereomers. All such isomeric forms are included within the present invention, including mixtures thereof. The compounds may also possess axial chirality which may result in atropisomers. Furthermore, some of the crystalline forms of the compounds may exist as polymorphs, which are included in the present invention. In addition, some of the compounds may also form solvates with water or other organic solvents. Such solvates are similarly included within the scope of this invention.

The oligomers described herein may be used in methods of inhibiting production of a protein or replication of a virus. Accordingly, in one embodiment a nucleic acid encoding such a protein is exposed to an oligomer as disclosed herein. In further embodiments of the foregoing, the antisense oligomer comprises either a 5' or 3' modified terminal group or combinations thereof, as disclosed herein, and the base pairing moieties B form a sequence effective to hybridize to a portion of the nucleic acid at a location effective to inhibit production of the protein. In one embodiment, the location is an ATG start codon region of an mRNA, a splice site of a pre-mRNA, or a viral target sequence as described below.

In one embodiment, the oligomer has a $T_m$ with respect to binding to the target sequence of greater than about 50° C., and it is taken up by mammalian cells or bacterial cells. In another embodiment, the oligomer may be conjugated to a transport moiety, for example an arginine-rich peptide, as described herein to facilitate such uptake. In another embodiment, the terminal modifications described herein can function as a transport moiety to facilitate uptake by mammalian and/or bacterial cells.

The preparation and properties of morpholino oligomers is described in more detail below and in U.S. Pat. No. 5,185,444 and WO/2009/064471, each of which is hereby incorporated by reference in their entirety.

D. Formulation and Administration of the Conjugates

The present disclosure also provides for formulation and delivery of the disclosed conjugate. Accordingly, in one embodiment the present disclosure is directed to a composition comprising a peptide-oligomer conjugate as disclosed herein and a pharmaceutically acceptable vehicle.

Effective delivery of the conjugate to the target nucleic acid is an important aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The conjugate may be administered in any convenient vehicle which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

The compounds (e.g., conjugates) of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, antisense inhibition is effective in treating infection of a host animal by a virus, by contacting a cell infected with the virus with an antisense agent effective to inhibit the replication of the specific virus. The antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

In one embodiment, the conjugate is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The conjugate may be administered at regular intervals for a short time period, e.g., daily for two weeks or less. However, in some cases the conjugate is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the conjugates of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of disease and/or infection, such as complete blood count (CBC), nucleic acid detection methods, immunodiagnostic tests, viral culture, or detection of heteroduplex.

The efficacy of an in vivo administered antiviral conjugate of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5):1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

E. Preparation of the Conjugates

The morpholino subunits, the modified intersubunit linkages and oligomers comprising the same can be prepared as described in the examples and in U.S. Pat. Nos. 5,185,444 and 7,943,762 which are hereby incorporated by reference in their entirety. The morpholino subunits can be prepared according to the following general Reaction Scheme I.

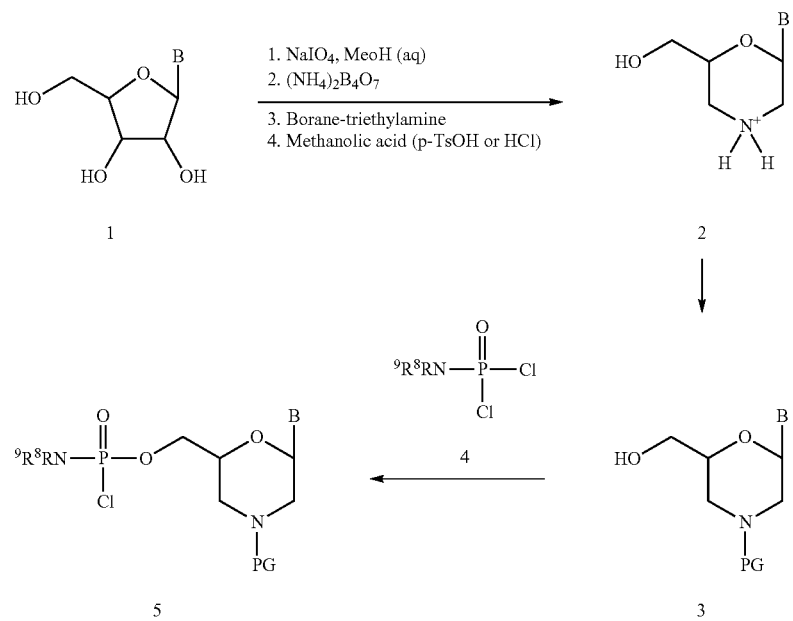

Reaction Scheme 1. Preparation of Morpholino Subunits

Referring to Reaction Scheme 1, wherein B represents a base pairing moiety and PG represents a protecting group, the morpholino subunits may be prepared from the corresponding ribinucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing poiety may be suitable protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271, 040, which is hereby incorporated by reference in its entirety.

Reaction of 3 with the activated phosphorous compound 4, results in morpholino subunints having the desired linkage moiety (5). Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762. Although the above scheme depicts preparation of linkages of type (B) (e.g., X is —$NR^8R^9$), linkages of type (A) (e.g., X is dimethyl amine) can be prepared in an analogous manner.

Figure 3:
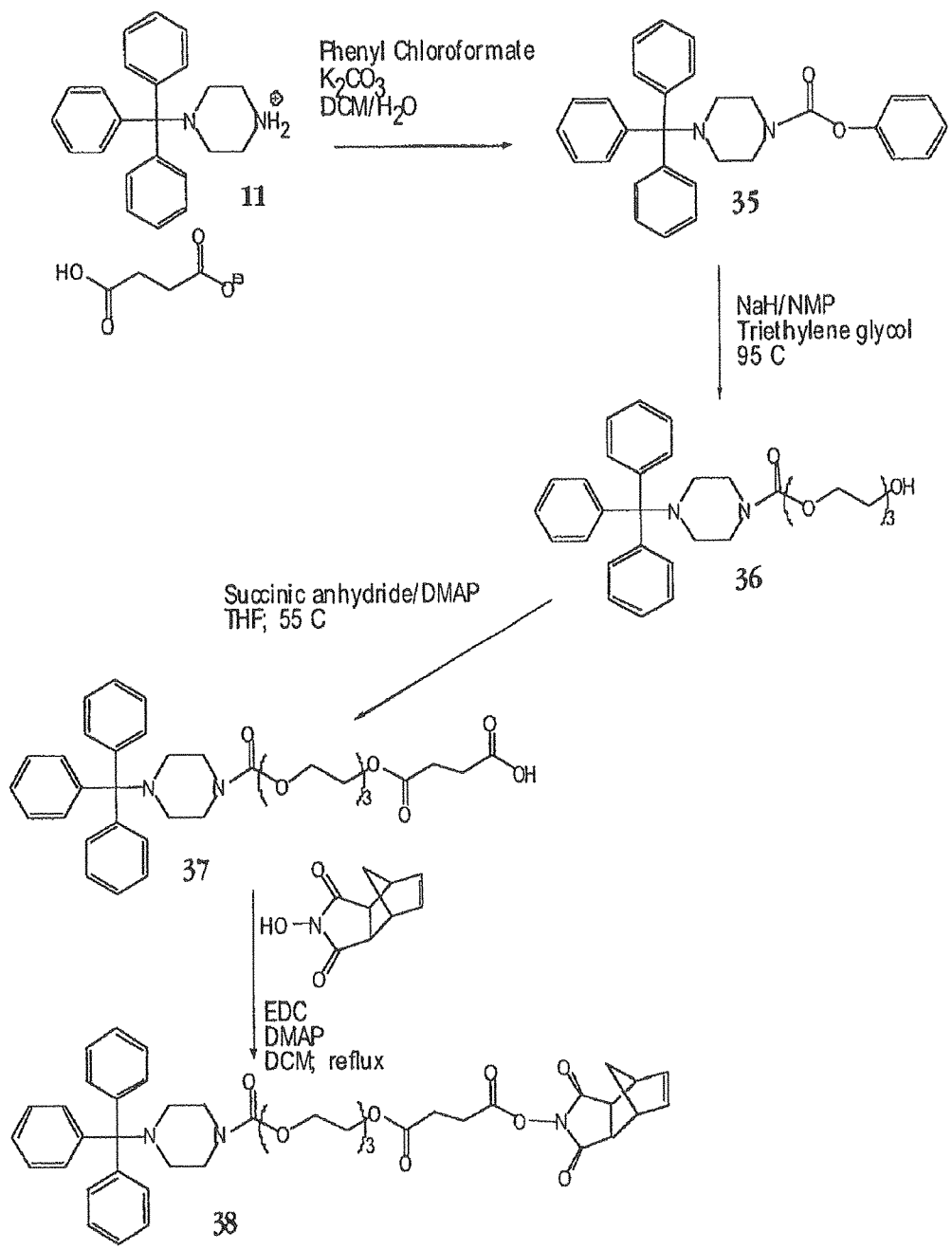
FIG. 3 is a reaction scheme showing preparation of a linker for solid-phase synthesis.
Figure 4:
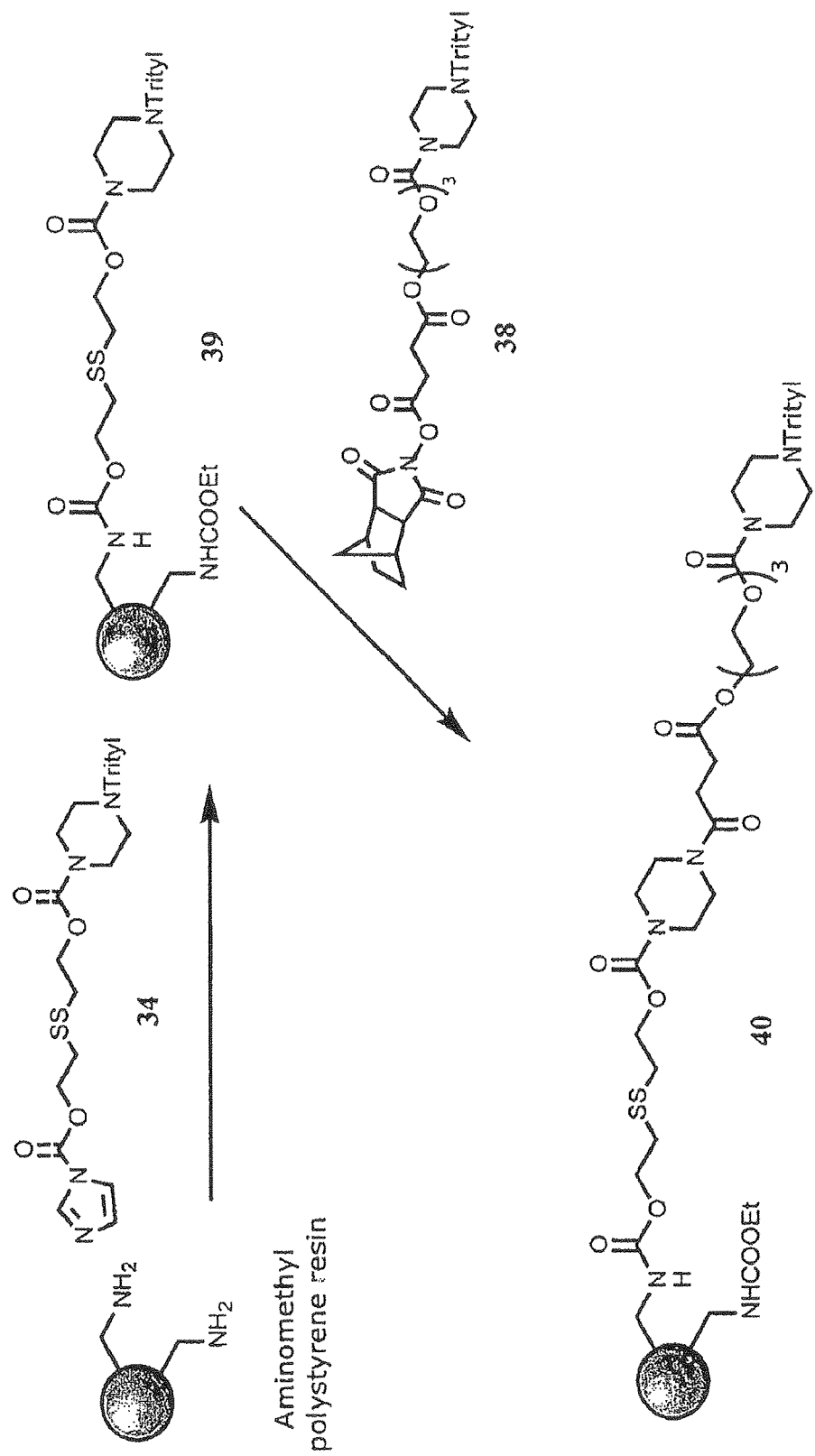
FIG. 4 demonstrates preparation of a solid support for oligomer synthesis.

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising $L^1$ and/or $R^{19}$. An exemplary method is demonstrated in FIGS. 3 and 4. In this manner, the oligo may comprise a 5'-terminal modification after oligomer synthsis is complete and the oligomer is cleaved from the solid support. Once supported, the protecting group of 5 (e.g., trityl) is removed and the free amine is reacted with an activated phosphorous moiety of a second compound of structure 5. This sequence is repeated until the desired length oligo is obtained. The protecting group in the terminal 5' end may either be removed or left on if a 5'-modification is desired. The oligo can be removed from the solid support using any number of methods, or example treatment with a base to cleave the linkage to the solid support.

Peptide oligomer conjugates can be prepared by coupling the desired peptide (prepared according to standard peptide synthetic methods known in the art) with an oligomer comprising a free NH (for example the 3' NH of amorpholino oligomer) in the presence of an appropriate activating reagent (e.g., HATU). Conjugates may be purified using a number of techniques known in the art, for example SCX chromatography.

The preparation of modified morpholino subunits and peptide oligomer conjugates are described in more detail in the Examples. The peptide oligomer conjugates containing any number of modified linkages may be prepared using methods described herein, methods known in the art and/or described by reference herein. Also described in the examples are global modifications of PMO+ morpholino oligomers prepared as previously described (see e.g., PCT publication WO2008036127).

F. Antisense Activity of the Oligomers

The present disclosure also provides a method of inhibiting production of a protein, the method comprising exposing a nucleic acid encoding the protein to a peptide-oligomer conjugate as disclosed herein. Accordingly, in one embodiment a nucleic acid encoding such a protein is exposed to a conjugate, as disclosed herein, where the base pairing moieties Pi form a sequence effective to hybridize to a portion of the nucleic acid at a location effective to inhibit production of the protein. The oligomer may target, for example, an ATG start codon region of an mRNA, a splice site of a pre-mRNA, or a viral target sequence as described below.

In another embodiment, the disclosure provides a method of enhancing antisense activity of a peptide oligomer conjugate comprising an oligonucleotide analogue having a sequence of morpholino subunits, joined by intersubunit linkages, supporting base-pairing moieties, the method comprises conjugating a carrier peptide as described herein to the oligonucleotide.

In some embodiments, enhancement of antisense activity may be evidenced by:

(i) a decrease in expression of an encoded protein, relative to that provided by a corresponding unmodified oligomer, when binding of the antisense oligomer to its target sequence is effective to block a translation start codon for the encoded protein, or (ii) an increase in expression of an encoded protein, relative to that provided by a corresponding unmodified oligomer, when binding of the antisense oligomer to its target sequence is effective to block an aberrant splice site in a pre-mRNA which encodes said protein when correctly spliced. Assays suitable for measurement of these effects are described further below. In one embodiment, modification provides this activity in a cell-free translation assay, a splice correction translation assay in cell culture, or a splice correction gain of function animal model system as described herein. In one embodiment, activity is enhanced by a factor of at least two, at least five or at least ten.

Described below are various exemplary applications of the conjugates of the invention including antiviral applications, treatment of neuromuscular diseases, bacterial infections, inflammation and polycystic kidney disease. This description is not meant to limit the invention in any way but serves to exemplify the range of human and animal disease conditions that can be addressed using the conjugates described herein.

G. Exemplary Therapeutic Uses of the Conjugates

The oligomers conjugated to the carrier peptide comprise good efficacy and low toxicity, thus resulting in a better therepuetic window than obtained with other oligomers or peptide-oligomer conjugates. The following description provides exemplary, but not limiting, example of therapeutic uses of the conjugates.

1. Targeting Stem-Loop Secondary Structure of ssRNA Viruses

One class of an exemplary antisense antiviral compound is a morpholino oligomer as described herein having a sequence of 12-40 subunits and a targeting sequence that is complementary to a region associated with stem-loop secondary structure within the 5'-terminal end 40 bases of the positive-sense RNA strand of the targeted virus. (See, e.g., PCT Pubn. No. WO/2006/033933 or U.S. Appn. Pubn. Nos. 20060269911 and 20050096291, which are incorporated herein by reference.)

The method comprises first identifying as a viral target sequence, a region within the 5'-terminal 40 bases of the positive strand of the infecting virus whose sequence is capable of forming internal stem-loop secondary structure. There is then constructed, by stepwise solid-phase synthesis, a morpholino oligomer having a targeting sequence of at least 12 subunits that is complementary to the virus-genome region capable of forming internal duplex structure, where the oligomer is able to form with the viral target sequence, a heteroduplex structure composed of the positive sense strand of the virus and the oligonucleotide compound, and characterized by a Tm of dissociation of at least 45° C. and disruption of such stem-loop structure. The oligomer is conjugated to a carrier peptide described herein.

The target sequence may be identified by analyzing the 5'-terminal sequences, e.g., the 5'-terminal 40 bases, by a computer program capable of performing secondary structure predictions based on a search for the minimal free energy state of the input RNA sequence.

In a related aspect, the conjugates can be used in methods of inhibiting in a mammalian host cell, replication of an infecting RNA virus having a single-stranded, positive-sense genome and selected from one of the Flaviviridae, Picornoviridae, Caliciviridae, Togaviridae, Arteriviridae, Coronaviridae, Astroviridae or Hepeviridae families. The method includes administering to the infected host cells, a virus-inhibitory amount of conjugate as described herein, having a targeting sequence of at least 12 subunits that is complementary to a region within the 5'-terminal 40 bases of the positive-strand viral genome that is capable of forming internal stem-loop secondary structure. The conjugate is effective, when administered to the host cells, to form a heteroduplex structure (i) composed of the positive sense strand of the virus and the oligonucleotide compound, and (ii) characterized by a Tm of dissociation of at least 45° C. and disruption of such stem-loop secondary structure. The conjugate may be administered to a mammalian subject infected with the virus, or at risk of infection with the virus.

Exemplary targeting sequences that target the terminal stem loop structures of the dengue and Japanese encephalitis viruses are listed below as SEQ ID NOs: 1 and 2, respectively.

Additional exemplary targeting sequences that target the terminal stem loop structures of ssRNA viruses can also be found in U.S. application Ser. No. 11/801,885 and PCT publication WO/2008/036127 which are incorporated herein by reference.

2. Targeting the First Open Reading Frame of ssRNA Viruses

A second class of exemplary conjugates is for use in inhibition of growth of viruses of the picornavirus, calicivirus, togavirus, coronavirus, and flavivirus families having a single-stranded, positive sense genome of less than 12 kb and a first open reading frame that encodes a polyprotein containing multiple functional proteins. In particular embodiments, the virus is an RNA virus from the coronavirus family or a West Nile, Yellow Fever or Dengue virus from the flavivirus family. The inhibiting conjugates comprise antisense oligomers described herein, having a targeting base sequence that is substantially complementary to a viral target sequence which spans the AUG start site of the first open reading frame of the viral genome. In one embodiment of the method, the conjugate is administered to a mammalian subject infected with the virus. See, e.g., PCT Pubn. No. WO/2005/007805 and US Appn. Pubn. No. 2003224353, which are incorporated herein by reference.

The preferred target sequence is a region that spans the AUG start site of the first open reading frame (ORF1) of the viral genome. The first ORF generally encodes a polyprotein containing non-structural proteins such as polymerases, helicases and proteases. By "spans the AUG start site" is meant that the target sequence includes at least three bases on one side of the AUG start site and at least two bases on the other (a total of at least 8 bases). Preferably, it includes at least four bases on each side of the start site (a total of at least 11 bases).

More generally, preferred target sites include targets that are conserved between a variety of viral isolates. Other favored sites include the IRES (internal ribosome entry site), transactivation protein binding sites, and sites of initiation of replication. Complex and large viral genomes, which may provide multiple redundant genes, may be efficiently targeted by targeting host cellular genes coding for viral entry and host response to viral presence.

A variety of viral-genome sequences are available from well known sources, such as the NCBI Genbank databases. The AUG start site of ORF1 may also be identified in the gene database or reference relied upon, or it may be found by scanning the sequence for an AUG codon in the region of the expected ORF1 start site.

The general genomic organization of each of the four virus families is given below, followed by exemplary target sequences obtained for selected members (genera, species or strains) within each family.

3. Targeting Influenza Virus

A third class of exemplary conjugates are used in inhibition of growth of viruses of the Orthomyxoviridae family and in the treatment of a viral infection. In one embodiment, the host cell is contacted with a conjugate as described herein, for example a conjugate comprising a base sequence effective to hybridize to a target region selected from the following: 1) the 5' or 3' terminal 25 bases of the negative sense viral RNA segments; 2) the terminal 25 bases of the 5' or 3' terminus of the positive sense cRNA; 3) 45 bases surrounding the AUG start codons of influenza viral mRNAs and; 4) 50 bases surrounding the splice donor or acceptor sites of influenza mRNAs subject to alternative splicing. (See, e.g., PCT Pubn. No. WO/2006/047683; U.S. Appn. Pubn. No. 20070004661; and PCT Appn. Num. 2010/056613 and U.S. application Ser. No. 12/945,081, which are incorporated herein by reference.)

Exemplary conjugates in this regard include conjugates comprising oligomers comprising SEQ ID NO:3.

TABLE 4

Influenza targeting sequences that incorporate modified intersubunit linkages or terminal groups

| NG-10-0038 | PMOhex   | CGG T$^h$TA GAA GAC $^h$TCA TC$^h$T TT |
| NG-10-0039 | PMOhex   | CGG T$^h$TA GAA GAC $^h$TCA $^h$TCT $^h$TT |
| NG-10-0096 | PMOapn   | CGG T$^a$TA GAA GAC $^a$TCA TC$^a$T TT |
| NG-10-0097 | PMOapn   | CGG $^a$T$^a$TA GAA GAC $^a$TCA $^a$TC$^a$T TT |
| NG-10-0099 | PMOpyr   | CGG $^p$T$^p$TA GAA GAC $^p$TCA $^p$TC$^p$T TT |
| NG-10-0107 | PMOthiol | CGG T$^{SH}$TA GAA GAC $^{SH}$TCA TC$^{SH}$T TT |

TABLE 4-continued

Influenza targeting sequences that incorporate modified intersubunit linkages or terminal groups

| | | |
|---|---|---|
| NG-10-0108 | PMOsucc | CGG T$^s$TA GAA GAC $^s$TCA TC$^s$T TT |
| NG-10-0111 | PMOguan | CGG T$^g$TA GAA GAC $^g$TCA TC$^g$T TT |
| NG-10-0141 | PMOpyr | CGG T$^p$TA GAA GAC $^p$TCA TC$^p$T TT |
| NG-10-0142 | PMOpyr | CGG T$^p$TA GAA GAC $^p$TCA $^p$TC$^p$T TT |
| NG-10-0158 | PMOglutaric | CGG T$^{glu}$TA GAA GAC $^{glu}$TCA TC$^{glu}$T TT |
| NG-10-0159 | PMOcyclo-glut | CGG T$^{cpglu}$TA GAA GAC $^{cpglu}$TCA TC$^{cpglu}$T TT |
| NG-10-0160 | PMOcholic acid | CGG T$^{ca}$TA GAA GAC $^{ca}$TCA TC$^{ca}$T TT |
| NG-10-0161 | PMOdeoxyCA | CGG T$^{dca}$TA GAA GAC $^{dca}$TCA TC$^{dca}$T TT |
| NG-10-0180 | PMOapn | TT$^a$TCGA CA$^a$T CGG T$^a$TA GAA GAC $^a$TCA T |
| NG-10-0174 | PMOm | CGG T$^a$TA GAA GAC $^a$TCA TC$^a$T TT |
| NG-10-0222 | PMO MeT | CGG T$^{Me}$TA GAA GAC +TCA TC +T TT |
| NG-10-0223 | PMO FarnT | CGG T$^{Farn}$TA GAA GAC +TCA TC +T TT |
| NG-10-0538 | PMOapn-trityl | CGG T$^a$TA GAA GAC $^a$TCA TC$^a$T TT |
| NG-10-0539 | PMOapn-trityl | CGG T$^p$TA GAA GAC $^p$TCA TC$^p$T TT |
| NG-10-0015 | PMO | CGG TTA GAA GAC TCA TCT TT |
| NG-11-0170 | PMOplus | CGG +TTA GAA GAC +TCA TC +T TT |
| NG-11-0145 | PMOplus-benzhydryl | CGG T +TA GAA GAC +TCA TC +T TT** |
| NG-11-0148 | PMOisopropylPip | CGG TiprpipT A GAA GAC iprpipTCA TCiprpipT TT |
| NG-11-0173 | PMOpyr | CGG pTTA GAA GAC pTCA TCpT TT |
| NG-11-0291 | Trimethyl Gly | CGG T*+TA GAA GAC *+TCA TC*+T TT |

**3'-benzhydryl; *+linkages are trimethyl glycine acylated at the PMOplus linkages; PMOm represents T bases with a methyl group on the 3-nitrogen position.

The conjugate s are particularly useful in the treatment of influenza virus infection in a mammal. The o conjugate may be administered to a mammalian subject infected with the influenza virus, or at risk of infection with the influenza virus.

4. Targeting Viruses of the Picornaviridae Family

A fourth class of exemplary conjugates are used in inhibition of growth of viruses of the Picornaviridae family and in the treatment of a viral infection. The conjugates are particularly useful in the treatment of Enterovirus and/or Rhinovirus infection in a mammal. In this embodiment, the conjugates comprise morpholino oligomers having a sequence of 12-40 subunits, including at least 12 subunits having a targeting sequence that is complementary to a region associated with viral RNA sequences within one of two 32 conserved nucleotide regions of the viral 5' untranslated region. (See, e.g., PCT Pubn. Nos. WO/2007/030576 and WO/2007/030691 or copending and co-owned U.S. application Ser. Nos. 11/518,058 and 11/517,757, which are incorporated herein by reference.) An exemplary targeting sequence is listed below as SEQ NO: 6.

5. Targeting Viruses of the Flavivirus Family

A fifth class of exemplary conjugates are used in inhibition of replication of a flavivirus in animal cells. An exemplary conjugate of this class comprises a morpholino oligomer of between 8-40 nucleotide bases in length and having a sequence of at least 8 bases complementary to a region of the virus' positive strand RNA genome that includes at least a portion of the 5'-cyclization sequence (5'-CS) or 3'-CS sequences of the positive strand flaviviral RNA. A highly preferred target is the 3'-CS and an exemplary targeting sequence for dengue virus is listed below as SEQ ID NO: 7. (See, e.g., PCT Pubn. No. (WO/2005/030800) or copending and co-owned U.S. Application Ser. No. 10/913,996, which are incorporated herein by reference.)

6. Targeting Viruses of the Nidovirus Family

A sixth class of exemplary conjugates are used in inhibition of replication of a nidovirus in virus-infected animal cells. An exemplary conjugate of this class comprises a morpholino oligomer containing between 8-25 nucleotide bases, and having a sequence capable of disrupting base pairing between the transcriptional regulatory sequences (TRS) in the 5' leader region of the positive-strand viral genome and negative-strand 3' subgenomic region (See, e.g., PCT Pubn. No. WO/2005/065268 or U.S. Appn. Pubn. No. 20070037763, which are incorporated herein by reference.)

7. Targeting of Filoviruses

In another embodiment, one or more conjugates as described herein can be used in a method of in inhibiting replication within a host cell of an Ebola virus or Marburg virus, by contacting the cell with a conjugate as described herein, for example a conjugate having a targeting base sequence that is complementary to a target sequence composed of at least 12 contiguous bases within an AUG start-site region of a positive-strand mRNA, as described further below.

The filovirus viral genome is approximately 19,000 bases of single-stranded RNA that is unsegmented and in the antisense orientation. The genome encodes 7 proteins from monocistronic mRNAs complementary to the vRNA.

Target sequences are positive-strand (sense) RNA sequences that span or are just downstream (within 25 bases) or upstream (within 100 bases) of the AUG start codon of selected Ebola virus proteins or the 3' terminal 30 bases of the minus-strand viral RNA. Preferred protein targets are the viral polymerase subunits VP35 and VP24, although L, nucleoproteins NP and VP30, are also contemplated. Among these early proteins are favored, e.g., VP35 is favored over the later expressed L polymerase.

In another embodiment, one or more conjugates as described herein can be used in a method of in inhibiting replication within a host cell of an Ebola virus or Marburg virus, by contacting the cell with a conjugate as described herein having a targeting base sequence that is complementary to a target sequence composed of at least 12 contiguous bases within an AUG start-site region of a positive-strand mRNA of the Filovirus mRNA sequences. (See, e.g., PCT Pubn. No. WO/2006/050414 or U.S. Pat. Nos. 7,524,829 and 7,507,196, and continuation applications with U.S. application Ser. Nos. 12/402,455; 12/402,461; 12/402,464; and 12/853,180 which are incorporated herein by reference.)

8. Targeting of Arenaviruses

In another embodiment, a conjugate as described herein can be used in a method for inhibiting viral infection in mammalian cells by a species in the Arenaviridae family. In one aspect, the conjugates can be used in treating a mammalian subject infected with the virus. (See, e.g., PCT Pubn. No. WO/2007/103529 or U.S. Pat. No. 7,582,615, which are incorporated herein by reference.)

Table 5 is an exemplary list of targeted viruses targeted by conjugates of the invention as organized by their Old World or New World Arenavirus classification.

TABLE 5

Targeted Arenaviruses

| Family | Genus | Virus |
|---|---|---|
| | | Old World Arenaviruses |
| Arenaviridae | *Arenavirus* | Lassa virus (LASV) |
| | | Lymphocytic choriomeningitis virus (LCMV) |
| | | Mopeia virus (MOPV) |
| | | New World Arenaviruses |
| | | Guanarito virus (GTOV) |
| | | Junín virus (JUNV) |
| | | Machupo virus (MACV) |
| | | Pichinide virus (PICV) |
| | | Pirital virus (PIRV) |
| | | Sabiá virus (SABV) |
| | | Tacaribe virus (TCRV) |
| | | Whitewater Arroyo virus (WWAV) |

The genome of Arenaviruses consists of two single-stranded RNA segments designated S (small) and L (large). In virions, the molar ratio of S- to L-segment RNAs is roughly 2:1. The complete S-segment RNA sequence has been determined for several arenaviruses and ranges from 3,366 to 3,535 nucleotides. The complete L-segment RNA sequence has also been determined for several arenaviruses and ranges from 7,102 to 7,279 nucleotides. The 3' terminal sequences of the S and L RNA segments are identical at 17 of the last 19 nucleotides. These terminal sequences are conserved among all known arenaviruses. The 5'-terminal 19 or 20 nucleotides at the beginning of each genomic RNA are imperfectly complementary with each corresponding 3' end. Because of this complementarity, the 3' and 5' termini are thought to base-pair and form panhandle structures.

Replication of the infecting virion or viral RNA (vRNA) to form an antigenomic, viral-complementary RNA (vcRNA) strand occurs in the infected cell. Both the vRNA and vcRNA encode complementary mRNAs; accordingly, Arenaviruses are classified as ambisense RNA viruses, rather than negative- or positive-sense RNA viruses. The ambisense orientation of viral genes are on both the L- and S-segments. The NP and polymerase genes reside at the 3' end of the S and L vRNA segments, respectively, and are encoded in the conventional negative sense (i.e., they are expressed through transcription of vRNA or genome-complementary mRNAs). The genes located at the 5' end of the S and L vRNA segments, GPC and Z, respectively, are encoded in mRNA sense but there is no evidence that they are translated directly from genomic vRNA. These genes are expressed instead through transcription of genomic-sense mRNAs from antigenomes (i.e., the vcRNA), full-length complementary copies of genomic vRNAs that function as replicative intermediates.

An exemplary targeting sequence for the arenavirus family of viruses is listed below as SEQ ID NO: 8.

9. Targeting of Respiratory Syncytial Virus

Respiratory syncytial virus (RSV) is the single most important respiratory pathogen in young children. RSV-caused lower respiratory conditions, such as bronchiolitis and pneumonia, often require hospitalization in children less than one-year-old. Children with cardiopulmonary diseases and those born prematurely are especially prone to experience severe disorders from this infection. RSV infection is also an important illness in elderly and high-risk adults, and it is the second-most commonly identified cause of viral pneumonia in older persons (Falsey, Hennessey et al. 2005). The World Health Organization estimates that RSV is responsible for 64 million clinical infections and 160 thousand deaths annually worldwide. No vaccines are currently available for the prevention of RSV infection. Although many major advances in our understanding of RSV biology, epidemiology, pathophysiology, and host-immune-response have occurred over the past few decades, there continues to be considerable controversy regarding the optimum management of infants and children with RSV infection. Ribavirin is the only licensed antiviral drug for treating RSV infection, but its use is limited to high-risk or severely-ill infants. The utility of Ribavirin has been limited by its cost, variable efficacy, and tendency to generate resistant viruses (Marquardt 1995; Prince 2001). The current need for additional effective anti-RSV agents is well-acknowledged.

It is known that peptide conjugated PMO (PPMO) can be effective in inhibiting RSV both in tissue culture and in an in vivo animal model system (Lai, Stein et al. 2008). Two antisense PPMOs, designed to target the sequence that includes the 5'-terminal region and translation start-site region of RSV L mRNA, were tested for anti-RSV activity in cultures of two human airway cell lines. One of them, (RSV-AUG-2; SEQ ID NO 10), reduced viral titers by >2.0 $\log_{10}$. Intranasal (i.n.) treatment of BALB/c mice with RSV-AUG-2 PPMO before the RSV inoculation produced a reduction in viral titer of 1.2 $\log_{10}$ in lung tissue at day 5 postinfection (p.i.), and attenuated pulmonary inflammation at day 7 postinfection. These data showed that RSV-AUG-2 provided potent anti-RSV activity worthy of further investigation as a candidate for potential therapeutic application (Lai, Stein et al. 2008). Despite the success with RSV-AUG-2 PPMO as described above, it is desirable to use conjugates as disclosed herein to address toxicity associated with previous peptide conjugates. Therefore, in another embodiment of the present invention, one or more conjugates as described herein can be used in a method of inhibiting replication within a host cell of RSV, by contacting the cell with a conjugate as described herein, for example a conjugate having a targeting base sequence that is complementary to a target sequence composed of at least 12 contiguous bases within an AUG start-site region of an mRNA from RSV, as described further below.

The L gene of RSV codes for a critical component of the viral RNA dependent RNA polymerase complex. Antisense PPMO designed against the sequence spanning the AUG translation start-site codon of the RSV L gene mRNA in the form of RSV-AUG-2 PPMO is complementary to sequence from the 'gene-start' sequence (GS) present at the 5' terminus of the L mRNA to 13 nt into the coding sequence. A preferred L gene targeting sequence is therefore complementary to any 12 contiguous bases from the 5' end of the L gene mRNA extending 40 bases in the 3' direction or 22 bases into the L gene coding sequence as shown below in Table 6 as SEQ ID NO: 9. Exemplary RSV L gene targeting sequences are listed below in Table 6 as SEQ ID NOs: 10-14. Any of the intersubunit modifications of the invention described herein can be incorporated in the oligomers to provide increased antisense activity, improved intracellular delivery and/or tissue specificity for improved therapeutic activity. Exemplary oligomers sequences containing intersubunit linkages of the invention are listed below in Table 6.

contiguous bases in a target region of the human myostatin mRNA identified by SEQ ID NO: 18, for treating a muscle wasting condition, as described previously (See, e.g., U.S. patent application Ser. No. 12/493,140, which is incorporated herein by reference; and PCT publication WO2006/086667). Exemplary murine targeting sequences are listed as SEQ ID NOs: 19-20; and (b) an antisense oligomer capable of producing exon skipping in the DMD protein (dystrophin), such as a PMO having a sequence selected from SEQ ID NOs: 22 to 35, to restore partial activity of the dystrophin protein, for treating DMD, as described previously (See, e.g., PCT Pubn. Nos. WO/2010/048586 and WO/2006/000057 or U.S. Patent Publication No. US09/061960 all of which are incorporated herein by reference).

Several other neuromuscular diseases can be treated using the modified linkages and terminal groups of the present invention. Exemplary compounds for treating spinal muscle atrophy (SMA) and myotonic dystrophy (DM) are discussed below.

SMA is an autosomal recessive disease caused by chronic loss of alpha-motor neurons in the spinal cord and can affect both children and adults. Reduced expression of survival motor neuron (SMN) is responsible for the disease (Hua, Sahashi et al. 2010). Mutations that cause SMA are located in the SMN1 gene but a paralogous gene, SMN2, can allow viability by compensating for loss of SMN1 if expressed from an alternative splice form lacking exon 7 (delta7 SMN2). Antisense compounds targeted to inton 6, exon 7 and intron 7 have all been shown to induce exon 7 inclusion to varying degrees. Antisense compounds targeted to intron 7 are preferred (see e.g., PCT Publication Nos. WO/2010/148249, WO/2010/120820, WO/2007/002390 and U.S. Pat. No. 7,838,657). Exemplary antisense sequences that target

TABLE 6

RSV target and targeting sequences

| Name | Sequence (5' to 3') | SEQ ID NO |
|---|---|---|
| L target | GGGACAAAATGGATCCCATTATTAATGGAAATTCTGCTAA | 9 |
| RSV-AUG-2 | TAATGGGATCCATTTTGTCCC | 10 |
| RSV-AUG3 | AATAATGGGATCCATTTTGTCCC | 11 |
| RSV-AUG4 | CATTAATAATGGGATCCATTTTGTCCC | 12 |
| RSV-AUG5 | GAATTTCCATTAATAATGGGATCCATTTG | 13 |
| RSV-AUG6 | CAGAATTTCCATTAATAATGGGATCCATT | 14 |
| RSV-AUG3apn* | AATAA$^{apn}$TGGGA$^{apn}$TCCA$^{apn}$TT$^{apn}$TTG$^{apn}$TCCC | 11 |
| RSV-AUG3guan | AATAA$^{guan}$TGGGA$^{guan}$TCCA$^{guan}$TT$^{guan}$TTG$^{guan}$TCCC | 11 |

10. Neuromuscular Diseases

In another embodiment, a therapeutic conjugate is provided for use in treating a disease condition associated with a neuromuscular disease in a mammalian subject. Antisense oligomers (e.g., SEQ ID NO: 16) have been shown to have activity in the MDX mouse model for Duchene Muscular Dystrophy (DMD). Exemplary oligomer sequences that incorporate the linkages used in some embodiments are listed below in Table 7. In some embodiments, the conjugates comprise an oligomer selected from:

(a) an antisense oligomer targeted against human myostatin, having a base sequence complementary to at least 12 the SMN2 pre-mRNA and induce improved exon 7 inclusion are listed below as SEQ ID NOs: 36-38. It is contemplated that selected modifications of these oligomer sequences using the modified linkages and terminal groups described herein would have improved properties compared to those known in the art. Furthermore, it is contemplated that any oligomer targeted to intron 7 of the SMN2 gene and incorporating the features of the present invention has the potential to induce exon 7 inclusion and provide a therapeutic benefit to SMA patients. Myotonic Dystrophy type 1 (DM1) and type 2 (DM2) are dominantly inherited disorders caused by expression of a toxic RNA leading to neuromuscular degeneration. DM1 and DM2 are associated with long polyCUG and polyCCUG repeats in the 3'-UTR and intron 1 regions of the transcript dystrophia myotonica protein kinase (DMPK) and zinc finger protein 9 (ZNF9), respectively (see e.g., WO2008/036406). While normal individuals have as many as 30 CTG repeats, DM1 patients carry a larger number of repeats ranging from 50 to thousands. The severity of the disease and the age of onset correlates with the number of repeats. Patients with adult onsets show milder symptoms and have less than 100 repeats, juvenile onset DM1 patients carry as many as 500 repeats and congenital cases usually have around a thousand CTG repeats. The expanded transcripts containing CUG repeats form a secondary structure, accumulate in the nucleus in the form of nuclear foci and sequester RNA-binding proteins (RNA-BP). Several RNA-BP have been implicated in the disease, including muscleblind-like (MBNL) proteins and CUG-binding protein (CUGBP). MBNL proteins are homologous to *Drosophila* muscleblind (Mbl) proteins necessary for photoreceptor and muscle differentiation. MBNL and CUGBP have been identified as antagonistic splicing regulators of transcripts affected in DM1 such as cardiac troponin T (cTNT), insulin receptor (IR) and muscle-specific chloride channel (ClC-1).

It is known in the art that antisense oligonucleotides targeted to the expanded repeats of the DMPK gene can displace RNA-BP sequestration and reverse myotonia symptoms in an animal model of DM1 (WO2008/036406). It is contemplated that oligomers incorporating features of the present invention would provide improved activity and therapeutic potential for DM1 and DM2 patients. Exemplary sequences targeted to the polyCUG and polyCCUG repeats described above are listed below as SEQ ID NOs: 39-55 and further described in U.S. application Ser. No. 13/101,942 which is incorporated herein in its entirety.

Additional embodiments of the present invention for treating neuralmuscular disorders are anticipated and include oligomers designed to treat other DNA repeat instability genetic disorders. These diseases include Huntington's disease, spino-cerebellar ataxia, X-linked spinal and bulbar muscular atrophy and spinocerebellar ataxia type 10 (SCA10) as described in WO2008/018795.

TABLE 7

M23D sequences (SEQ ID NO: 15) that incorporate modified intersubunit linkages and/or 3' and/or 5' terminal groups

| NG | PMO-X Modification | 5' | Sequence | 3' |
|---|---|---|---|---|
| NG-10-0383 | PMO | EG3 | GGC CAA ACC TCG GCT TAC CTG AAA T | triphenylacetyl |
| NG-10-0325 | triphenylphos | OH | GGC CAA ACC FCG GCF TAC CFG AAA T | triphenylphos |
| NG-10-0272 | PMO-farnesyl | OH | GGC CAA ACC TCG GCT TAC CTG AAA T | farnesyl |
| NG-10-0102 | PMO | OH | GGC CAA ACC TCG GCT TAC CTG AAA T | trityl |
| NG-10-0330 | trimethoxybenzoyl | EG3 | GGC CAA ACC TCG GCT TAC CTG AAA T | trimethoxybenzoyl |
| NG-10-0056 | PMOplus 5'-pol | EG3 | GGC C$^+$A$^+$A $^+$ACC TCG GCT TAC CTG AAA T | H |
| NG-07-0064 | PMO-3'-trityl | H-Pip | GGC CAA ACC TCG GCT TAC CTG AAA T | trityl |
| NG-10-0382 | PMO | EG3 | GGC CAA ACC TCG GCT TAC CTG AAA T | triphenylpropionyl |
| NG-10-0278 | PMOpyr | EG3 | GGC CAA ACC pTCG GCpT pTAC CpTG AAA pT | H |
| NG-10-0210 | PMOapn | EG3 | GGC C$^a$A$^a$A $^a$ACC TCG GCT TAC CTG AAA T | H |
| NG-10-0098 | PMOpyr | EG3 | GGC CAA ACC $^p$TCG GC$^p$T TAC C$^p$TG AAA T | H |
| NG-10-0070 | PMOapn | EG3 | GGC CAA ACC $^a$TCG GC$^a$T TAC C$^a$TG AAA $^a$T | H |
| NG-10-0095 | PMOapn | EG3 | GGC CAA ACC $^a$TCG GC$^a$T $^a$TAC C$^a$TG AAA $^a$T | H |
| NG-10-0317 | PMO | EG3 | GGC CAA ACC TCG GCT TAC CTG AAA T | farnesyl |
| NG-10-0477 | PMO triMe Gly | EG3 | GGC CAA ACC FCG GCF TAC CFG AAA F | trimethyl Glycine |
| NG-10-0133 | PMOapn | OH | GGC C$^a$AA $^a$ACC $^a$TCG GC$^a$T $^a$TAC C$^a$TG AAA $^a$T | H |

TABLE 7-continued

M23D sequences (SEQ ID NO: 15) that incorporate modified intersubunit linkages and/or 3' and/or 5' terminal groups

| NG | PMO-X Modification | 5' | Sequence | 3' |
|---|---|---|---|---|
| NG-10-0387 | PMO | EG3 | GGC CAA ACC TCG GCT TAC CTG AAA T | 2-OH, diphenylacet |
| NG-10-0104 | PMOguan | EG3 | GGC CAA ACC $^g$TCG GC$^g$T TAC C$^g$T G AAA T | $\Delta^g$ |
| NG-10-0420 | PMOplus methyl | EG3 | GGC CAA ACC $^{m+}$TCG GC$^{+}$T TAC C$^{+}$TG AAA $^{m+}$T | Trityl |
| NG-10-0065 | PMOtri | EG3 | GGC CAA ACC $^t$TCG GC$^t$T TAC C$^t$T G AAA T | H |
| NG-10-0607 | PMO-X | EG3 | GGC CAA ACC TCG GCT TAC CTG AAA T | 9-fluorene-carboxyl |
| NG-10-0060 | PMOcp | EG3 | GGC CAA ACC $^{cp}$TCG GC$^{cp}$T TAC C$^{cp}$T G AAA T | H |
| NG-10-0162 | PMO-COCH$_2$SH | EG3 | GGC CAA ACC TCG GCT TAC CTG AAA T | COCH$_2$SH |
| NG-10-0328 | diphenylacetyl | EG3 | GGC CAA ACC TCG GCT TAC CTG AAA T | diphenylacetyl |
| NG-10-0134 | PMOapnPMOtri | OH | GGC C$^a$AA $^a$ACC $^t$TCG GC$^t$T $^t$TAC C$^t$TG AAA $^t$T | H |
| NG-10-0386 | PMO | DPA | GGC CAA ACC TCG GCT TAC CTG AAA T | 5'-diphenylac, 3'-trity |
| NG-07-0064 | PMO-3'-trityl | H-Pip | GGC CAA ACC TCG GCT TAC CTG AAA T | trityl |
| NG-10-0059 | PMOcp | EG3 | GGC CAA ACC $^{cp}$TCG GC$^{cp}$T $^{cp}$TAC C$^{cp}$T G AAA $^{cp}$T | H |
| NG-10-0135 | PMOtri | OH | GGC CAA ACC $^t$TCG GC$^t$T $^t$TAC C$^t$TG AAA $^t$T | H |
| NG-10-0168 | PMOapn PMOcys | OH | GGC CAA ACC $^a$TCG GC$^t$T $^a$TAC C$^t$TG AAA $^{SHc}$T | H |
| NG-10-0113 | PMOapnPMOtri | OH | GGC CAA ACC $^a$TCG GC$^t$T $^a$TAC C$^t$TG AAA $^a$T | H |
| NG-10-0385 | PMO | EG3 | GGC CAA ACC TCG GCT TAC CTG AAA T | diphenylphosphoryl |
| NG-10-0279 | PMO | OH | GGC CAA ACC TCG GCT TAC CTG AAA T | geranyl |
| NG-10-0055 | PMOplus disp | EG3 | GGC C$^+$AA $^+$ACC $^+$ACG GC$^+$T TAC C$^+$AG AAA T | H |
| NG-10-0105 | PMOsucc | EG3 | GGC CAA ACC $^+$ACG GC$^+$T TAC C$^s$T G AAA T | $\Delta^s$ |
| NG-10-0805 | PMO-X | EG3 | GGC CAA ACC $^{EtpiP}$TCG GC$^{EtpiP}$T TAC C$^{EtpiP}$TG AAA $^{EtpiP}$T | H |
| NG-10-0811 | PMO-X | EG3 | GGC CAA ACC $^{pyrQMe}$TCG GC$^{pyrQMe}$T TAC CG AAA $^{pyrQMe}$T $^{pyrQMe}$T | H |
| NG-10-0057 | PMOplus 3'-pol | EG3 | GGC CAA ACC TCG GCT TAC C$^+$TG $^+$A$^+$A$^+$A T | H |
| NG-10-0625 | PMO-X | EG3 | GGC CAA ACC TCG GCT TAC CTG AAA T | 5-carboxyfluorescein |
| NG-10-0804 | dimer | EG3 | GGC CAA ACC TCG GCT TAC CTG AAA T | dimerized |

TABLE 7-continued

M23D sequences (SEQ ID NO: 15) that incorporate modified intersubunit linkages and/or 3' and/or 5' terminal groups

| NG | PMO-X Modification | 5' | Sequence | 3' |
|---|---|---|---|---|
| NG-10-0066 | PMOtri | EG3 | GGC CAA ACC ᵗTCG GCᵗT TAC CᵗT G AAA ᵗT | H |
| NG-10-0280 | PMO disulfide | EG3 | GGC CAA ACC TCG GCT TAC CTG AAA T | COCH₂CH₂SSPy |
| NG-10-0212 | PMOapn | EG3 | GGC CaAaA aACC aTCG GCaT aTaAC CaTG aAaAaA aT | H |
| NG-10-0156 | 3'-MeOtrityl | EG3 | GGC CAA ACC TCG GCT TAC CTG AAA T | MeO-Tr |
| NG-10-0062 | PMOhex | EG3 | GGC CAA ACC ʰTCG GCʰT TAC Cʰ T G AAA ʰT | H |
| NG-11-0043 | PMO-X | EG3 | GGC CAA ACC TCG GCT TAC CTG AAA T | guanidinyl |
| NG-10-0206 | PMOplus | EG3 | GGC C⁺A⁺A ⁺AACC ⁺TCG GC⁺T ⁺TAC C⁺TG ⁺A⁺A⁺A ⁺T | H |
| NG-10-0383 | PMO | EG3 | GGC CAA ACC TCG GCT TAC CTG AAA T | triphenylacetyl |
| NG-10-0325 | triphenylphos | OH | GGC CAA ACC FCG GCF TAC CFG AAA T | triphenylphos |
| NG-10-0272 | PMO-farnesyl | OH | GGC CAA ACC TCG GCT TAC CTG AAA T | farnesyl |

*Dimerized indicates the oligomer is dimerized by a linkage linking the 3' ends of the two monomers. For example, the linkage may be —COCH₂CH₂—S—CH(CONH₂)CH₂—CO—NHCH₂CH₂CO— or any other suitable linkage. EG3 refers to a triethylene glycol tail (see e.g., conjugates in examples 30 and 31).

11. Antibacterial Applications

The invention includes, in another embodiment, a conjugate comprising an antibacterial antisense oligomer for use in treating a bacterial infection in a mammalian host. In some embodiments, the oligomer comprises between 10-20 bases and a targeting sequence of at least 10 contiguous bases complementary to a target region of the infecting bacteria's mRNA for acyl carrier protein (acpP), gyrase A subunit (gyrA), ftsZ, ribosomal protein S10 (rpsJ), leuD, mgtC, pirG, pcaA, and cmal genes, where the target region contains the translational start codon of the bacterial mRNA, or a sequence that is within 20 bases, in an upstream (i.e., 5') or downstream (i.e., 3') direction, of the translational start codon, and where the oligomer binds to the mRNA to form a heteroduplex thereby to inhibit replication of the bacteria.

12. Modulating Nuclear Hormone Receptors

In another embodiment the present invention relates to compositions and methods for modulating expression of nuclear hormone receptors (NHR) from the nuclear hormone receptor superfamily (NHRSF), mainly by controlling or altering the splicing of pre-mRNA that codes for the receptors. Examples of particular NHRs include glucocorticoid receptor (GR), progesterone receptor (PR) and androgen receptor (AR). In certain embodiments, the conjugates described herein lead to increased expression of ligand-independent or other selected forms of the receptors, and decreased expression of their inactive forms.

Embodiments of the present invention include conjugates comprising oligomers, for example oligomers that are complementary to selected exonic or intronic sequences of an NHR, including the "ligand-binding exons" and/or adjacent introns of a NHRSF pre-mRNA, among other NHR-domains described herein. The term "ligand-binding exons" refers to exon(s) that are present in the wild-type mRNA but are removed from the primary transcript (the "pre-mRNA") to make a ligand-independent form of the mRNA. In certain embodiments, complementarity can be based on sequences in the sequence of pre-mRNA that spans a splice site, which includes, but is not limited to, complementarity based on sequences that span an exon-intron junction. In other embodiments, complementarity can be based solely on the sequence of the intron. In other embodiments, complementarity can be based solely on the sequence of the exon. (See, e.g., U.S. application Ser. No. 13/046,356, which is incorporated herein by reference.)

NHR modulators may be useful in treating NHR-associated diseases, including diseases associated with the expression products of genes whose transcription is stimulated or repressed by NHRs. For instance, modulators of NHRs that inhibit AP-1 and/or NF-κB can be useful in the treatment of inflammatory and immune diseases and disorders such as osteoarthritis, rheumatoid arthritis, multiple sclerosis, asthma, inflammatory bowel disease, transplant rejection, and graft vs. host disease, among others described herein and known in the art. Compounds that antagonize transactivation can be useful in treating metabolic diseases associated with increased levels of glucocorticoid, such as diabetes, osteoporosis and glaucoma, among others. Also, compounds that agonize transactivation can be useful in treating metabolic diseases associated with a deficiency in glucocorticoid, such as Addison's disease and others.

Embodiments of the present invention include methods of modulating nuclear NHR activity or expression in a cell, comprising contacting the cell with a conjugate comprising the carrier protein and an antisense oligomer composed of morpholino subunits linked by phosphorus-containing inter-subunit linkages joining a morpholino nitrogen of one subunit to a 5' exocyclic carbon of an adjacent subunit, wherein the oligonucleotide contains between 10-40 bases and a targeting sequence of at least 10 contiguous bases complementary to a target sequence, wherein the target sequence is a pre-mRNA transcript of the NHR, thereby modulating activity or expression of the NHR. In certain embodiments, the oligomer alters splicing ofthe pre-mRNA transcript and increases expression of a variant of the NHR. In some embodiments, the oligomer induces full or partial exon-skipping of one or more exons of the pre-mRNA transcript. In certain embodiments, the one or more exons encode at least a portion of a ligand-binding domain of the NHR, and the variant is a ligand independent form of the NHR. In certain embodiments, the one or more exons encode at least a portion of a transactivation domain of the NHR, and the variant has reduced transcriptional activation activity. In certain embodiments, the one or more exons encode at least a portion of a DNA-binding domain of the NHR. In certain embodiments, the one or more exons encode at least a portion of an N-terminal activation domain of the NHR. In certain embodiments, the one or more exons encode at least a portion of a carboxy-terminal domain of the NHR. In specific embodiments, the variant binds to NF-KB, AP-1, or both, and reduces transcription of one or more of their pro-inflammatory target genes. In certain embodiments, the oligomer agonizes a transactivational transcriptional activity of the NHR. In other embodiments, the oligomer antagonizes a transactivational transcriptional activity of the NHR. In certain embodiments, the oligomer agonizes a transrepression activity of the NHR. In other embodiments, the oligomer antagonizes a transrepression activity of the NHR. In specific embodiments, the oligomer antagonizes a transactivational transcriptional activity of the NHR and agonizes a transrepression activity of the NHR. (See, e.g., U.S. Appn. No. 61/313,652, which is incorporated herein by reference.)

EXAMPLES

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO, PMO+, PPMO and PMO containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detritylation step is omitted.

Example 1

Tert-Butyl 4-(2,2,2-trifluoroacetamido)piperidine-1-carboxylate

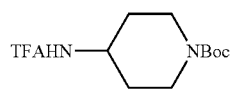

To a suspension of tert-butyl 4-aminopiperidine-1-carboxylate (48.7 g, 0.243 mol) and DIPEA (130 mL, 0.749 mol) in DCM (250 mL) was added ethyl trifluoroacetate (35.6 mL, 0.300 mol) dropwise while stirring. After 20 hours, the solution was washed with citric acid solution (200 mL×3, 10% w/v aq) and sodium bicarbonate solution (200 mL×3, conc aq), dried (MgSO$_4$), and filtered through silica (24 g). The silica was washed with DCM and the combined eluant was partially concentrated (100 mL), and used directly in the next step. APCl/MS calcd. for $C_{12}H_{19}F_3N_2O_3$ 296.1, found m/z=294.9 (M−1).

Example 2

2,2,2-trifluoro-N-(piperidin-4-yl)acetamide hydrochloride

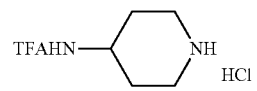

To a stirred DCM solution of the title compound of Example 1 (100 mL) was added dropwise a solution of hydrogen chloride (250 mL, 1.0 mol) in 1,4-dioxane (4 M). Stirring was continued for 6 hours, then the suspension was filtered, and the solid washed with diethyl ether (500 mL) to afford the title compound (54.2 g, 96% yield) as a white solid. APCl/MS calcd. for $C_7H_{11}F_3N_2O$ 196.1, found m/z=196.9 (M+1).

Example 3

(4-(2,2,2-trifluoroacetamido)piperidin-1-yl)phosphonic dichloride

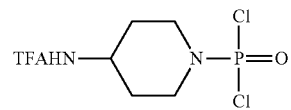

To a cooled (ice/water bath) suspension of the title compound of Example 2 (54.2 g, 0.233 mol) in DCM (250 mL) was added dropwise phosphorus oxychloride (23.9 mL, 0.256 mol) and DIPEA (121.7 mL, 0.699 mol) and stirred. After 15 minutes, the bath was removed and with continued stirring the mixture allowed to warm to ambient temperature. After 1 hour, the mixture was partially concentrated (100 mL), the suspension filtered, and the solid washed with diethyl ether to afford the title compound (43.8 g, 60% yield) as a white solid. The elutant was partially concentrated (100 mL), the resulting suspension filtered, and the solid washed with diethyl ether to afford additional title compound (6.5 g, 9% yield). ESI/MS calcd. for 1-(4-nitrophenyl)piperazine derivative $C_{17}H_{22}ClF_3N_5O_4P$ 483.1, found m/z=482.1 (M−1).

Example 4

((2S,6S)-6-((R)-5-methyl-2,6-dioxo-1,2,3,6-tetrahydropyridin-3-yl)-4-tritylmopholin-2-yl)methyl (4-(2,2,2-trifluoroacetamido)piperidin-1-yl)phosphonochloridate

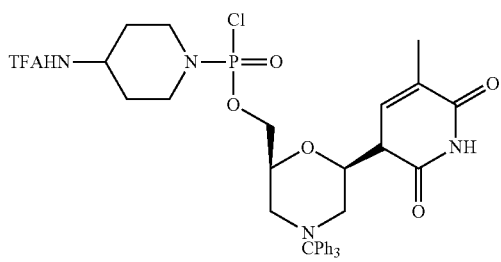

To a stirred, cooled (ice/water bath) solution of the title compound of Example 3 (29.2 g, 93.3 mmol) in DCM (100 mL) was added dropwise over 10 minutes a DCM solution (100 mL) of Mo(Tr)T # (22.6 g, 46.7 mmol), 2,6-Lutidine (21.7 mL, 187 mmol), and 4-(dimethylamino)pyridine (1.14 g, 9.33 mmol). The bath was allowed to warm to ambient temperature. After 15 hours, the solution was washed with a citric acid solution (200 mL×3, 10% w/v aq), dried (MgSO$_4$), concentrated, and the crude oil was loaded directly onto column. Chromatography [SiO$_2$ column (120 g), hexanes/EtOAc eluant (gradient 1:1 to 0:1), repeated×3] fractions were concentrated to provide the title compound (27.2 g, 77% yield) as a white solid. ESI/MS calcd. for the 1-(4-nitrophenyl)piperazine derivative $C_{46}H_{50}F_3N_8O_8P$ 930.3, found m/z=929.5 (M−1).

Example 5

((2S,6R)-6-(6-Benzamido-9H-purin-9-yl)-4-tritylmorpholin-2-yl)methyl (4-(2,2,2-trifluoroacetamido)piperidin-1-yl)phosphonochloridate

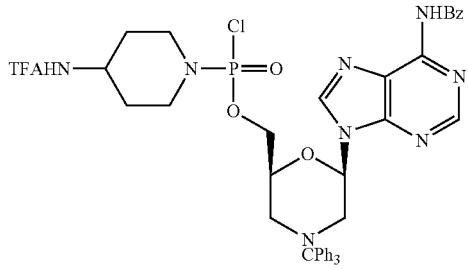

The title compound was synthesized in a manner analogous to that described in Example 4 to afford the title compound (15.4 g, 66% yield) as a white solid. ESI/MS calcd. for 1-(4-nitrophenyl)piperazine derivative $C_{53}H_{53}F_3N_{11}O_7P$ 1043.4, found m/z=1042.5 (M−1).

Example 6

(R)-methyl(1-phenylethyl)phosphoramidic dichloride

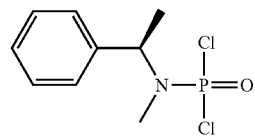

To a cooled (ice/water bath) solution of phosphorus oxychloride (2.83 mL, 30.3 mmol) in DCM (30 mL) was added sequentially, dropwise, and with stirring 2,6-lutidine (7.06 mL, 60.6 mmol) and a DCM solution of (R)-(+)-N,a-dimethylbenzylamine (3.73 g, 27.6 mmol). After 5 minutes, the bath was removed and reaction mixture allowed to warm to ambient temperature. After 1 hour, the reaction solution was washed with a citric acid solution (50 mL×3, 10% w/v aq), dried (MgSO$_4$), filtered through SiO$_2$ and concentrated to provide the title compound (3.80 g) as a white foam. ESI/MS calcd. for 1-(4-nitrophenyl)piperazine derivative $C_{19}H_{25}N_4O_4P$ 404.2, found m/z=403.1 (M−1).

Example 7

(S)-methyl(1-phenylethyl)phosphoramidic dichloride

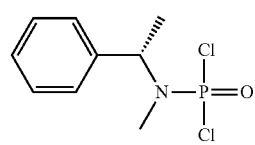

The title compound was synthesized in a manner analogous to that described in Example 6 to afford the title compound (3.95 g) as a white foam. ESI/MS calcd. for 1-(4-nitrophenyl)piperazine derivative $C_{19}H_{25}N_4O_4P$ 404.2, found m/z=403.1 (M−1).

Example 8

((2S,6R)-6-(5-methyl-2,4-dioxo-3,4-dihydropyrimidin-1(2H)-yl)-4-tritylmorpholin-2-yl)methyl methyl (R)-1-phenylethyl)phosphoamidochloridate

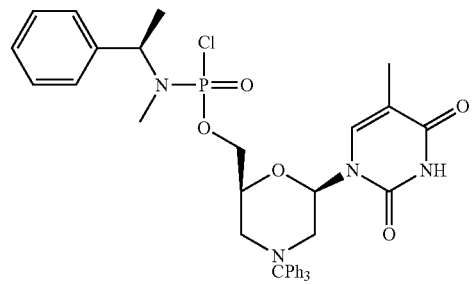

The title compound was synthesized in a manner analogous to that described in Example 4 to afford the title chlorophosphoroamidate (4.46 g, 28% yield) as a white solid. ESI/MS calcd. for $C_{38}H_4OClN_4O_5P$ 698.2, found m/z=697.3 (M−1).

Example 9

((2S,6R)-6-(5-methyl-2,4-dioxo-3,4-dihydropyrimidin-1(2H)-yl)-4-Tritylmorpholin-2-yl)methyl methyl ((S)-1-phenylethyl)phosphoramidochloridate

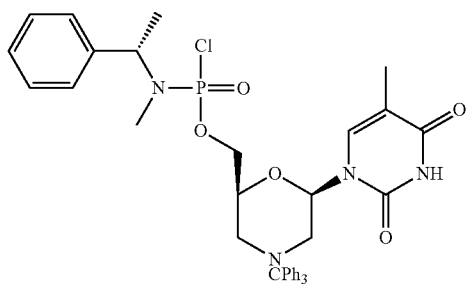

The title compound was synthesized in a manner analogous to that described in Example 4 to afford the title chlorophosphoroamidate (4.65 g, 23% yield) as a white solid. ESI/MS calcd. for $C_{38}H_4OClN_4O_5P$ 698.2, found m/z=697.3 (M−1).

Example 10

(4-(pyrolidin-1-yl)piperidin-1-yl)phosphoronic dichloride hydrochloride

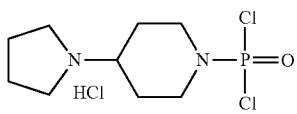

To a cooled (ice/water bath) solution of phosphorus oxychloride (5.70 mL, 55.6 mmol) in DCM (30 mL) was added 2,6-lutidine (19.4 mL, 167 mmol) and a DCM solution (30 mL) of 4-(1-pyrrolidinyl)-piperidine (8.58 g, 55.6 mmol) and stirred for 1hour. The suspension was filtered and solid washed with excess diethyl ether to afford the title pyrrolidine (17.7 g, 91% yield) as a white solid. ESI/MS calcd. for 1-(4-nitrophenyl)piperazine derivative $C_{19}H_{30}N_5O_4P$ 423.2, found m/z=422.2 (M−1).

Example 11

((2S,6R)-6-(5-methyl-2,4-dioxo-3,4-dihtdropyrimidin-1(2H)-yl)-4-Triylporpholin-2-yl)methyl (4-(pyrrolidin-1-yl)peperidin-1-yl)phosphonochloridate hydrochloride

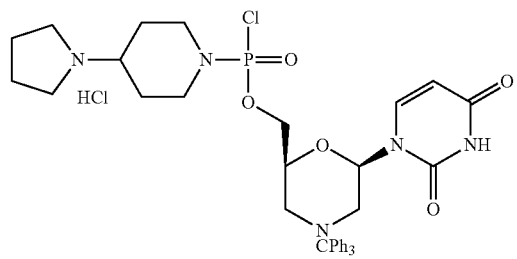

To a stirred, cooled (ice/water bath) solution of the dichlorophosphoramidate 8 (17.7 g, 50.6 mmol) in DCM (100 mL) was added a DCM solution (100 mL) of Mo(Tr)T # (24.5 g, 50.6 mmol), 2,6-Lutidine (17.7 mL, 152 mmol), and 1-methylimidazole (0.401 mL, 5.06 mmol) dropwise over 10 minutes. The bath was allowed to warm to ambient temperature as suspension was stirred. After 6 hours, the suspension was poured onto diethyl ether (1 L), stirred 15 minutes, filtered and solid washed with additional ether to afford a white solid (45.4 g). The crude product was purified by chromatography [$SiO_2$ column (120 gram), DCM/MeOH eluant (gradient 1:0 to 6:4)], and the combined fractions were poured onto diethyl ether (2.5 L), stirred 15 min, filtered, and the resulting solid washed with additional ether to afford the title compound (23.1 g, 60% yield) as a white solid. ESI/MS calcd. for 1-(4-nitrophenyl)piperazine derivative $C_{48}H_{57}N_8O_7P$ 888.4, found m/z=887.6 (M−1).

Example 12

3-(Tert-butyldisulfanyl)-2-(isobutoxycarbonylamino) proanoic acid

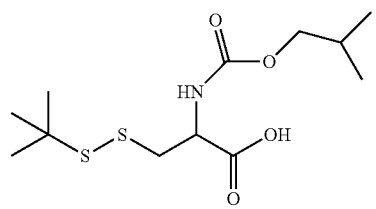

2

To S-tert-butylmercapto-L-cysteine (10 g, 47.8 mmol) in $CH_3CN$ (40 mL) was added $K_2CO_3$ (16.5 g, 119.5 mmol) in $H_2O$ (20 mL). After stirring for 15 minutes, iso-butyl chloroformate (9.4 mL, 72 mmol) was injected slowly. The reaction was allowed to run for 3 hours. The white solid was filtered through Celite; the filtrate was concentrated to remove $CH_3CN$. The residue was dissolved in ethyl acetate (200 mL), washed with 1N HCl (40 ml×3), brine (40×1), dried over $Na_2SO_4$. Desired product (2) was obtained after chromatography (5% MeOH/DCM).

Example 13

Tert-butyl 4-(3-(tert-butyldisulfanyl)-2-(isobutoxycarbonylamino)propanamido)piperidine-1-carboxylate

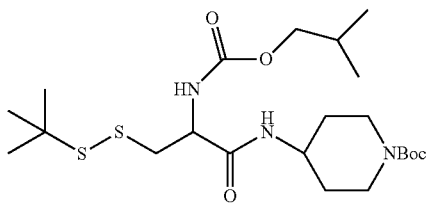

3

To the acid (compound 2 from Example 12, 6.98 g, 22.6 mmol) in DMF (50 ml was added HATU (8.58 g, 22.6 mmol). After 30 min, Hunig base (4.71 ml, 27.1 mmol) and 1-Boc-4-amino piperidine (5.43 g, 27.1 mmol) were added to the mixture. The reaction was continued stirring at RT for another 3 h. DMF was removed at high vacuum, the crude residue was dissolved in EtAc (300 ml), washed with H₂O (50 ml×3). The final product (3) was obtained after ISCO purification (5% MeOH/DCM).

Example 14

Isobutyl 3-(tert-butyldisulfanyl)-1-oxo-1-(piperidin-4-ylamino)propan-2-ylcarbamate

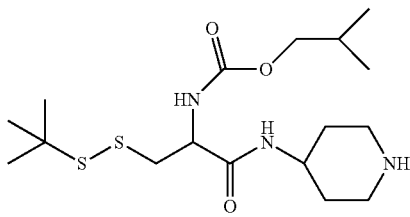

4

To compound 3 prepared in Example 13 (7.085 g, 18.12 mmol) was added 30 ml of 4M HCl/Dioxane. The reaction was completed after 2 h at RT. The HCl salt (4) was used for the next step without further purification.

Example 15

Isobutyl 3-(tert-butyldisulfanyl)-1-(1-(dichlorophosphoryl)piperidin-4-ylamino)-1-oxopropan-2-ylcarbamate

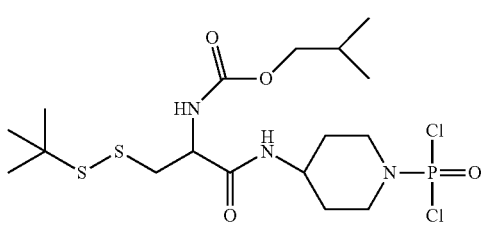

5

To compound 4 prepared in Example 15 (7.746 g, 18.12 mmol) in DCM (200 ml) at −78° C. was slowly injected POCl₃ (1.69 ml, 18.12 mmol) under Ar, followed by the addition of Et₃N (7.58 ml, 54.36 mmol). The reaction was stirred at RT for 5 h, concentrated to remove excess base and solvent. The product (5) was given as white solid after ISCO purification (50% EtAc/Hexane).

Example 16

Isobutyl 3-(tert-butyldisulfanyl)-1-(1-(chloro(((2S,6R)-6-(5-methyl-2,4-dioxo-3,4-dihydropyrimidin-1(2H)-yl)-4-tritylmorpholin-2-ylmethoxy)phosphoryl)piperidin-4-ylamino)-1-oxopropan-2-ylcarbamate

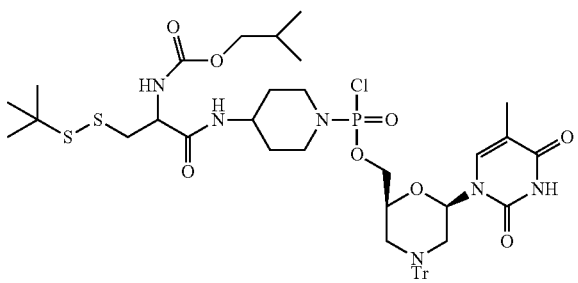

6

To 1-((2R,6S)-6-(hydroxymethyl)-4-tritylmorpholin-2-yl)-5-methylpyrimidine-2,4(1H,3H)-dione (moT(Tr)) (5.576 g, 10.98 mmol) in DCM (100 ml) at 0° C., was added lutidine (1.92 ml, 16.47 mmol) and DMAP (669 mg, 5.5 mmol), followed by the addition of 4 (6.13 g, 12.08 mmol). The reaction was left stirring at RT for 18 h. The desired product (6) was obtained after ISCO purification (50% EtAc/Hexane).

Example 17

((2S,6R)-6-(5-methyl-2,4-dioxol-3,4-dihydropyrimidin-1(2H)-yl)-4-tritylmorpholin-2-yl)methyl hexyl (methyl)phosphoramidochloridate

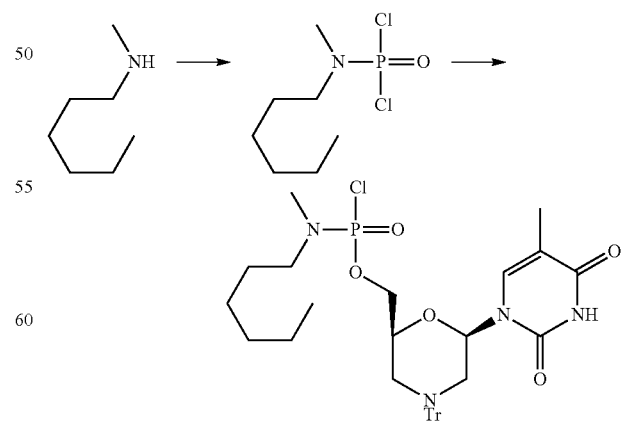

A DCM (80 ml) solution of N-hydroxylmethylamine (4.85 ml, 32 mmol) was cooled down to −78° C. under N2.

A solution of phosphoryl chloride (2.98 ml, 32 mmol) in DCM (10 ml), followed by a solution of Et₃N (4.46 ml, 32 mmol) in DCM (10 ml), was added slowly. The stirring was continued while the reaction was allowed to warm to RT overnight. The desired product (1) was given as clear oil after ISCO purification (20% EtAc/Hexane).

To moT(Tr) (5.10 g, 10.54 mmol) in DCM (100 ml) at 0° C., was added lutidine (3.68 ml, 31.6 mmol) and DMAP (642 mg, 5.27 mmol), followed by the addition of 1 (4.89 g, 21.08 mmol). The reaction was left stirring at RT for 18 h. The desired product (2) was obtained after ISCO purification (50% EtOAc/Hexane).

Example 18

((2S,6R)-6-(5-methyl-2,4-dioxo-3,4-dihydropyrimidin-1(2H)-yl)-4-trotylmorpholin-2-yl)methyl dodecyl(methyl)phosphoramidochloridate

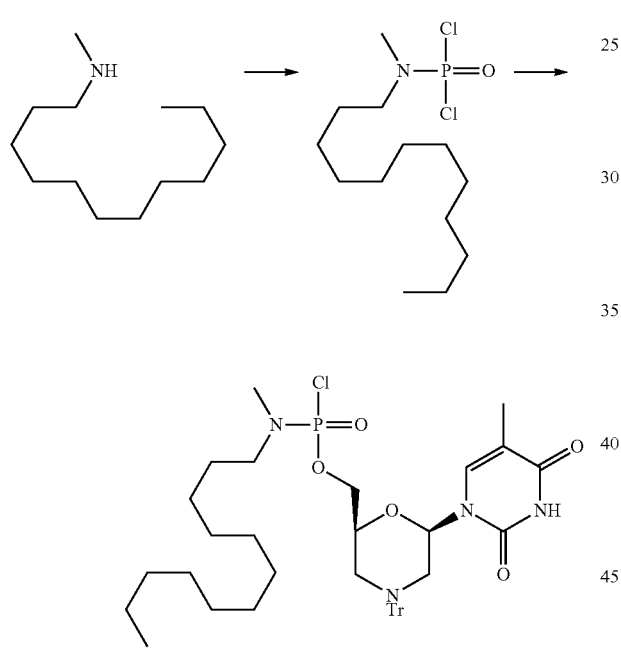

The title compound was prepared according to the general procedures described in Examples 6 and 8.

Example 19

((2S,6R)-6-(5-methyl-2,4-dioxo-3,4-dihydropyrimidin-1(2H)-yl)-4-tritylmorpholin-2-yl)methyl morpholinophosphonochloridate

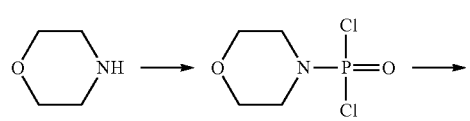

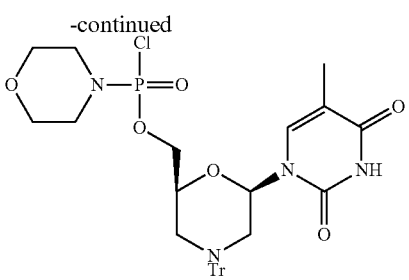

The title compound was prepared according to the general procedures described in Examples 6 and 8.

Example 20

((2S,6R)-6-(5-methyl-2,4-dioxo-3,4-dihydropyrimidin-1(2H)-yl)-4-tritylmorhpholin-2-yl)methyl (S)-2-(methoxymethyl)pyrrolidin-1-ylphosphonochloridate

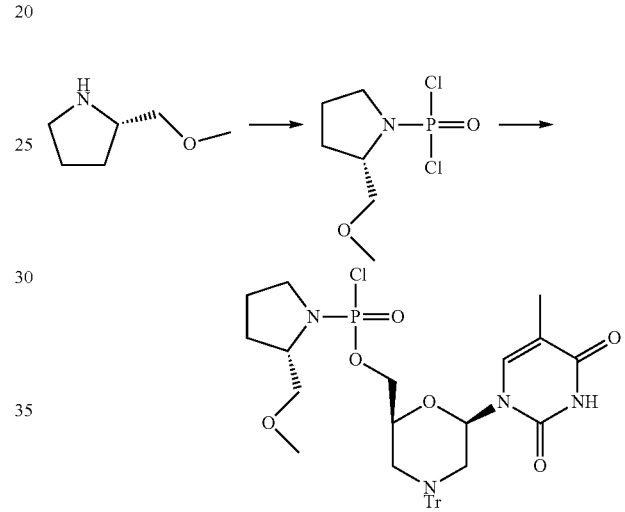

The title compound was prepared according to the general procedures described in Examples 6 and 8.

Example 21

((2S,6R)-6-(5-methyl-2,4-dioxo-3,4-dihydropyrimidin-1(2H)-yl)-4-tritylmorpholin-2-yl)methyl 4-(3,4,5-trimethoxybenzamido)piperidin-1-ylphosphonochloridate

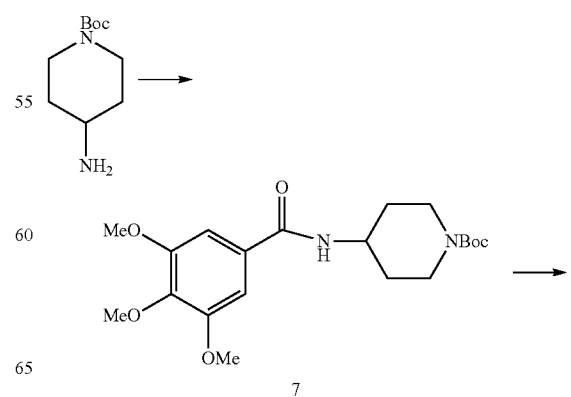

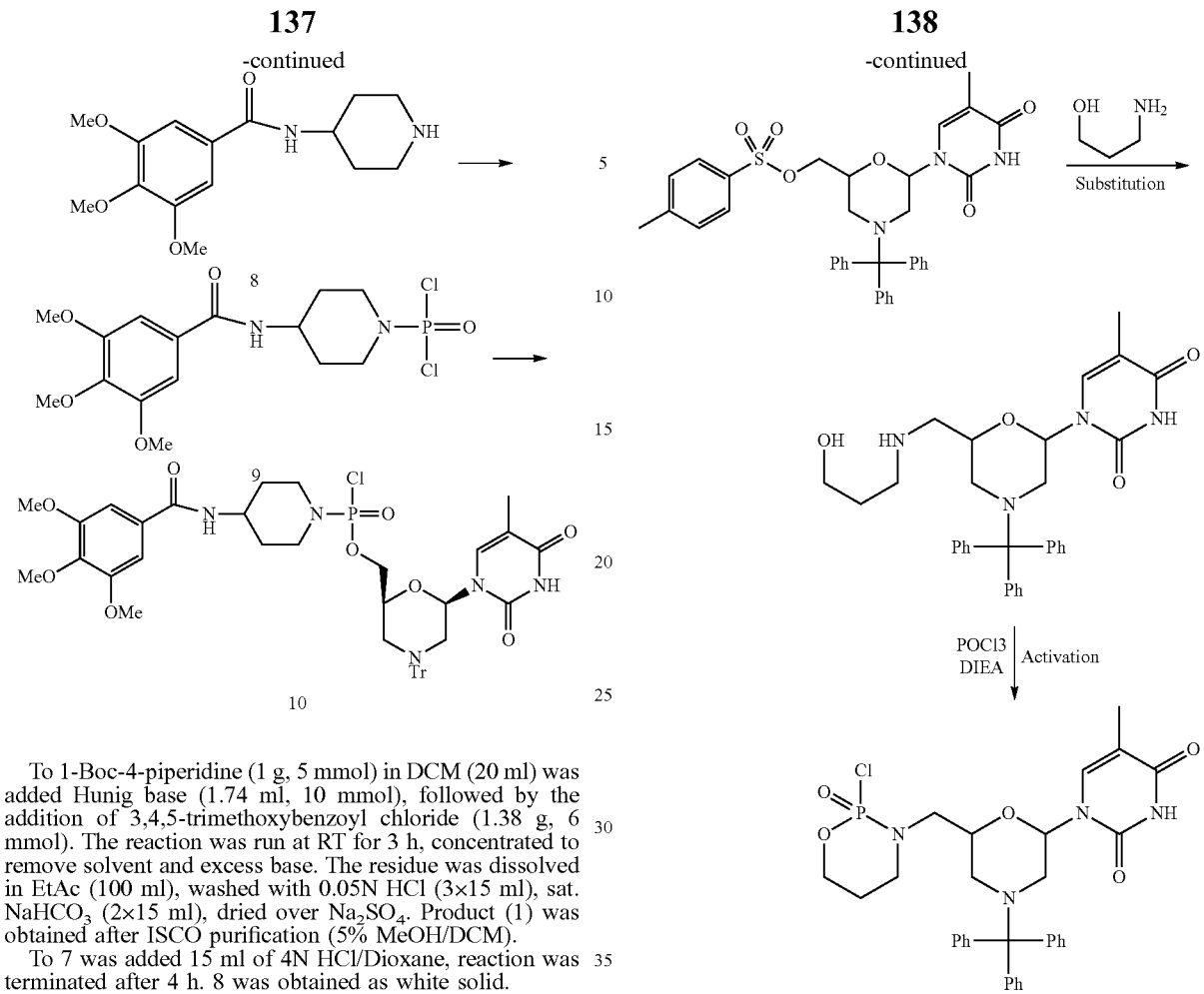

To 1-Boc-4-piperidine (1 g, 5 mmol) in DCM (20 ml) was added Hunig base (1.74 ml, 10 mmol), followed by the addition of 3,4,5-trimethoxybenzoyl chloride (1.38 g, 6 mmol). The reaction was run at RT for 3 h, concentrated to remove solvent and excess base. The residue was dissolved in EtAc (100 ml), washed with 0.05N HCl (3×15 ml), sat. NaHCO$_3$ (2×15 ml), dried over Na$_2$SO$_4$. Product (1) was obtained after ISCO purification (5% MeOH/DCM).

To 7 was added 15 ml of 4N HCl/Dioxane, reaction was terminated after 4 h. 8 was obtained as white solid.

A DCM (20 ml) solution of 8 (1.23 g, 4.18 mmol) was cooled down to −78° C. under N$_2$. A solution of phosphoryl chloride (0.39 ml, 4.18 mmol) in DCM (2 ml), followed by a solution of Et$_3$N (0.583 ml, 4.18 mmol) in DCM (2 ml), was added slowly. The stirring was continued while the reaction was allowed to warm to RT overnight. The desired product (9) was obtained after ISCO purification (50% EtAc/Hexane).

To moT(Tr) (1.933 g, 4.0 mmol) in DCM (20 ml) at 0° C., was added lutidine (0.93 ml, 8 mmol) and DMAP (49 mg, 0.4 mmol), followed by the addition of 9 (1.647 g, 4 mmol). The reaction was left stirring at RT for 18 h. The desired product (10) was obtained after ISCO purification (50% EtAc/Hexane).

Example 22

Synthesis of Cyclophosphoramide Containing Subunit ($^{CP}$T)

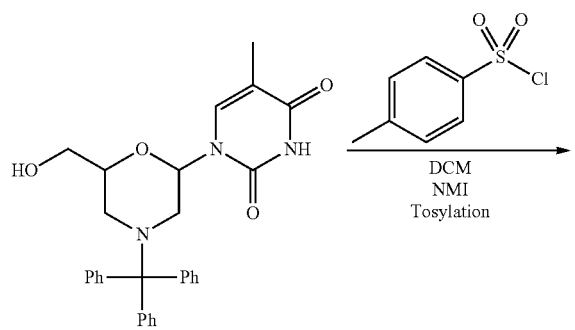

The moT subunit (25 g) was suspended in DCM (175 ml) and NMI (N-methylimidazole, 5.94 g, 1.4 eq.) was added to obtain a clear solution. Tosyl chloride was added to the reaction mixture, and the reaction progress was monitored by TLC until done (about 2 hours). An aqueous workup was performed by washing with 0.5 M citric acid buffer (pH=5), followed by brine. The organic layer was separated and dried over Na2SO4. Solvent was removed with a rotavaporator to obtain the crude product which was used in the next step without further purification.

The moT Tosylate prepared above was mixed with propanolamine (1 g/10 ml). The reaction mixture was then placed in an oven at 45° C. overnight followed by dilution with DCM (10 ml). An aqueous workup was performed by washing with 0.5 M citric acid buffer (pH=5), followed by brine. The organic layer was separated and dried over Na$_2$SO$_4$. Solvent was removed with a rotavaporator to obtain the crude product. The curde product was analyzed by NMR and HPLC and determined to be ready for the next step without further purification.

The crude product was dissolved in DCM (2.5 ml DCM/g, 1 eq.) and mixed with DIEA (3 eq.). This solution was cooled with dry ice-acetone and POCl$_3$ was added dropwise (1.5 eq.). The resultant mixture was stirred at room temperature overnight. An aqueous workup was performed by washing with 0.5 M citric acid buffer (pH=5), followed by brine. The organic layer was separated and dried over Na$_2$SO$_4$. Solvent was removed with a rotavaporator to obtain the crude product as a yellowish solid. The crude product was purified by silica gel chromatography (crude product/silica=1 to 5 ratio, gradient DCM to 50% EA/DCM), and fractions were pooled according to TLC analysis. Solvent was removed to obtain the desired product as a mixture of diastereomers. The purified product was analyzed by HPLC (NPP quench) and NMR (H-1 and P-31).

The diastereomeric mixture was separated according to the following procedure. The mixture (2.6 g) was dissolved in DCM. This sample was loaded on a RediSepRf column (80 g normal phase made by Teledyne Isco) and eluted with 10% EA/DCM to 50% EA/DCM over 20 minutes. Fractions were collected and analyzed by TLC. Fractions were pooled according to TLC analysis, and solvent was removed with a rotavaporator at room temperature. The diastereomeric ratio of ther pooled fractions was determined by P-31 NMR and NPP-TFA analysis. If needed, the above procedure was repeated until the diastereomeric ratio reached 97%.

Example 23

Global Cholic Acid Modification of PMOplus

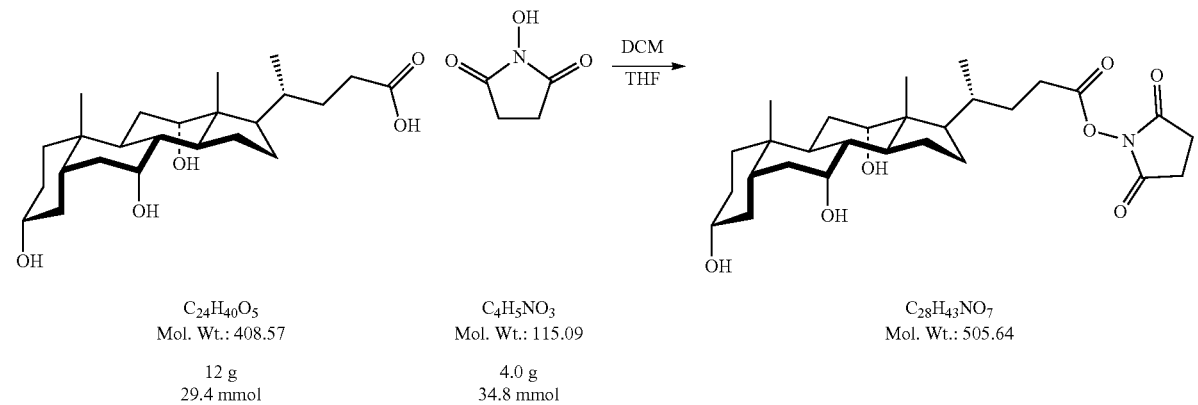

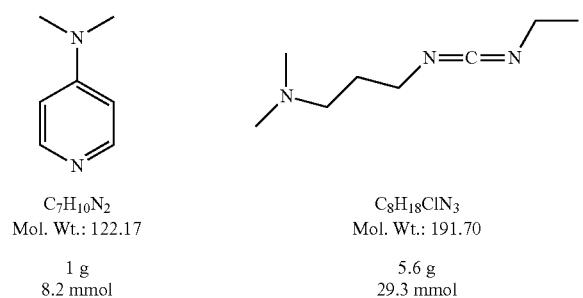

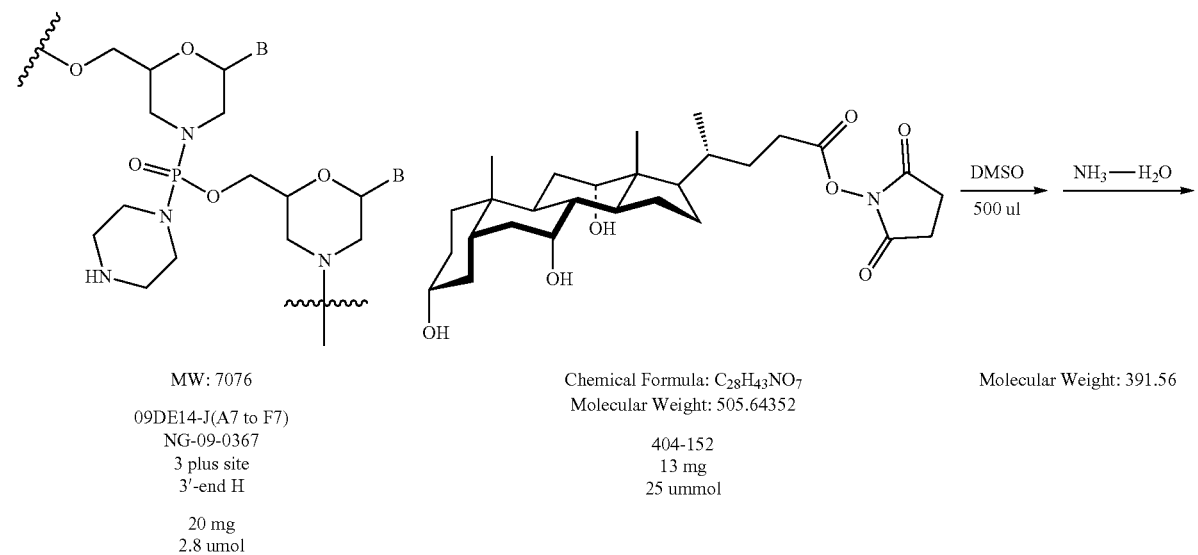

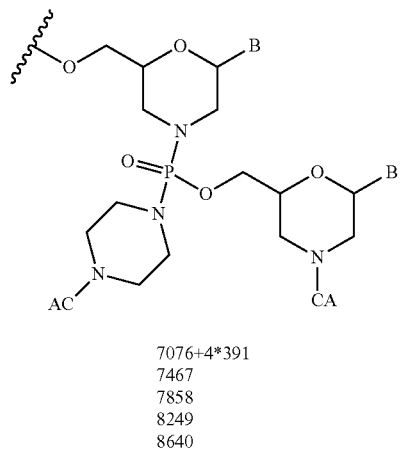

7076+4*391
7467
7858
8249
8640

The succinimide activated cholic acid derivative was prepared according to the following procedure. Cholic acid (12 g, 29.4 mmol), N-hydroxysuccinimide (4.0 g, 34.8 mmol), EDCI (5.6 g, 29.3 mmol), and DMAP (1 g, 8.2 mmol) were charged to a round bottom flask. DCM (400 ml) and THF (40 ml) were added to dissolve. The reaction mixture was stirred at room temperature overnight. Water (400 ml) was then added to the reaction mixture, the organic layer separated and washed with water (2×400 ml), followed by sat. NaHCO$_3$ (300 ml) and brine (300 ml). The organic layer was then dried over Na$_2$SO$_4$. Solvent was removed with rotavaporator to obtain a white solid. The crude product was dissolved in chloroform (100 ml) and precipitated into heptane (1000 ml). The solid was collected by filtration, analyzed by HPLC and NMR and used without further purification.

An appropriate amount of PMOplus (20 mg, 2.8 µmol) was weighed into a vial (4 ml) and dissolved in DMSO (500 ul). The activated cholate ester (13 mg, 25 µmol) was added to the reaction mixture according to the ratio of two equivalent of active ester per modification site followed by stirring at room temperature overnight. Reaction progress was determined by MALDI and HPLC (C-18 or SAX).

After the reaction was complete (as determined by disappearance of starting PMOplus), 1 ml of concentrated ammonia was added to the reaction mixture once the reaction is complete. The reaction vial was then placed in an oven (45° C.) overnight (18 hours) followed by cooling to room temperature and dilution with 1% ammonia in water (10 ml). This sample was loaded on to an SPE column (2 cm), and the vial rinsed with 1% ammonia solution (2×2 ml). The SPE column was washed with 1% ammonia in water (3×6 ml), and the product eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

This same procedure is applicable to deoxycholic acid activation and conjugation to a PMO$^+$.

Example 24

Global Guanidynylation of PMOplus

An appropriate amount of PMOplus (25 mg, 2.8 µmol) was weighed into a vial (6 ml). 1H-Pyrozole-1-carboxamidine chloride (15 mg, 102 µmol) and potassium carbonate (20 mg, 0.15 mmol) were added to the vial. Water was added (500 ul), and the reaction mixture was stirred at room temperature overnight (about 18 hours). Reaction completion was determined by MALDI.

Once complete, the reaction was diluted with 1% ammonia in water (10 ml) and loaded on to an SPE column (2 cm). The vial was rinsed with 1% ammonia solution (2×2 ml), and the SPE column was washed with 1% ammonia in water (3×6 ml). Product was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

Example 25
Global Thioacetyl Modification of PMOplus (M23D)
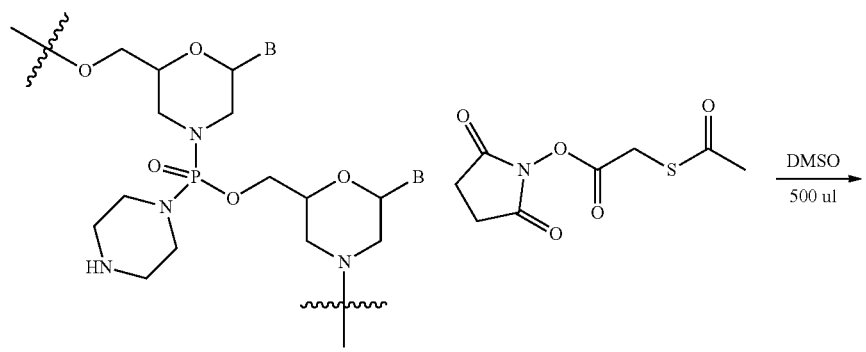
MW: 8710
10Feb 16-J(D1)
NG-09-0719
M23D
3 plus site
3'-end H
20 mg
2.3 umol
Chemical Formula: $C_8H_9NO_5S$
Exact Mass: 231.0
SATA
N-succinimidyl-S-acetylthioacetate
7 mg
28 umol
3 eq.
DMSO
500 ul
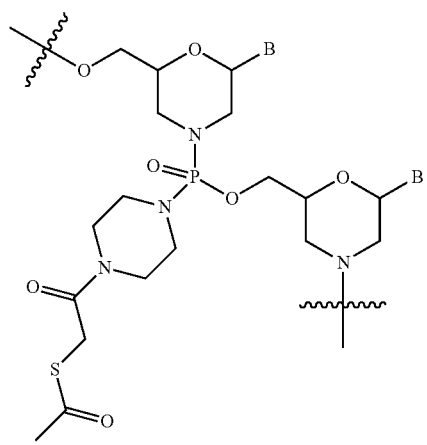
Exact Mass: 117.0
MW: 8710*117n
8827
8944
9061
9178
Ammonolysis

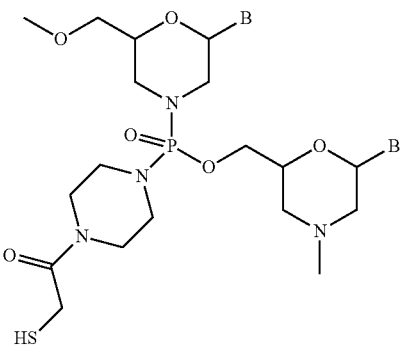

Exact Mass: 75.0

8710+n*75
8785
8860
8935
9010

An appropriate amount of PMOplus (20 mg, 2.3 μmol) was weighed in to a vial (4 ml) and dissolved in DMSO (500 ul). N-succinimidyl-S-acetylthioacetate (SATA) (7 mg, 28 μmol) was added to the reaction mixture, and it was allowed to stir at room temperature overnight. Reaction progress was monitored by MALDI and HPLC.

Once complete, 1% ammonia in water was added to the reaction mixture, and it was stirred at room temperature for 2 hours. This solution was loaded on to an SPE column (2 cm), The vial was rinsed with 1% ammonia solution (2×2 ml), and the SPE column was washed with 1% ammonia in water (3×6 ml). Product was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

Example 26

Global Succinic Acid Modification of PMOplus

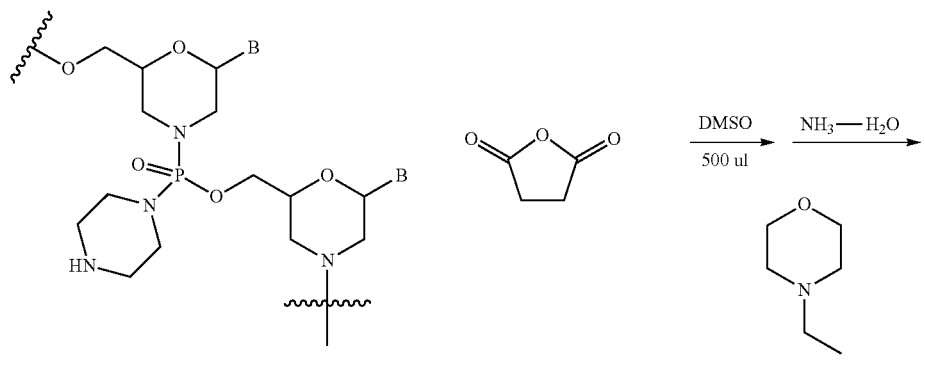

MW: 8710
10FE02-R(A7)
NG-09-0719
3 plus site
3'-end H 32 mg
3.7 umol

Chemical Formula: $C_4H_4O_3$
Molecular Weight: 100.07276

10 mg
100 umol

Chemical Formula: $C_6H_{13}NO$
Molecular Weight: 115.17352 d = 0.91
100 umol
12 mg
13 ul

-continued

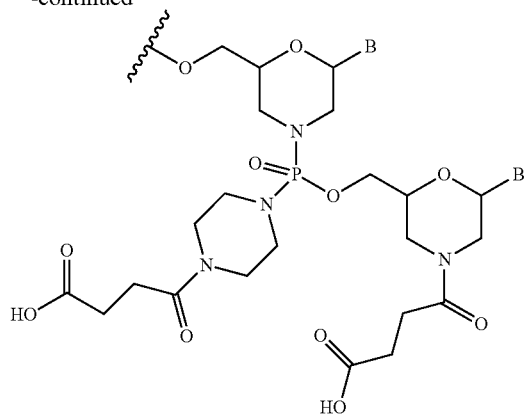

Chemical Formula: C₄H₅O₃⁻
Molecular Weight: 101.08070

8710+4*100
8810
8910
9010
9110

An appropriate amount of PMOplus (32 mg, 3.7 μmol) was weighed in to a vial (4 ml) and dissolved in DMSO (500 ul). N-ethyl morpholino (12 mg, 100 μmol) and succinic anhydride (10 mg, 100 μmol) were added to the reaction mixture, and it was allowed to stir at room temperature overnight. Reaction progress was monitored by MALDI and HPLC.

Once complete, 1% ammonia in water was added to the reaction mixture, and it was stirred at room temperature for 2 hours. This solution was loaded on to an SPE column (2 cm), The vial was rinsed with 1% ammonia solution (2×2 ml), and the SPE column was washed with 1% ammonia in water (3×6 ml). Product was eluted with 45% acetonitrile in 1% ammonia in water (6 ml). Fractions containing oligomer were identified by UV optical density measurement. Product was isolated by lyophilization. Purity and identity were determined by MALDI and HPLC (C-18 and/or SAX).

The above procedure is applicable to glutartic acid (glutaric anhydride) and tetramethyleneglutaric acid (tetramethyleneglutaric anhydride) modification of PMOplus as well.

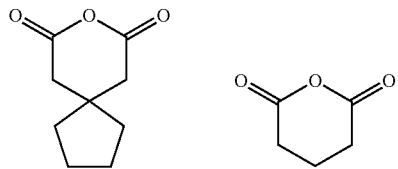

Tetramethylenglutaric anhydride    Glutaric anhydride

Example 27

Preparation of an Oligonucleotide Analogue Comprising a Modified Terminal Group

To a solution of a 25-mer PMO containing a free 3'-end (27.7 mg, 3.226 μmol) in DMSO (300 μL) was added farnesyl bromide (1.75 μl, 6.452 μmol) and diisopropylethylamine (2.24 μL, 12.9 mol). The reaction mixture was stirred at room temperature for 5 hours. The crude reaction mixture was diluted with 10 mL of 1% aqueous NH₄OH, and then loaded onto a 2 mL Amberchrome CG300M column. The column was then rinsed with 3 column volumes of water, and the product was eluted with 6 mL of 1:1 acetonitrile and water (v/v). The solution was then lyophilized to obtain the title compound as a white solid.

Example 28

Preparation of Morpholino Oligomers

Preparation of trityl piperazine phenyl carbamate 35 (see FIG. 3): To a cooled suspension of compound 11 in dichloromethane (6 mL/g 11) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile. Yield=80%

Preparation of carbamate alcohol 36: Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane. Yield=90%.

Preparation of Tail acid 37: To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous NaHCO$_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

Preparation of 38: To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of 38 from compound 36. Introduction of the activated "Tail" onto the disulfide anchor-resin was performed in NMP by the procedure used for incorporation of the subunits during solid phase synthesis.

Preparation of the Solid Support for Synthesis of Morpholino Oligomers: This procedure was performed in a silanized, jacketed peptide vessel (custom made by ChemGlass, NJ, USA) with a coarse porosity (40-60 µm) glass frit, overhead stirrer, and 3-way Teflon stopcock to allow N2 to bubble up through the frit or a vacuum extraction. Temperature control was achieved in the reaction vessel by a circulating water bath.

The resin treatment/wash steps in the following procedure consist of two basic operations: resin fluidization and solvent/solution extraction. For resin fluidization, the stopcock was positioned to allow N2 flow up through the frit and the specified resin treatment/wash was added to the reactor and allowed to permeate and completely wet the resin. Mixing was then started and the resin slurry mixed for the specified time. For solvent/solution extraction, mixing and N2 flow were stopped and the vacuum pump was started and then the stopcock was positioned to allow evacuation of resin treatment/wash to waste. All resin treatment/wash volumes were 15 mL/g of resin unless noted otherwise.

To aminomethylpolystyrene resin (100-200 mesh; ~1.0 mmol/g N2 substitution; 75 g, 1 eq, Polymer Labs, UK, part #1464-X799) in a silanized, jacketed peptide vessel was added 1-methyl-2-pyrrolidinone (NMP; 20 ml/g resin) and the resin was allowed to swell with mixing for 1-2 hr. Following evacuation of the swell solvent, the resin was washed with dichloromethane (2×1-2 min), 5% diisopropylethylamine in 25% isopropanol/dichloromethane (2×3-4 min) and dichloromethane (2×1-2 min). After evacuation of the final wash, the resin was fluidized with a solution of disulfide anchor 34 in 1-methyl-2-pyrrolidinone (0.17 M; 15 mL/g resin, ~2.5 eq) and the resin/reagent mixture was heated at 45° C. for 60 hr. On reaction completion, heating was discontinued and the anchor solution was evacuated and the resin washed with 1-methyl-2-pyrrolidinone (4×3-4 min) and dichloromethane (6×1-2 min). The resin was treated with a solution of 10% (v/v) diethyl dicarbonate in dichloromethane (16 mL/g; 2×5-6 min) and then washed with dichloromethane (6×1-2 min). The resin 39 (see FIG. 4) was dried under a N2 stream for 1-3 hr and then under vacuum to constant weight (±2%). Yield: 110-150% of the original resin weight.

Determination of the Loading of Aminomethylpolystyrene-disulfide resin: The loading of the resin (number of potentially available reactive sites) is determined by a spectrometric assay for the number of triphenylmethyl (trityl) groups per gram of resin.

A known weight of dried resin (25±3 mg) is transferred to a silanized 25 ml volumetric flask and ~5 mL of 2% (v/v) trifluoroacetic acid in dichloromethane is added. The contents are mixed by gentle swirling and then allowed to stand for 30 min. The volume is brought up to 25 mL with additional 2% (v/v) trifluoroacetic acid in dichloromethane and the contents thoroughly mixed. Using a positive displacement pipette, an aliquot of the trityl-containing solution (500 µL) is transferred to a 10 mL volumetric flask and the volume brought up to 10 mL with methanesulfonic acid.

The trityl cation content in the final solution is measured by UV absorbance at 431.7 nm and the resin loading calculated in trityl groups per gram resin (µmol/g) using the appropriate volumes, dilutions, extinction coefficient (ε: 41 µmol-1 cm-1) and resin weight. The assay is performed in triplicate and an average loading calculated.

The resin loading procedure in this example will provide resin with a loading of approximately 500 µmol/g. A loading of 300-400 in µmol/g was obtained if the disulfide anchor incorporation step is performed for 24 hr at room temperature.

Tail loading: Using the same setup and volumes as for the preparation of aminomethylpolystyrene-disulfide resin, the Tail can be introduced into the molecule. For the coupling step, a solution of 38 (0.2 M) in NMP containing 4-ethylmorpholine (NEM, 0.4 M) was used instead of the disulfide anchor solution. After 2 hr at 45° C., the resin 39 was washed twice with 5% diisopropylethylamine in 25% isopropanol/dichloromethane and once with DCM. To the resin was added a solution of benzoic anhydride (0.4 M) and NEM (0.4 M). After 25 min, the reactor jacket was cooled to room temperature, and the resin washed twice with 5% diisopropylethylamine in 25% isopropanol/dichloromethane and eight times with DCM. The resin 40 was filtered and dried under high vacuum. The loading for resin 40 is defined to be the loading of the original aminomethylpolystyrene-disulfide resin 39 used in the Tail loading.

Solid Phase Synthesis: Morpholino Oligomers were prepared on a Gilson AMS-422 Automated Peptide Synthesizer in 2 mL Gilson polypropylene reaction columns (Part #3980270). An aluminum block with channels for water flow was placed around the columns as they sat on the synthesizer. The AMS-422 will alternatively add reagent/wash solutions, hold for a specified time, and evacuate the columns using vacuum.

For oligomers in the range up to about 25 subunits in length, aminomethylpolystyrene-disulfide resin with loading near 500 µmol/g of resin is preferred. For larger oligomers, aminomethylpolystyrene-disulfide resin with loading of 300-400 µmol/g of resin is preferred. If a molecule with 5'-Tail is desired, resin that has been loaded with Tail is chosen with the same loading guidelines.

The following reagent solutions were prepared:
Detritylation Solution: 10% Cyanoacetic Acid (w/v) in 4:1 dichloromethane/acetonitrile; Neutralization Solution: 5% Diisopropylethylamine in 3:1 dichloromethane/isopropanol; Coupling Solution: 0.18 M (or 0.24 M for oligomers having grown longer than 20 subunits) activated Morpholino Subunit of the desired base and linkage type and 0.4

M N ethylmorpholine, in 1,3-dimethylimidazolidinone. Dichloromethane (DCM) was used as a transitional wash separating the different reagent solution washes.

On the synthesizer, with the block set to 42° C., to each column containing 30 mg of aminomethylpolystyrene-disulfide resin (or Tail resin) was added 2 mL of 1-methyl-2-pyrrolidinone and allowed to sit at room temperature for 30 min. After washing with 2 times 2 mL of dichloromethane, the following synthesis cycle was employed:

| Step | Volume | Delivery | Hold time |
|---|---|---|---|
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| Detritylation | 1.5 mL | Manifold | 15 seconds |
| DCM | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| Coupling | 350 uL-500 uL | Syringe | 40 minutes |
| DCM | 1.5 mL | Manifold | 30 seconds |
| Neutralization | 1.5 mL | Manifold | 30 seconds |
| Neutralization | 1.5 mL | Manifold | 30 seconds |
| DCM | 1.5 mL | Manifold | 30 seconds |
| DCM | 1.5 mL | Manifold | 30 seconds |
| DCM | 1.5 mL | Manifold | 30 seconds |

The sequences of the individual oligomers were programmed into the synthesizer so that each column receives the proper coupling solution (A,C,G,T,I) in the proper sequence. When the oligomer in a column had completed incorporation of its final subunit, the column was removed from the block and a final cycle performed manually with a coupling solution comprised of 4-methoxytriphenylmethyl chloride (0.32 M in DMI) containing 0.89 M 4-ethylmorpholine.

Cleavage from the resin and removal of bases and backbone protecting groups: After methoxytritylation, the resin was washed 8 times with 2 mL 1-methyl-2-pyrrolidinone. One mL of a cleavage solution consisting of 0.1 M 1,4-dithiothreitol (DTT) and 0.73 M triethylamine in 1-methyl-2-pyrrolidinone was added, the column capped, and allowed to sit at room temperature for 30 min. After that time, the solution was drained into a 12 mL Wheaton vial. The greatly shrunken resin was washed twice with 300 μL of cleavage solution. To the solution was added 4.0 mL conc aqueous ammonia (stored at −20° C.), the vial capped tightly (with Teflon lined screw cap), and the mixture swirled to mix the solution. The vial was placed in a 45° C. oven for 16-24 hr to effect cleavage of base and backbone protecting groups.

Initial Oligomer Isolation: The vialed ammonolysis solution was removed from the oven and allowed to cool to room temperature. The solution was diluted with 20 mL of 0.28% aqueous ammonia and passed through a 2.5×10 cm column containing Macroprep HQ resin (BioRad). A salt gradient (A: 0.28% ammonia with B: 1 M sodium chloride in 0.28% ammonia; 0-100% B in 60 min) was used to elute the methoxytrityl containing peak. The combined fractions were pooled and further processed depending on the desired product.

Demethoxytritylation of Morpholino Oligomers: The pooled fractions from the Macroprep purification were treated with 1 M H3PO4 to lower the pH to 2.5. After initial mixing, the samples sat at room temperature for 4 min, at which time they are neutralized to pH 10-11 with 2.8% ammonia/water. The products were purified by solid phase extraction (SPE).

Amberchrome CG-300M (Rohm and Haas; Philadelphia, Pa.) (3 mL) is packed into 20 mL fitted columns (BioRad Econo-Pac Chromatography Columns (732-1011)) and the resin rinsed with 3 mL of the following: 0.28% NH4OH/80% acetonitrile; 0.5M NaOH/20% ethanol; water; 50 mM H3PO4/80% acetonitrile; water; 0.5 NaOH/20% ethanol; water; 0.28% NH4OH.

The solution from the demethoxytritylation was loaded onto the column and the resin rinsed three times with 3-6 mL 0.28% aqueous ammonia. A Wheaton vial (12 mL) was placed under the column and the product eluted by two washes with 2 mL of 45% acetonitrile in 0.28% aqueous ammonia. The solutions were frozen in dry ice and the vials placed in a freeze dryer to produce a fluffy white powder. The samples were dissolved in water, filtered through a 0.22 micron filter (Pall Life Sciences, Acrodisc 25 mm syringe filter, with a 0.2 micron HT Tuffryn membrane) using a syringe and the Optical Density (OD) was measured on a UV spectrophotometer to determine the OD units of oligomer present, as well as dispense sample for analysis. The solutions were then placed back in Wheaton vials for lyophilization.

Analysis of Morpholino Oligomers: MALDI-TOF mass spectrometry was used to determine the composition of fractions in purifications as well as provide evidence for identity (molecular weight) of the oligomers. Samples were run following dilution with solution of 3,5-dimethoxy-4-hydroxycinnamic acid (sinapinic acid), 3,4,5-trihydoxyacetophenone (THAP) or alpha-cyano-4-hydoxycinnamic acid (HCCA) as matrices.

Cation exchange (SCX) HPLC was performed using a Dionex ProPac SCX-10, 4×250 mm column (Dionex Corporation; Sunnyvale, Calif.) using 25 mM pH=5 sodium acetate 25% acetonitrile (Buffer A) and 25 mM pH=5 sodium acetate 25% acetonitrile 1.5 M potassium chloride (buffer B) (Gradient 10-100% B in 15 min) or 25 mM KH2PO4 25% acetonitrile at pH=3.5 (buffer A) and 25 mM KH2PO4 25% acetonitrile at pH=3.5 with 1.5 M potassium chloride (buffer B) (Gradient 0-35% B in 15 min). The former system was used for positively charged oligomers that do not have a peptide attached, while the latter was used for peptide conjugates.

Purification of Morpholino Oligomers by Cation Exchange Chromatography: The sample is dissolved in 20 mM sodium acetate, pH=4.5 (buffer A) and applied to a column of Source 30 cation exchange resin (GE Healthcare) and eluted with a gradient of 0.5 M sodium chloride in 20 mM sodium acetate and 40% acetonitrile, pH=4.5 (buffer B). The pooled fractions containing product are neutralized with conc aqueous ammonia and applied to an Amberchrome SPE column. The product is eluted, frozen, and lyophilized as above.

Example 29

Preparation of an Exemplary Conjugate

The peptide sequence $AcR_6G$ was prepared according to standard peptide synthetic methods known in the art. To a solution of the PMO (NG-05-0225, 3'-H: M23D: 5'-EG3, a sequence for binding to exon 23 of the mdx mouse, 350 mg, 1 eq), AcR6G (142 mg, 2 eq), HATU (31 mg, 2 eq) in DMSO (3 mL) was added diisopropylethylamine (36 µL, 5 eq) at room temperature. After 1 hour, the reaction was worked up and the desired peptide-oligomer conjugate was purified by SCX chromatography (eluting with a gradient: A: 20 mM NaH2PO4 in 25% acetonitrile/H2O, pH 7.0; B: 1.5 M guanidine HCl and 20 mM NaH2PO4 in 25% acetonitrile/H2O, pH 7.0). The combined fractions were subjected to solid phase extraction (1M NaCl, followed by water elution). The conjugate was obtained as a white powder (257 mg, 65.5% yield) after lyophilization.

Example 30

Treatment of MDX Mice With Exemplary Conjugates of the Invention

The MDX mouse is an accepted and well-characterized animal model for Duchene muscular dystrophy (DMD) containing a mutation in exon 23 of the dystrophin gene. The M23D antisense sequence (SEQ ID NO:15) is known to induce exon 23 skipping and restoration of functional dystrophin expression. MDX mice were dosed once (50 mg/kg) by tail vein injection with one of the following conjugates:
1. 5'-EG3-M23D-BX(RXRRBR)$_2$ (AVI5225);
2. 5'-EG3-M23D-G(R)$_5$ (NG-11-0045);
3. 5'-EG3-M23D-G(R)$_6$ (NG-11-0009);
4. 5'-EG3-M23D-G(R)$_7$ (NG-11-0010); or
5. 5'-EG3-M23D-G(R)$_8$ (NG-11-0216)
wherein M23D is a morpholino olionucleotide having the sequence GGCCAAACCTCGGCTTACCTGAAAT (SEQ ID NO:15) and "EG3" refers to the following structure:

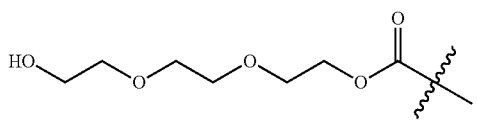 [SMILES: *C(=O)OCCOCCOCCO]

linked to the 5' end of the oligomer via a piperazine linker (i.e., structure XXIX).

Figure 5A:
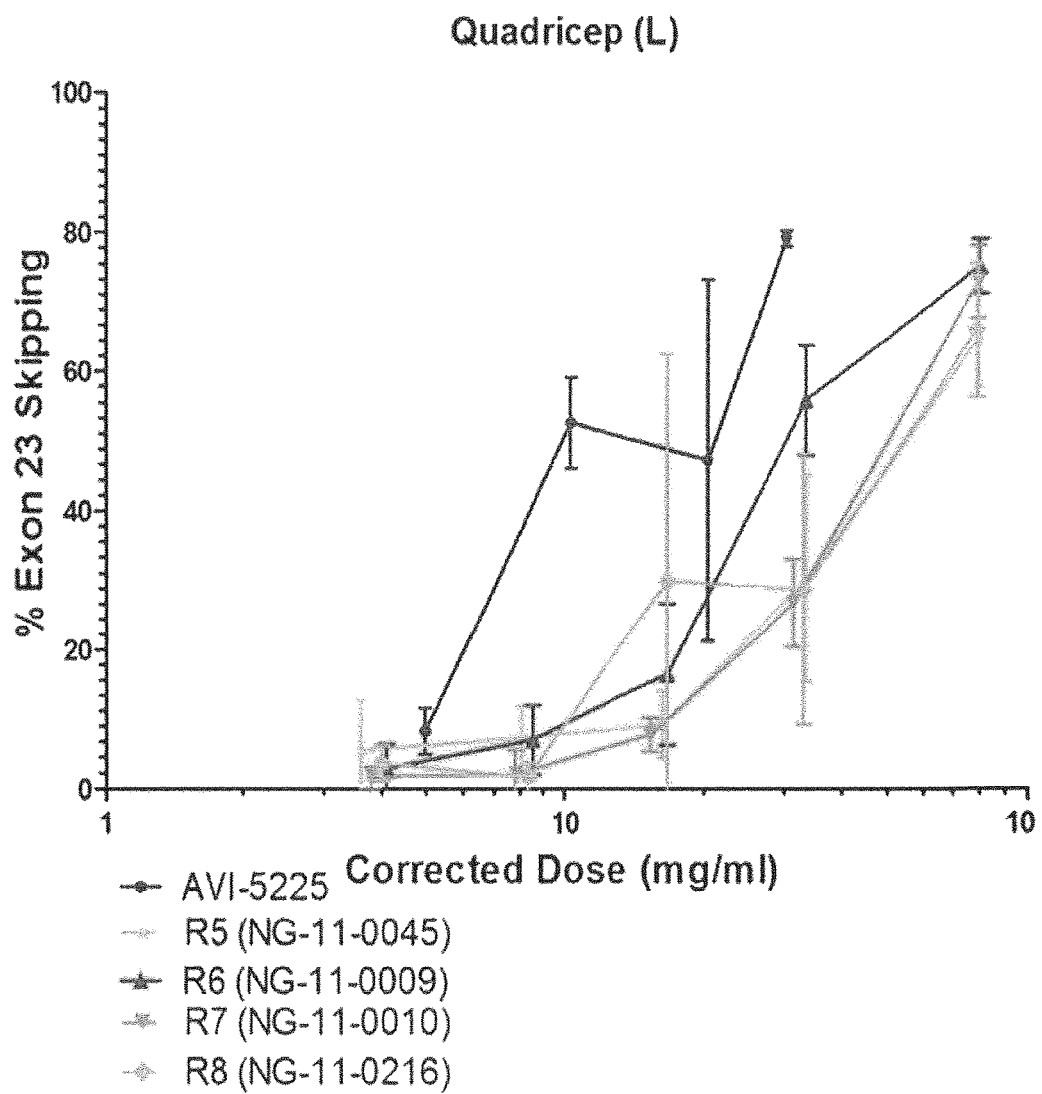
FIGS. 5A, 5B and 5C show exon skipping data for exemplary conjugates compared to a known conjugate in mouse quadriceps, diaphragm and heart, respectively.
Figure 5B:
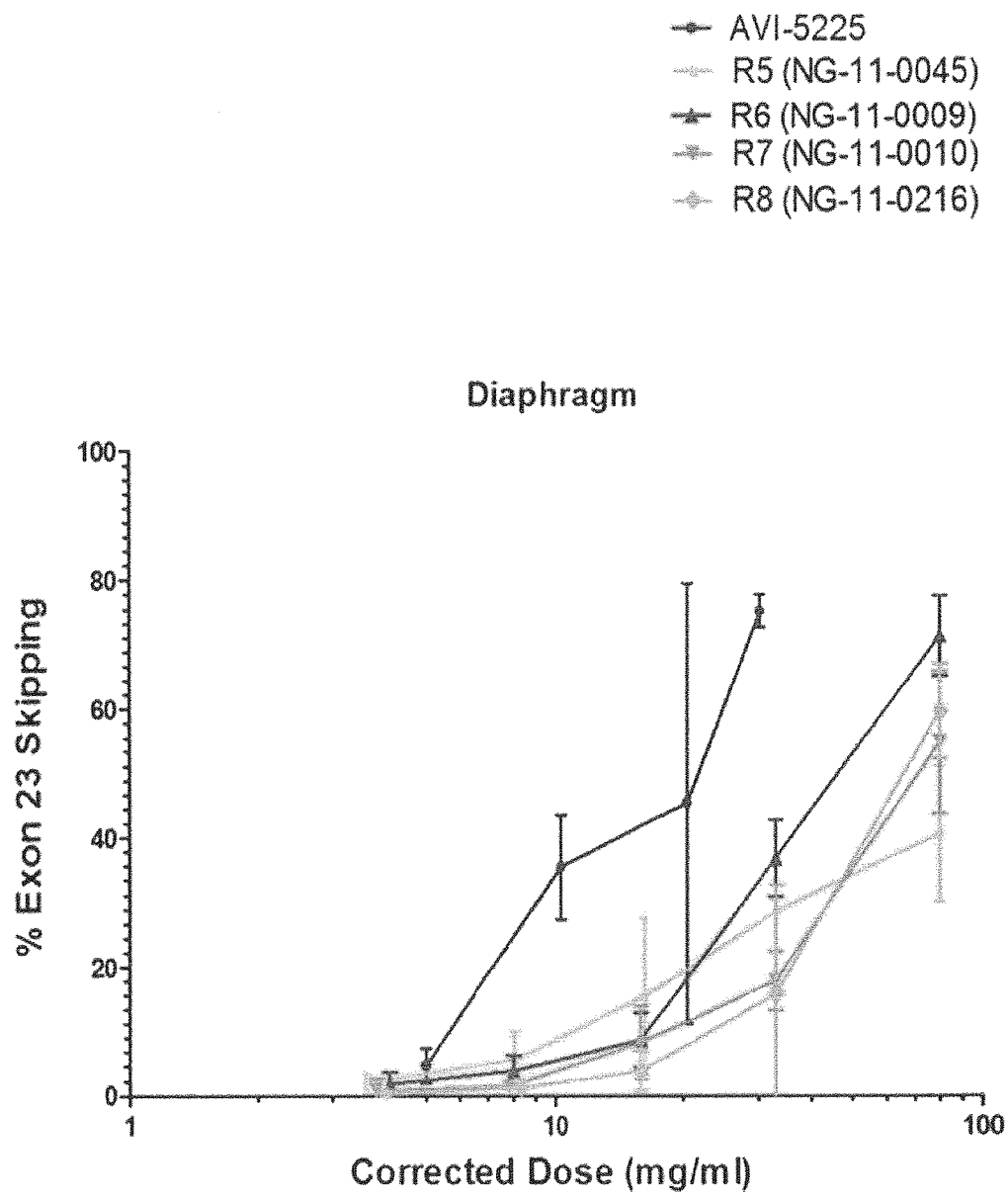
Figure 5C:
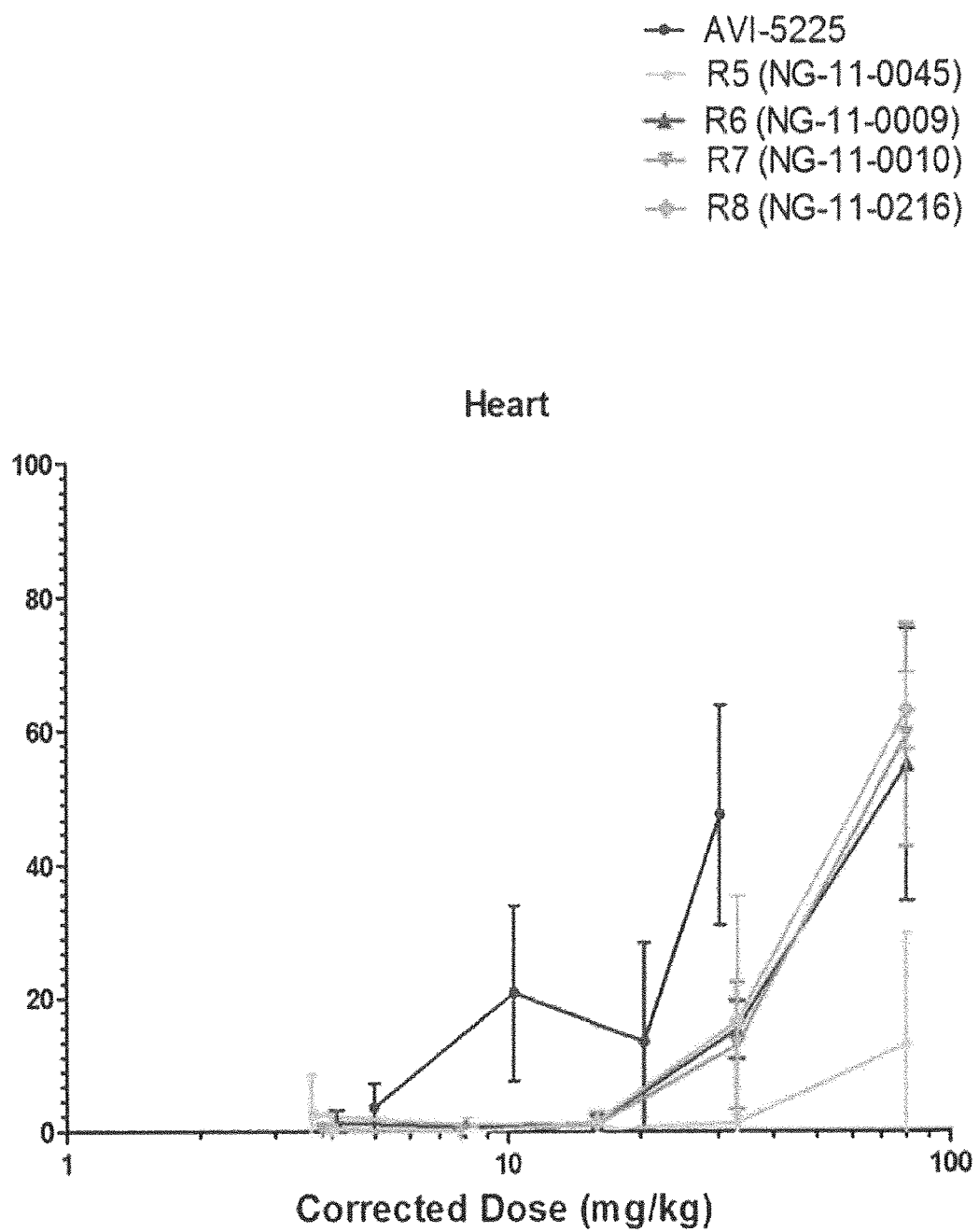
Figure 6A:
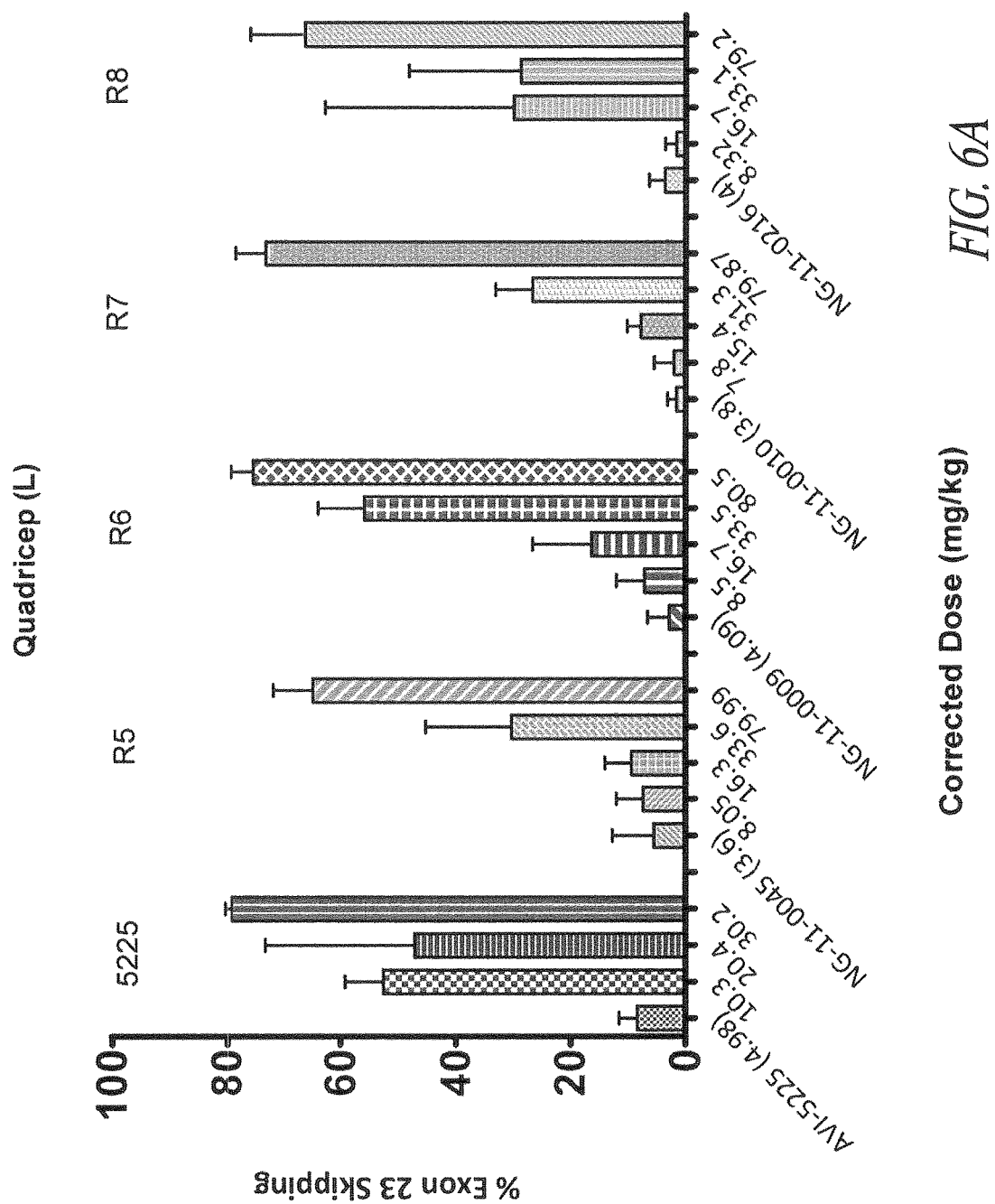
FIGS. 6A, 6B and 6C are alternate representations of exon skipping data for exemplary conjugates compared to a known conjugate in mouse quadriceps, diaphragm and heart, respectively.
Figure 6B:
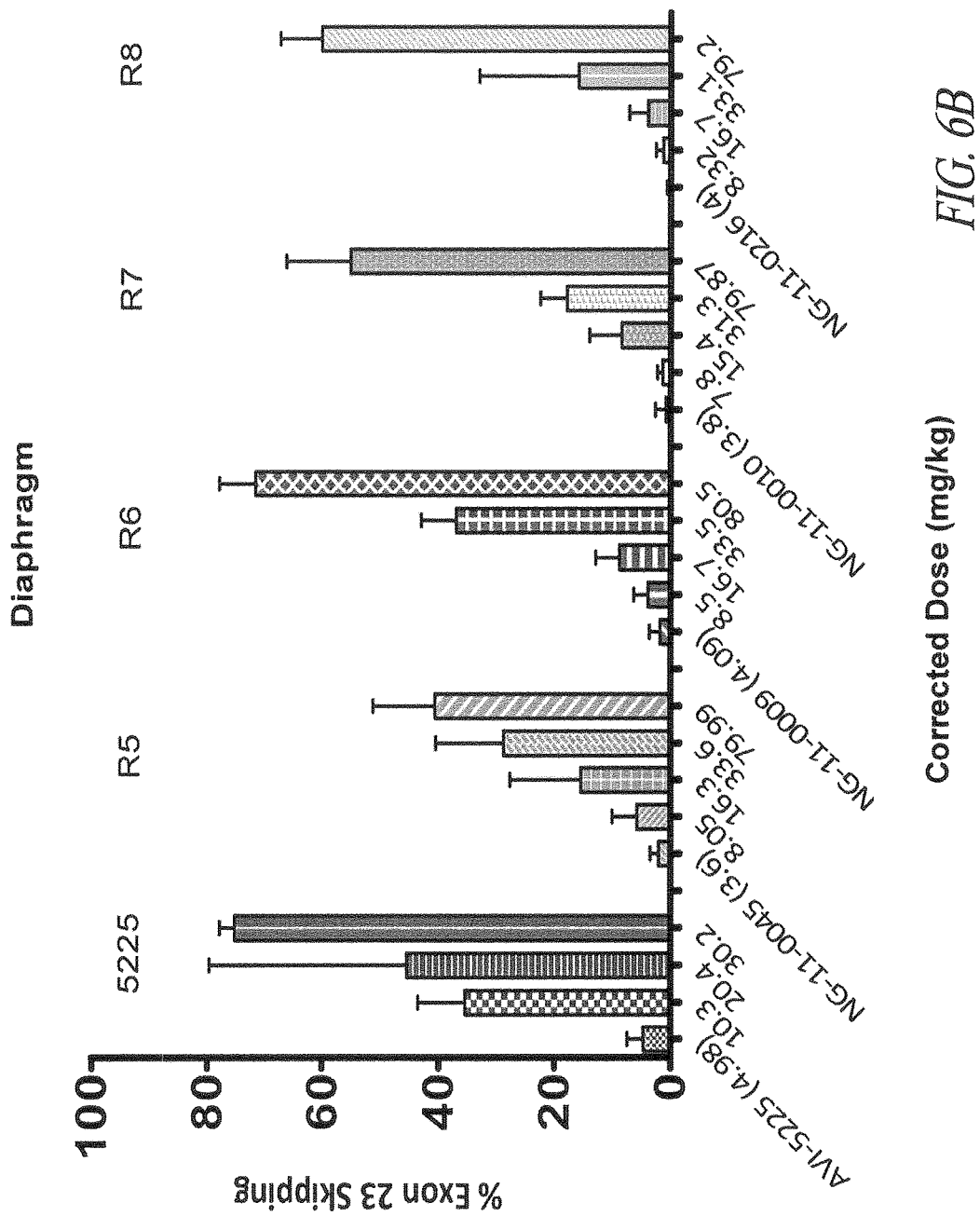
Figure 6C:
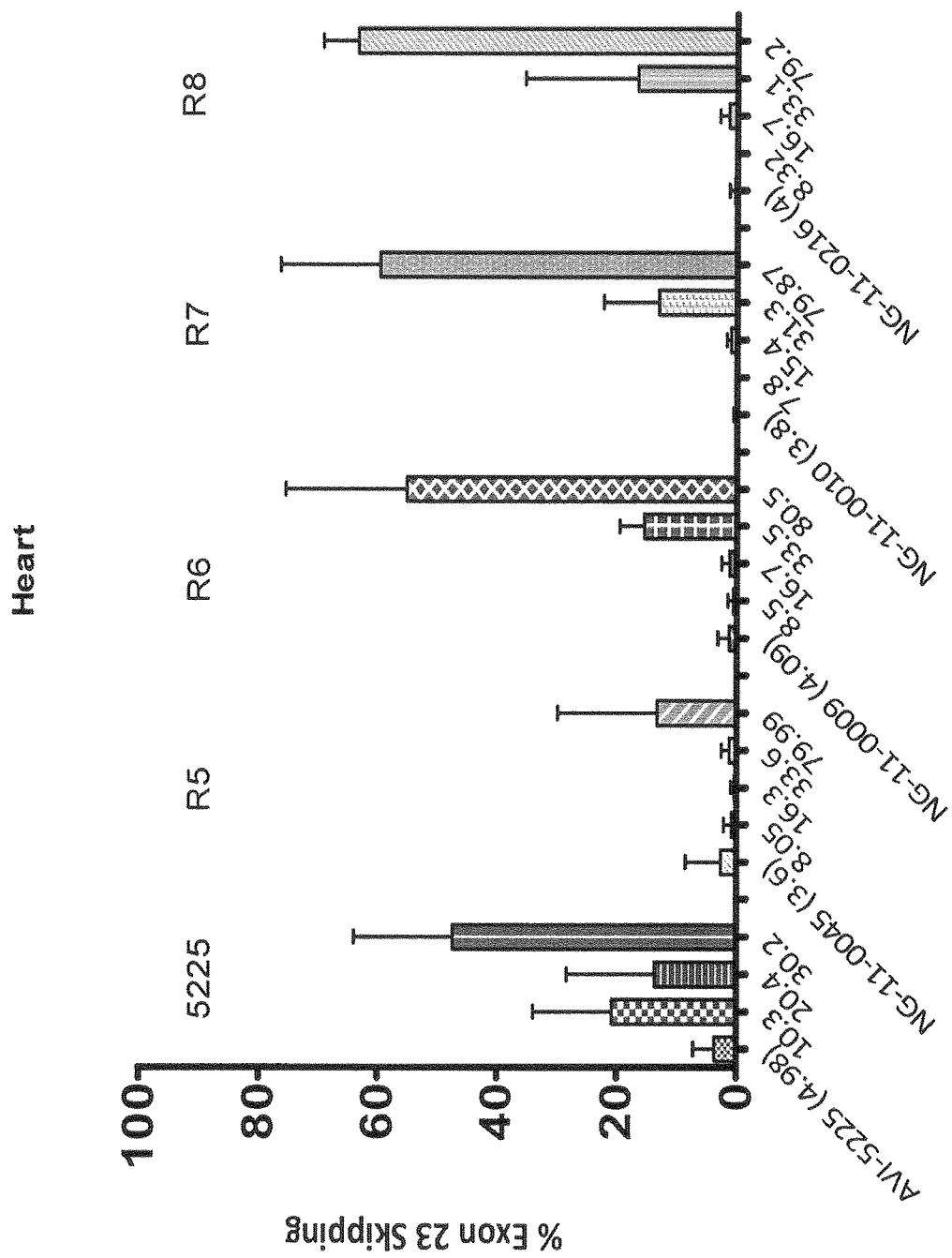

One week post-injection, the MDX mice were sacrificed and RNA was extracted from various muscle tissues. Endpoint PCR was used to determine the relative abundance of dystrophin mRNA containing exon 23 and mRNA lacking exon 23 due to antisense-induced exon skipping. Percent exon 23 skipping is a measure of antisense activity in vivo. FIGS. 5 and 6 show shows the results from the quadriceps (QC, FIGS. 5A and 6A), diaphragm (DT, FIGS. 5B and 6B) and heart (HT, FIGS. 5C and 5C), respectively one week post-treatment. The dose response between AVI-5225 and the other conjugates was similar Amongst the arginine series, the R$_6$G peptide has the highest efficacy in quadriceps and diaphragm and was similar to the other arginine series peptides in heart.

Example 31

BUN Levels and Survival Rates of Mice Treated With Exemplary Conjugates

Figure 7A:
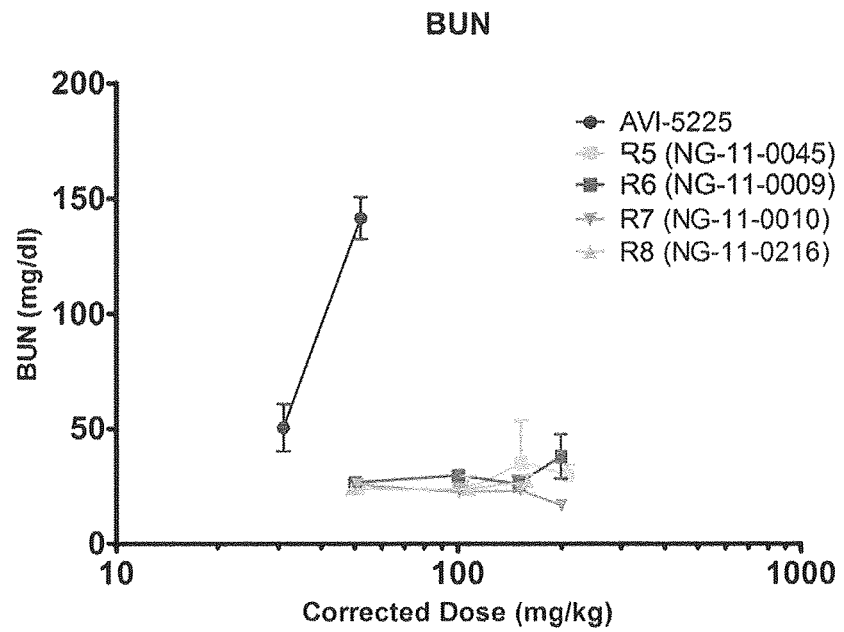
FIGS. 7A and 7B are graphs depicting blood urea nitrogen (BUN) levels and survival rate of mice treated with various peptide-oligomer conjugates, respectively.
Figure 7B:
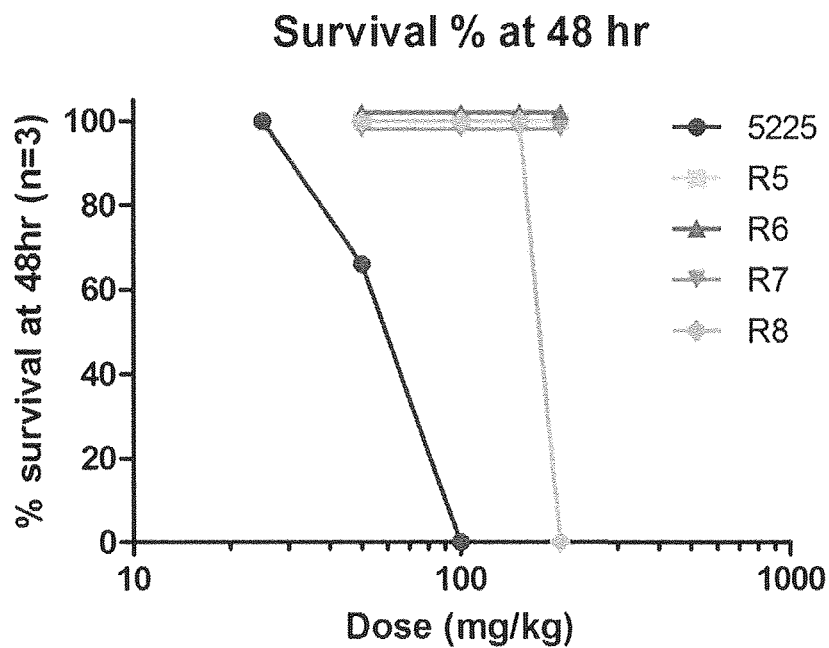

Mice were treated with the conjugates described in Example 30, and KIM-1 levels, BUN levels and survival rate were determined according to the general procedures described in Example 32 below and known in the art. Surprisingly, FIG. 7A shows that all glycine linked conjugates had significantly lower BUN levels than the XB linked conjugate (AVI-5225). In addition, mice treated with glycine linked conjugates survived longer at higher doses than the XB linked conjugate (FIG. 7B), with the R$_8$G conjugate being the least tolerated of the arginine polymers. All mice treated with the R$_6$G conjugate (NG-11-0009) survived at doses up to 400 mg/kg (data not shown).

Figure 8A:
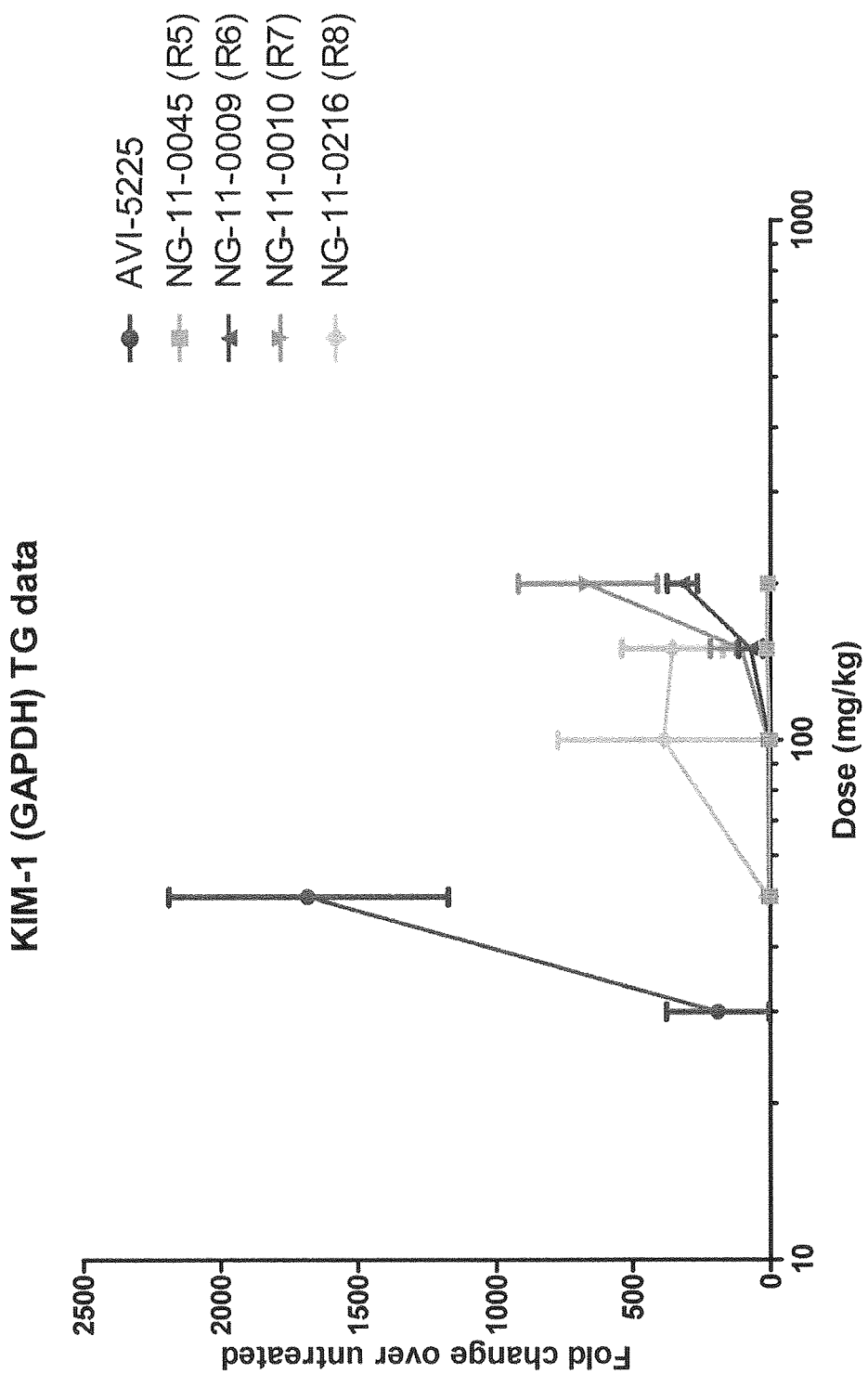
FIGS. 8A and 8B show kidney injury marker (KIM) data and Clusterin (Clu) data for mice treated with various peptide-oligomer conjugates, respectively.
Figure 8B:
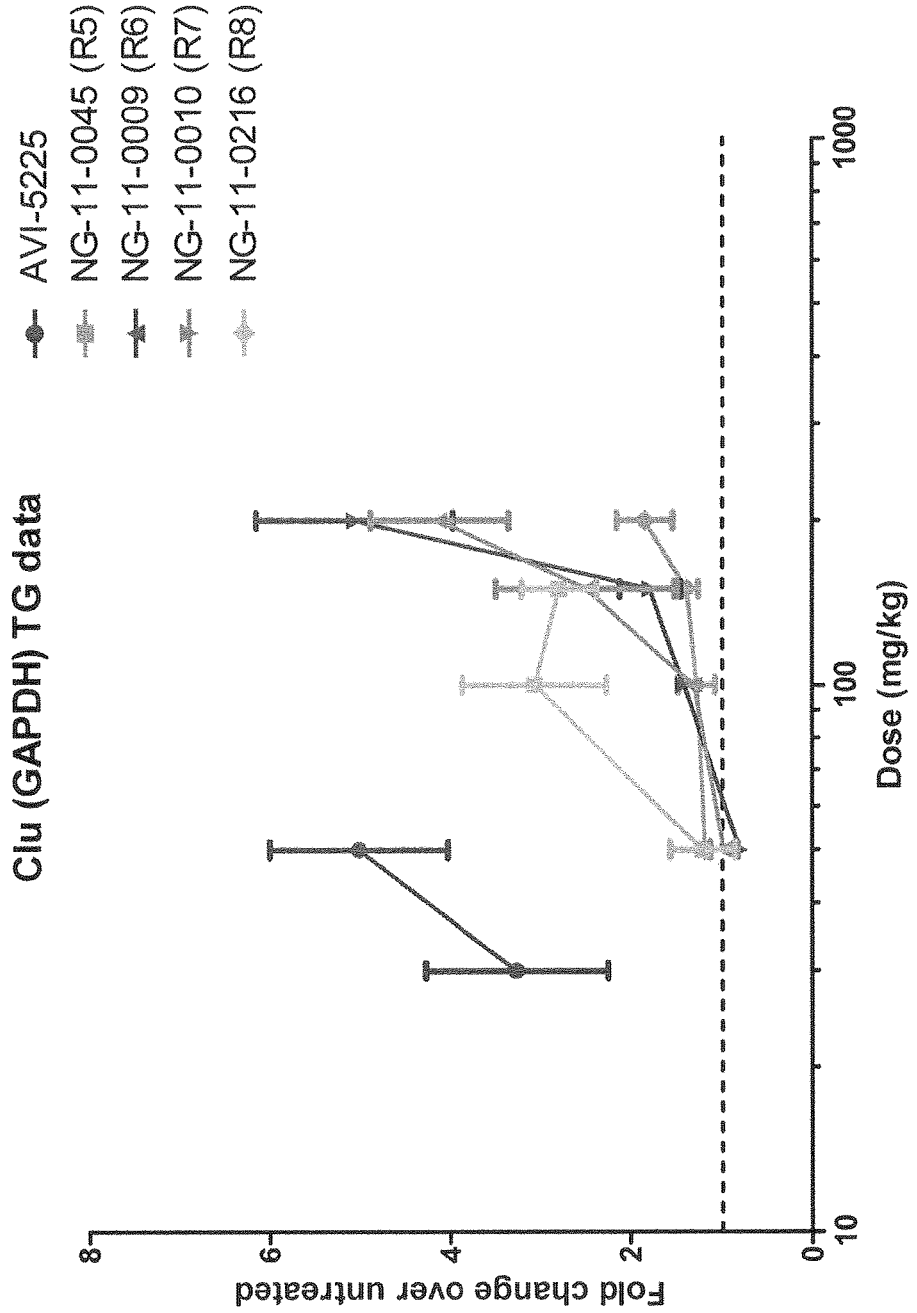
Figure 9A:
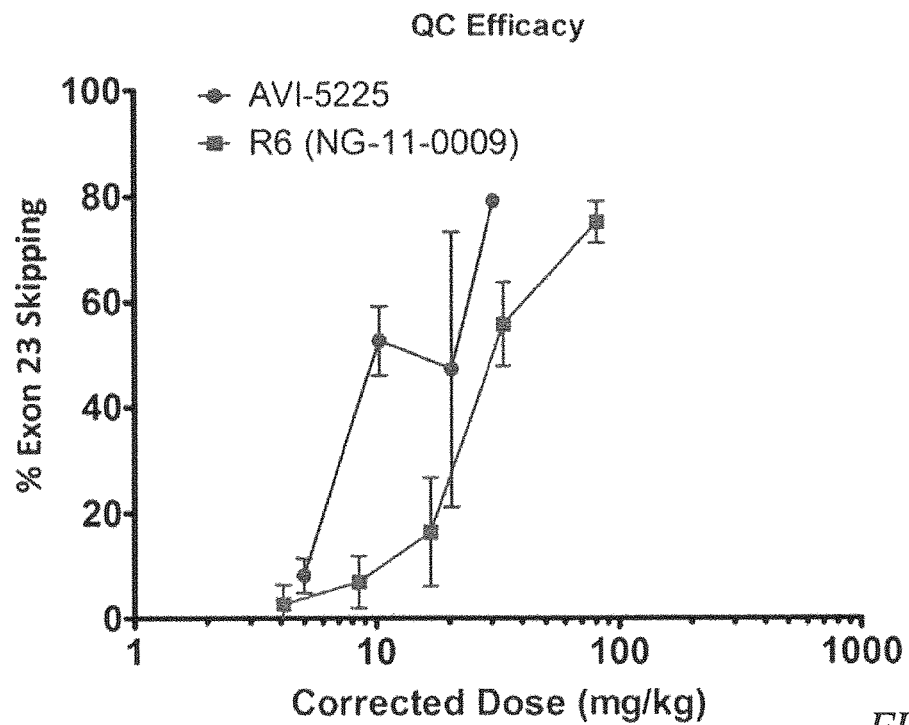
FIGS. 9A, 9B, 9C and 9D are graphs comparing the exon skipping, BUN levels, precent survival and KIM levels, respectively, in mice treated with an exemplary conjugate compared to a known conjugate.
Figure 9B:
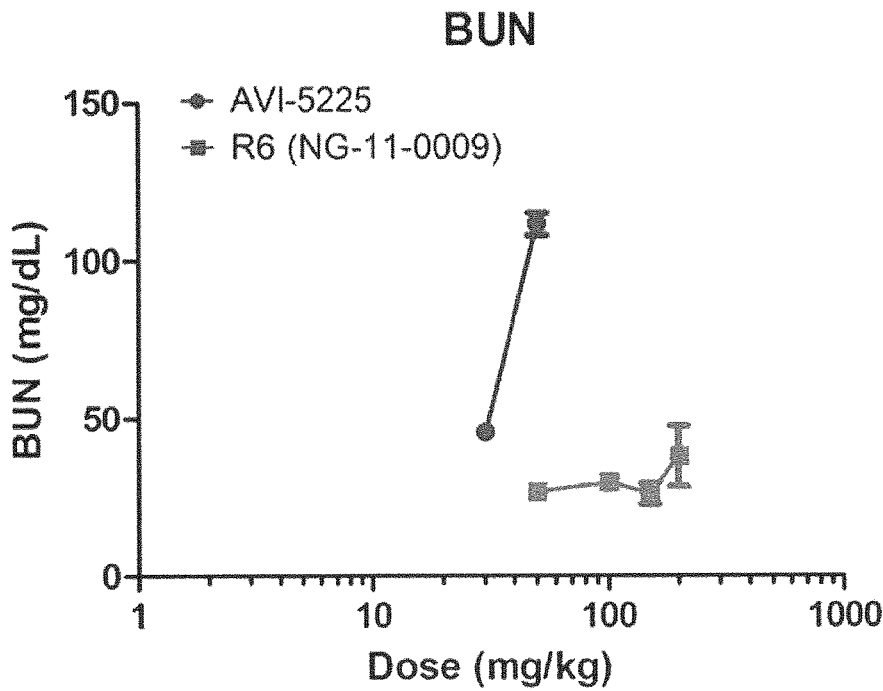
Figure 9C:
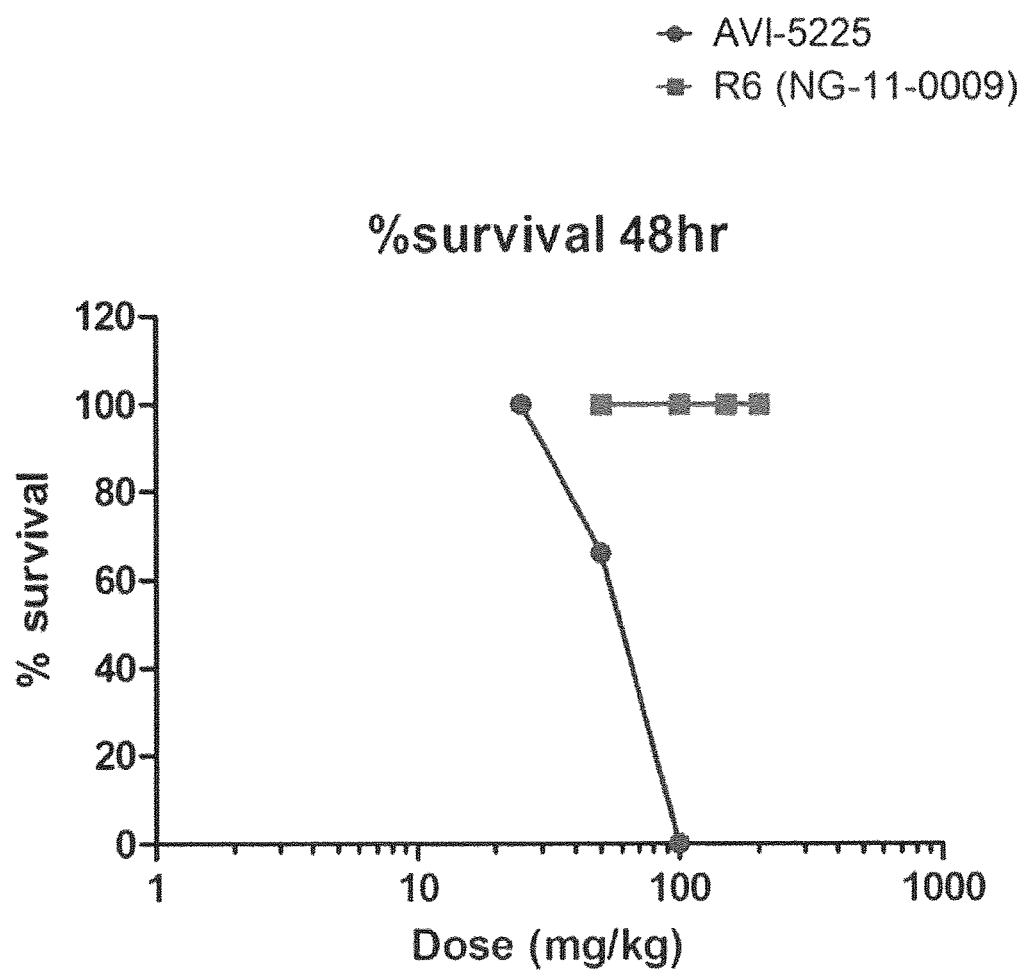
Figure 9D:
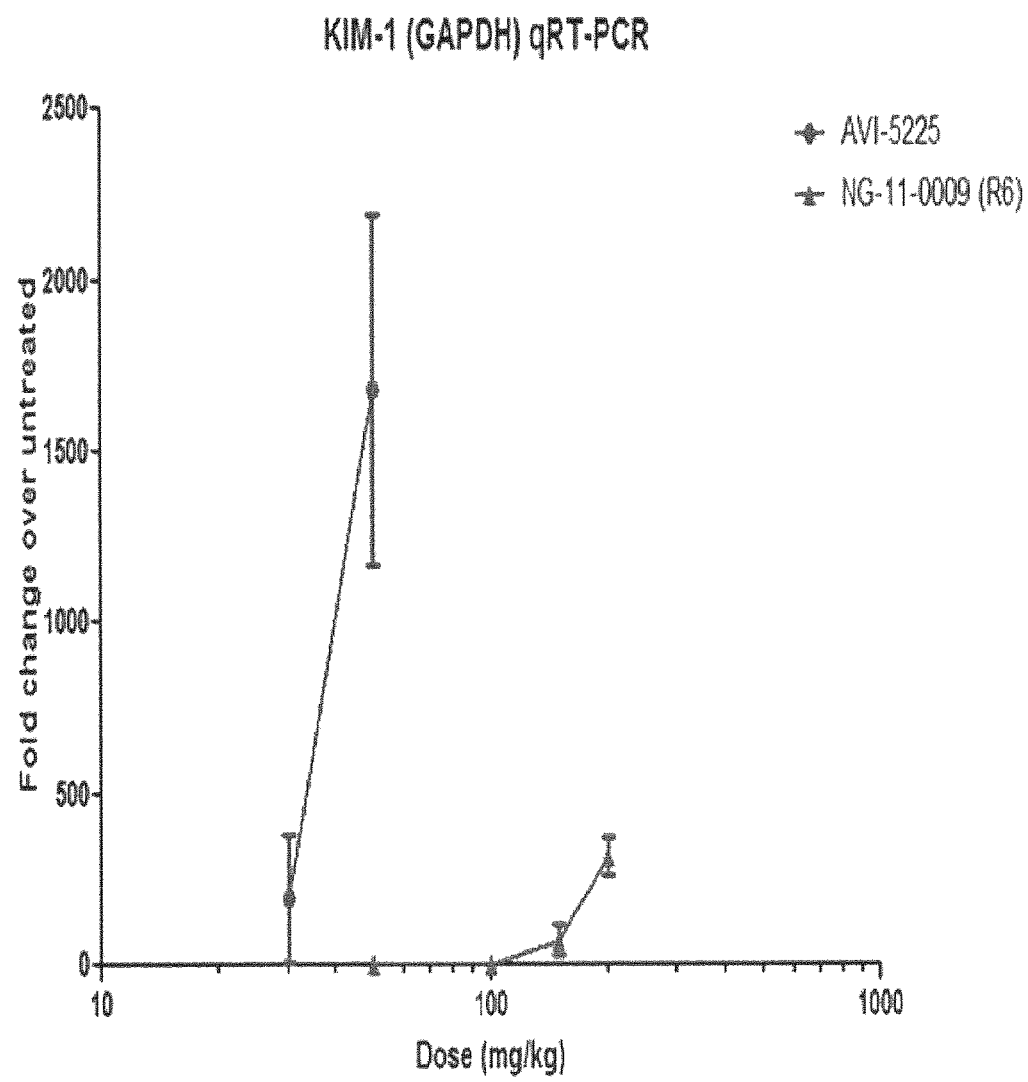

The KIM-1 (FIG. 8A) and Clusterin (FIG. 8B) levels of mice treated with the glycine linked conjugates was significantly lower than mice treated with AVI-5225. This data indicates that the conjugates of the present invention have lower toxicity than prior conjugates, and as shown above in Example 30, the efficacy of the conjugates is not decreased. Accordingly, the present conjugates have a better therapeutic window than other known conjugates and are potentially better drug candidates.

Example 32

Toxicology of Exemplary Conjugates

Four exemplary conjugates of the invention were tested for their toxicology in mice. The conjugates were as follows:
1. 5'-EG3-M23D-BX(RXRRBR)$_2$ (AVI5225);
2. 5'-EG3-M23D-G(RXRRBR)$_2$ (NG-11-0654);
3. 5'-EG3-M23D-BX(R)$_6$ (NG-11-0634); and
4. 5'-EG3-M23D-G(R)$_6$ (NG-11-0009)
wherein M23D is a morpholino olionucleotide having the sequence GGCCAAACCTCGGCTTACCTGAAAT and "EG3" refers to the following structure:

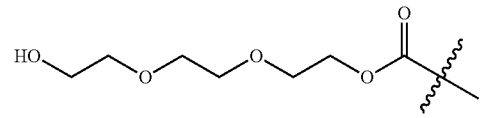 [SMILES: *C(=O)OCCOCCOCCO]

linked to the 5' end of the oligomer via a piperazine linker (i.e., structure XXIX).

Eight week old male mice (C57/BL6; Jackson Laboratories, 18-22 grams) were treated with the above conjugates formulated in saline. The mice were acclimated for a minimum of five days prior to the commencement of the experimental procedures.

The animals were housed up to 3 per cage in clear polycarbonate microisolator cages with certified irradiated contact bedding. The cages conformed to standards set forth in the Animal Welfare Act (with all amendments) and the Guide for the Care and Use of Laboratory Animals, National Academy Press, Wash., D.C., 2010.

Animals were randomized into treatment groups based on cage weights specified in the table below. Group allocation was documented in the study records.

TABLE 8

Toxicology Study Design

| Group n = 3 | Oligo | Dose per injection (mg/kg) | Regimen | Route of Admin. |
|---|---|---|---|---|
| 1 | NG-11-0654 | 50 | Single | Tail Vein, i.v. |
| 2 | NG-11-0654 | 100 | injection | 200 µl |
| 3 | NG-11-0654 | 150 | | |
| 4 | NG-11-0654 | 200 | | |
| 5 | NG-11-0634 | 50 | | |
| 6 | NG-11-0634 | 100 | | |
| 7 | NG-11-0634 | 150 | | |
| 8 | NG-11-0634 | 200 | | |

TABLE 8-continued

Toxicology Study Design

| Group n = 3 | Oligo | Dose per injection (mg/kg) | Regimen | Route of Admin. |
|---|---|---|---|---|
| 9 | NG-11-0009 | 50 | | |
| 10 | NG-11-0009 | 100 | | |
| 11 | NG-11-0009 | 150 | | |
| 12 | NG-11-0009 | 200 | | |
| 13 | AVI-5225 | 25 | | |
| 14 | AVI-5225 | 50 | | |
| 15 | AVI-5225 | 100 | | |
| 16 | Vehicle | 0 | | |

The day of dosing on the study was designated as Study Day 1. Conjugate was administered via tail vein as a slow push bolus (~5 seconds). All animals were dosed over two days. Groups 1-8 were dosed on the first day and Groups 9-16 were dosed on the second day. Treatment Groups (TG) 13-16 were dosed per the table above. Results from these TGs did not affect progression to other TG. The first 2 TG of each conjugate were dosed per the table above. If all animals in 100 mg/kg group died then the remaining TGs of that test article would not be dosed and the study would end. If at least one animal survived 2 hours post-dose in the 100 mg/kg group, then the 150 mg/kg group was dosed. If all animals in the 150 mg/kg group died then the remaining TGs of that test article would not be dosed and the study would end. If at least one animal survived 2 hours post-dose in the 150 mg/kg group, then the 200 mg/kg group was dosed.

Animals were observed for moribundity and mortality once daily. Any animal showing signs of distress, particularly if death appeared imminent was humanely euthanized according to Numira Biosciences Standard Operating Procedures. Body weights were recorded on the day after arrival, the day of dosing, and the day of necropsy. Detailed clinical observations were conducted and recorded at 0 minutes, 15 minutes, and 2 hours post-dose to assess tolerability of injections.

Blood samples (maximum volume, approximately 1 mL) were obtained from all animals via cardiac puncture 3 days post-dose prior to necropsy. Blood samples were collected into red top microtainer tubes and held at room temperature for at least 30 minutes but no longer than 60 minutes prior to centrifugation. Samples were centrifuged at approximately 1500-2500 rpm for 15-20 minutes to obtain serum.

Animals unlikely to survive until the next scheduled observation were weighed and euthanized. Animals found dead were weighed and the time of death was estimated as closely as possible. Blood and tissue samples were not collected.

Day 3 (2 days post-dose), all animals were humanely euthanized with carbon dioxide. Euthanasia was performed in accordance with accepted American Veterinary Medical Association (AVMA) guidelines on Euthanasia, June 2007.

The partial gross necropsy included examination and documentation of findings. All external surfaces and orifices were evaluated. All abnormalities observed during the collection of the tissues were described completely and recorded. No additional tissues were taken.

The right and left kidneys were collected. Tissues were collected within 15 minutes or less of euthanasia. All instruments and tools used were changed between treatment groups. All tissues were flash frozen and stored at <−70° C. as soon as possible after collection.

Kidney injury marker data was obtained as follows. RNA from mouse kidney tissue was purified using Quick Gene Mini80 Tissue Kit SII (Fuji Film). Briefly, approximately 40 mg of tissue was added to 0.5 ml lysis buffer (5 μl 2-mercaptoethanol in 0.5 ml lysis buffer) in a MagnaLyser Green Bead vial (Roche) and homogenized using MagNA Lyser (Roche) with 2 sets of 3×3800 RPM and 3 sets of 1× 6500 RPM. Samples were cooled on ice 3-4 minutes between each low speed set and between each higher speed run. Homogenates were centrifuged 5 minute at 400×g at room temperature. The homogenate was immediately processed for RNA purification according to the Quick Gene Mini80 protocol. Samples underwent an on-column DNA digestion with DNase I (Qiagen) for 5 minutes. Total RNA was quantitated with a NanoDrop 2000 spectrophotometer (Thermo Scientific).

qRT-PCR was performed using Applied Biosystems reagents (One-step RT-PCR) and pre-designed primer/probe sets (ACTB, GAPDH, KIM-1, Clusterin-FAM reporter)

| Reagent | Company | Cat. No. |
|---|---|---|
| One-step PCR kit | Applied Biosystems | 4309169 |
| GAPDH mouse primer/probe set | Applied Biosystems | 4352932E |
| KIM-1 mouse primer/probe set | Applied Biosystems | Mm00506686_m1 |

Each reaction contained the following (30 ul total):
15 ul 2×qRT-PCR Buffer from ABI One-Step Kit
1.5 ul Primer/Probe mix
8.75 ul Nuclease-free water
0.75 ul 40× multiscript+RNase inhibitor
4 ul RNA template (100 ng/ul)
The qRT One-Step Program was run as follows:
1. 48 C for 30 minutes
2. 95 C for 10 minutes
3. 95 C for 15 seconds
4. 60 C for 1 minute
5. Repeat Steps 3-4 39 times for a total of 40 cycles Samples were run in triplicate wells and averaged for further analysis. Analysis was performed using $\Delta\Delta Ct$ method. Briefly, Experimental $\Delta Ct$ [Ct(Target)−Ct(Reference)] subtracted by Control $\Delta Ct$ [Ct(Target)−Ct(Reference)]=$\Delta\Delta Ct$. Fold change range calculated: $2^\wedge-(\Delta\Delta Ct+SD)$ to $2^\wedge-(\Delta\Delta Ct-SD)$. Control=vehicle treated animal group (pooled), Target=KIM-1; Reference=GAPDH; SD=Sqrt [(SDtarget^2)+(SDref^2)].

Figure 10:
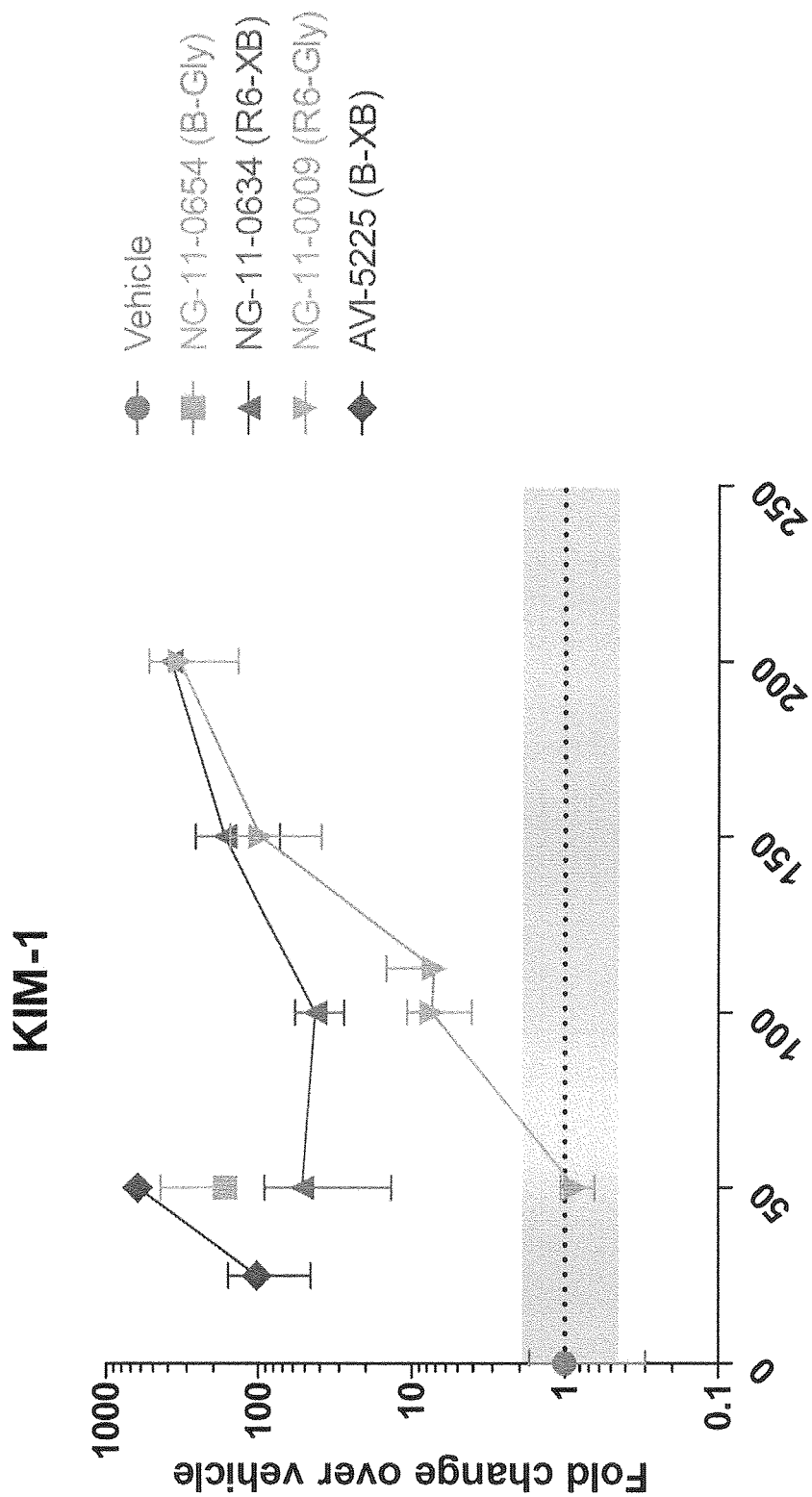
FIG. 10 presents KIM data for mice treated with various conjugates.

Results of KIM data are shown in FIG. 10. Conjugates comprising carrier peptides with terminal glycines had lower KIM concentrations with the $R_6G$ peptide having the lowest. Both the terminal G and the presence of unnatural amino acids (aminohexanoic acid) appear to play a role in the toxicity of the conjugates.

Figure 11:
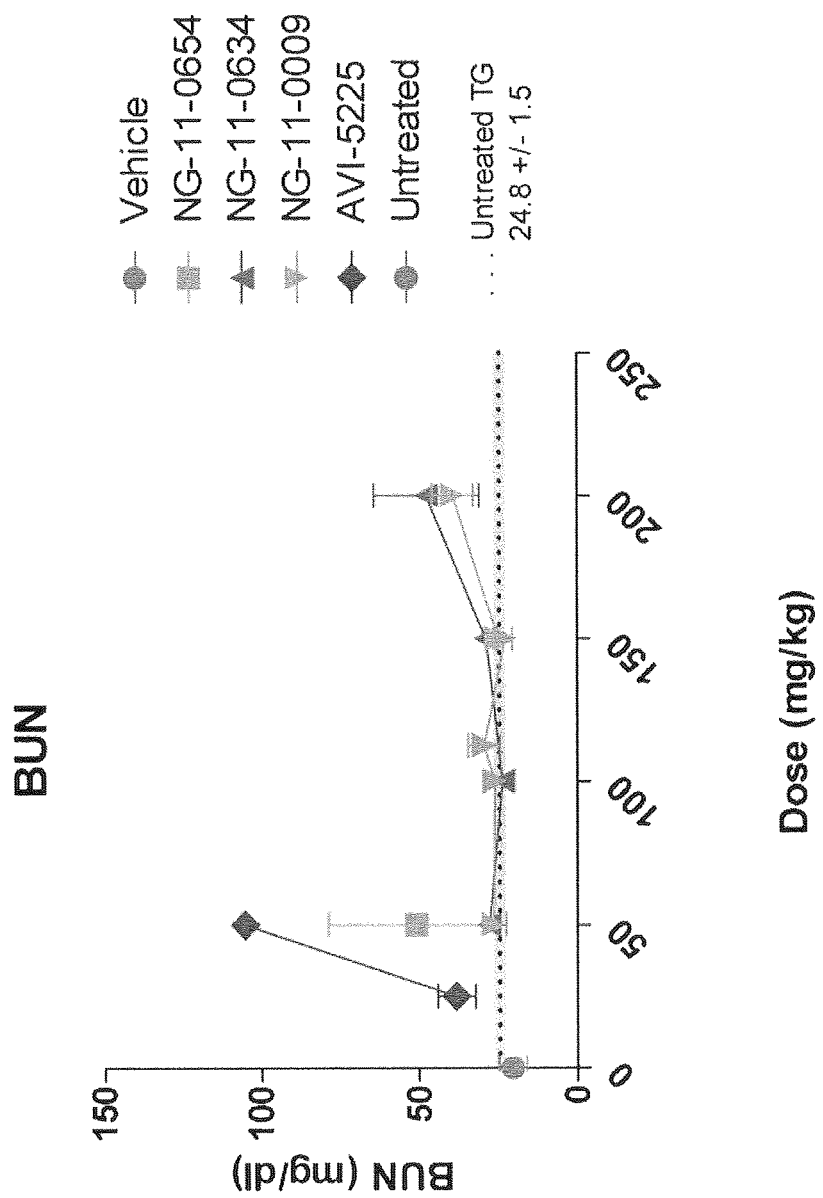
FIG. 11 shows results of BUN analysis of mice treated with various conjugates.

Frozen serum samples were sent on dry ice to IDEXX Laboratories (West Sacramento, Calif.) for processing. Serum dilution was performed per IDEXX Standard Operating Procedures (SOPs) when necessary. Blood chemistry results were were analyzed. Blood urea nitrogen levels are shown in FIG. 11. Again, the G-linked conjugate had lower BUN levels and the both the terminal G and overall peptide sequence appear to play a role in the toxicological profile of the conjugates.

Kidney tissues (approx. 150 mg) were weighed accurately in a 2 mL screw cap vial partially filled with ceramic beads. Five volume parts Tissue PE LB buffer (G Biosciences) containing 10 U/mL Proteinase K (Sigma) were added to 1 part tissue. Samples were homogenized with a Roche MagnaLyser (4×40 sec @7,000 rpm, with cooling between runs)

and incubated for 30 min at 40° C. When required, tissue homogenates were diluted with BSAsal (3 mg/mL BSA+20 mM NaCl) to bring high sample concentrations into the calibration range.

Calibration samples were prepared by spiking a solution of 3 mg/mL of BSA in 20 mM NaCl with known amounts of an appropriate analytical reference standard. Duplicate sets of eight samples each were prepared. The ULOQ was 40 µg/mL and LLOQ was 0.065536 µg/mL. An internal standard (NG-07-0775) was added to all samples except some blank samples designated as double blanks (no drug, no internal standard). Samples were extracted by vortexing 100 µL aliquots with 3 volumes of methanol.

After centrifugation (15 min, 14,000 rpm) supernatants were transferred to new tubes and dried in a Speedvac. Dried samples were reconstituted with an appropriate amount of FDNA (5' d FAM-ATTTCAGGTAAGCCGAGGTTTG-GCC 3') in [10 mM Tris pH 8.0+1 mM EDTA+100 mM NaCl]–acetonitrile (75-25).

Samples were analyzed on the Dionex UltiMate 3000 HPLC using anion-exchange chromatography (Dionex DNAPac 4×250 mm column). Injection volume was 5 µL. Mobile phase was composed of 20% acetonitrile and 80% water containing 25 mM Tris pH 8.0 and a gradient of increasing NaCl concentration. Flow rate was 1 mL/min, and run time was 10 min per sample. The fluorescence detector was set to EX 494 nm and EM 520 nm. Peak identification was based on retention time. Peak height ratios (analyte:internal standard) were used for quantitation. Calibration curves were calculated based on the averaged response factors of duplicate calibration samples (one set run at the beginning of the batch, the other at the end of the batch. Linear curve fit with 1/xweighting factor was used. Blank samples (calibration sample with no reference compound added) and double blank samples (on internal standard added) were used to ensure assay specificity and absence of carryover.

Figure 12:
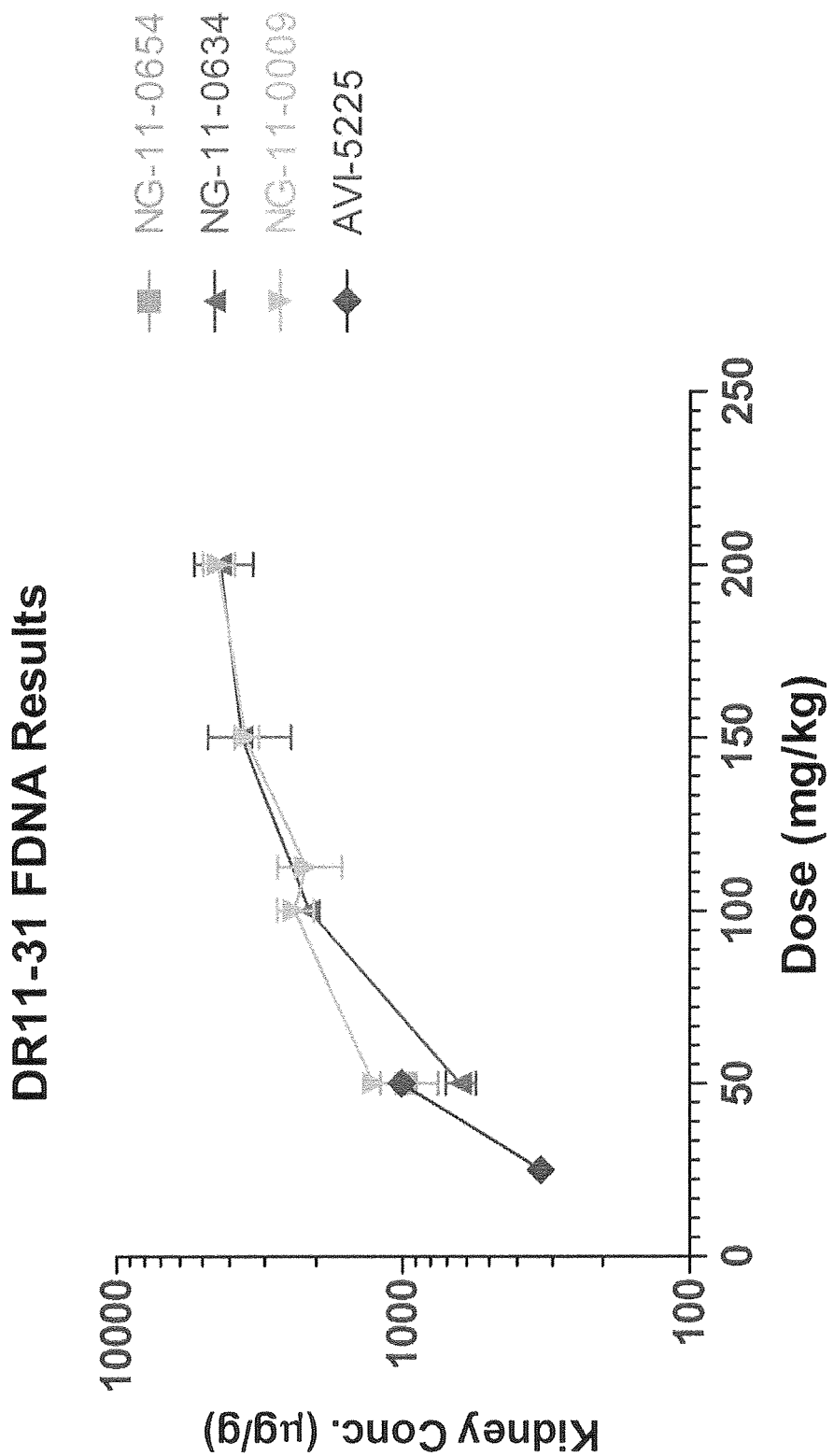
FIG. 12 is a graph showing the concentration of various oligomers in mouse kidney tissue.

FIG. 12 shows that kidney concentrations were similar amongst the tested conjugates.

The above data shows that conjugates of the invention have similar efficacy and improved toxicity compared to other conjugates. FIGS. 9A-D summarizes these results with respect to an $R_6G$ conjugate (NG-11-0009).

The various embodiments described above can be combined to provide further embodiments. All of the U.S. patents, U.S. patent application publications, U.S. patent applications, foreign patents, foreign patent applications and non-patent publications referred to in this specification and/ or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A conjugate comprising:
   (a) a carrier peptide comprising amino acid subunits, the carrier peptide comprising a glycine (G) amino acid subunit at the carboxy terminus of the carrier peptide;
   (b) a nucleic acid analogue comprising a substantially uncharged backbone and a targeting base sequence for sequence-specific binding to a target nucleic acid, wherein the nucleic acid analog is 8 to 40 bases in length; and
   (c) a covalent attachment between the nucleic acid analog and the carrier peptide, the covalent attachment comprising the carboxy-terminal glycine and an optional linker group; wherein:
   two or more of the amino acid subunits are positively charged amino acids, no more than seven contiguous amino acid subunits are arginine, and the covalent attachment between the nucleic acid analog and the carrier peptide is not 6-aminohexanoic acid or β-alanine.

2. The conjugate of claim 1, wherein the nucleic acid analog is 8 to 20 bases in length.

3. The conjugate of claim 1, wherein the nucleic acid analog is 8 to 16 bases in length.

4. The conjugate of claim 1, wherein the nucleic acid analog is 10 to 30 bases in length.

5. The conjugate of claim 1, wherein the nucleic acid analog is 12 to 25 bases in length.

6. The conjugate of claim 1, wherein the nucleic acid analog is 8 to 12 bases in length.

7. The conjugate of claim 1, wherein the carrier peptide is selected from SEQ ID NOS: 60, 69, 70, 89-121, 125, 130-160, 162-257, 276, 277, 281-288, 293-297, 300, 302-412, 419-552, and 554-566.

8. The conjugate of claim 1, wherein the carrier peptide is selected from SEQ ID NOS: 130, 157-160, 251, 256, 386-388, and 540.

9. The conjugate of claim 1, wherein the carrier peptide is SEQ ID NO: 159.

10. The conjugate of claim 1, wherein the carrier peptide is of a formula selected from:

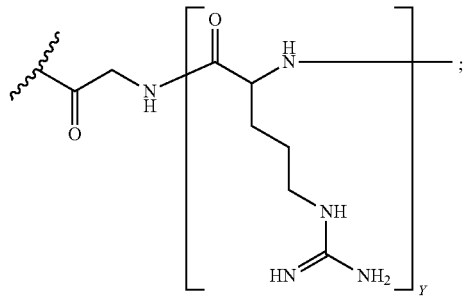

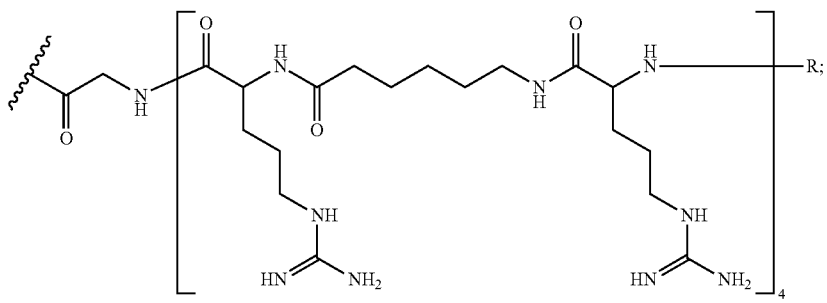

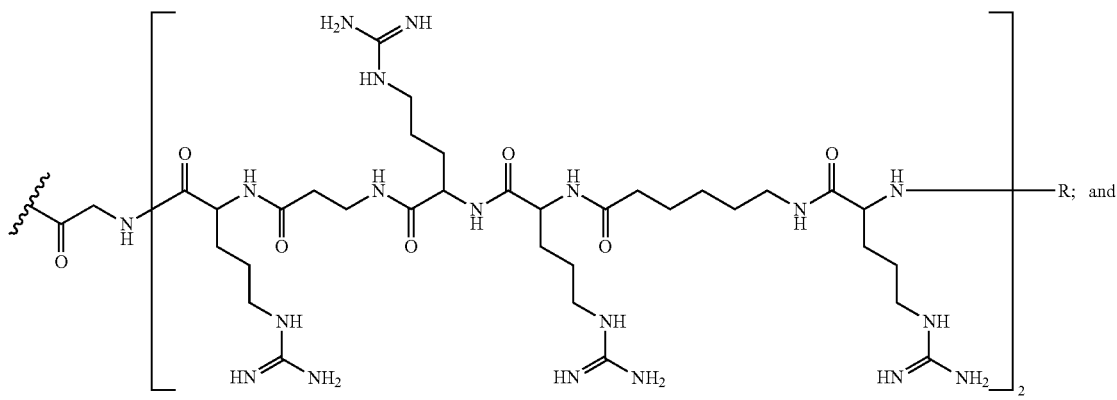

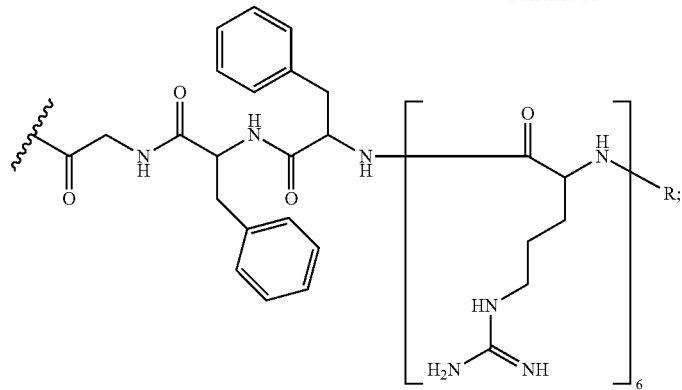
wherein:
Y is an integer from 4 to 7; and
R is selected from H, acetyl, benzoyl, and stearoyl.
11. The conjugate of claim 10, wherein the carrier peptide is of the formula:
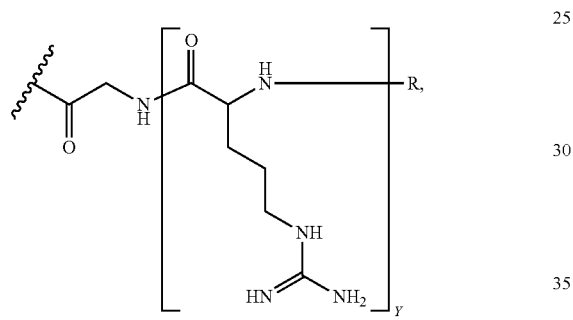
and Y is 6.
12. The conjugate of claim 1, wherein the conjugate is selected from:
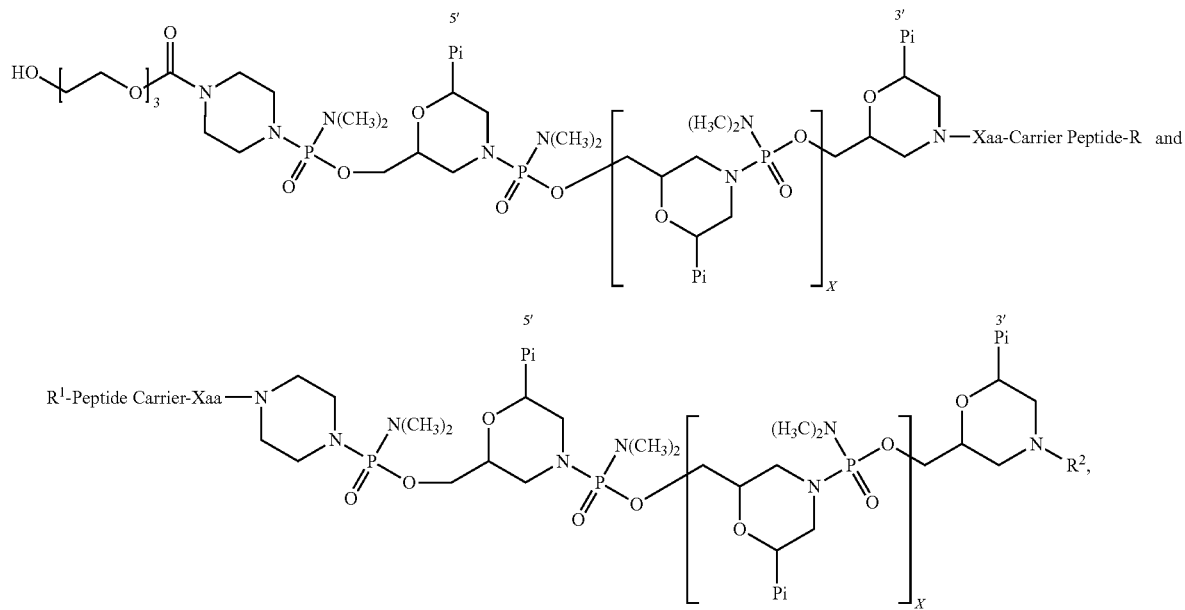

or a pharmaceutically acceptable salt of either of the foregoing, wherein:

X is an integer from 6 to 38;

R is selected from H, acetyl, benzoyl, and stearoyl;

$R^1$ is selected from H, acetyl, benzoyl, and stearoyl;

$R^2$ is selected from H, acetyl, benzoyl, stearoyl, trityl, and 4-methoxytrityl;

each Pi is a purine or pyrimidine base-pairing moiety which taken together form a targeting base sequence; and the carrier peptide is selected from SEQ ID NOS: 60, 69, 70, 89-121, 125, 130-160, 162-257, 276, 277, 281-288, 293-297, 300, 302-412, 419-552, and 554-566, wherein Xaa is the carboxy-terminal glycine.

13. The conjugate of claim 12, wherein X is 6 to 18.

14. The conjugate of claim 12, wherein X is 6 to 14.

15. The conjugate of claim 12, wherein X is 8 to 28.

16. The conjugate of claim 12, wherein X is 10 to 23.

17. The conjugate of claim 12, wherein X is 6 to 10.

18. The conjugate of claim 12, wherein the carrier peptide is selected from SEQ ID NOS: 130, 157-160, 251, 256, 386-388, and 540.

19. The conjugate of claim 12, wherein the carrier is SEQ ID NO: 159.

20. The conjugate of claim 12, wherein each Pi is independently selected from adenine, cytosine, guanine, uracil, thymine, and inosine.

21. A conjugate selected from:

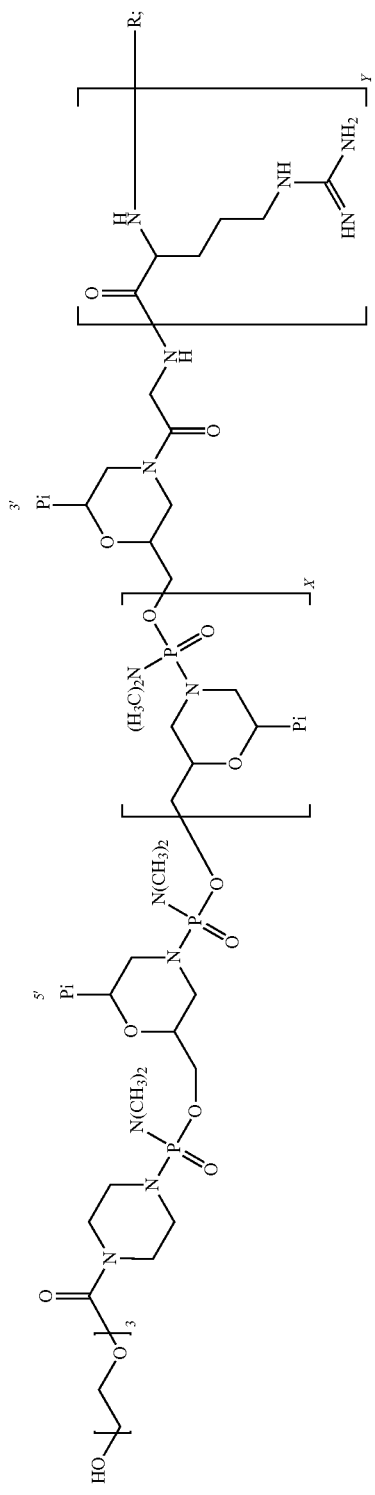
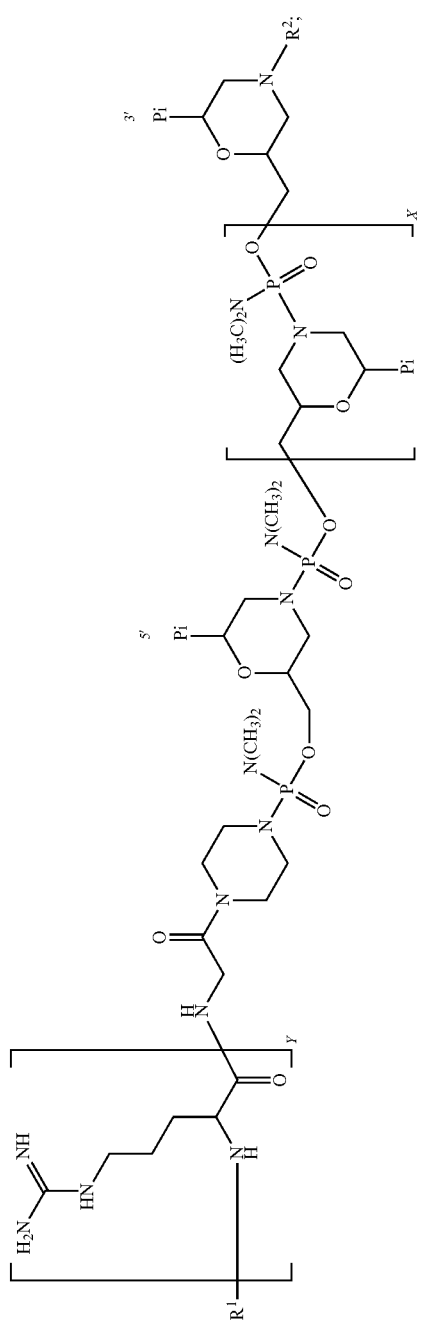

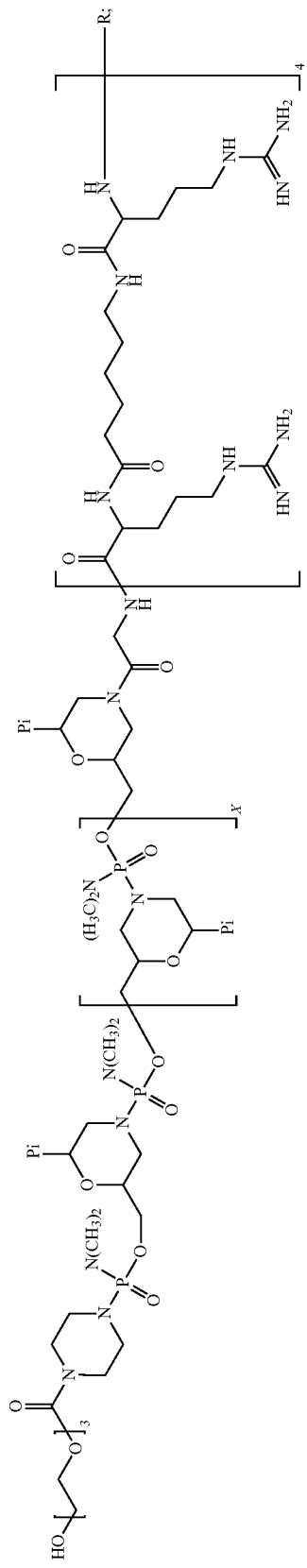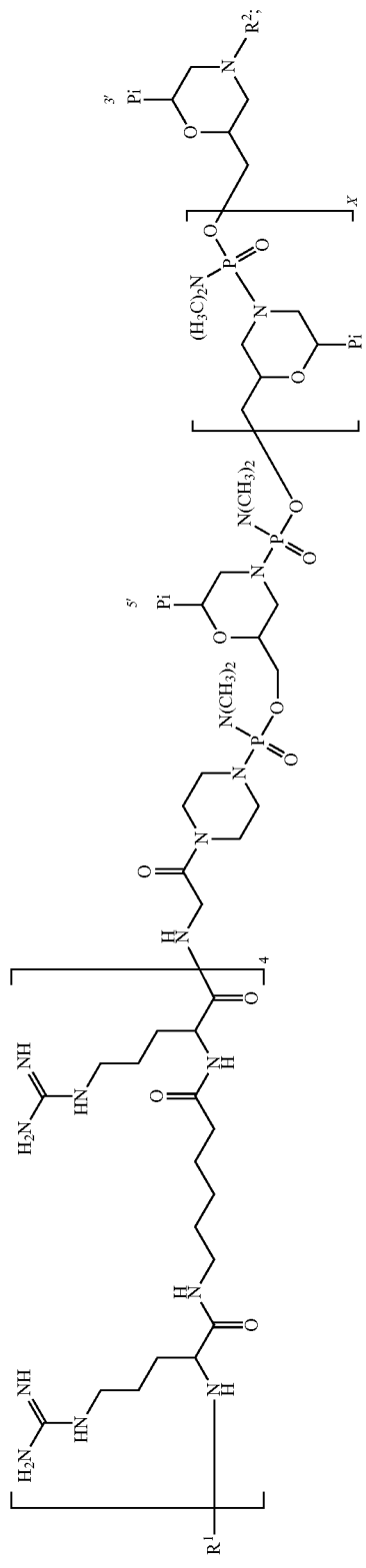

-continued
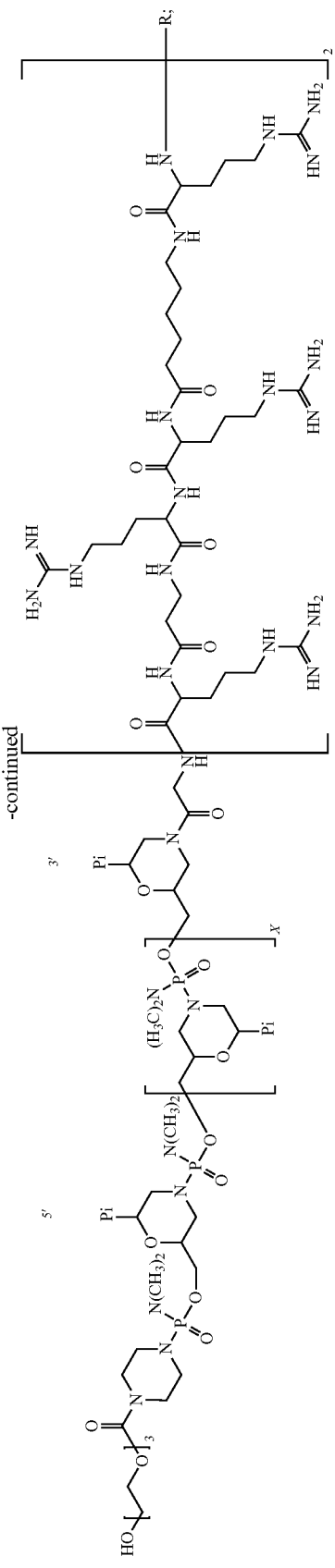
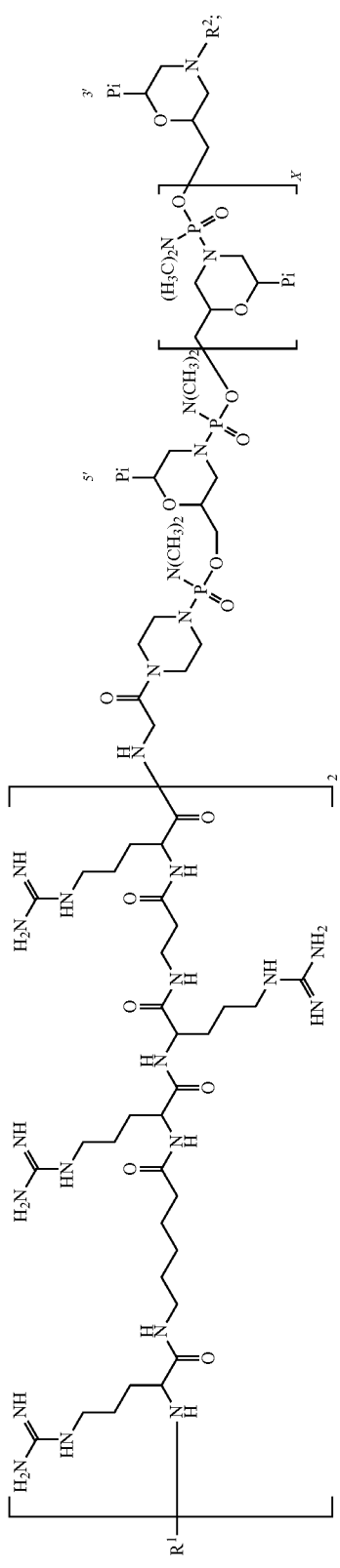

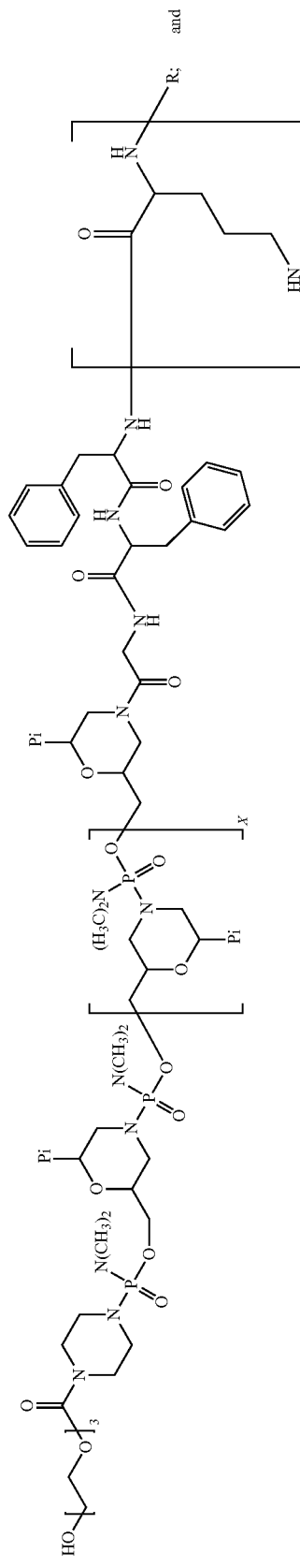
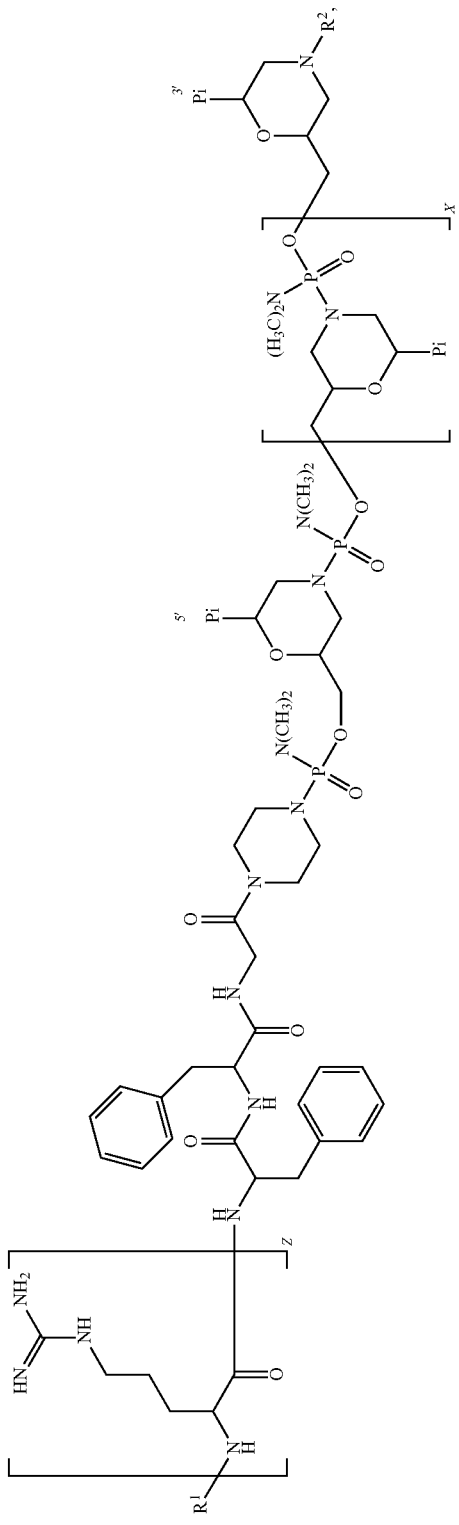

or a pharmaceutically acceptable salt of any of the foregoing, wherein:
X is an integer from 6 to 38;
Y is an integer from 4 to 9;
Z is 6 or 9;
R is selected from H, acetyl, benzoyl, and stearoyl;
R¹ is selected from H, acetyl, benzoyl, and stearoyl;
R² is selected from H, acetyl, benzoyl, stearoyl, trityl, and 4-methoxytrityl; and
each Pi is a purine or pyrimidine base-pairing moiety which taken together form a targeting base sequence.

22. The conjugate of claim 21, wherein X is 6 to 18.
23. The conjugate of claim 21, wherein X is 6 to 14.
24. The conjugate of claim 21, wherein X is 8 to 28.
25. The conjugate of claim 21, wherein X is 10 to 23.
26. The conjugate of claim 21, wherein X is 6 to 10.
27. The conjugate of claim 21, wherein each Pi is independently selected from adenine, cytosine, guanine, uracil, thymine, and inosine.
28. The conjugate of claim 21, wherein the compound is:

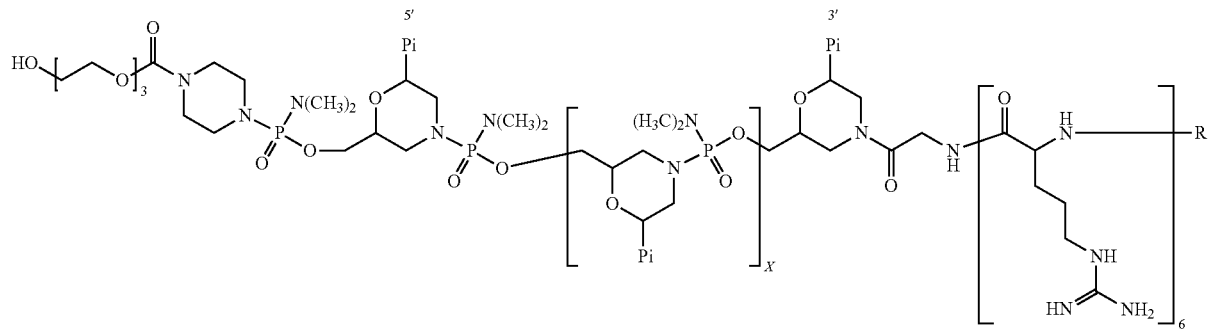

or a pharmaceutically acceptable salt thereof.
29. The conjugate of claim 28, wherein R is H.
30. The conjugate of claim 28, wherein R is acetyl.
31. The conjugate of claim 28, wherein X is 6 to 18.
32. The conjugate of claim 28, wherein X is 6 to 14.
33. The conjugate of claim 28, wherein X is 8 to 28.
34. The conjugate of claim 28, wherein X is 10 to 23.
35. The conjugate of claim 28, wherein X is 6 to 10.
36. The conjugate of claim 28, wherein each Pi is independently selected from adenine, cytosine, guanine, uracil, thymine, and inosine.
37. The conjugate of claim 1, wherein the conjugate is the compound of the formula:

EG3-M23D-G(R)₆ wherein M23D is a nucleic acid analogue having the sequence GGCCAAACCTCGGCTTACCTGAAAT (SEQ ID No. 15);
EG3 is

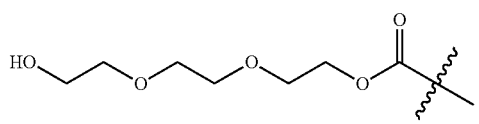 [SMILES: *C(=O)OCCOCCOCCO]

linked to the 5' end of the oligomer via a piperazine linker;
G is glycine; and
R is arginine.

* * * * *